(12) United States Patent
Suzuki et al.

(10) Patent No.: US 8,337,395 B2
(45) Date of Patent: Dec. 25, 2012

(54) ANASTOMOSIS SYSTEM

(75) Inventors: Keita Suzuki, Kokubunji (JP); Tetsuya Yamamoto, Hidaka (JP); Yoshio Onuki, Hino (JP); Satoshi Miyamoto, Nishitama-gun (JP); Masahiro Ishikawa, Hino (JP); Anthony Nicholas Kalloo, Glenn Dale, MD (US); Sergey Veniaminovich Kantsevoy, Silver Spring, MD (US); Pankaj Jay Pasricha, Houston, TX (US); Sydney Sheung Chee Chung, Hong Kong (CN)

(73) Assignees: Olympus Corporation, Tokyo (JP); Apollo Endosurgery, Inc., Austin, TX (US)

( * ) Notice: Subject to any disclaimer, the term of this patent is extended or adjusted under 35 U.S.C. 154(b) by 213 days.

(21) Appl. No.: 12/435,144

(22) Filed: May 4, 2009

(65) Prior Publication Data
US 2009/0216081 A1 Aug. 27, 2009

Related U.S. Application Data

(63) Continuation of application No. 10/390,443, filed on Mar. 17, 2003, now Pat. No. 7,527,590.

(60) Provisional application No. 60/365,687, filed on Mar. 19, 2002.

(51) Int. Cl.
*A61B 1/00* (2006.01)

(52) U.S. Cl. ........ 600/115; 600/114; 600/116; 600/146; 600/156; 600/158

(58) Field of Classification Search ........... 600/114–116
See application file for complete search history.

(56) References Cited

U.S. PATENT DOCUMENTS

| | | | | |
|---|---|---|---|---|
| 3,913,565 A | * | 10/1975 | Kawahara | 600/585 |
| 4,066,070 A | * | 1/1978 | Utsugi | 600/116 |
| 4,224,929 A | * | 9/1980 | Furihata | 600/116 |
| 4,577,621 A | * | 3/1986 | Patel | 600/114 |
| 4,899,787 A | * | 2/1990 | Ouchi et al. | 138/131 |
| 4,911,148 A | * | 3/1990 | Sosnowski et al. | 600/136 |
| 5,174,276 A | * | 12/1992 | Crockard | 600/104 |
| 5,251,611 A | * | 10/1993 | Zehel et al. | 600/141 |
| 5,279,610 A | * | 1/1994 | Park et al. | 606/108 |
| 5,284,128 A | * | 2/1994 | Hart | 600/208 |
| 5,337,733 A | * | 8/1994 | Bauerfeind et al. | 600/139 |
| 5,441,507 A | | 8/1995 | Wilk | |
| 5,571,119 A | | 11/1996 | Atala | |
| 5,741,429 A | * | 4/1998 | Donadio et al. | 216/8 |

(Continued)

OTHER PUBLICATIONS

Takashi, A., et al., "Gastrojejunostomy", Outline of Standard Surgical Procedures, New Surgical Atlas, Gastroenterological Surgery 6, Supplemental Edition, vol. 18, No. 7, Jun. 1995, published by Health Publications (Japan).

(Continued)

*Primary Examiner* — Matthew J Kasztejna
(74) *Attorney, Agent, or Firm* — Scully, Scott, Murphy & Presser, P.C.

(57) ABSTRACT

There is provided an endoscopic system.
The system comprises a flexible endoscope insertable into a first tubular organ from a natural opening of a human body. The system further comprises an opening member which forms on a wall part of the first tubular organ an opening used to insert the endoscope into an abdominal cavity from the first tubular organ in the body, an anastomosing member which is able to anastomoses the first tubular organ with a second tubular organ in the abdominal cavity, and a cutting member with which the second tubular organ is able to be cut.

6 Claims, 105 Drawing Sheets

U.S. PATENT DOCUMENTS

| | | | |
|---|---|---|---|
| 5,759,151 A * | 6/1998 | Sturges | 600/146 |
| 5,871,488 A | 2/1999 | Tovey et al. | |
| 5,879,371 A | 3/1999 | Gardiner et al. | |
| 6,200,313 B1 | 3/2001 | Abe et al. | |
| 6,234,958 B1 | 5/2001 | Snoke et al. | |
| 6,306,081 B1 * | 10/2001 | Ishikawa et al. | 600/127 |
| 6,527,753 B2 | 3/2003 | Sekine et al. | |
| 6,689,130 B2 | 2/2004 | Arai et al. | |
| 6,719,765 B2 | 4/2004 | Bonutti | |
| 7,721,742 B2 * | 5/2010 | Kalloo et al. | 600/115 |
| 2001/0049497 A1 * | 12/2001 | Kalloo et al. | 604/164.01 |
| 2002/0026094 A1 * | 2/2002 | Roth | 600/121 |
| 2003/0216749 A1 | 11/2003 | Ishikawa et al. | |

OTHER PUBLICATIONS

Stedman's Medical Dictionary, 26$^{th}$ Edition, Williams & Wilkins, 1995.

* cited by examiner

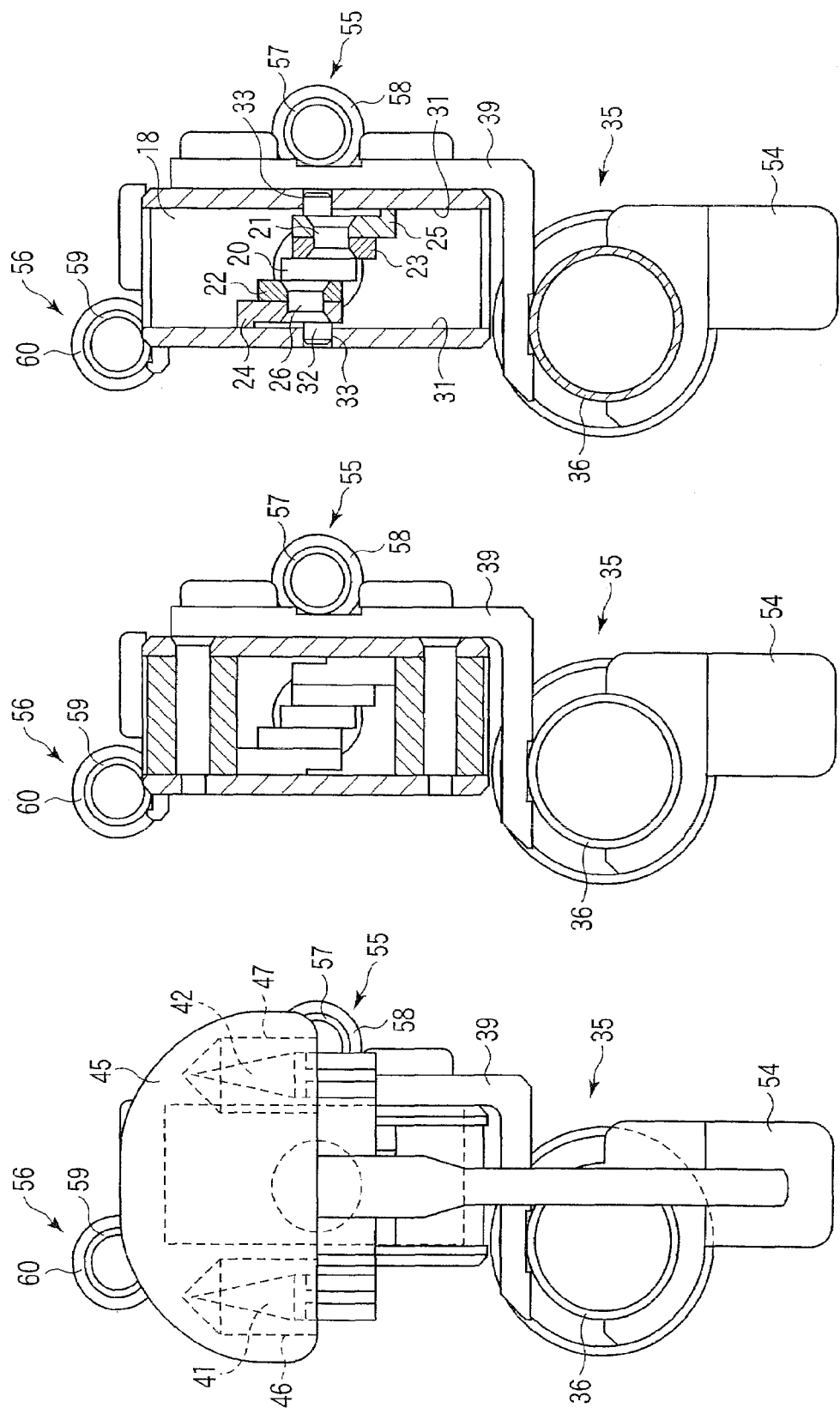

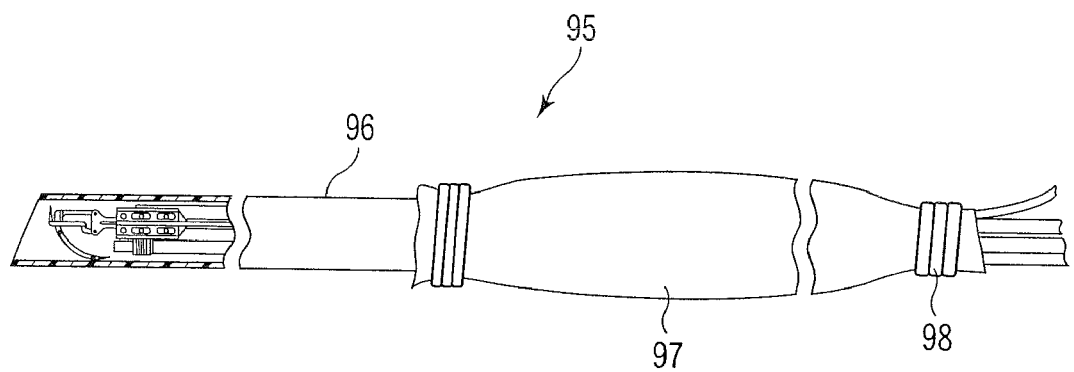
F I G. 20
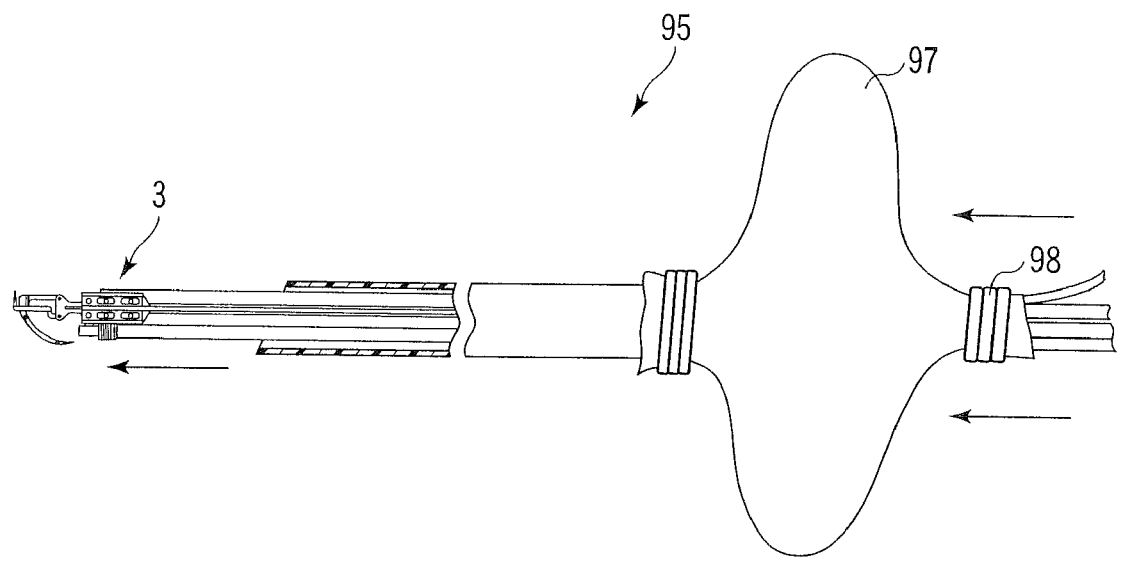
F I G. 21

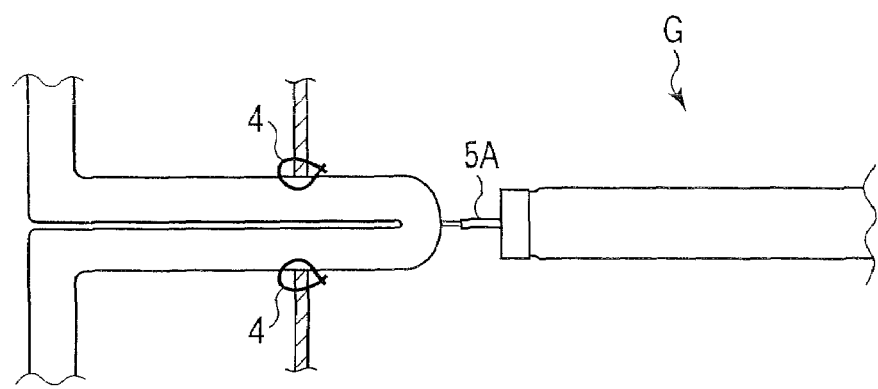
F I G. 30
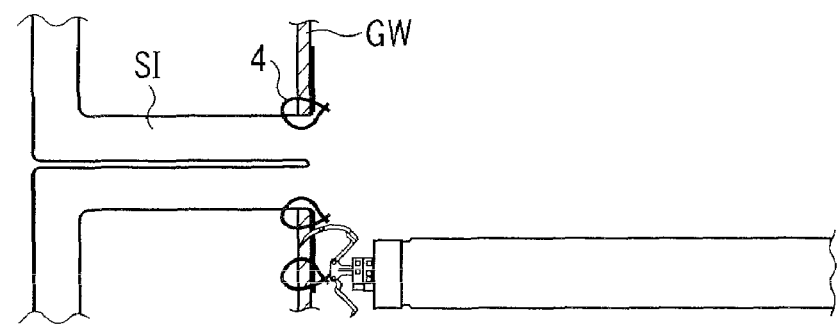
F I G. 31
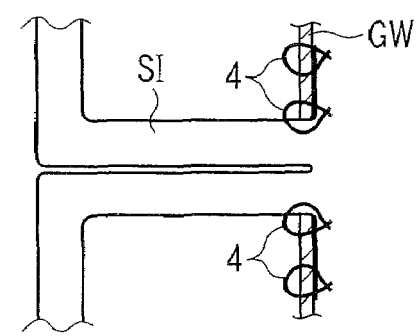
F I G. 32

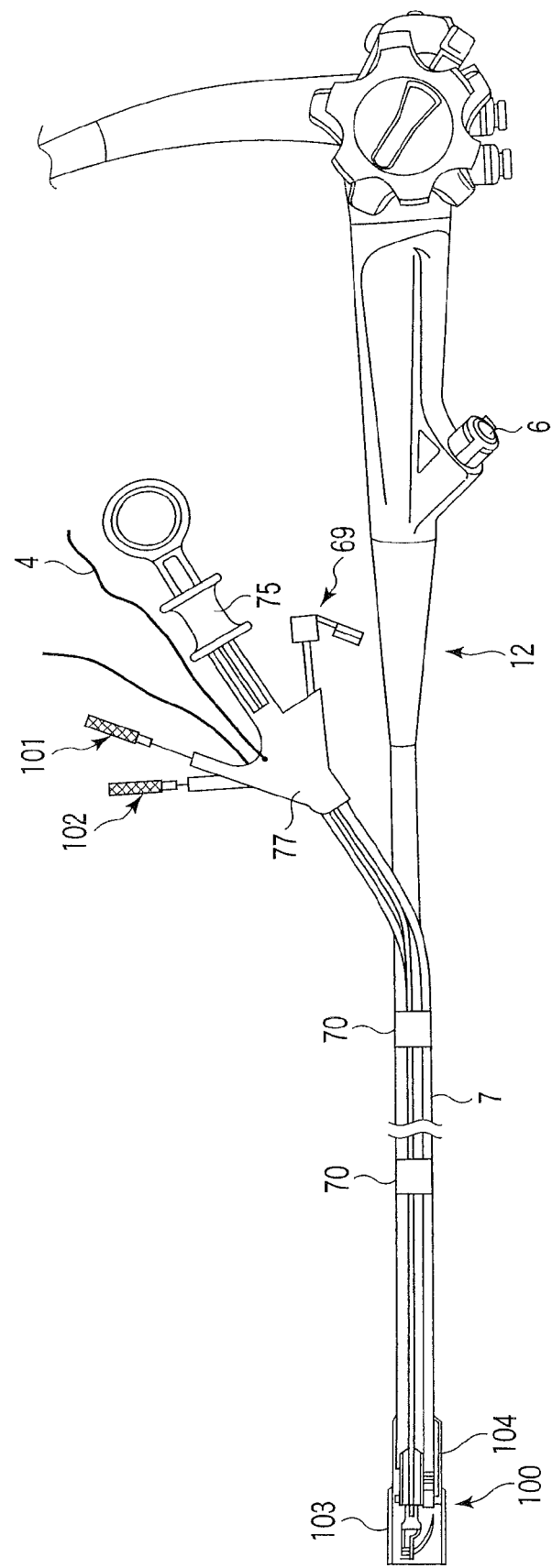
F I G. 41

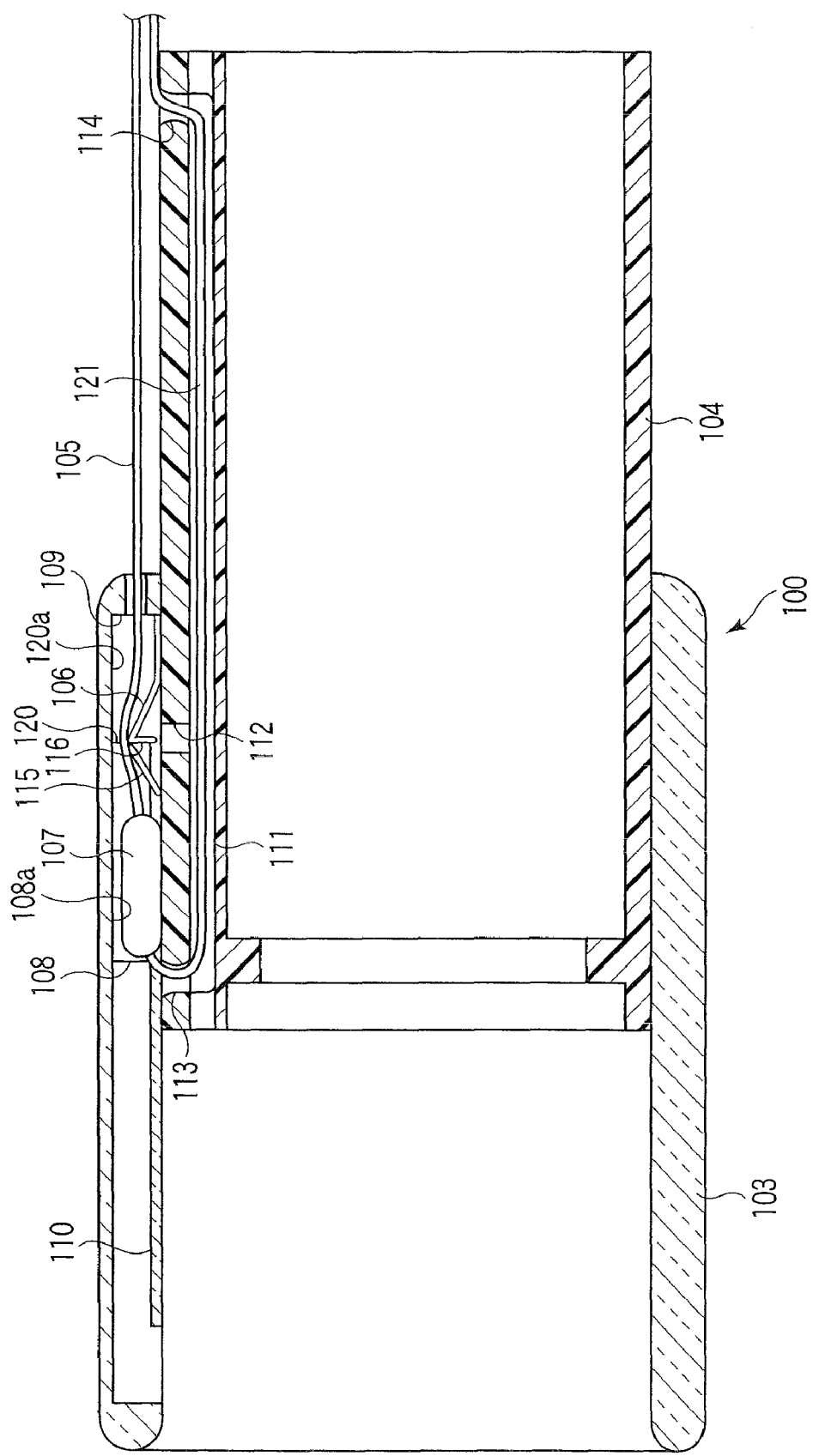
F I G. 43

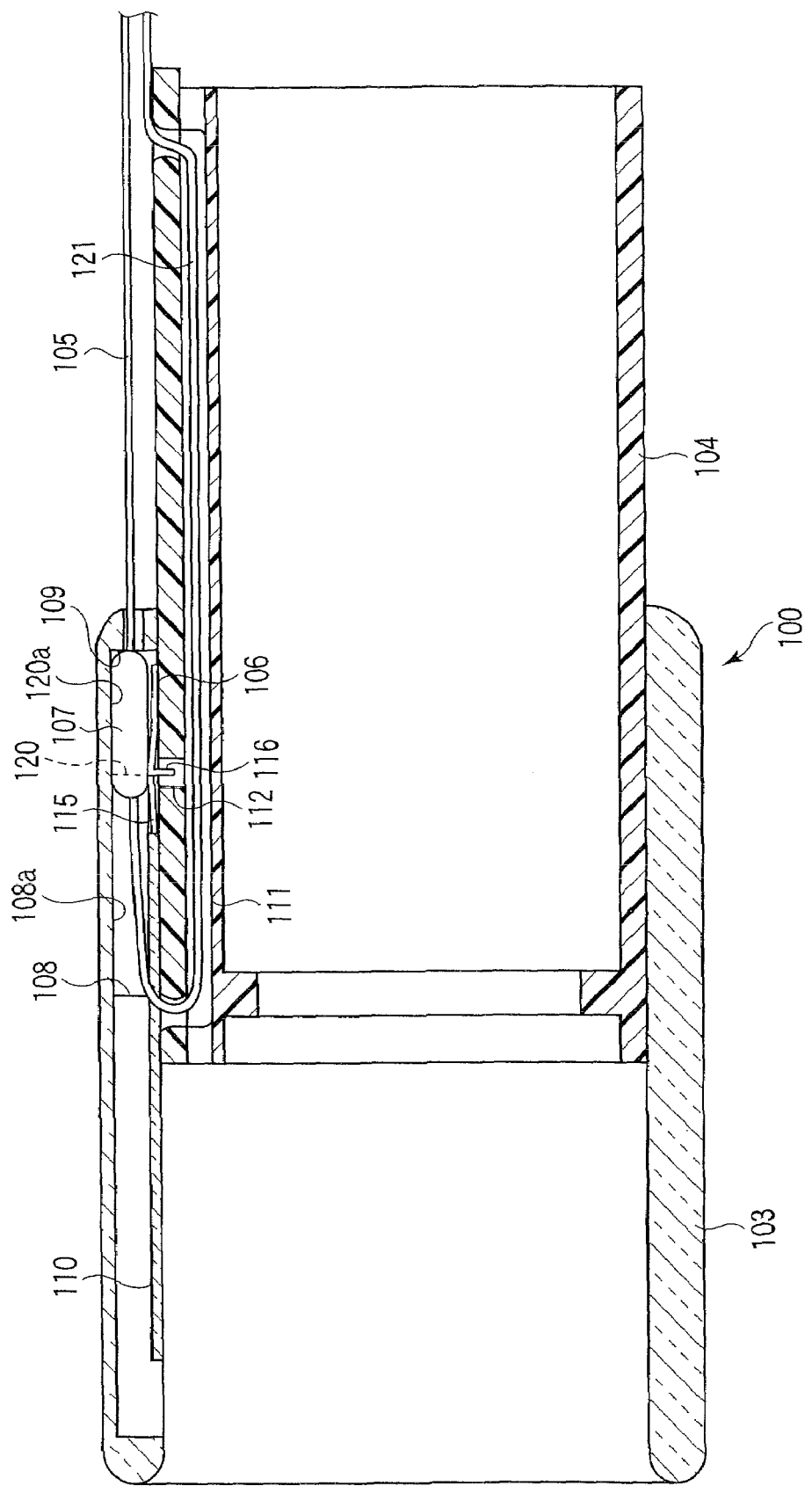
F I G. 44

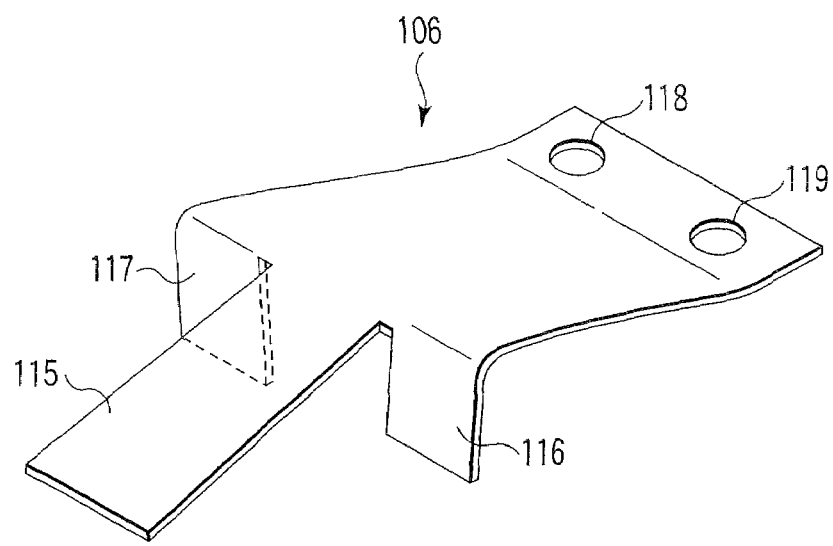
F I G. 46
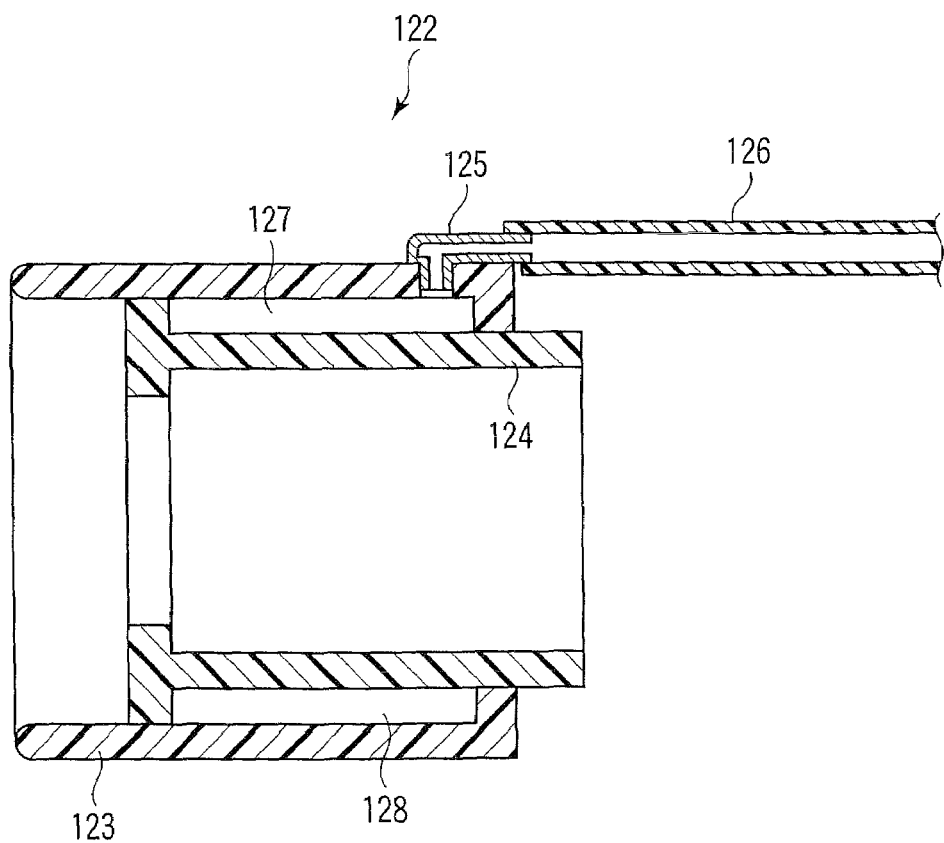
F I G. 47

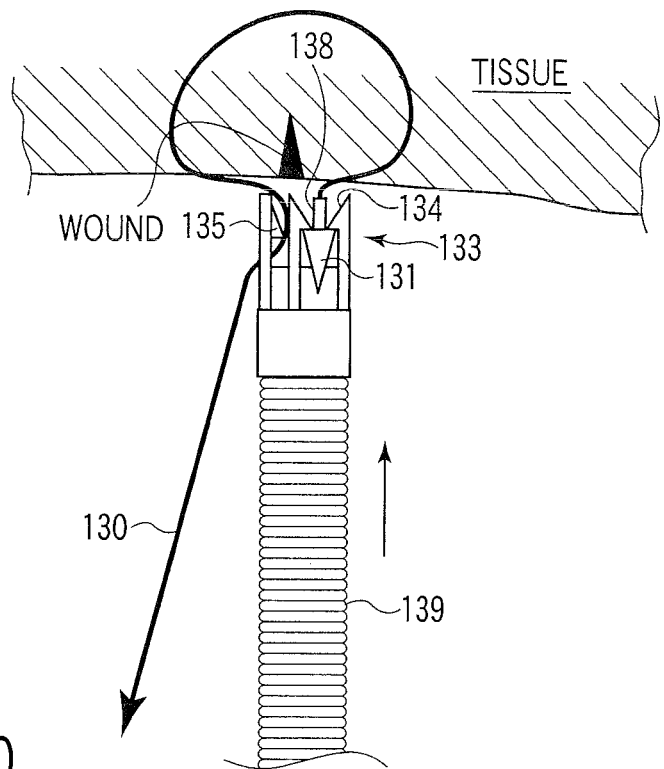
F I G. 50
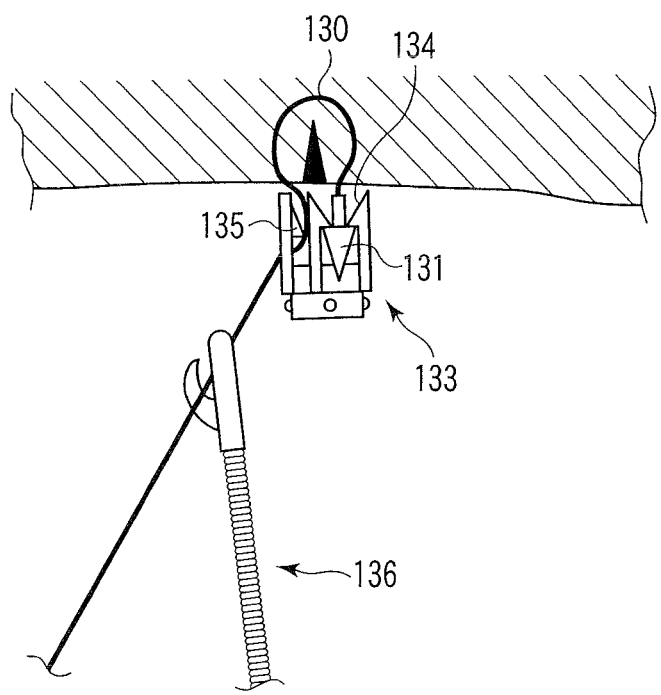
F I G. 51

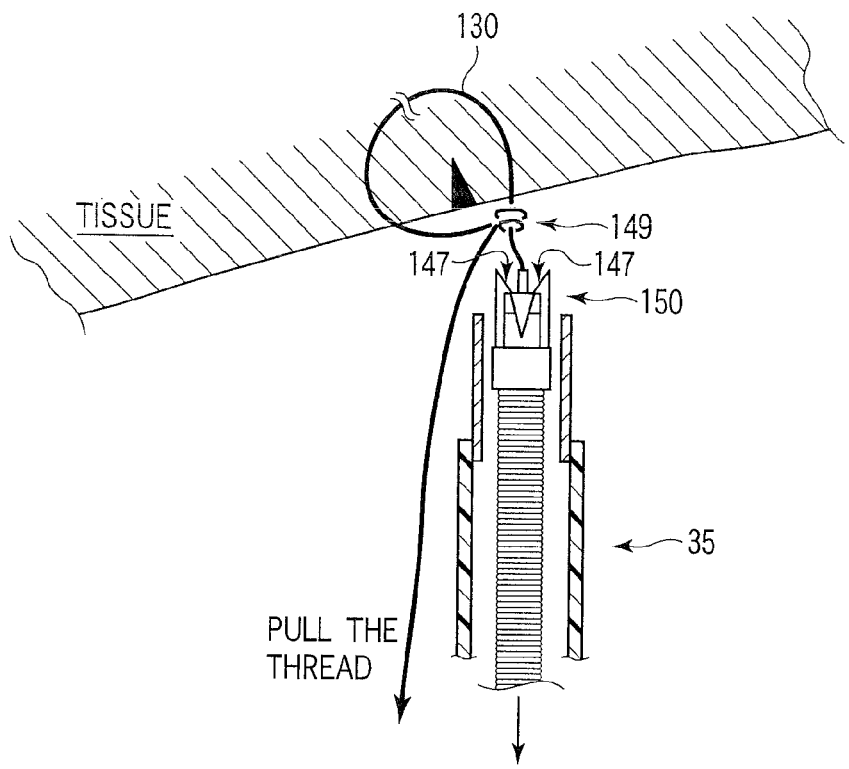
F I G. 59
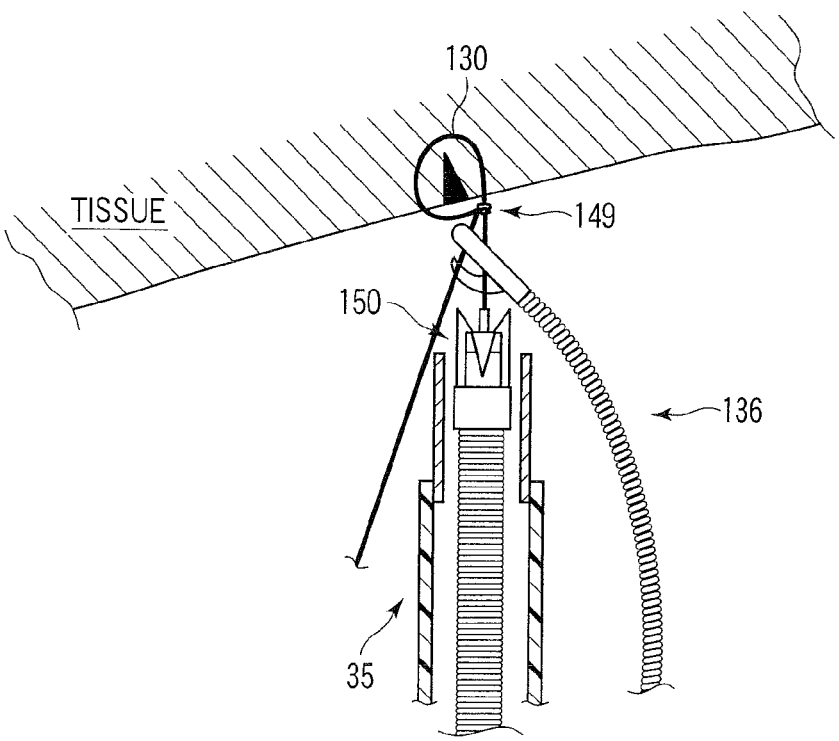
F I G. 60

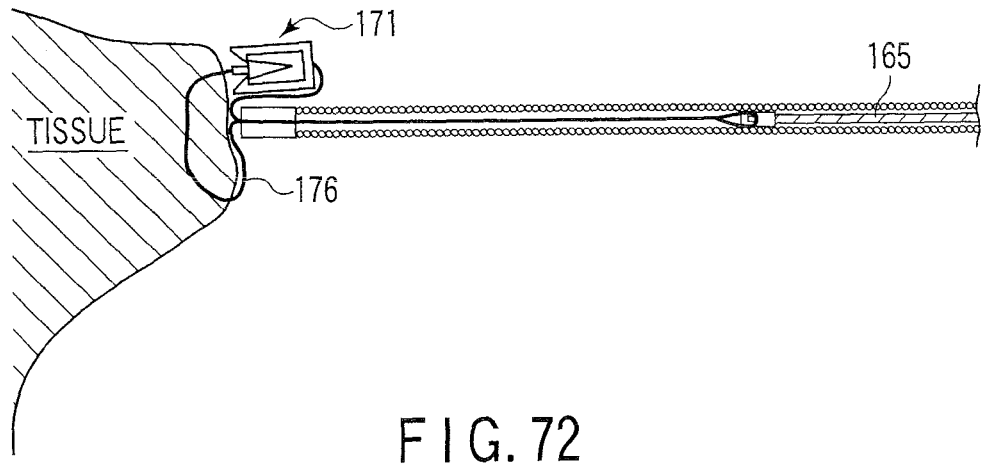
F I G. 72
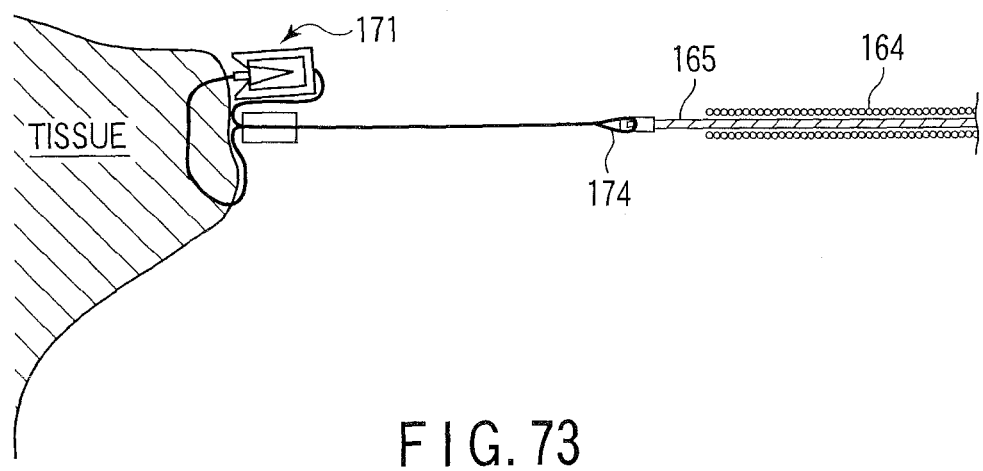
F I G. 73
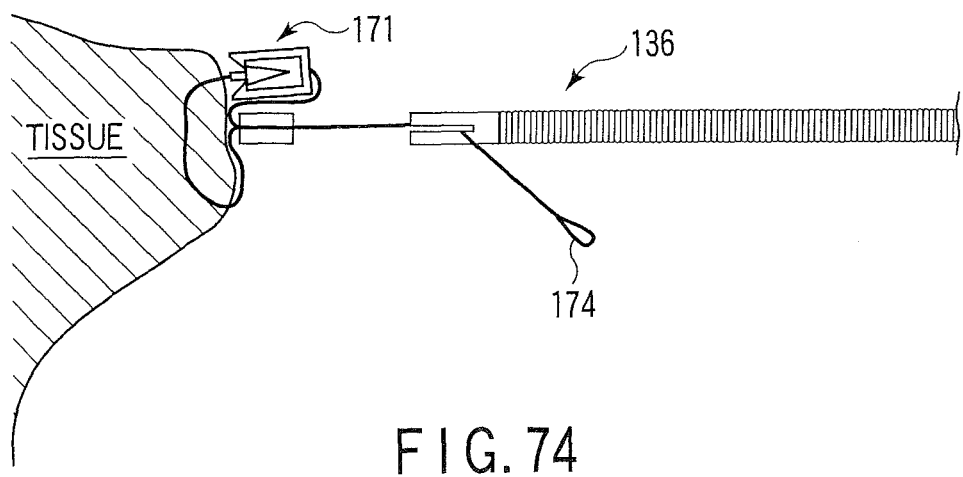
F I G. 74

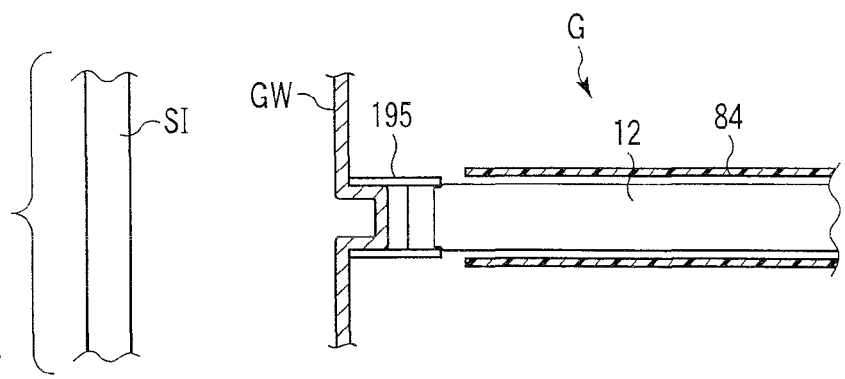
F I G. 78
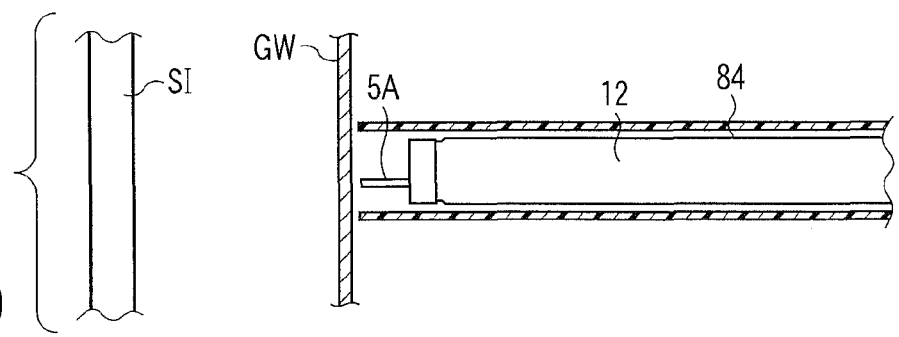
F I G. 79
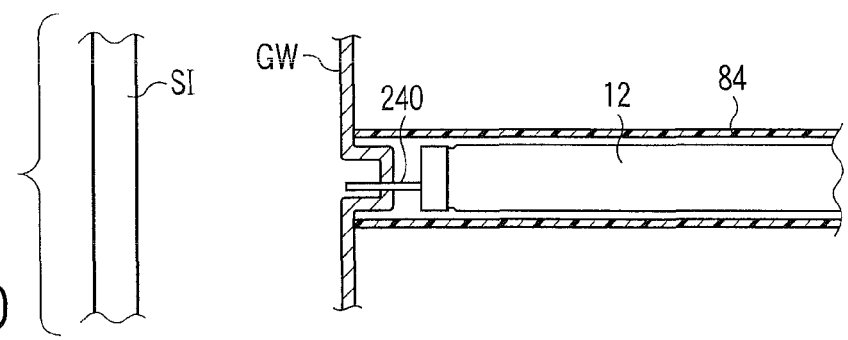
F I G. 80
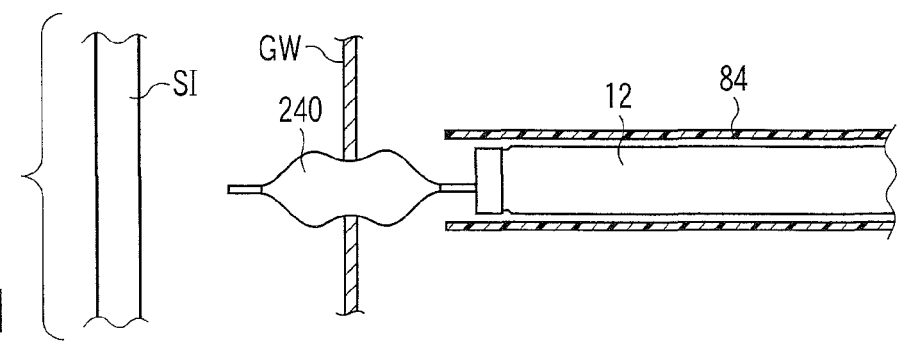
F I G. 81

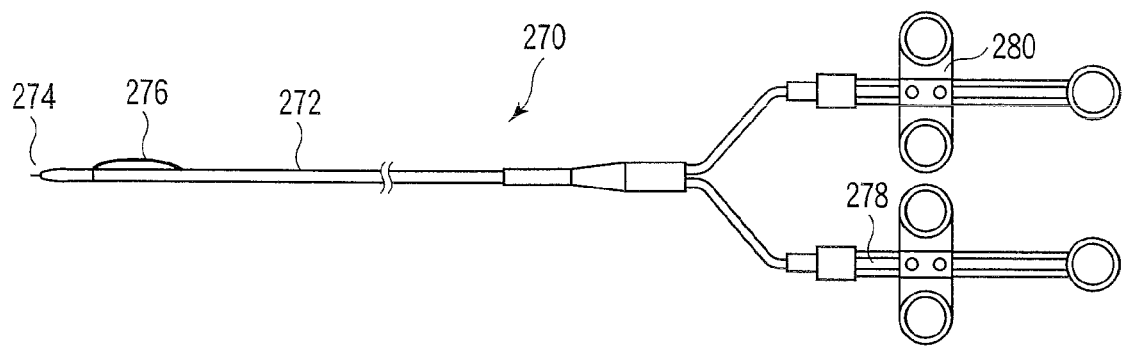
F I G. 94
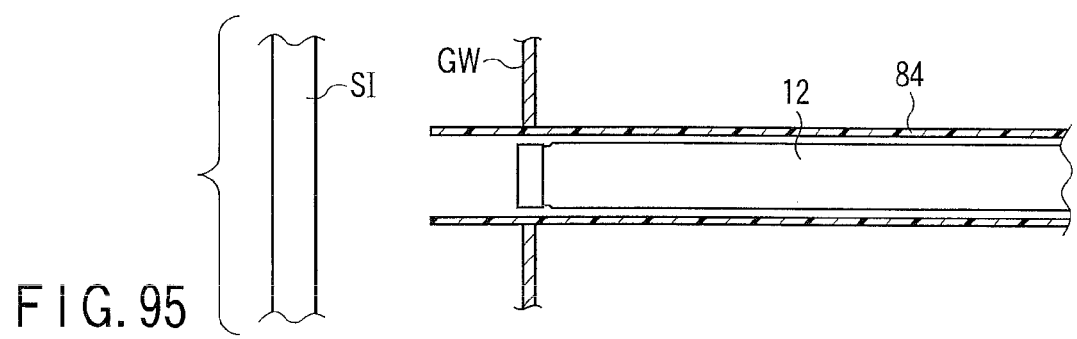
F I G. 95
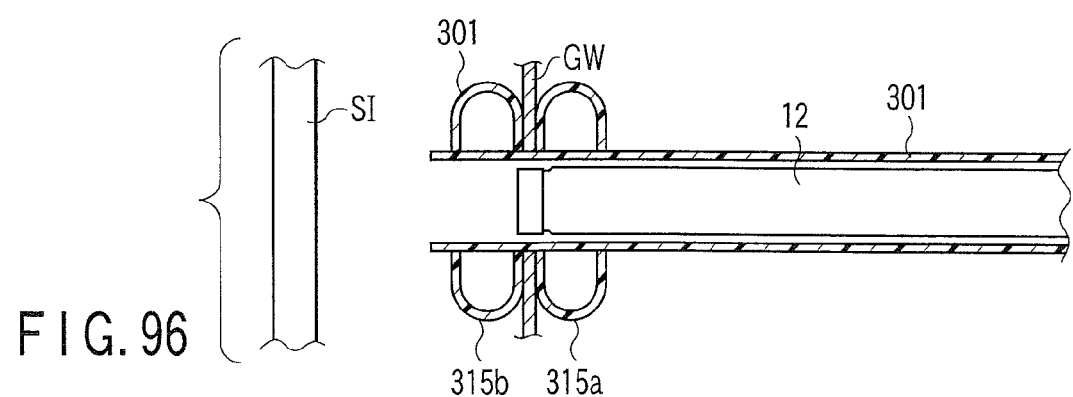
F I G. 96

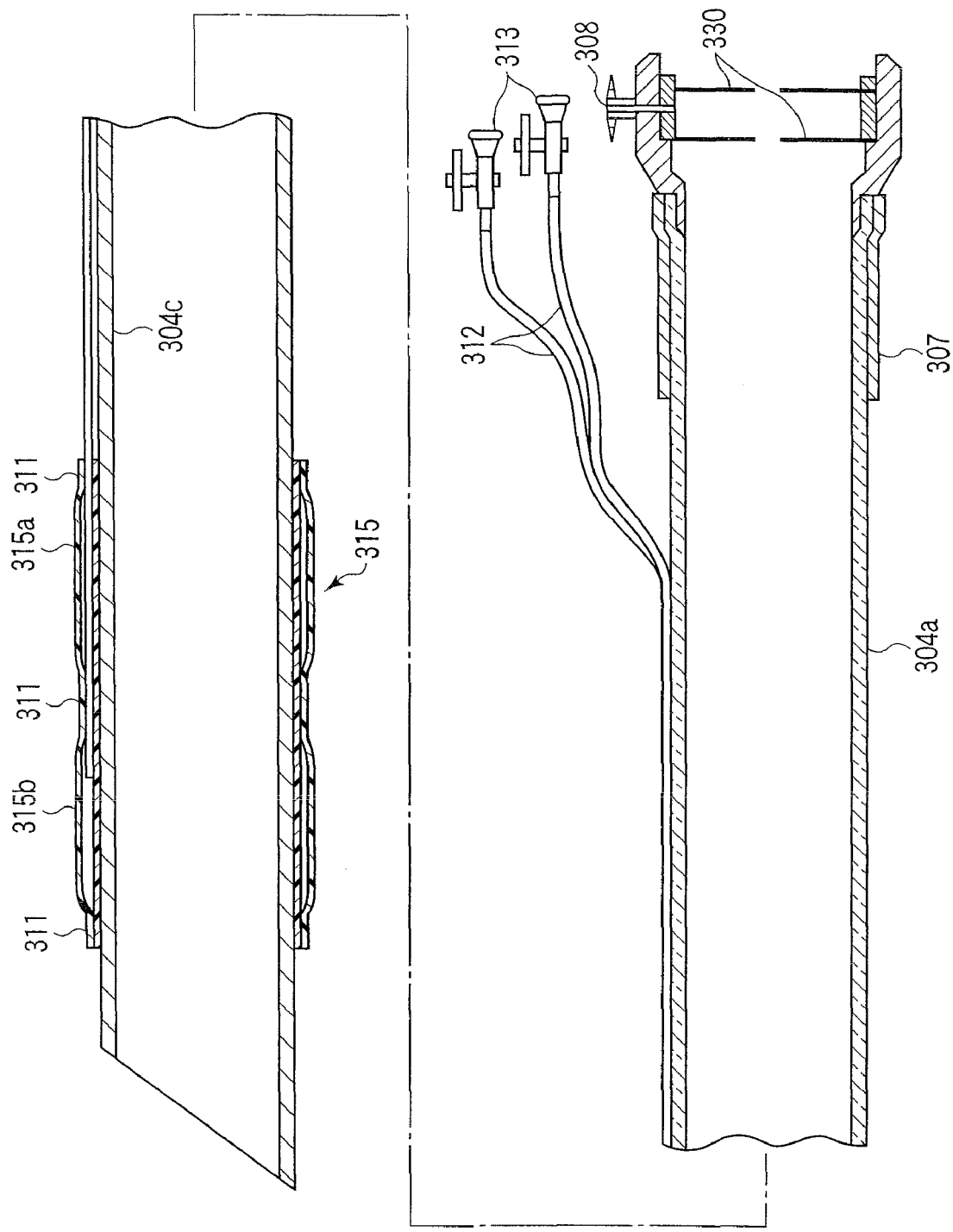
F I G. 100

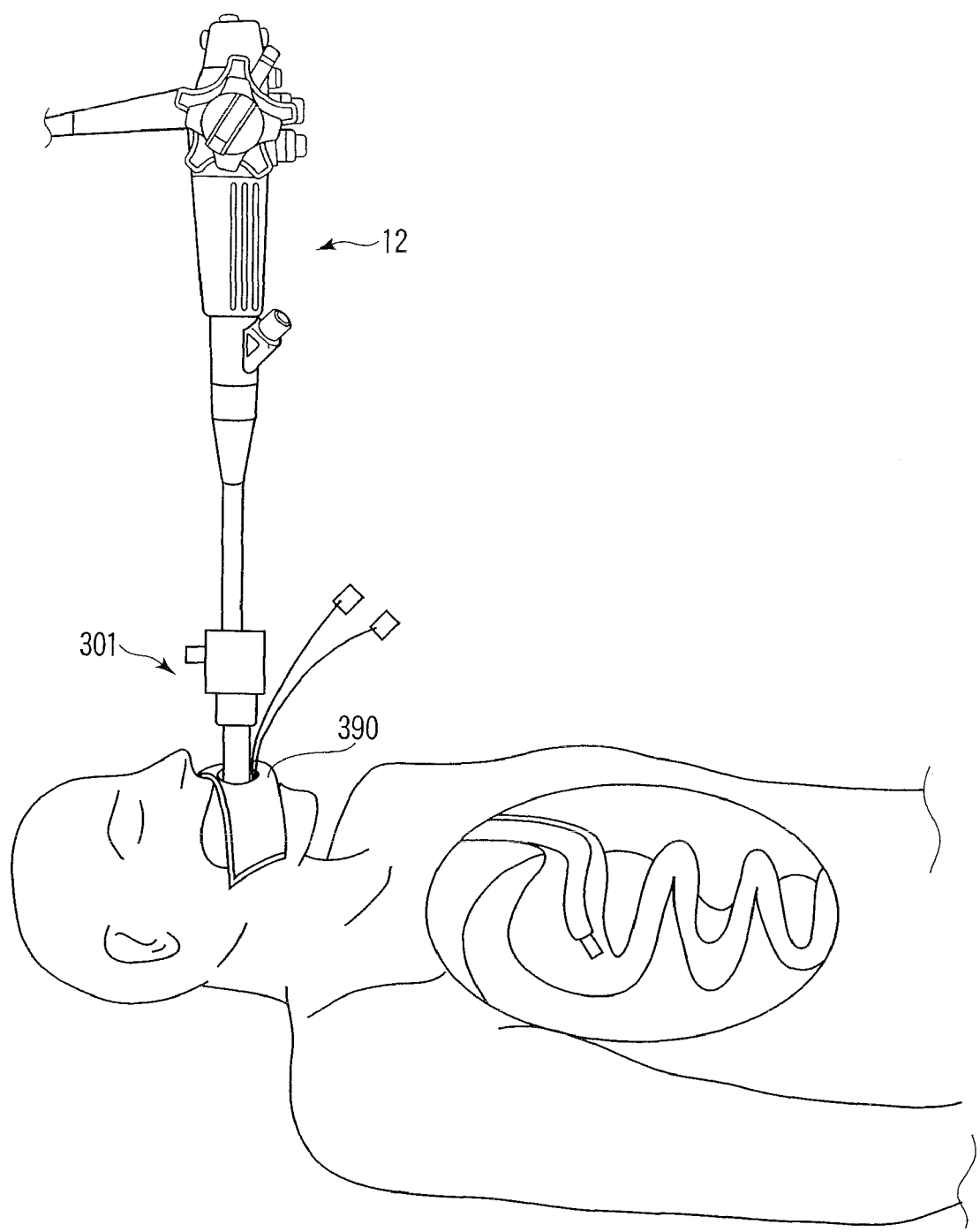
F I G. 101

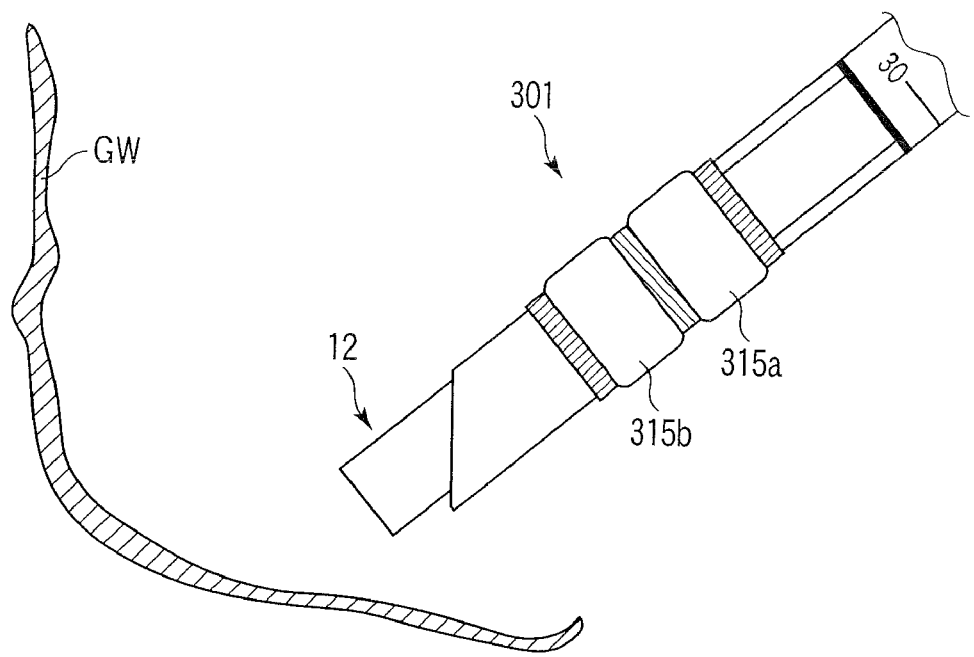
F I G. 102
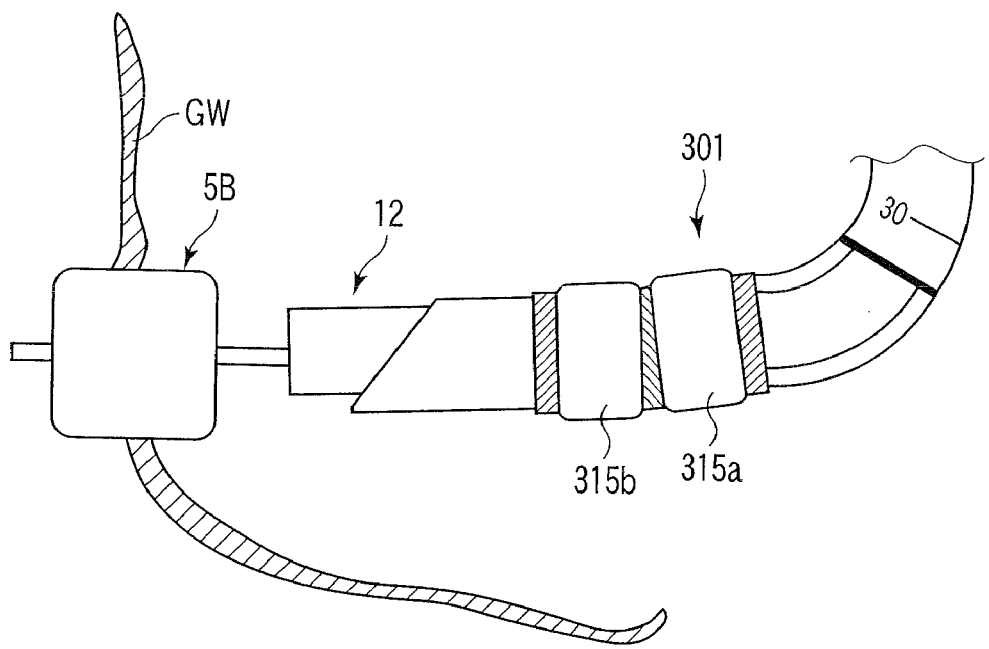
F I G. 103

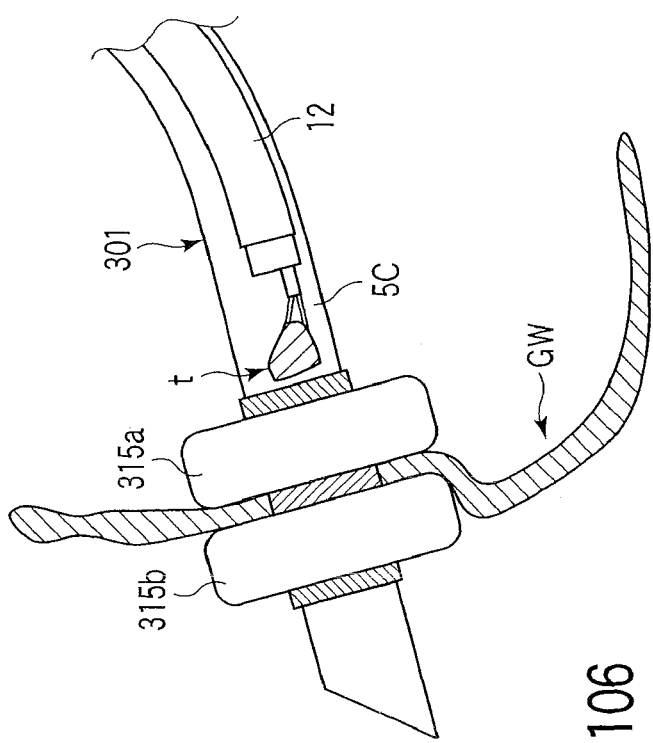
F I G. 106
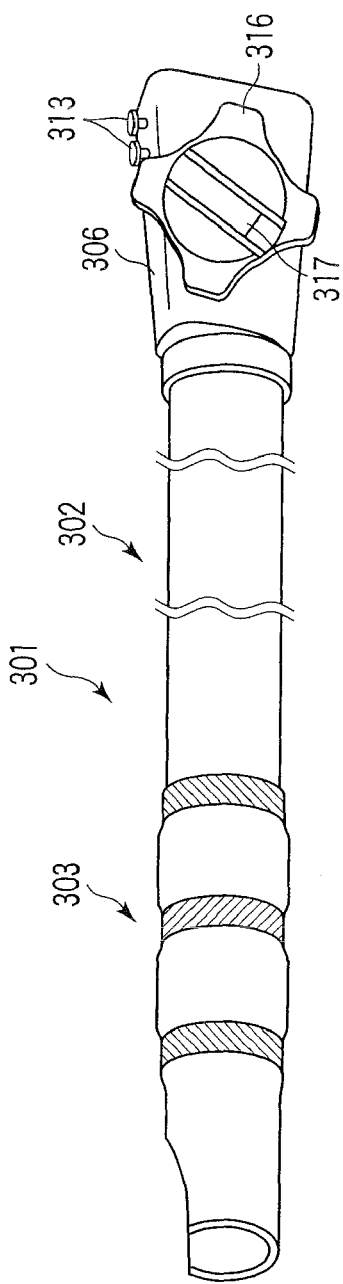
F I G. 107

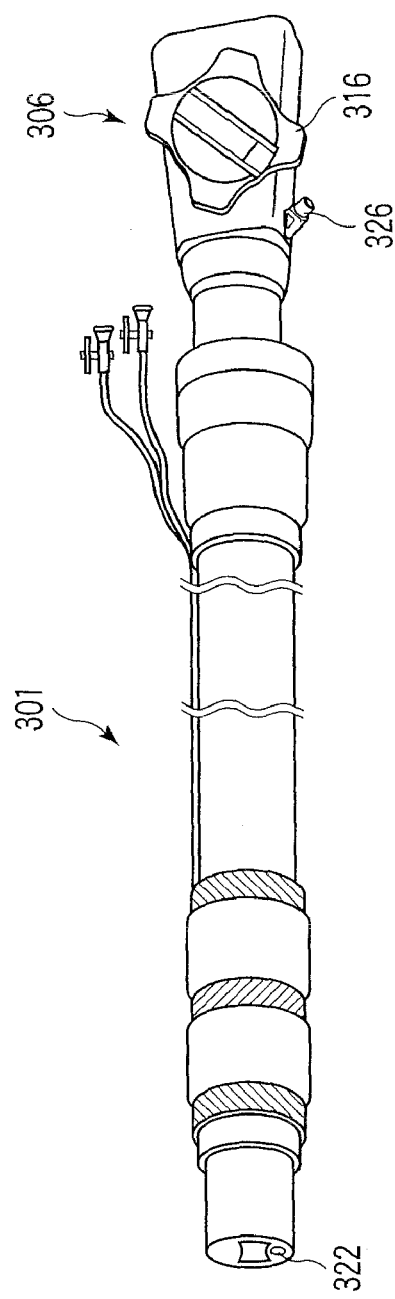
F I G. 113
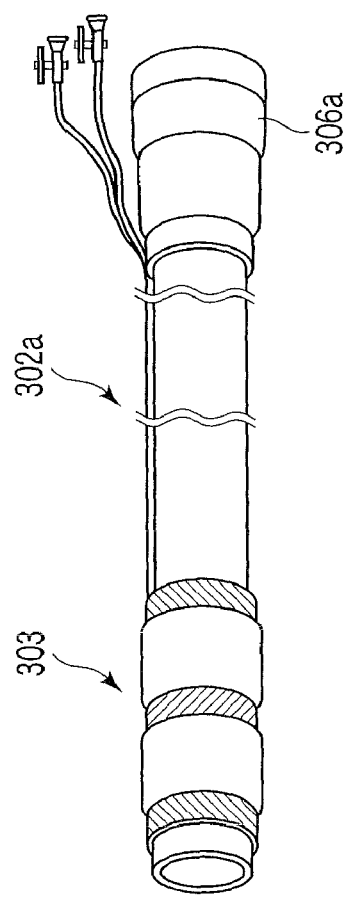
F I G. 114
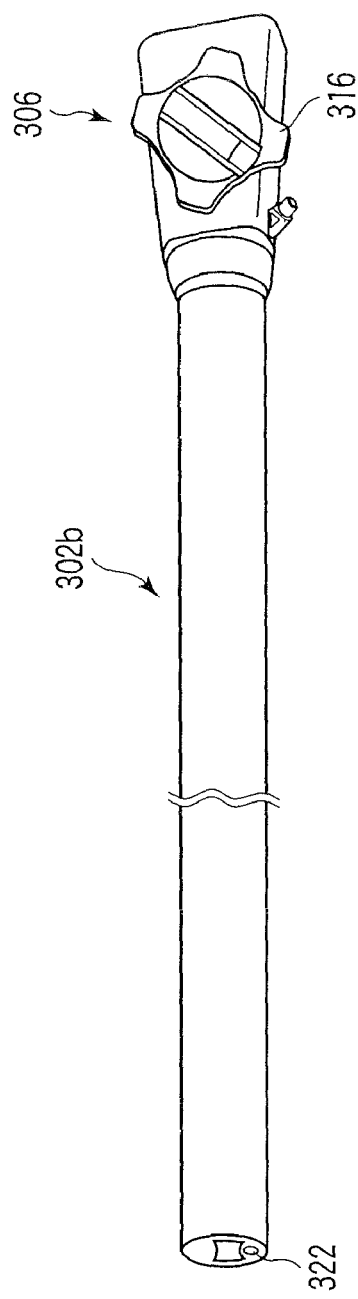
F I G. 115

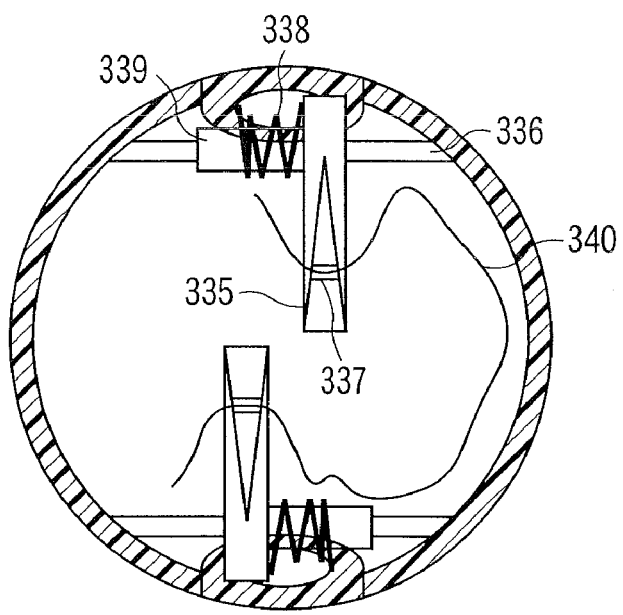
F I G. 123
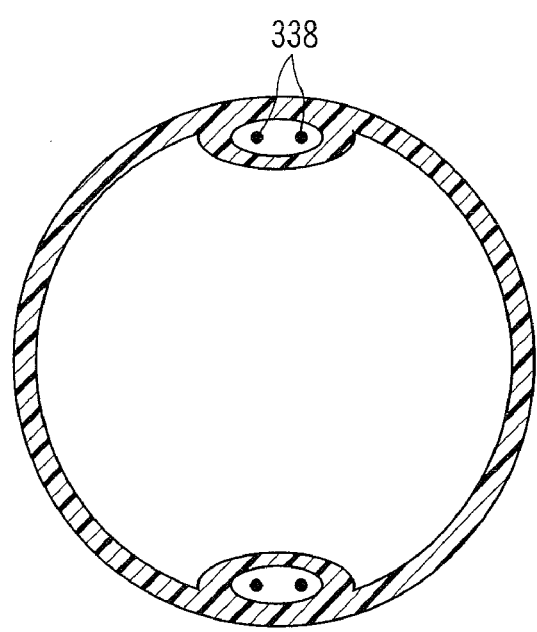
F I G. 124

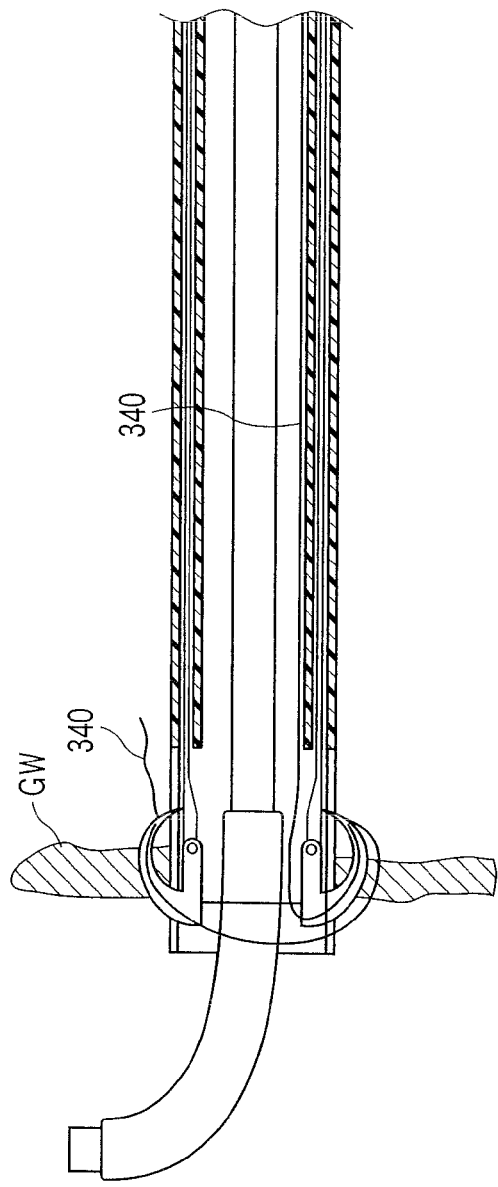
F I G. 125
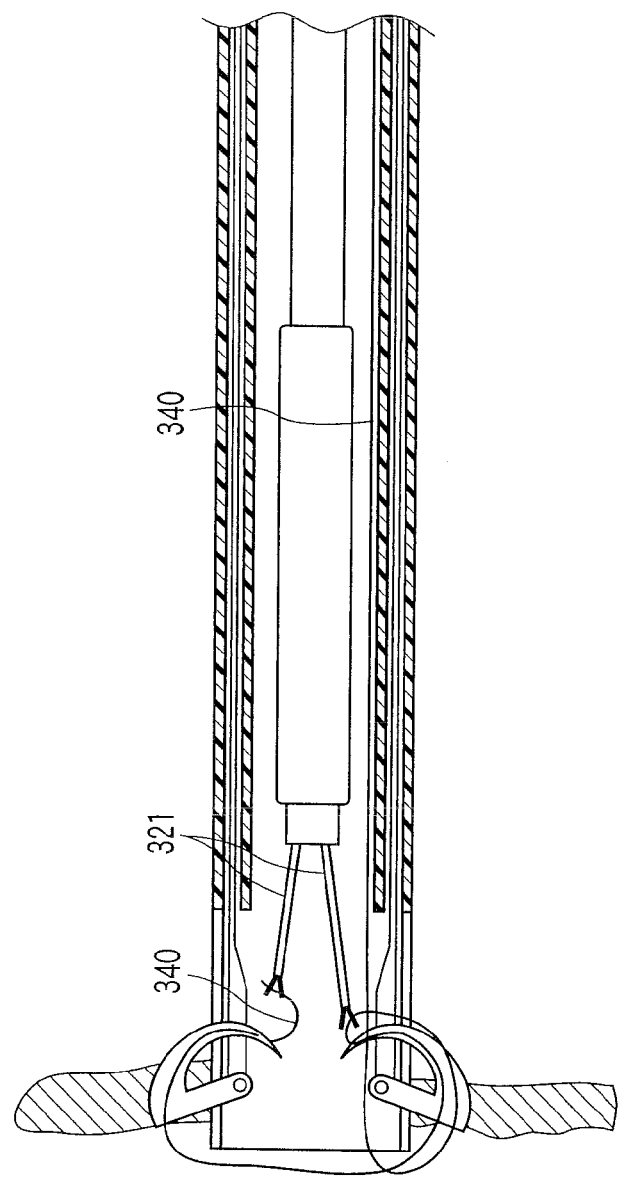
F I G. 126

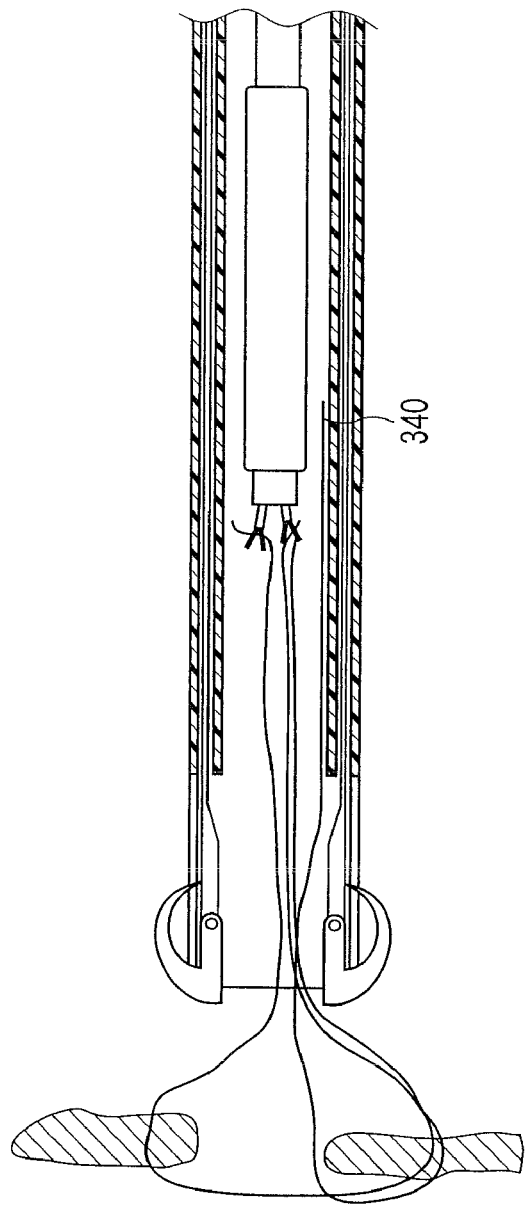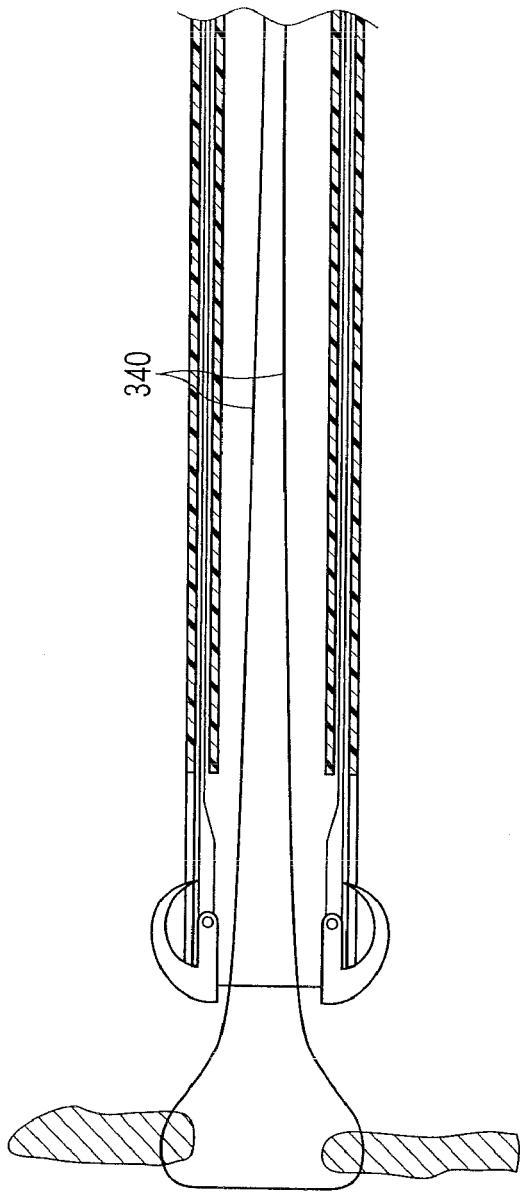
FIG. 127
FIG. 128

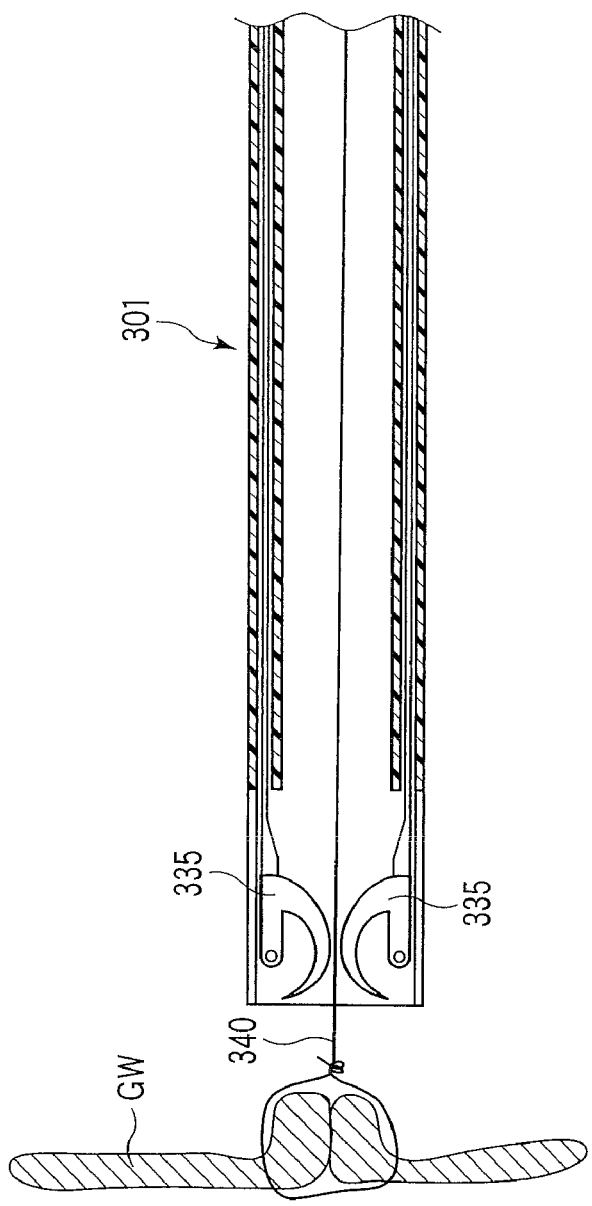
F I G. 129
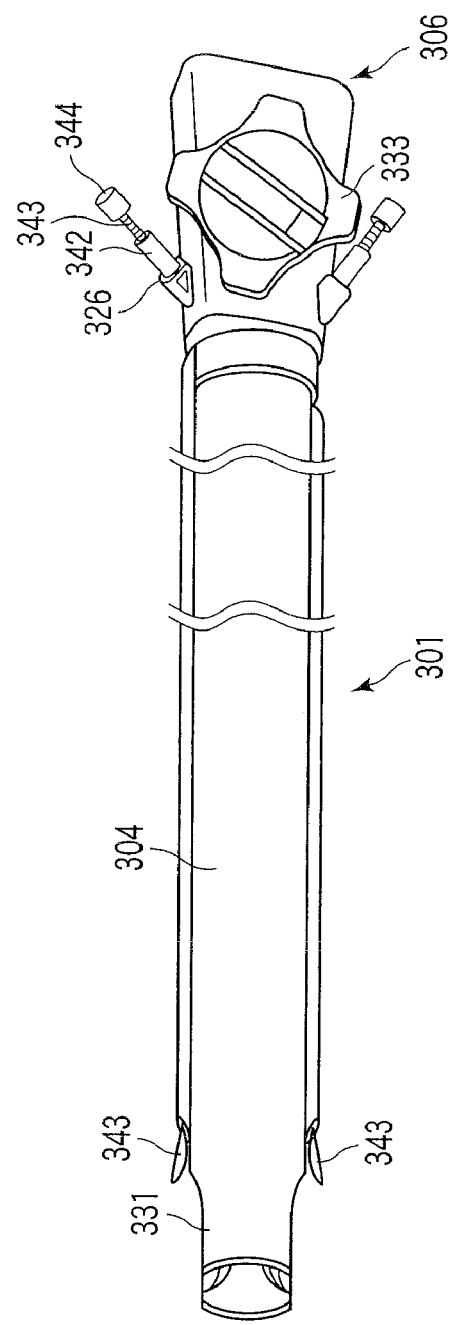
F I G. 130

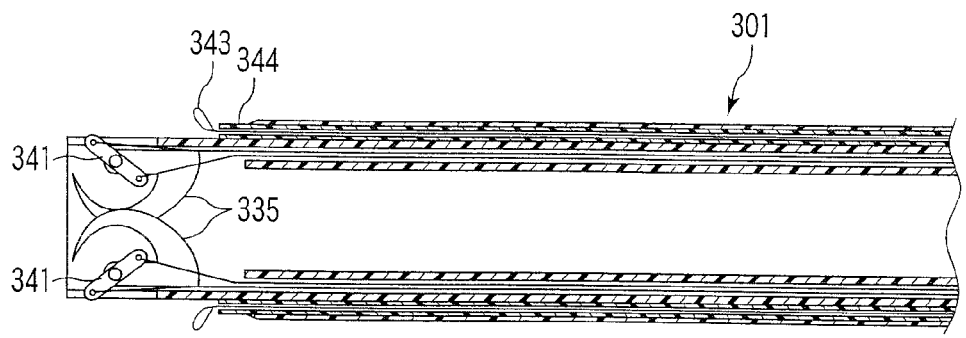
F I G. 131
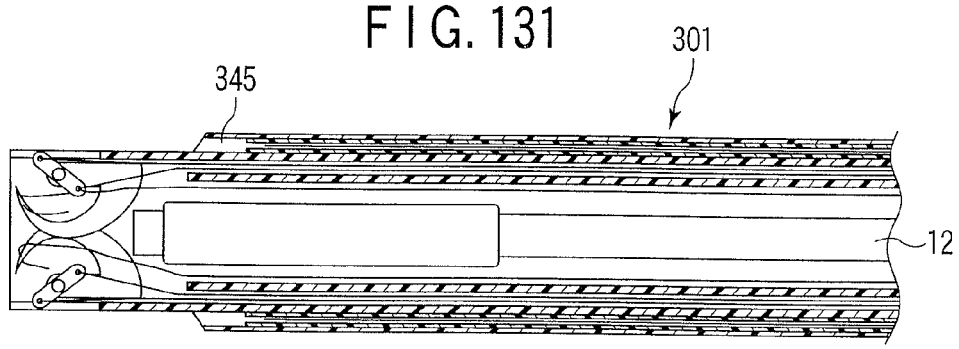
F I G. 132
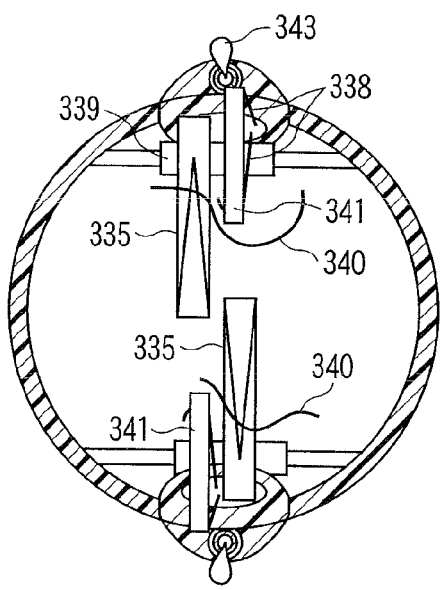
F I G. 133
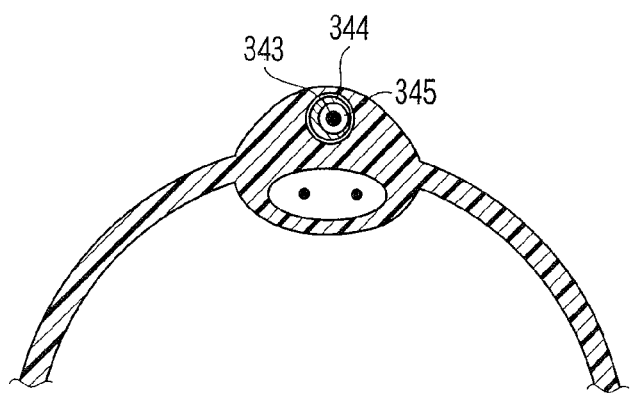
F I G. 134

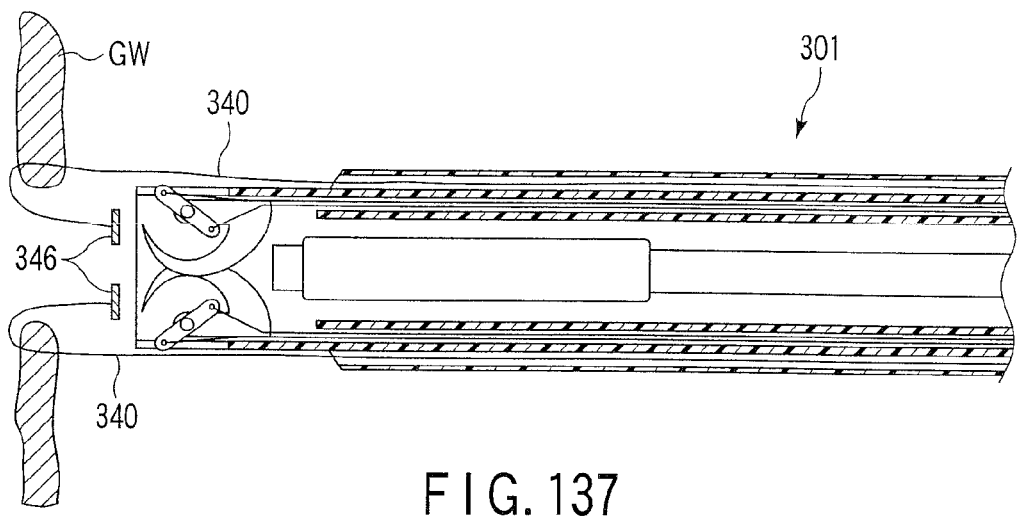
F I G. 137
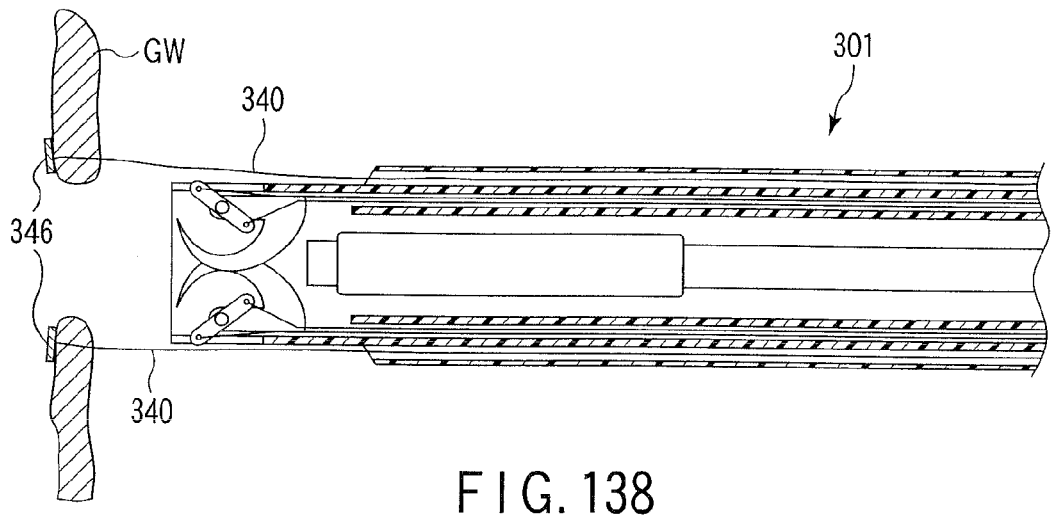
F I G. 138
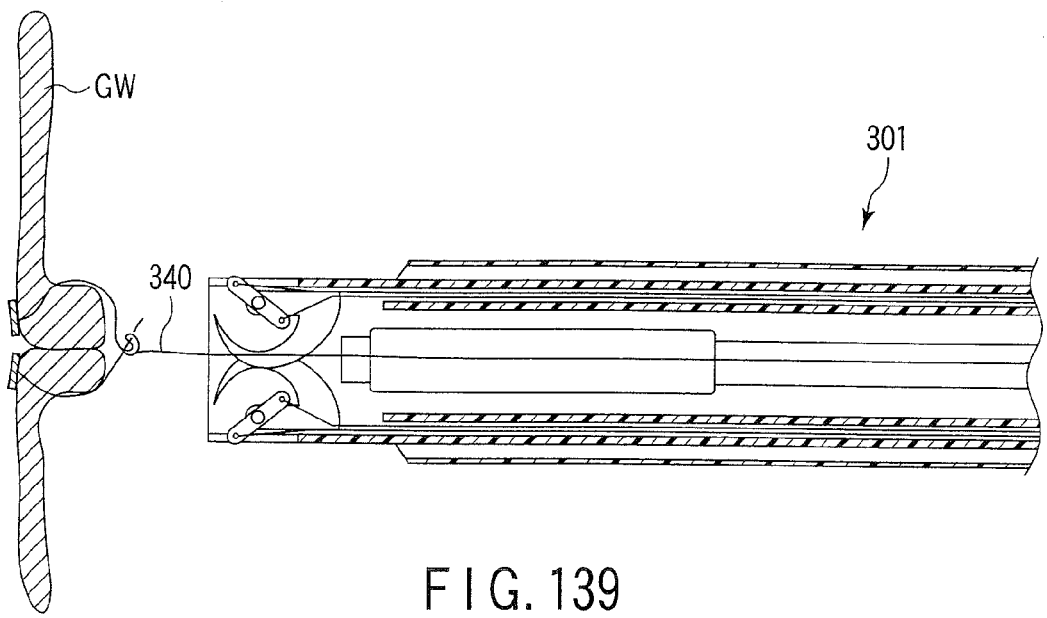
F I G. 139

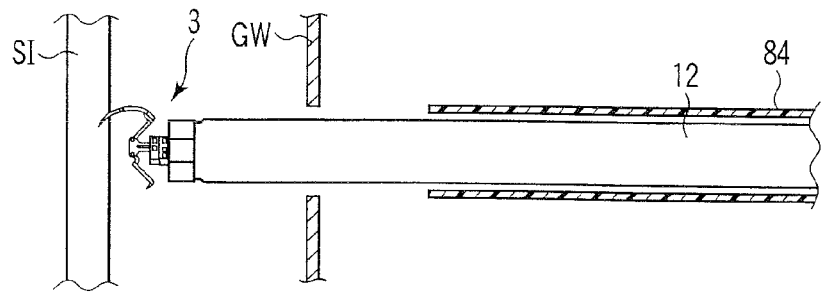
FIG. 140
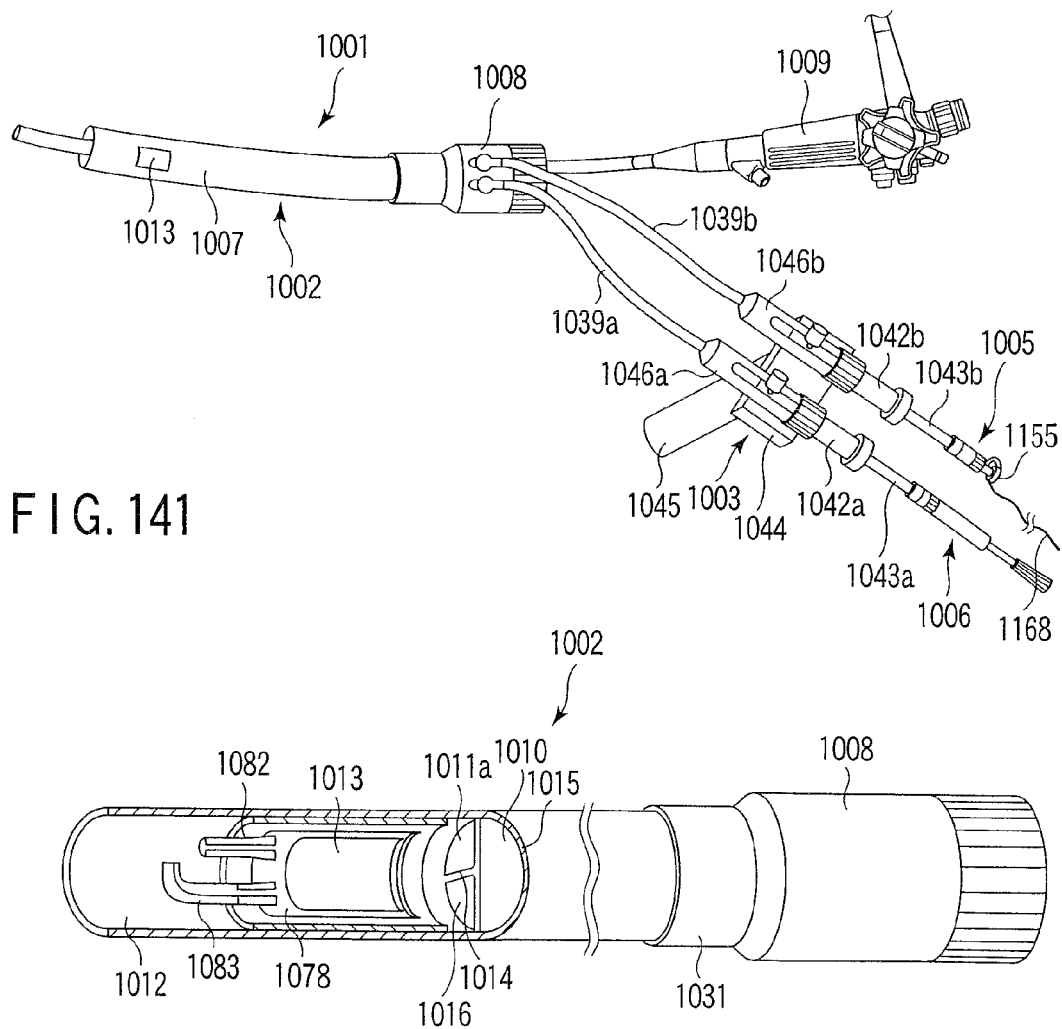
FIG. 141
FIG. 142

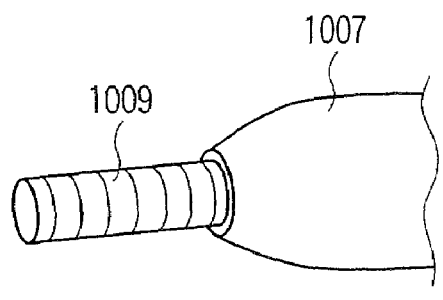
F I G. 155A
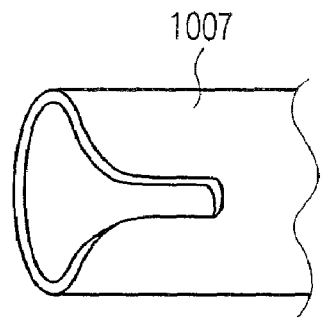
F I G. 155B
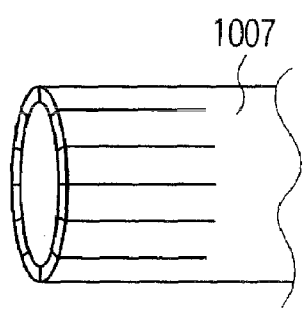
F I G. 155C
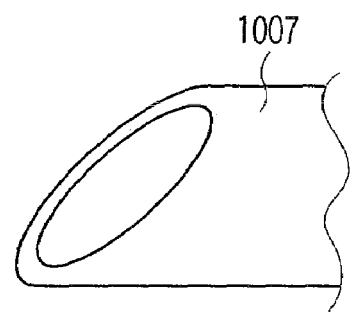
F I G. 155D

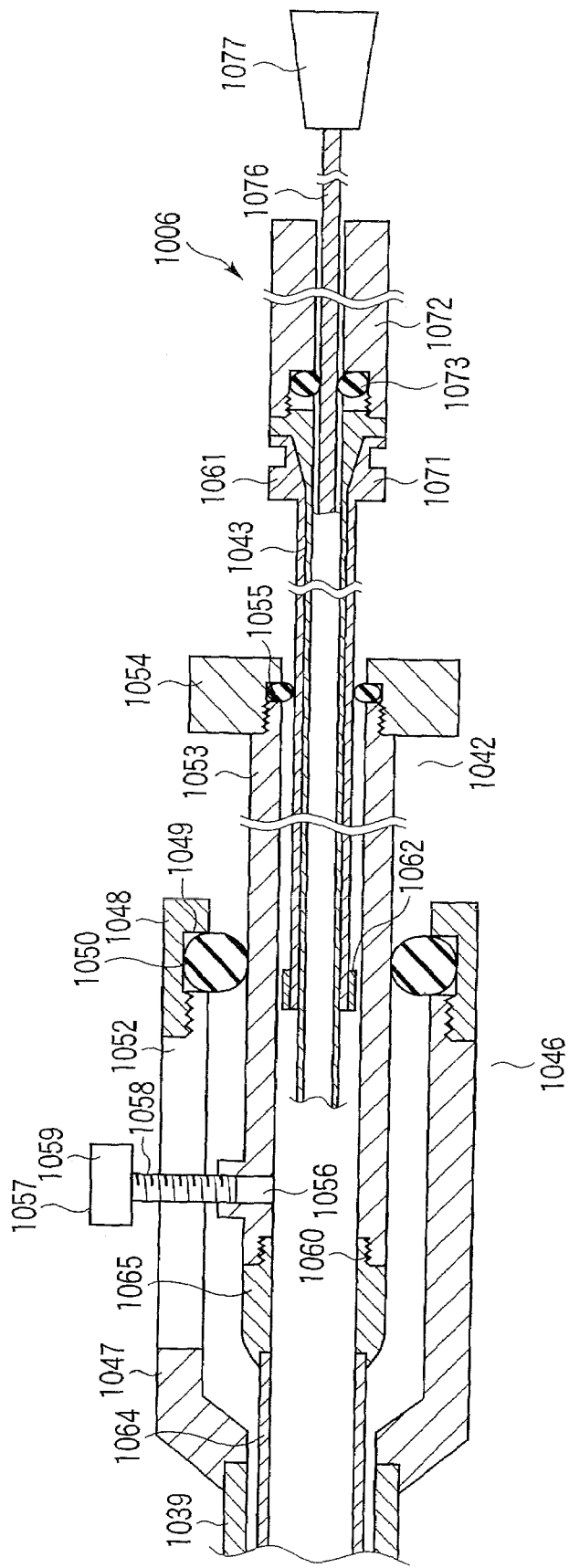
F I G. 161

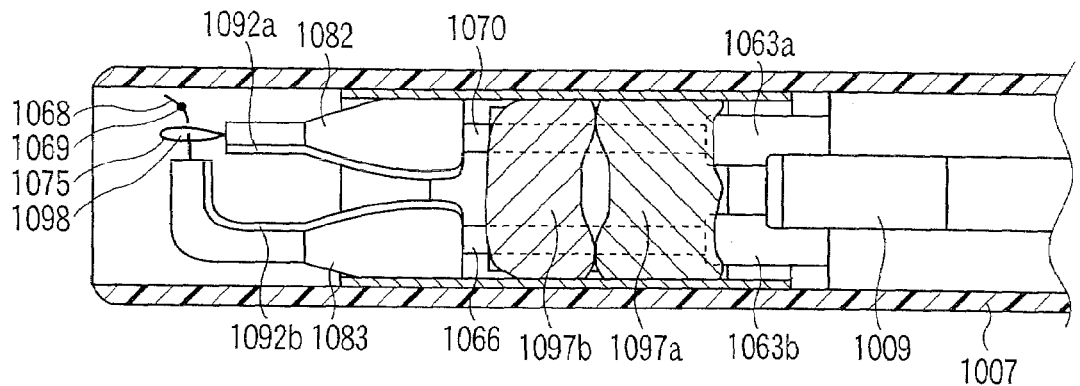
F I G. 165
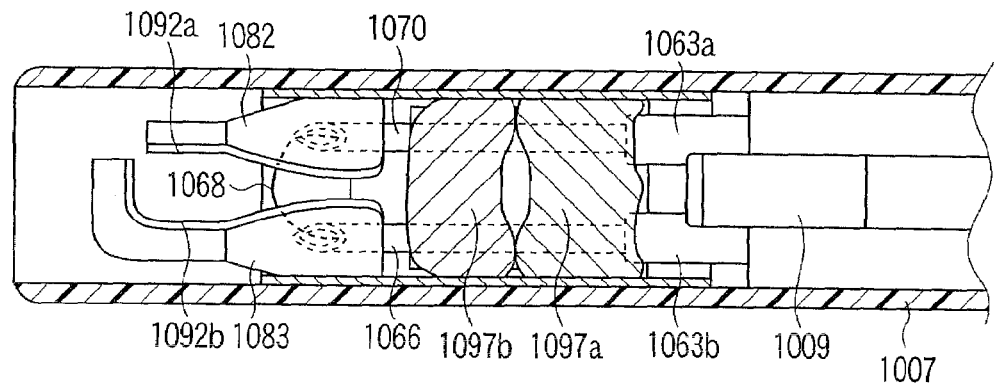
F I G. 166
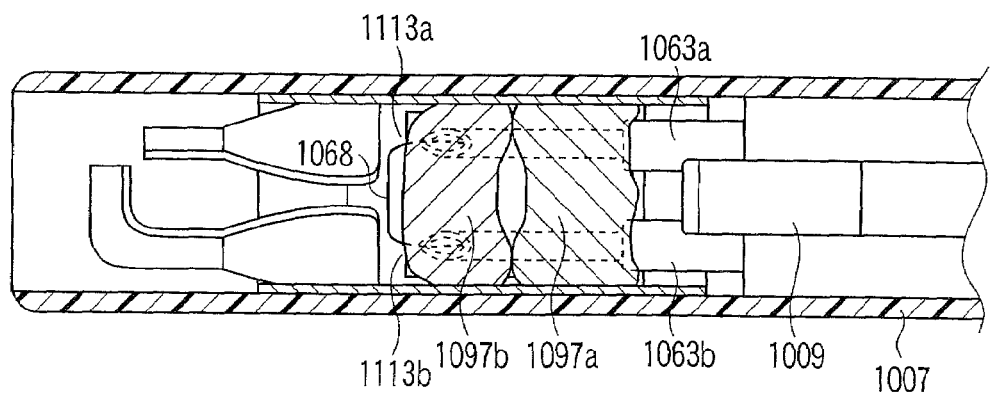
F I G. 167

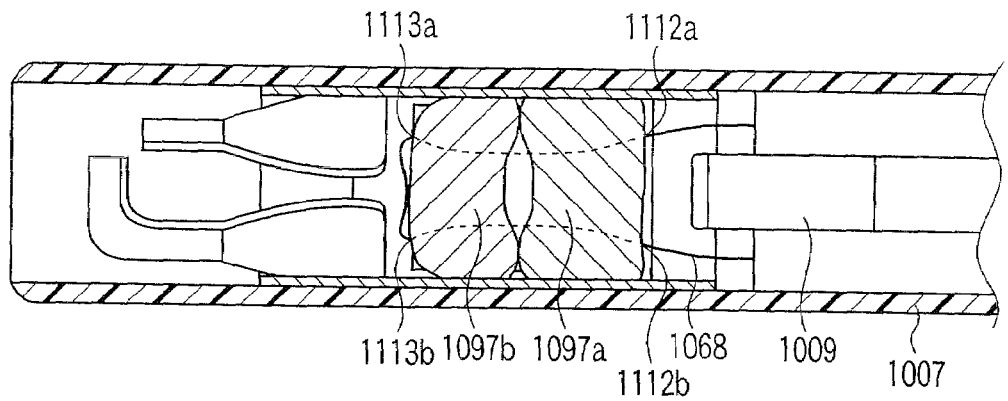
F I G. 168
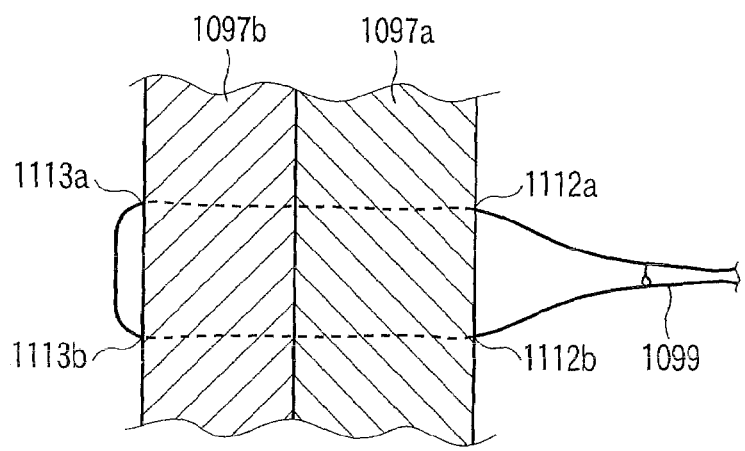
F I G. 169
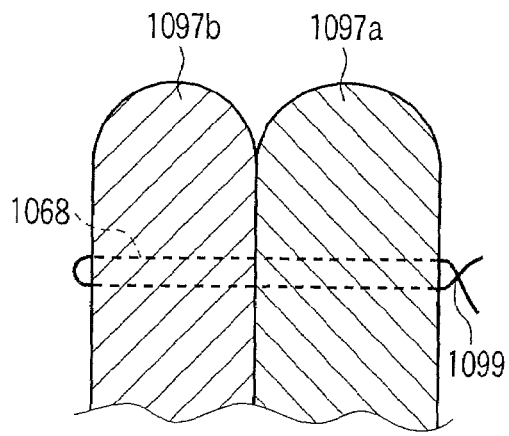
F I G. 170

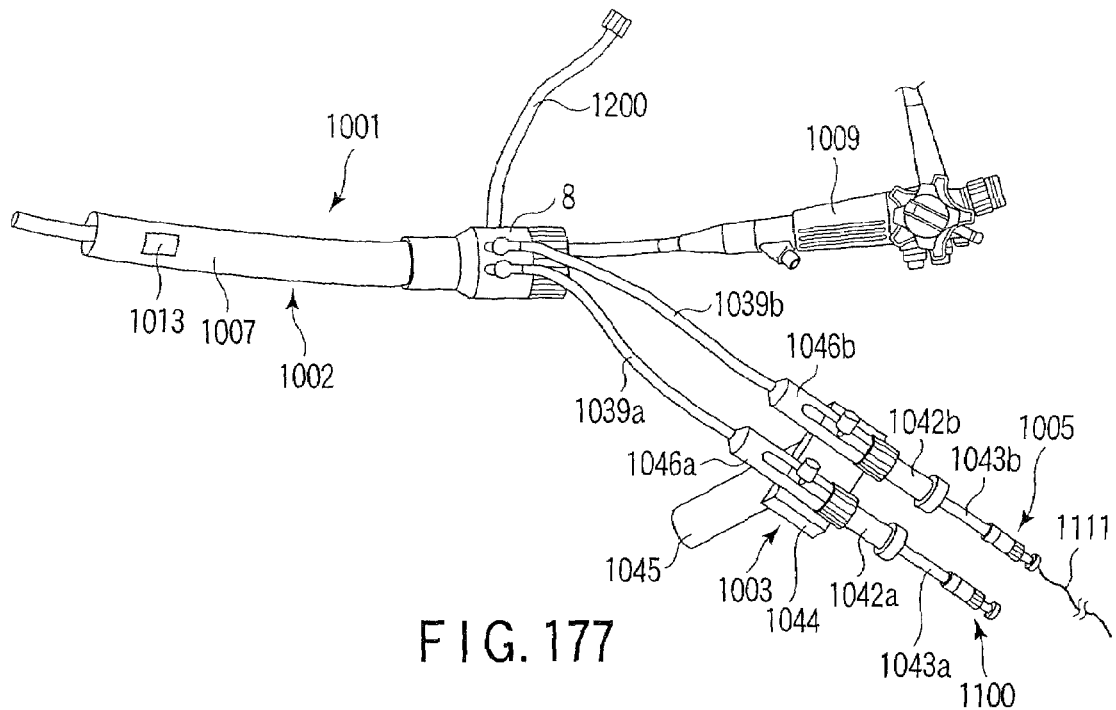
F I G. 177
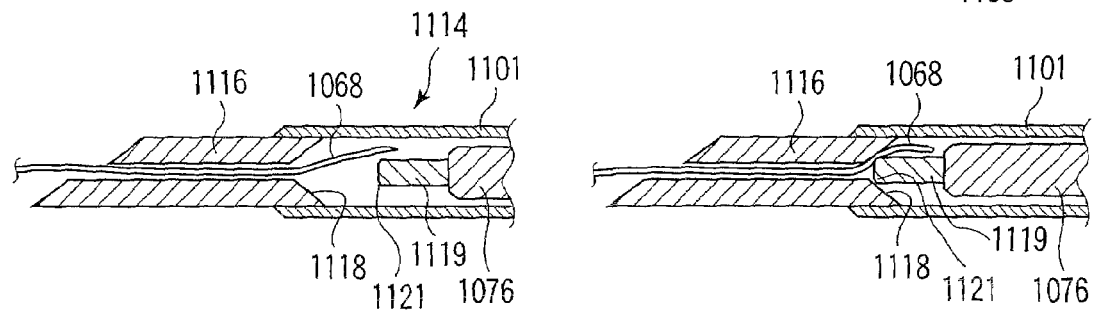
F I G. 178A  F I G. 178B
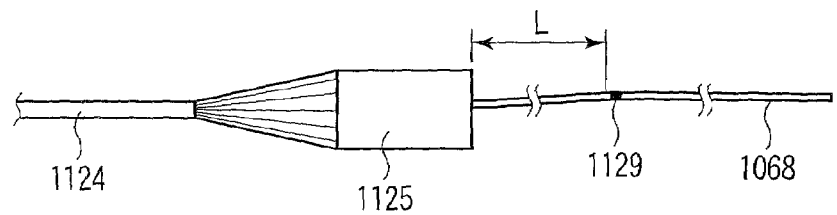
F I G. 179
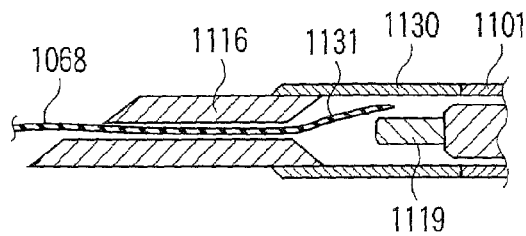
F I G. 180

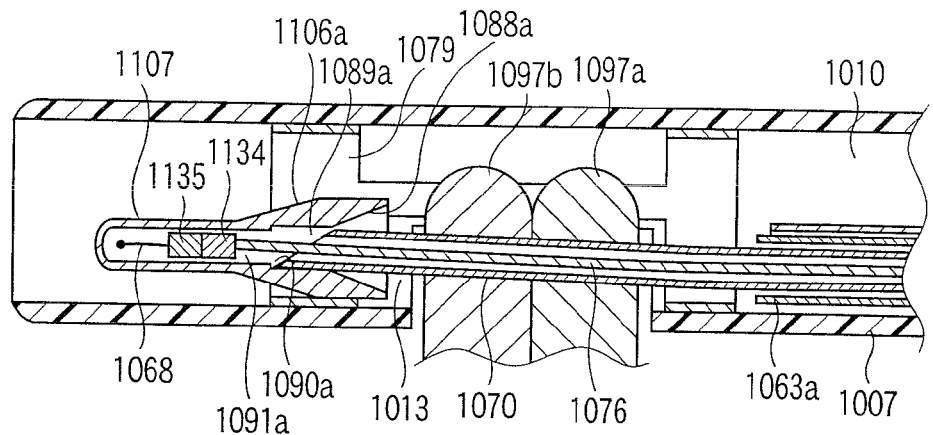
F I G. 184
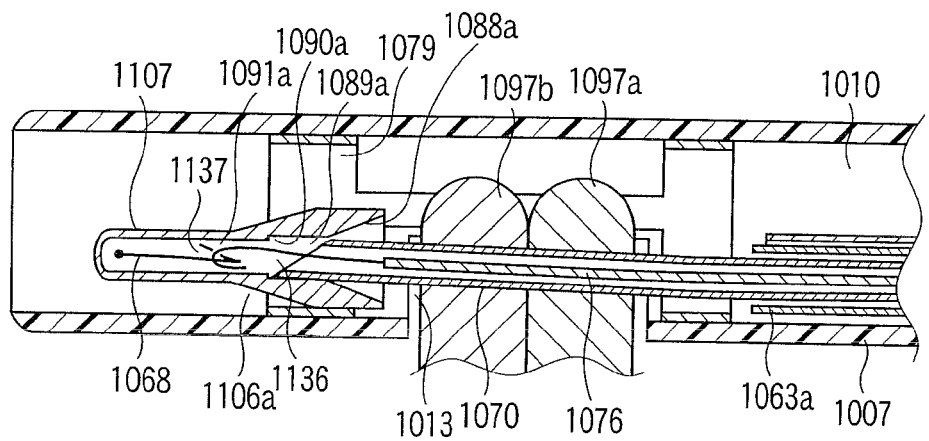
F I G. 185
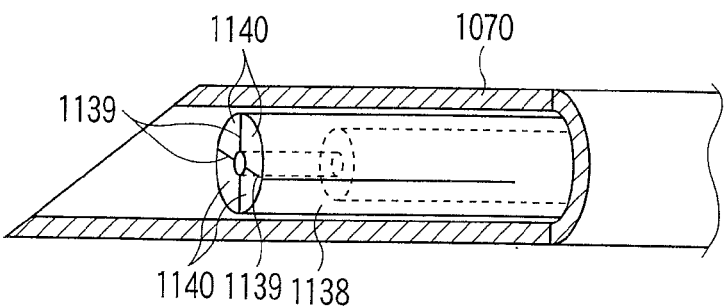
F I G. 186

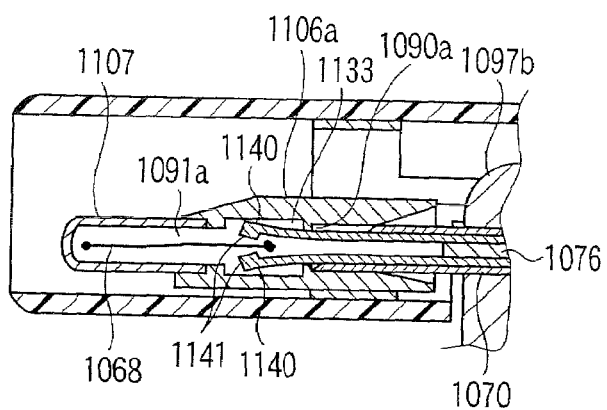
F I G. 187A
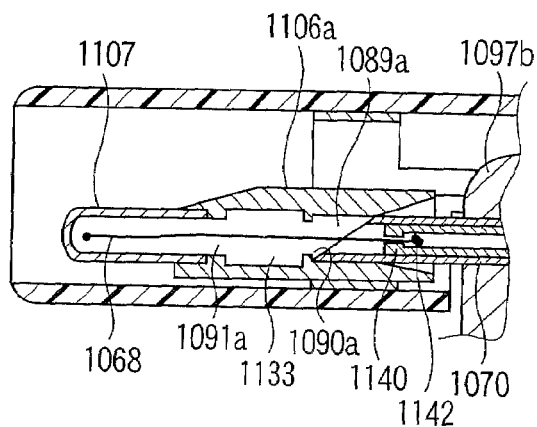
F I G. 187B
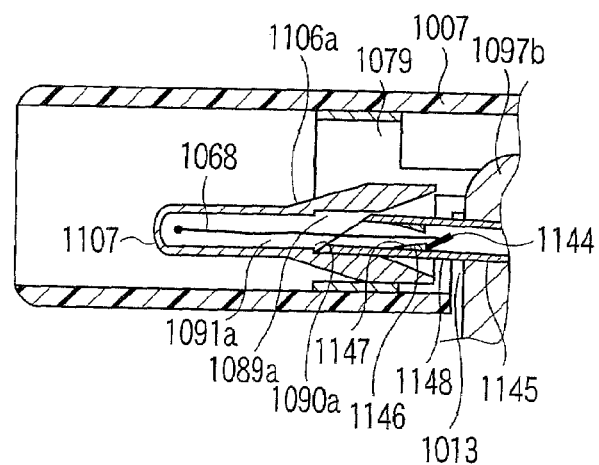
F I G. 188

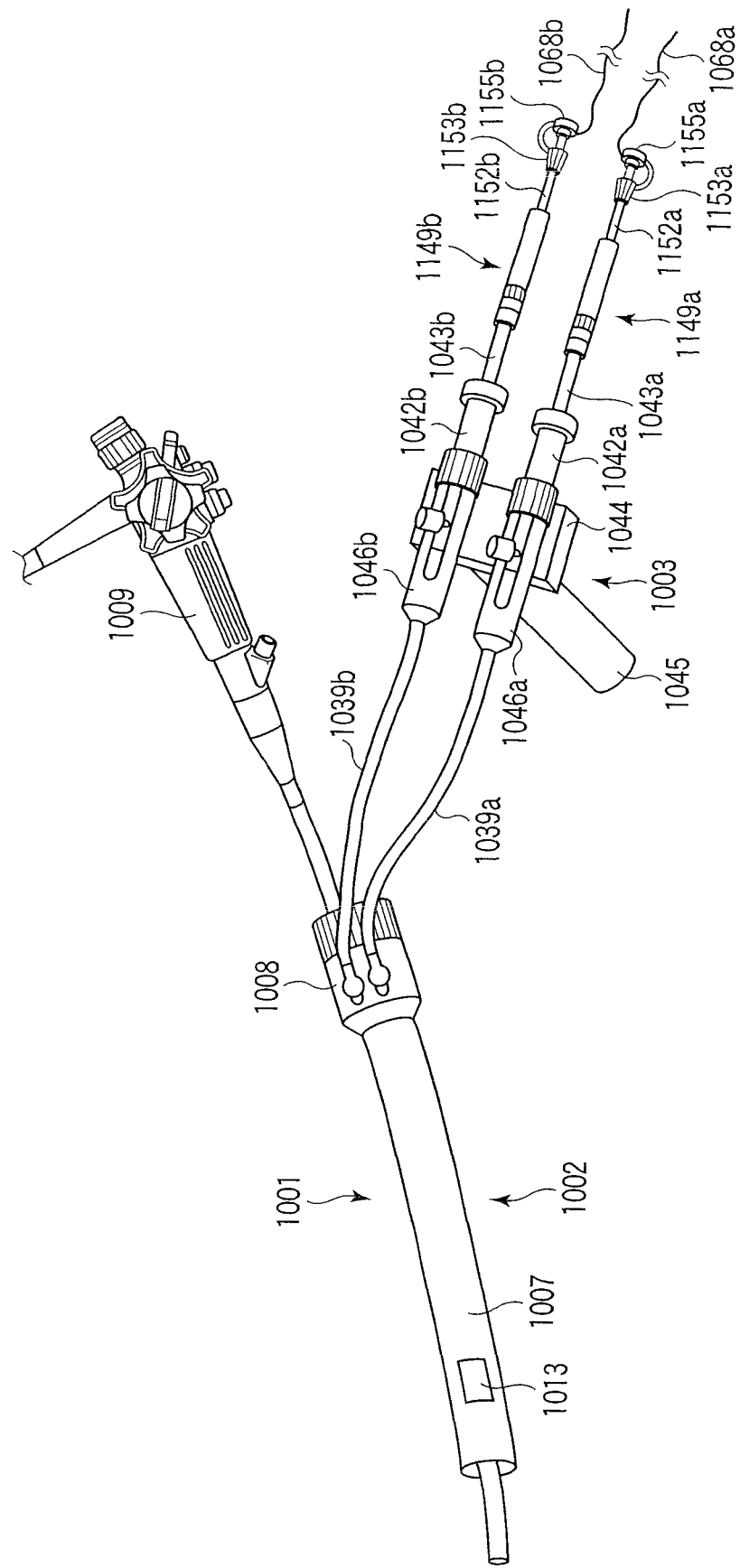
F I G. 189

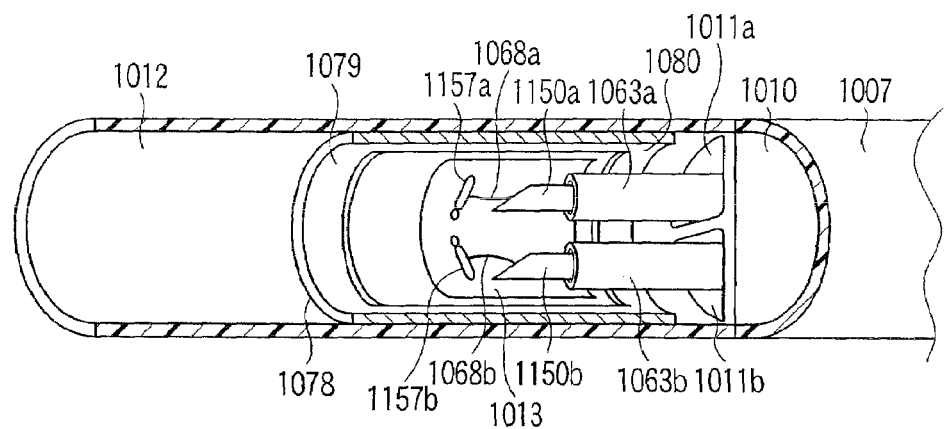
F I G. 190
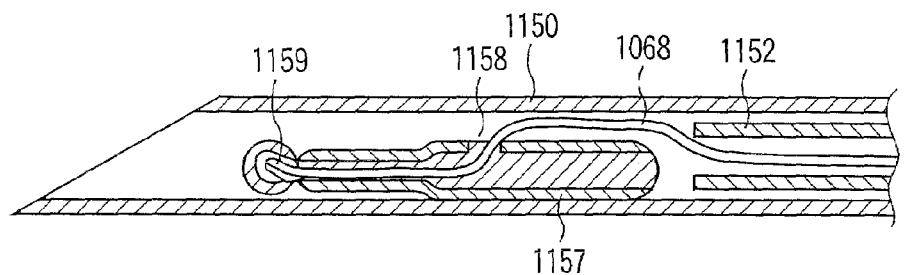
F I G. 191
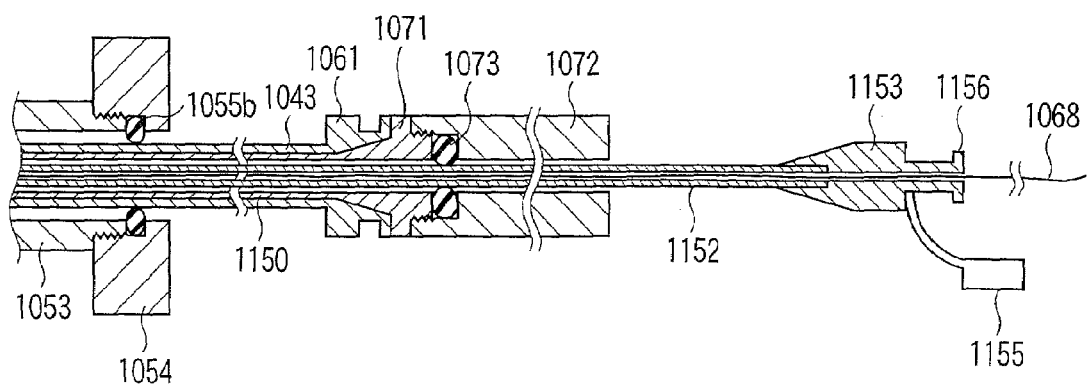
F I G. 192

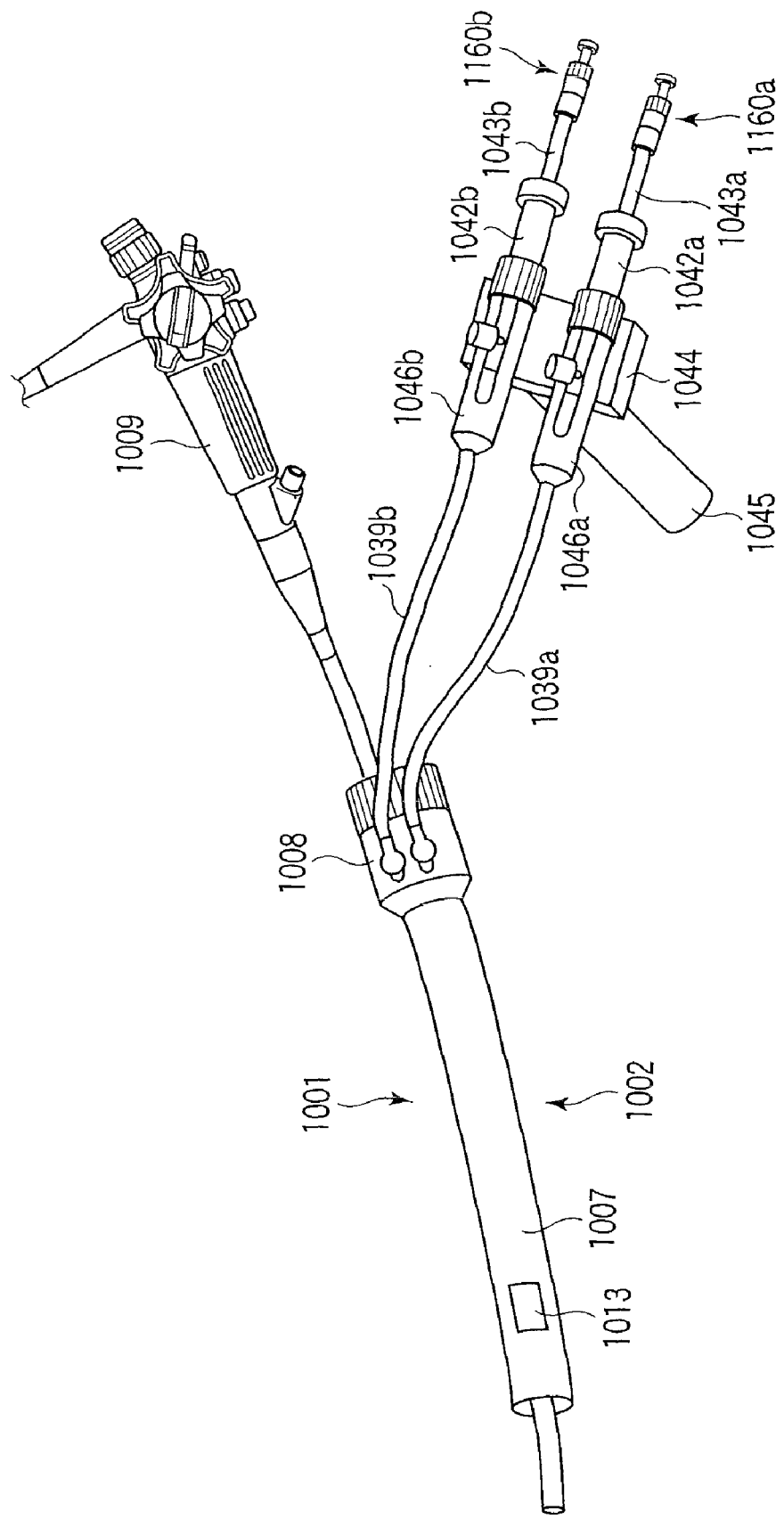
F I G. 196

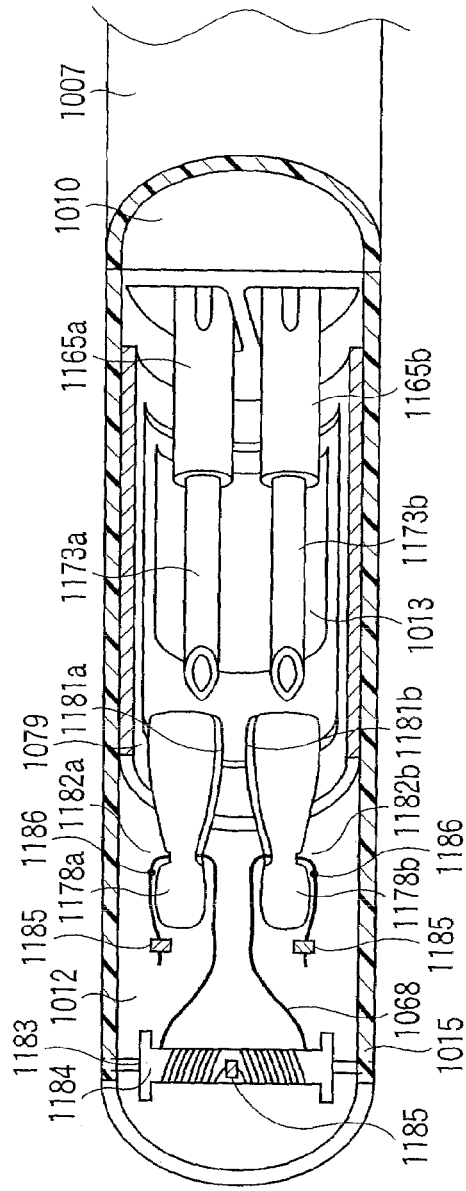
F I G. 203
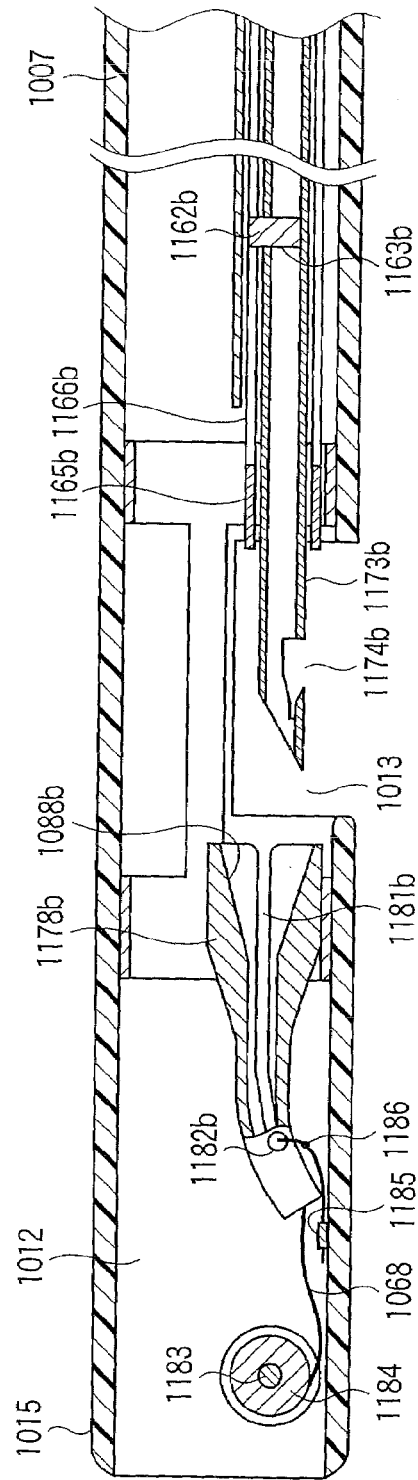
F I G. 204

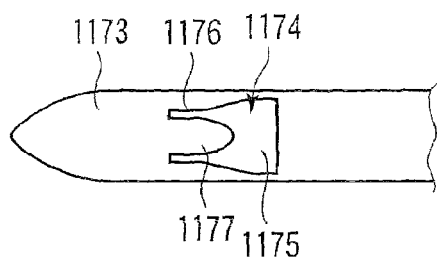
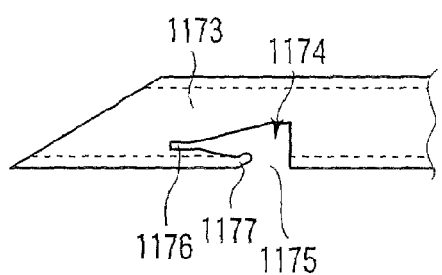
F I G. 205A    F I G. 205B
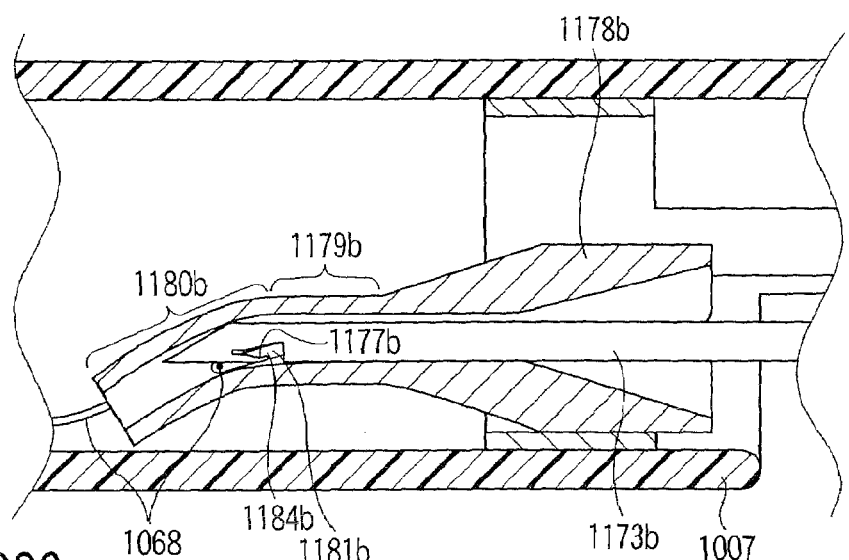
F I G. 206
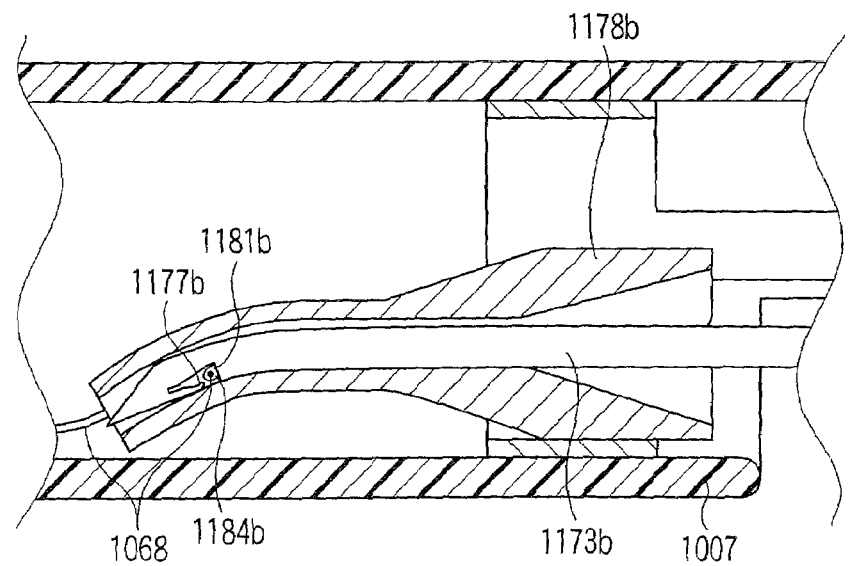
F I G. 207

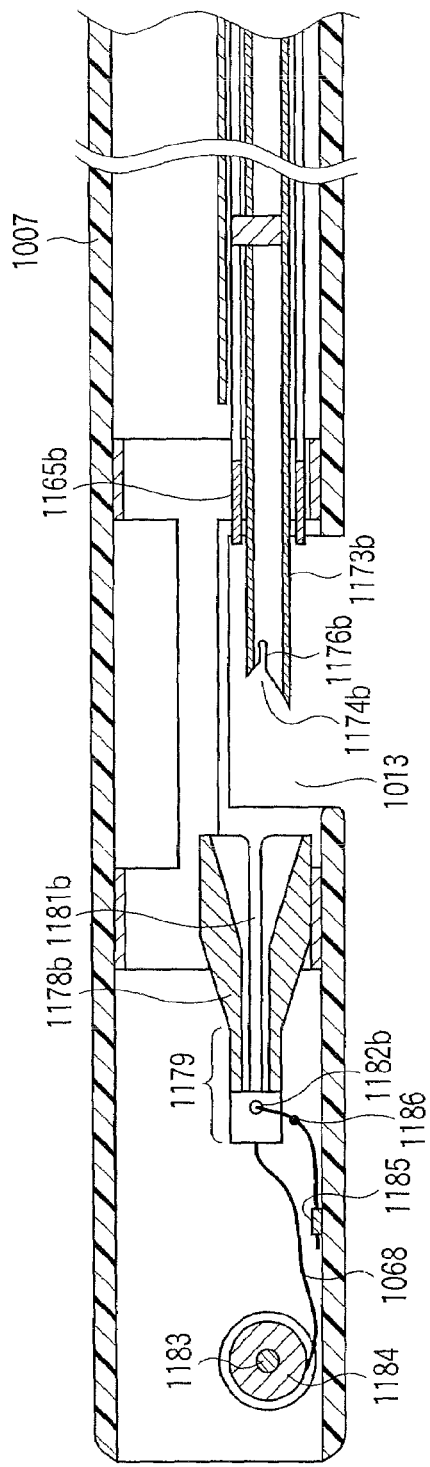
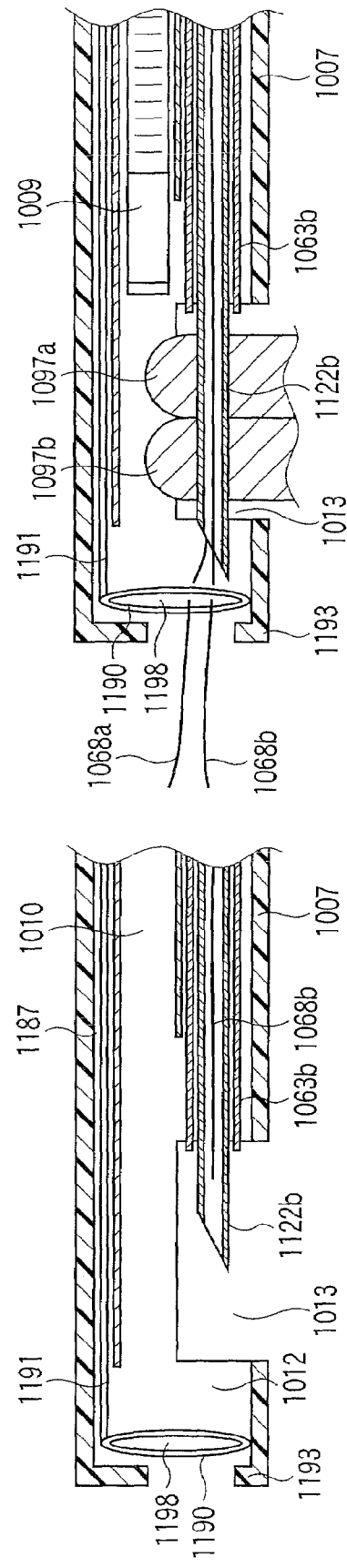
F I G. 211
F I G. 213
F I G. 214

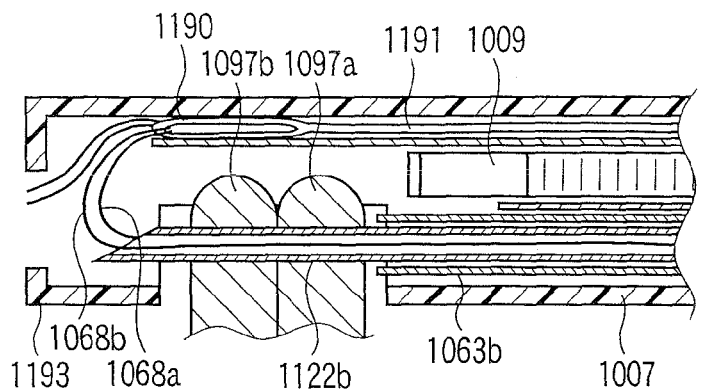
F I G. 215
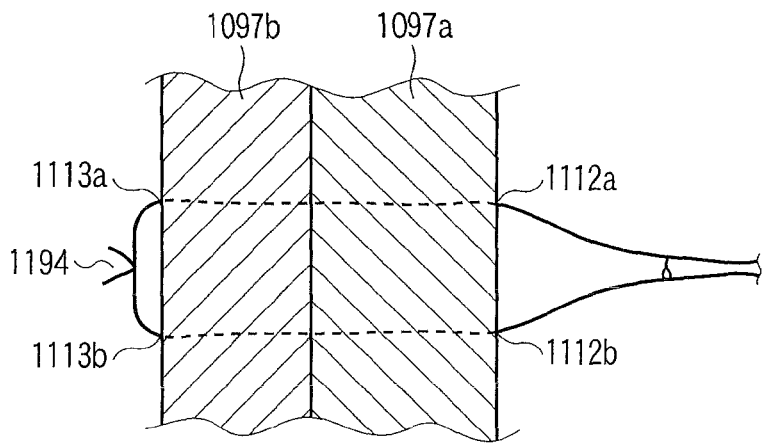
F I G. 216
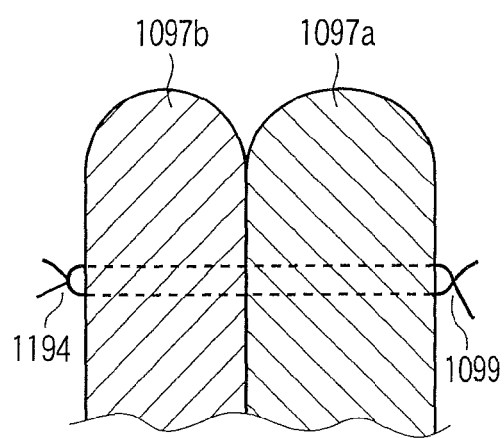
F I G. 217

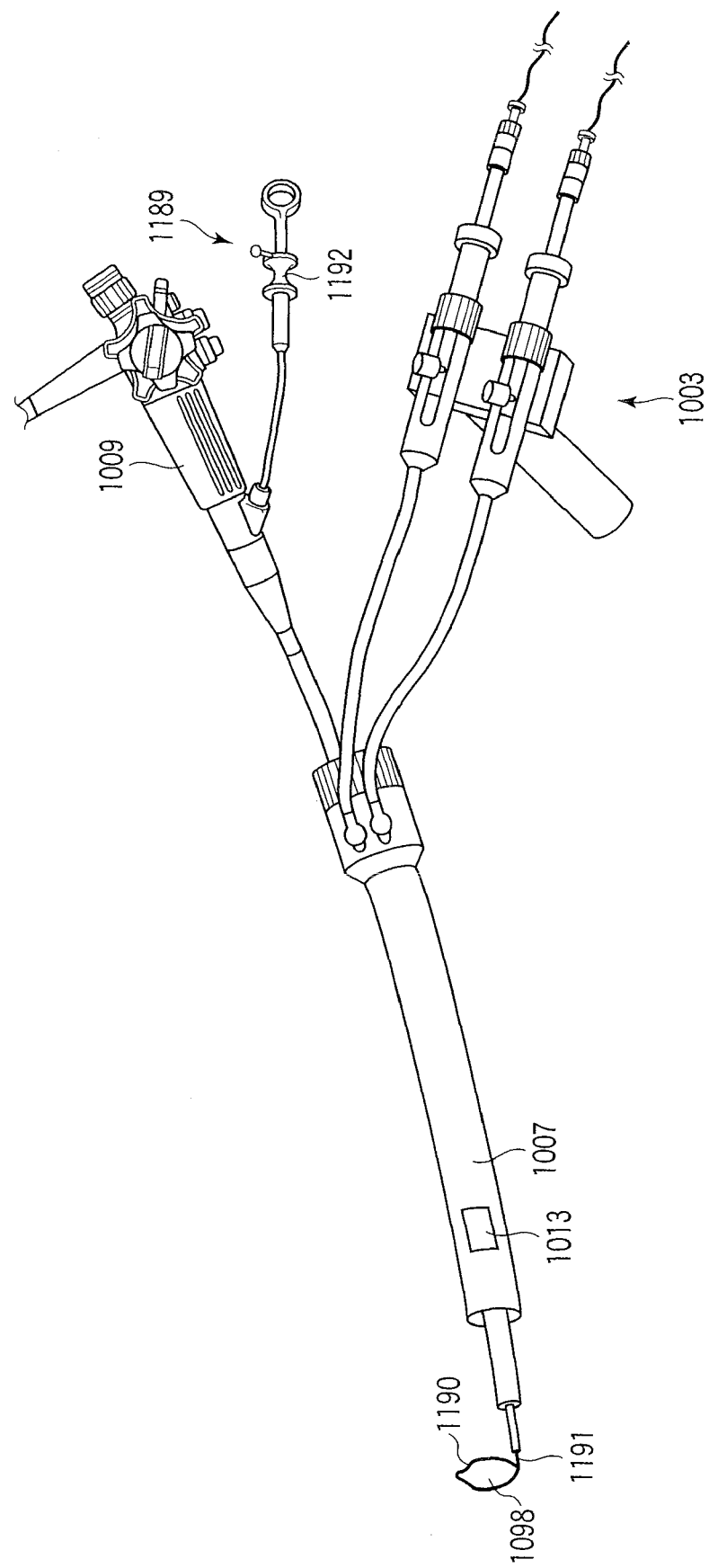
F I G. 218

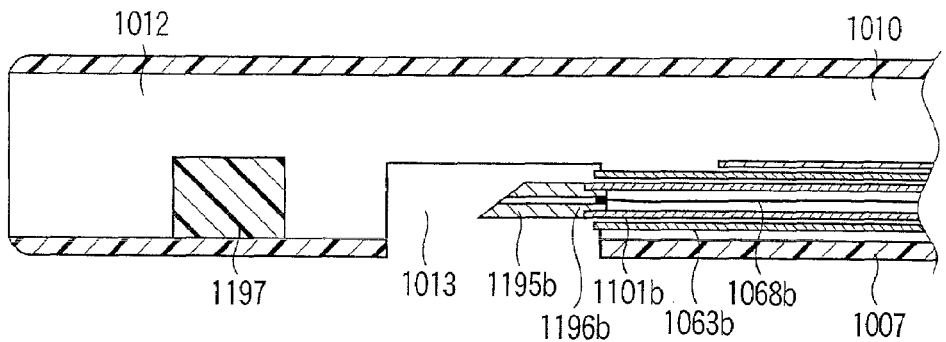
F I G. 219
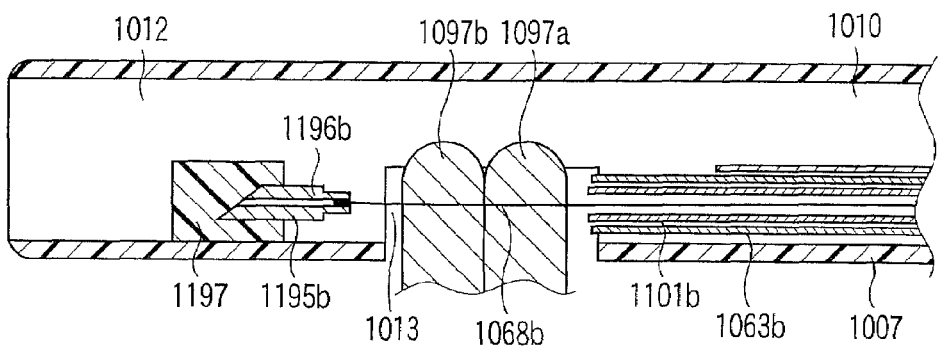
F I G. 220
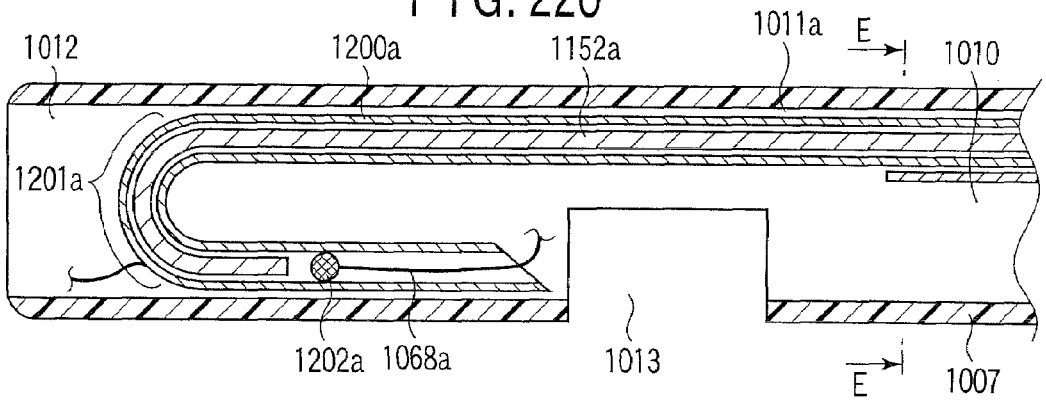
F I G. 222
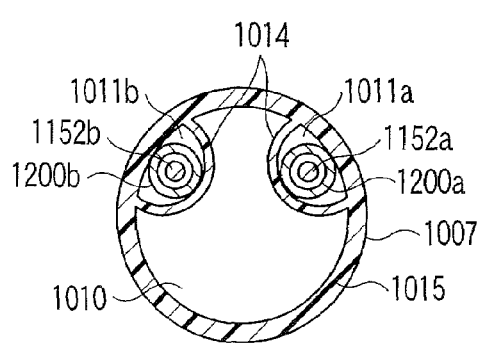
F I G. 223

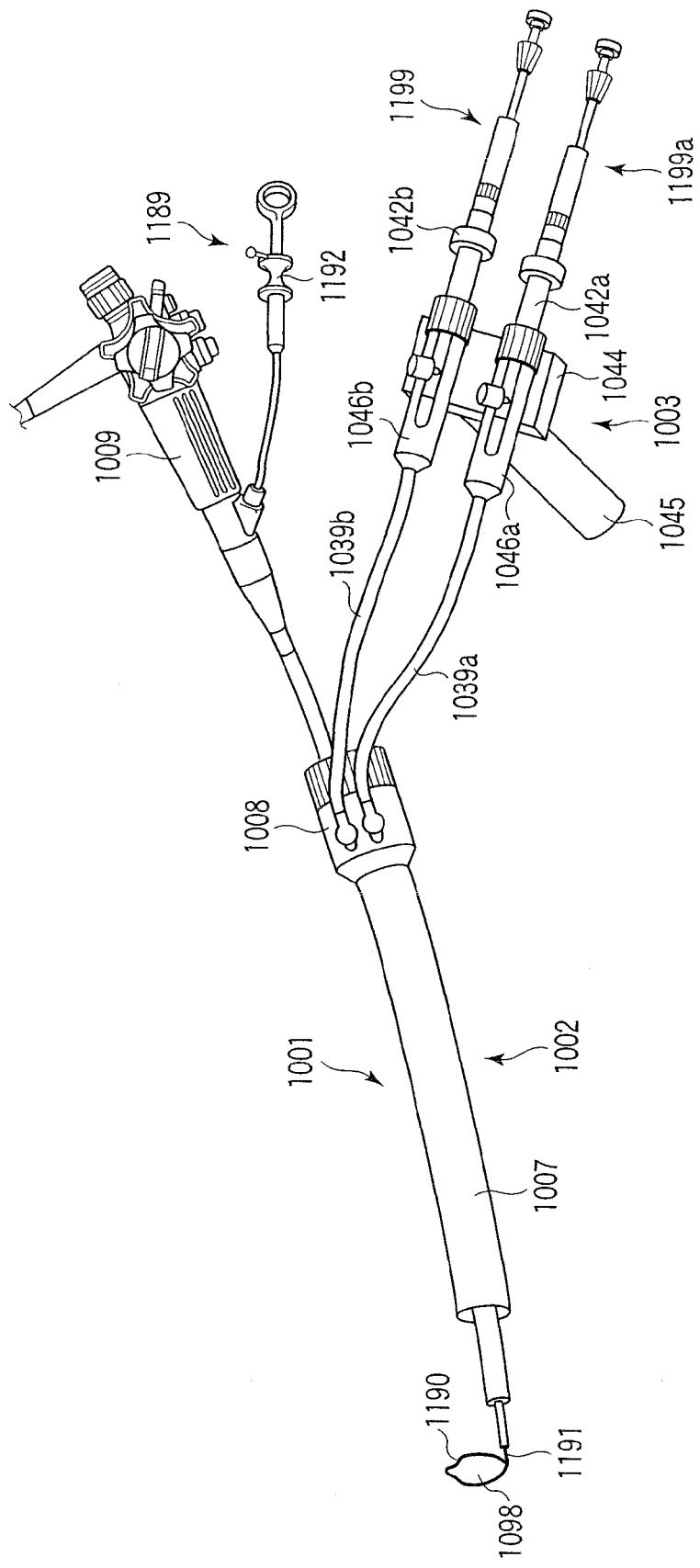
F I G. 221

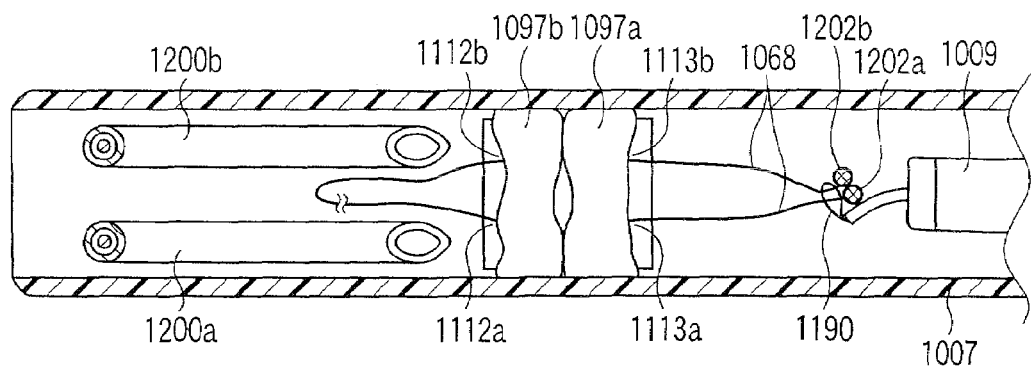
F I G. 230
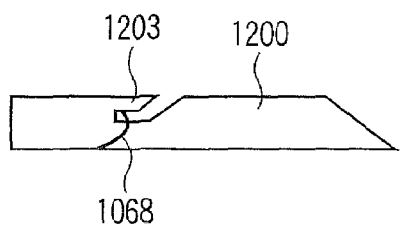
F I G. 231A
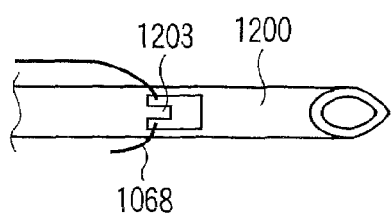
F I G. 231B
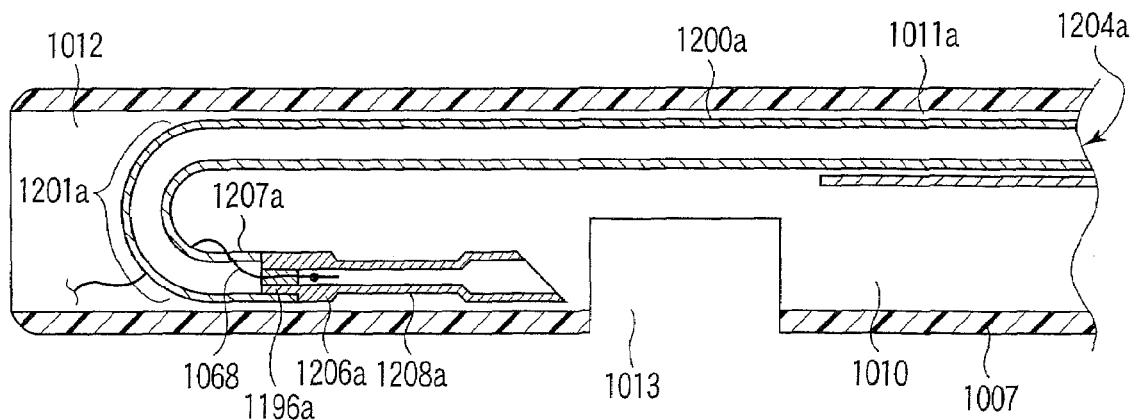
F I G. 232

ANASTOMOSIS SYSTEM

CROSS-REFERENCE TO RELATED APPLICATIONS

The present application is a continuation of copending U.S. patent application Ser. No. 10/390,443 filed on Mar. 17, 2003 and claims the benefit of U.S. Provisional Application No. 60/365,687, filed Mar. 19, 2002, the entire contents of which are incorporated herein by this reference.

BACKGROUND OF THE INVENTION

The present invention relates to an endoscopic system, and more particularly to an endoscopic system used in, e.g., gastrojejunostomy for connecting two internal tubular organs or lumen parts in a living body.

In recent years, treatments using an endoscope have considerably advanced, and it is possible to perform treatments without conducting the major surgery, e.g., dissecting the abdominal part. In particular, the anastomosis of tubular organs or vessels in the celoma is an important technique when performing the treatment using an endoscope. Therefore, various kinds of treatment techniques using an endoscope have been developed.

For example, the invasion to a patient can be greatly reduced by orally or gastrically performing by using the endoscope the gastrojejunostomy which allow the content of the gaster to pass to the jejunum through the pylorus of stomach or the duodenum.

BRIEF SUMMARY OF THE INVENTION

In view of the above-described circumstance, it is an object of the present invention to provide an endoscopic system which enables to orally or gastrically perform the gastrojejunostomy.

To accomplish the above object, according to the present invention, there is provided an endoscopic system comprising: a flexible endoscope which is insertable into a first tubular organ from a natural opening of a human body; an opening member which forms on a wall part of the first tubular organ an opening used to insert the endoscope into an abdominal cavity from the first tubular organ in the body; an anastomosing member which is able to anastomoses the first tubular organ with a second tubular organ in the abdominal cavity; and a cutting member with which the second tubular organ is able to be cut.

BRIEF DESCRIPTION OF THE SEVERAL VIEWS OF THE DRAWING

FIG. 8A is a view similar to FIG. 8, showing only the suture machine with the endoscope removed therefrom;

FIG. 9 is a cross-sectional view taken along the line C-C in FIG. 7;

FIG. 10 is a cross-sectional view taken along the line D-D in FIG. 7;

FIG. 20 is a view showing the over-tube according to the modification with the endoscope and the suture machine being accommodated;

FIG. 21 is a view showing the state that the endoscope and the suture machine are caused to protrude from the over-tube illustrated in FIG. 20;

FIGS. 22 to 32 show the procedures of the gastrojejunostomy using the anastomosis system illustrated in FIGS. 1 to 22, and FIG. 22 is a view showing the state that the endoscope and the over-tube are inserted into the gaster;

FIG. 23 is a view showing the state the gastric wall is sucked by the over-tube;

FIG. 24 is a view showing a bore hole is formed to the gastric wall by a needle-shaped knife;

FIG. 25 is a view showing the state that a balloon dilator is inserted into a bore hole of the gastric wall and expanded;

FIG. 26 is a view showing the state that the endoscope is inserted into the abdominal cavity;

FIG. 27 is a view showing the state that the small intestine is held by a grasping forceps and moved to the side of the gastric wall;

FIG. 28 is a view showing the state that a needle is put through the small intestine and a suspension thread is inserted in order to suspend the small intestine;

FIG. 29 is a view showing the state that the gaster and the small intestine are put into a suture by using a curved needle suture machine;

FIG. 30 is a view showing the state that the intestinum tenue is cut open by the needle-shaped forceps;

FIG. 31 is a view showing the state that the curved needle suture machine is used for suture so as to cut open the tunica mucosa of intestinum tenues;

FIG. 32 is a view showing the inside of the gaster with the suture system being removed from the gaster;

FIG. 33 is a view showing the state the a curved needle is moved closer to a tissue;

FIG. 34 is a view showing the state that the curved needle is struck into the tissue;

FIG. 35 is a view showing the state that the suture thread is caught by the thread gripper;

FIG. 36 is a view showing the state that the suture thread is pulled into a flexible tubular member together with the hook which has caught the suture thread;

FIG. 37 is a view showing the state that the thread gripper is removed from a channel member;

FIG. 38 is a view showing the state that the curved needle is removed from the tissue;

FIG. 41 is a view of an endoscopic anastomosis system according to a first modification similar to FIG. 2, showing the state that the suture machine is accommodated in a protection member;

FIGS. 43 to 46 show the protection member in the first modification, and FIG. 43 is a view showing the state that a movable portion is caused to protrude;

FIG. 44 is a view showing the state that a moving member releases engagement of a lock member;

FIG. 45 is a view showing the state that the movable portion is pulled back;

FIG. 46 is a detailed view of the lock member;

FIG. 47 is an explanatory view of the protection member for use in an endoscopic anastomosis system according to a second modification;

FIGS. 48 to 52 show an endoscopic anastomosis system according to a third modification, and FIG. 48 is a view showing the suture machine for use in this system;

FIG. 49 is a view showing the state that a detachable needle is engaged with a needle/thread fixture after a tissue is stuck;

FIG. 50 is a view showing the state that the suture thread is fastened to close a wound;

FIG. 51 is a view showing the state that a remaining part of the suture thread is cut by a thread cutter;

FIG. 52 is a cross-sectional view taken along the line H-H in FIG. 48;

FIG. 59 is a view showing the state that a knot is formed by a loop which comes off the engagement member when the first and second operation members are opened;

FIG. 60 is a view showing the state that the remaining part of the suture thread is cut by the thread cutter;

FIGS. 68 to 74 show the suture procedures by the endoscopic anastomosis system according to a seventh modification, and FIG. 68 is a view showing the state that the suture machine is moved close to the tissue to be put into a suture;

FIG. 69 is a view showing the state that the detachable needle is engaged with the needle fixture after centesis of the tissue;

FIG. 70 is a view showing the state that the needle holder is removed from the tissue;

FIG. 71 is a view showing the state that the suture machine and the endoscope are separated from the tissue with the needle/thread fixture being left;

FIG. 72 is a view showing the state that the tissue is tied with the suture thread;

FIG. 73 is a view showing the state that the suture thread can be separated;

FIG. 74 is a view showing the state that the remaining part of the suture thread is cut by the thread cutter;

FIG. 78 is a view showing the state that the gastric wall is sucked by using the anastomosis system according to a second embodiment;

FIG. 79 is a view showing the state that the gastric wall is cut open by using the anastomosis system according to a third embodiment;

FIG. 80 is a view showing the state that the gastric wall is bored by using the anastomosis system according to a fourth embodiment;

FIG. 81 is a view showing the state that a bore hole portion in FIG. 80 is expanded;

FIG. 88 is a cross-sectional view similar to FIG. 87, showing the state that the needle-shaped knife is pulled in;

FIG. 94 is a schematic view showing an entire arcate knife with the needle-shaped knife for use in the anastomosis system according to the sixth embodiment;

FIG. 95 is a view showing an additional procedure by the anastomosis system according to a seventh embodiment;

FIG. 96 is a view illustrating one procedure using the anastomosis system according to an eighth embodiment;

FIG. 100 is an enlarged vertical cross-sectional view of the over-tube of FIG. 97;

FIG. 101 is an explanatory view of the over-tube of FIG. 97, showing the state that the over-tube is orally inserted with the endoscope;

FIGS. 102 to 106 are conceptual views showing the part in the vicinity of the distal end portion, illustrating observation or treatment of the inside of the abdominal cavity by the over-tube of FIG. 7;

FIG. 107 is a perspective view illustrating the overall structure of the over-tube according to a first modification;

FIG. 113 is a perspective view illustrating the overall structure of the over-tube according to a second modification;

FIGS. 114 and 115 are perspective views of each part of the over-tube of FIG. 113;

FIG. 123 is an outside drawing of the distal end portion of the over-tube depicted in FIG. 121 showing from the front side;

FIG. 124 is a transverse cross-sectional view of the shaft portion of the over-tube depicted in FIG. 121;

FIGS. 125 to 129 are conceptual views showing the part in the vicinity of the distal end portion, illustrating observation or treatment of the inside of the abdominal cavity by the over-tube depicted in FIG. 121;

FIG. 130 is a perspective view illustrating the overall structure of the over-tube according to a fourth modification;

FIG. 131 is a vertical cross-sectional view showing the part in the vicinity of the distal end portion of the over-tube of FIG. 130;

FIG. 132 is a vertical cross-sectional view showing the part in the vicinity of the distal end portion combined with the suture thread;

FIG. 133 is an explanatory drawing showing the distal end portion of FIG. 132 from the distal end side;

FIG. 134 is a partially enlarged transverse cross-sectional view of a tubular main body;

FIGS. 135 to 139 are views illustrating observation or treatment of the inside of the abdominal cavity by the over-tube illustrated in FIG. 130;

FIG. 140 is a view showing a part of the anastomosis procedures by the anastomosis system according to a ninth embodiment of the present invention;

FIGS. 141 to 170 show a first example of a tissue centesis system for use in the anastomosis system according to a 10th embodiment, and FIG. 141 is an outside drawing of the same;

FIG. 142 is a view showing the inner structure of the over-tube of the system illustrated in FIG. 141;

FIG. 143 is a schematic view of an operation portion connected to the over-tube of FIG. 141;

FIG. 144 is a schematic view of a needle for use in the system illustrated in FIG. 141;

FIG. 145 is a schematic view of another needle;

FIG. 146 is a schematic view of an inner sheath;

FIG. 147 is a view showing a part of the over-tube in the form of cross-sectional view;

FIG. 148 is a vertical cross-sectional view of FIG. 147;

FIGS. 149, 150 and 151 are a cross-sectional view taken along the line A-A of FIG. 148, a cross-sectional view taken along the line B-B of the same, and a cross-sectional view taken along the line C-C of the same;

Figure 152:
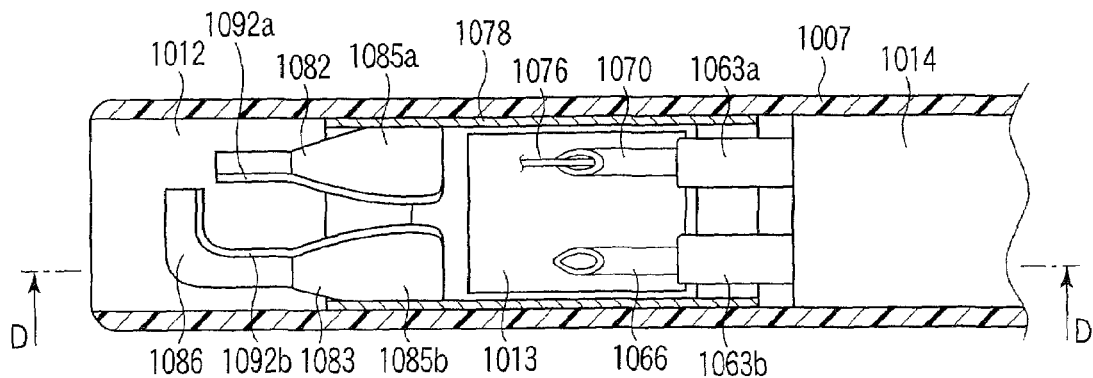
Figure 153:
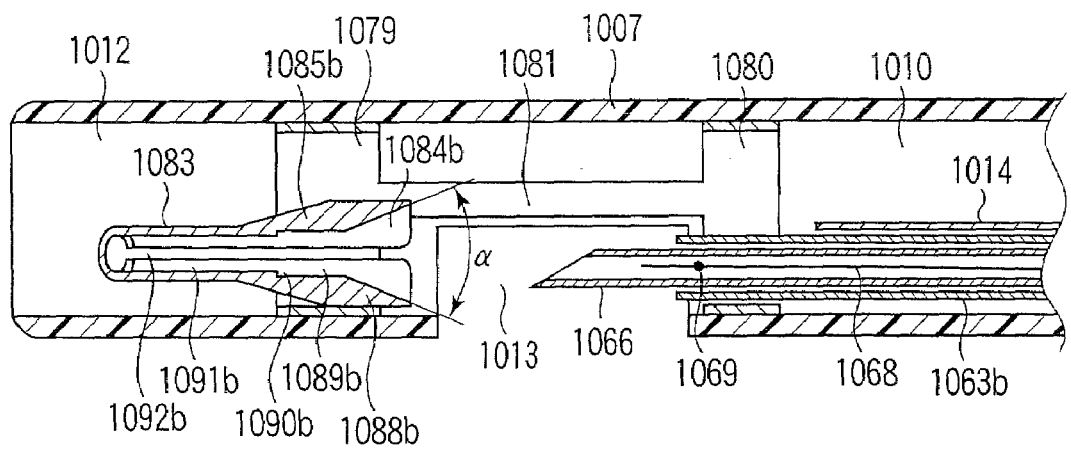
Figure 154:
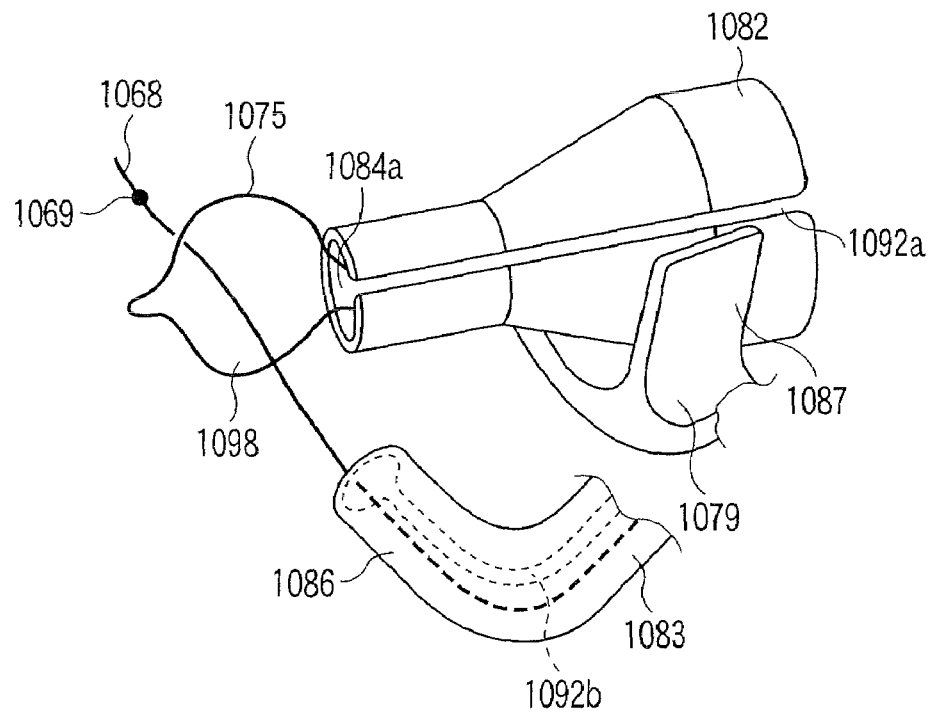
Figure 156:
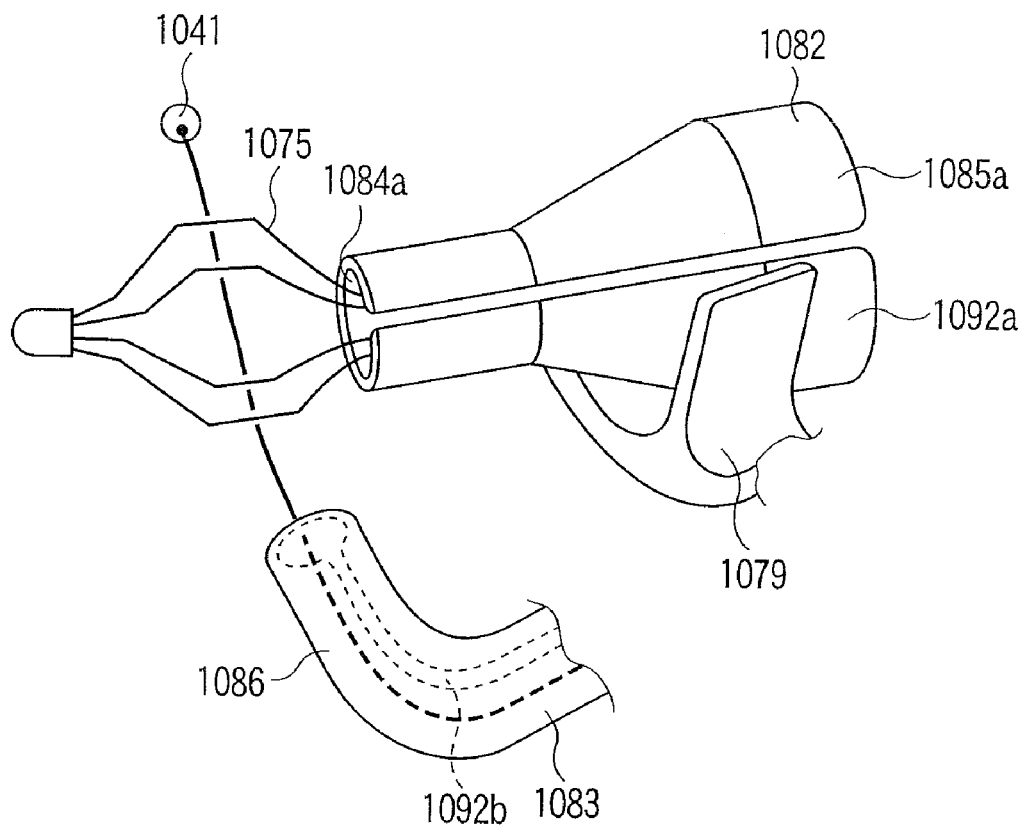
Figure 157:
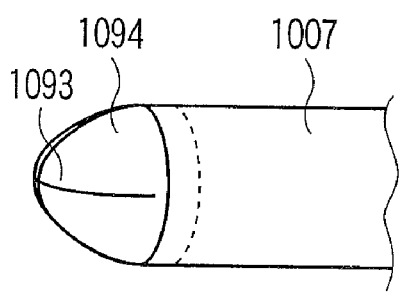
Figure 158:
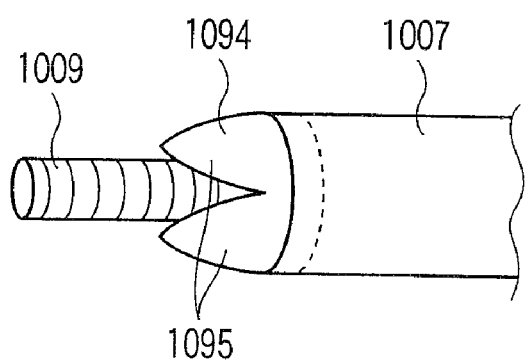
Figure 159:
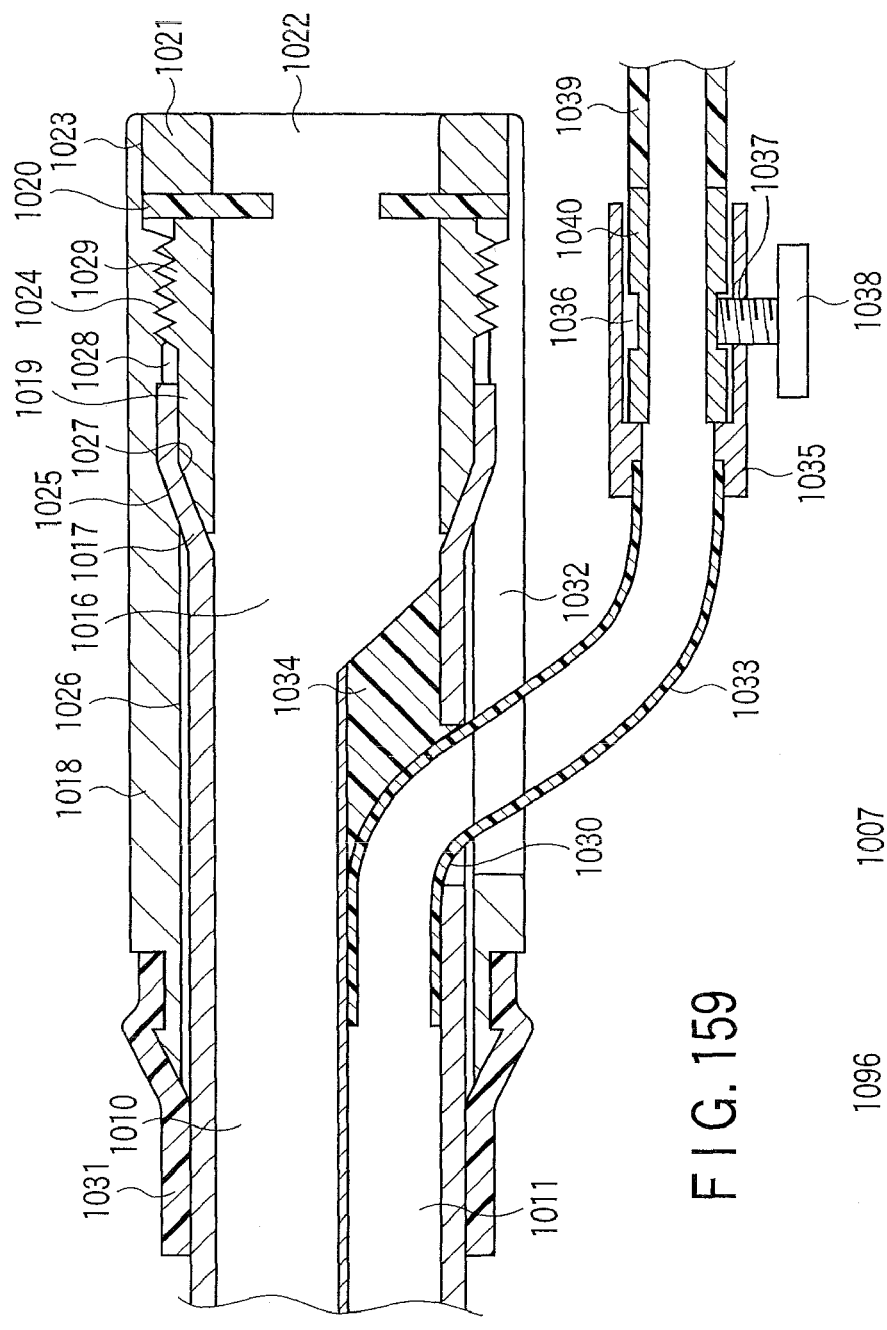
Figure 160:
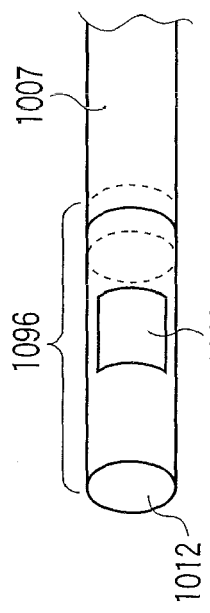
Figure 162:
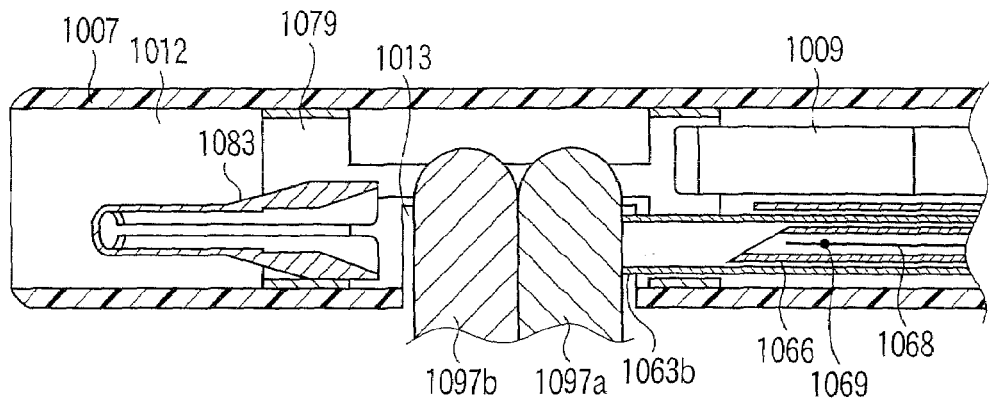
Figure 163:
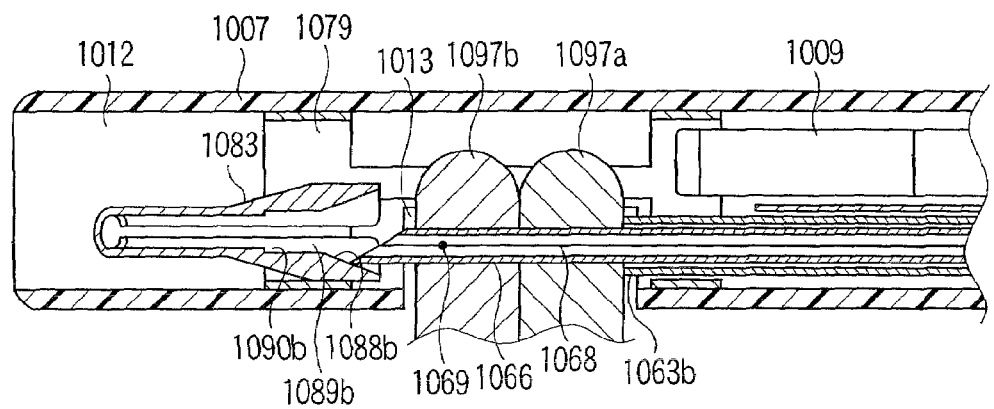
Figure 164:
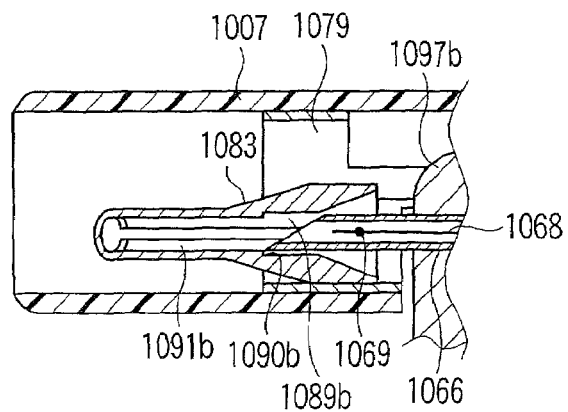
Figure 171:
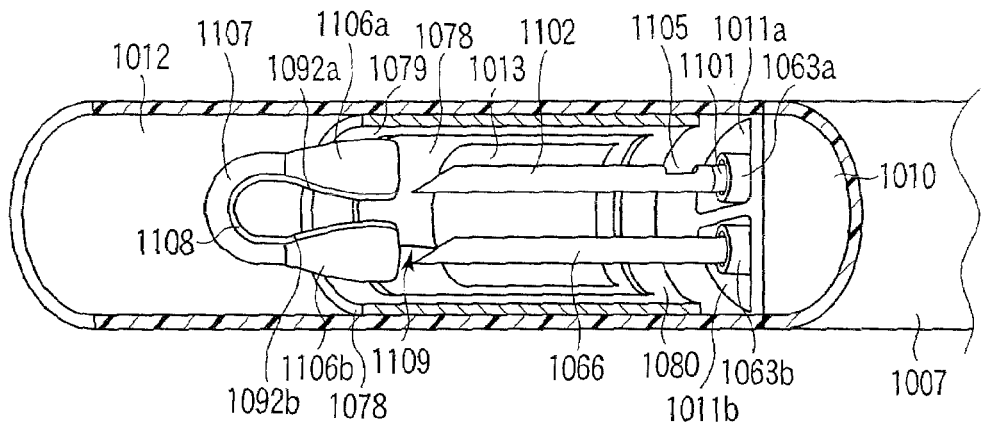
Figure 172A:
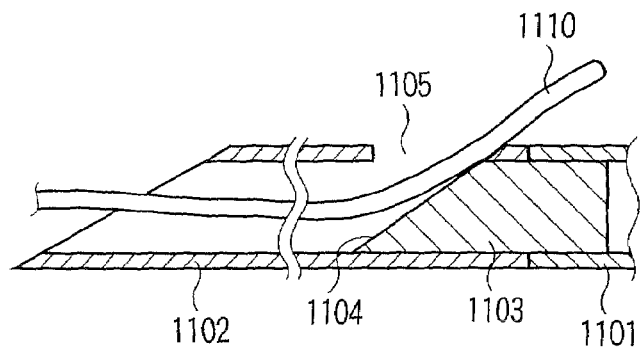
Figure 172B:
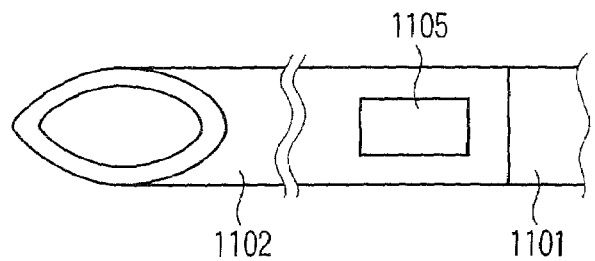
Figure 173:
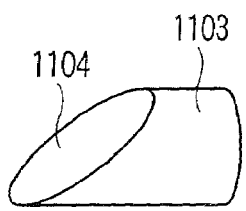
Figure 174:
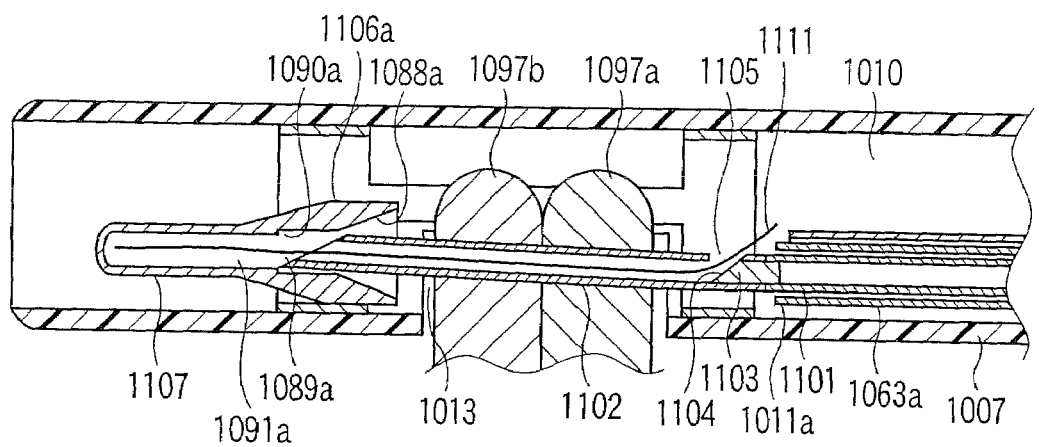
Figure 175:
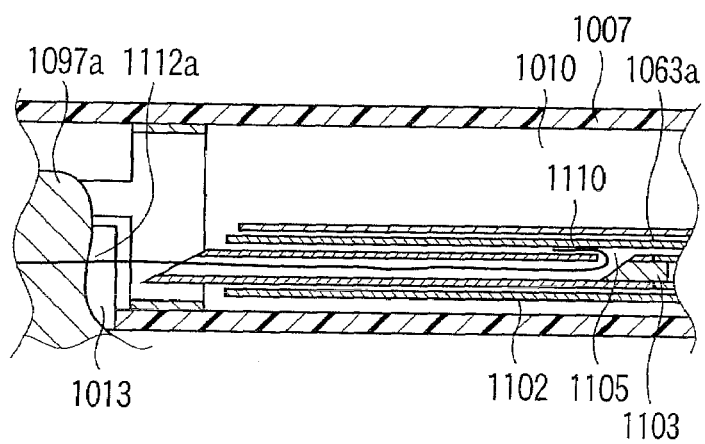
Figure 176:
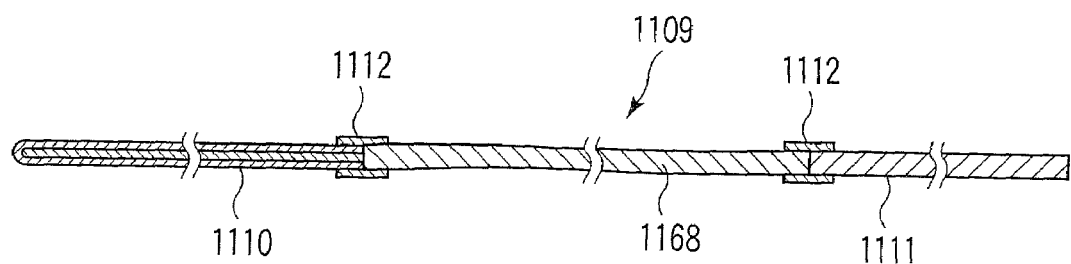
Figure 181:
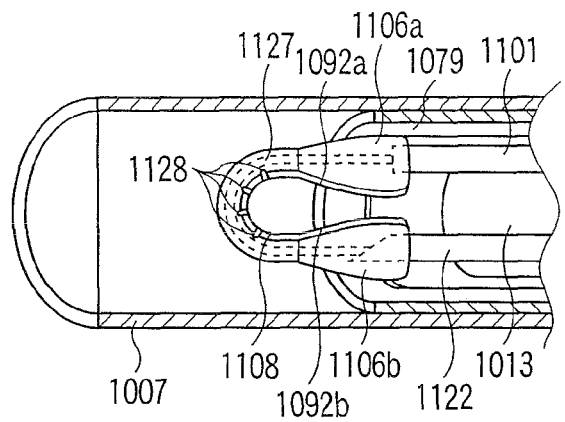
Figure 182:
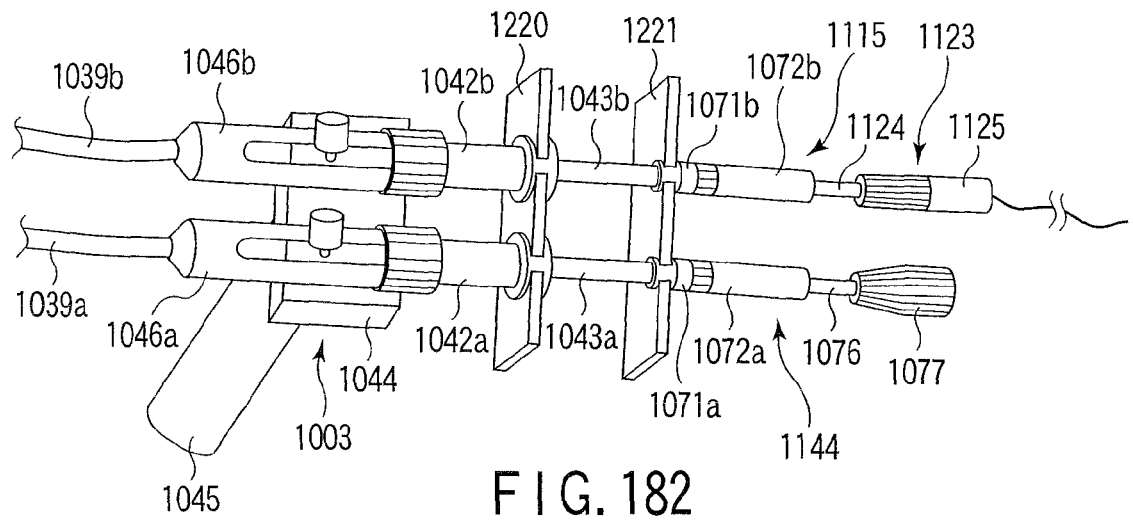
Figure 183:
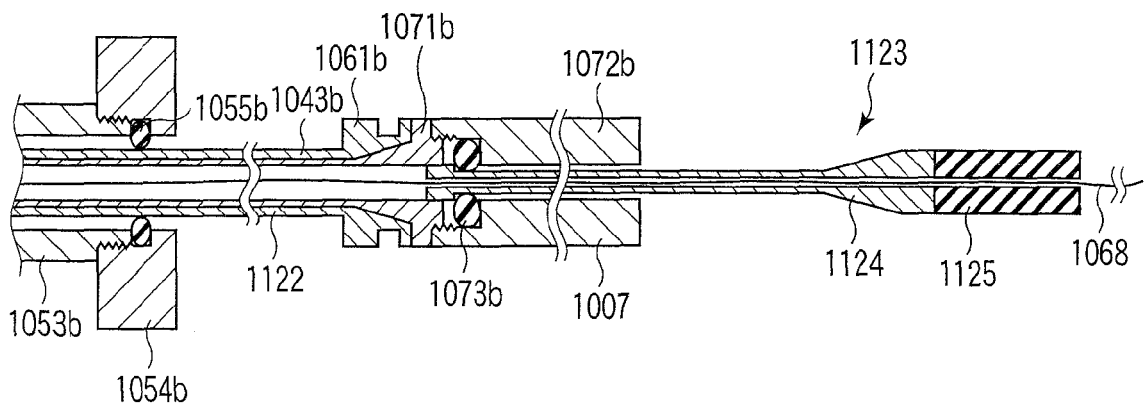
Figure 193:
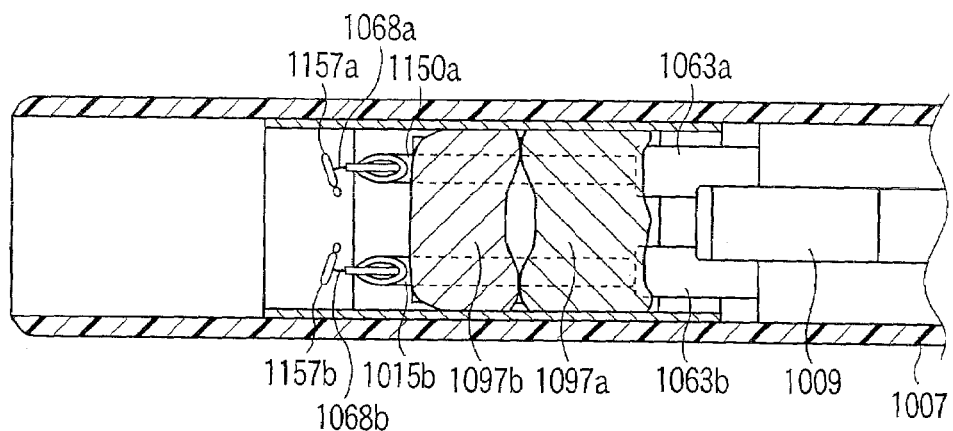
Figure 194:
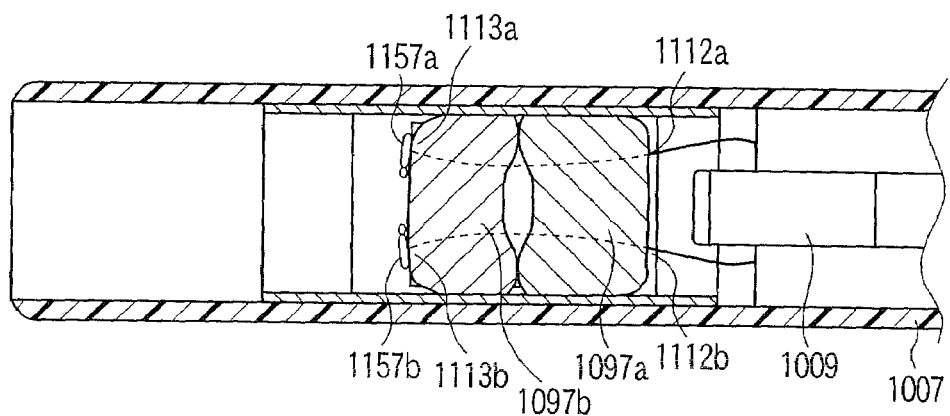
Figure 195:
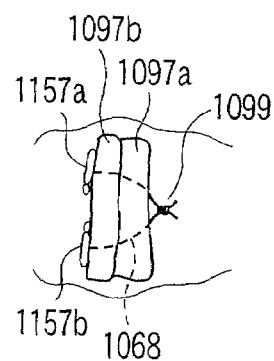
Figure 197:
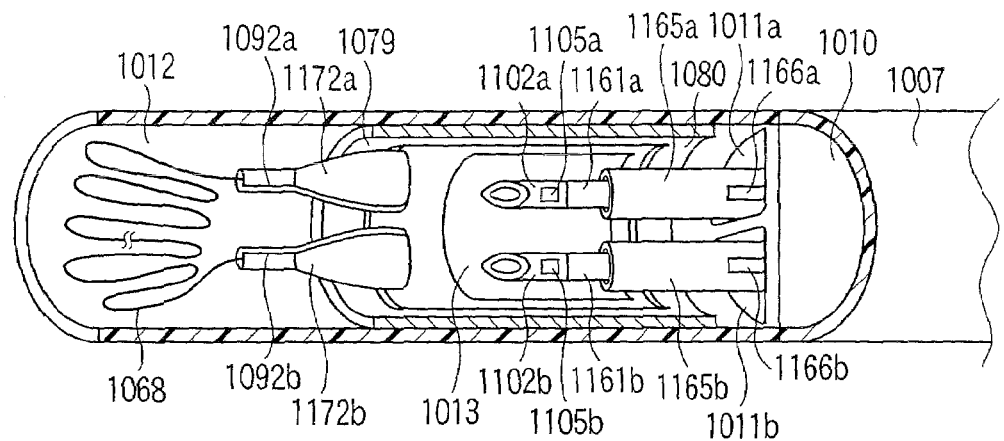
Figure 198:
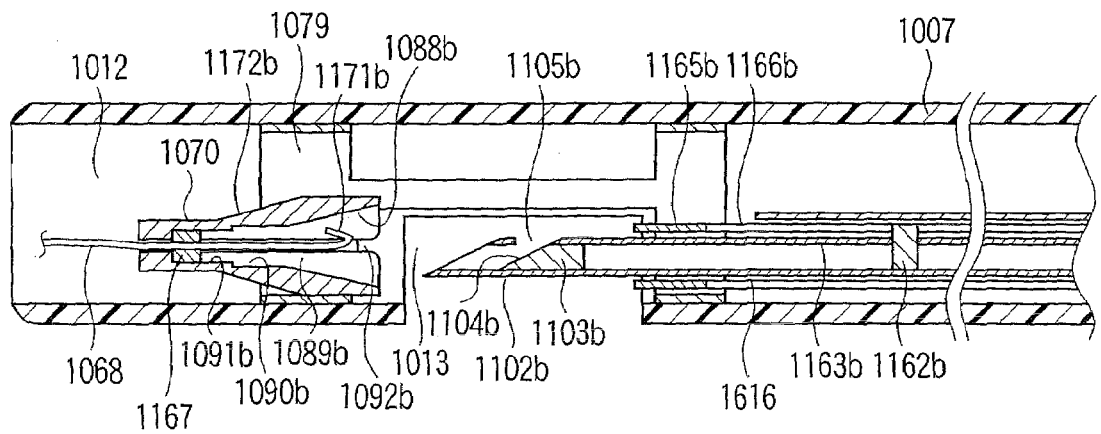
Figure 199:
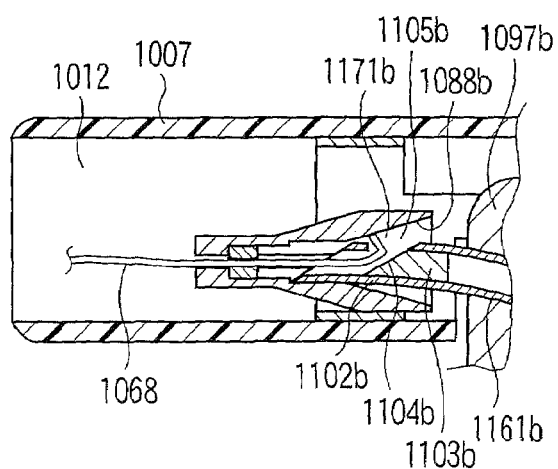
Figure 200:
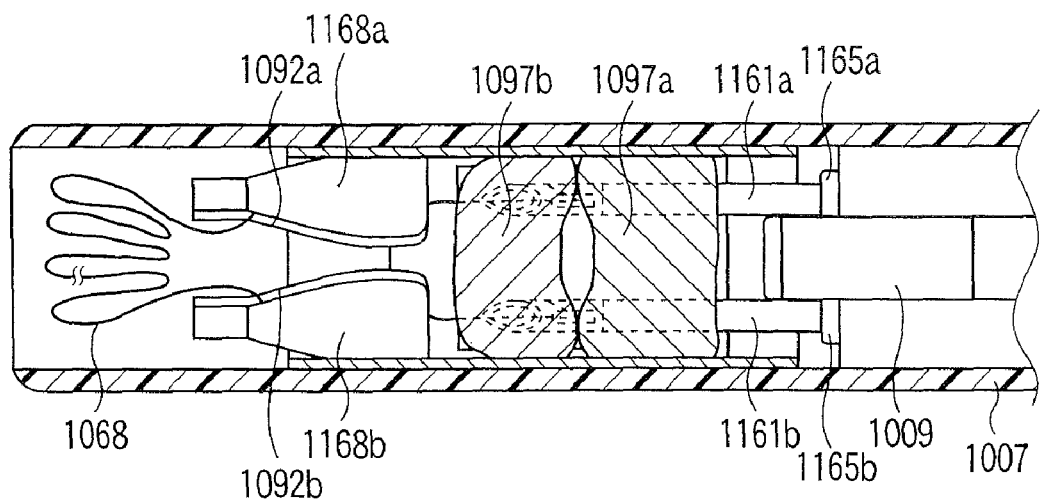
Figure 201:
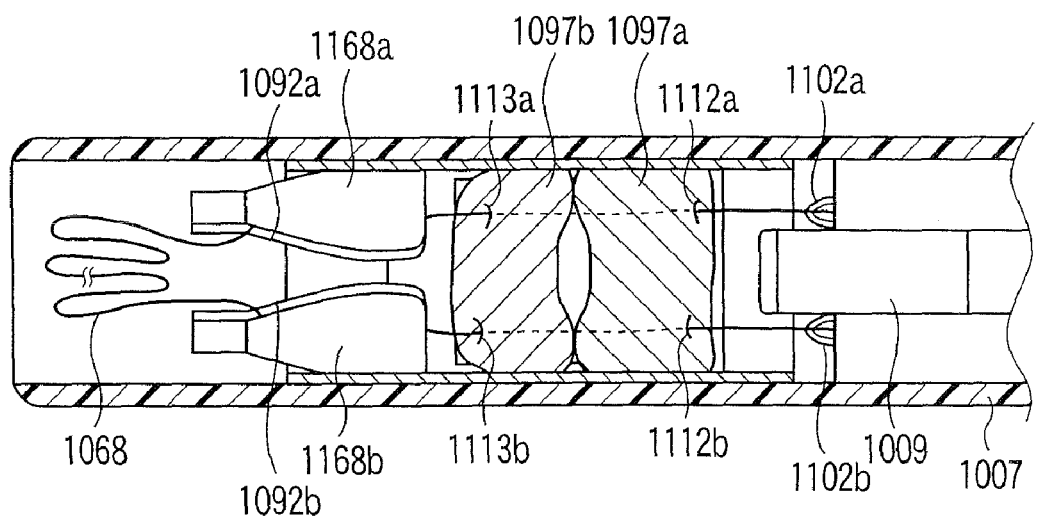
Figure 202:
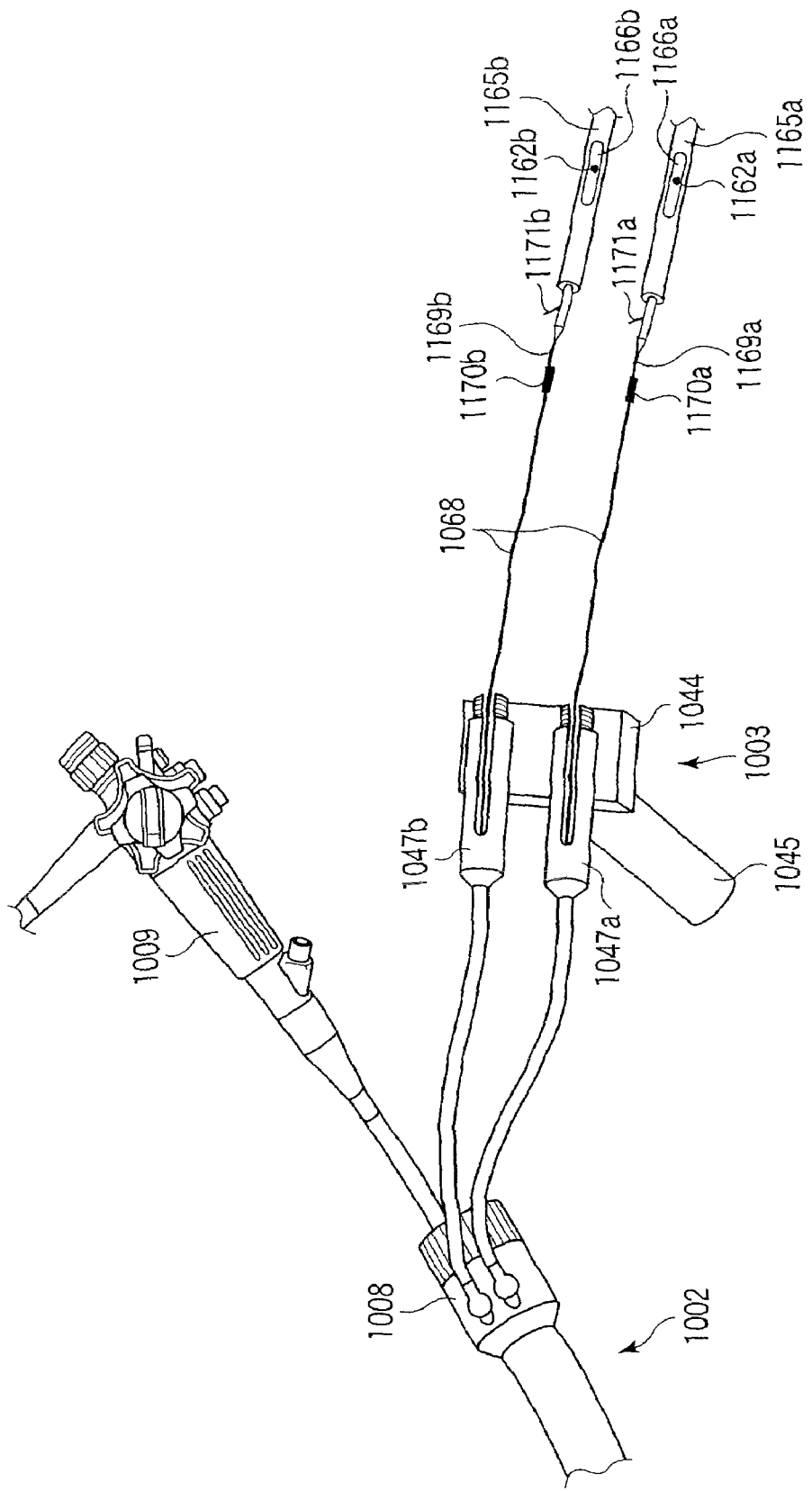
Figure 208:
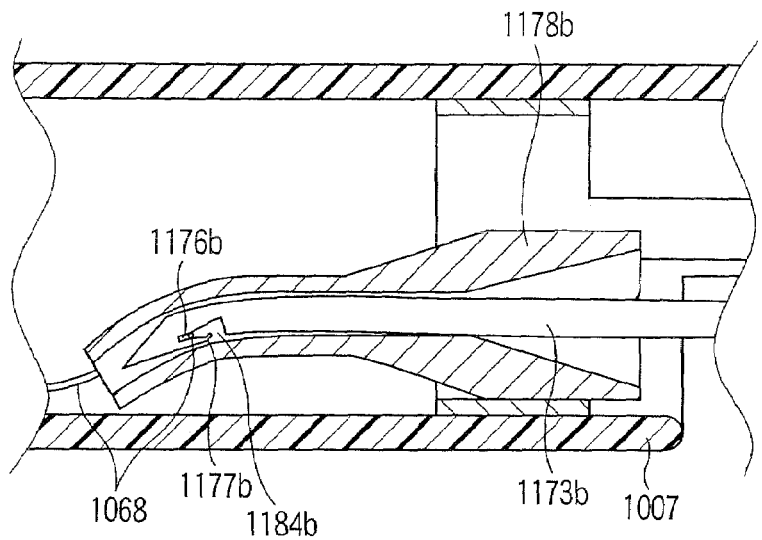
Figure 209:
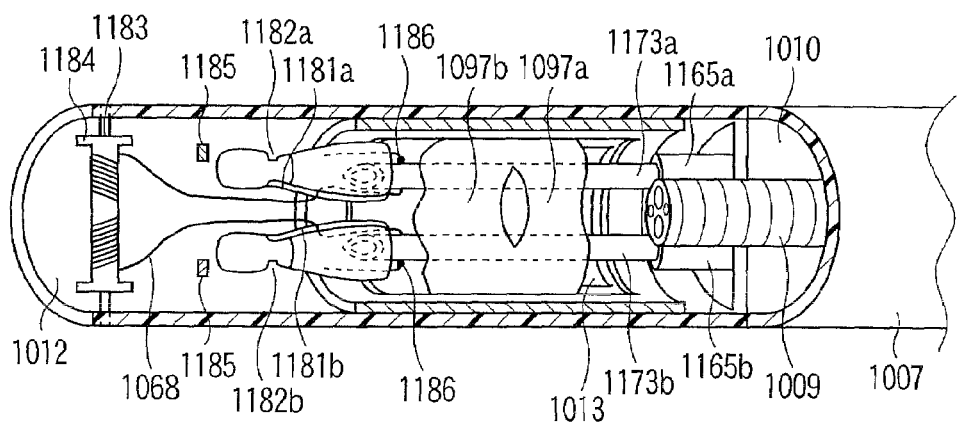
Figure 210:
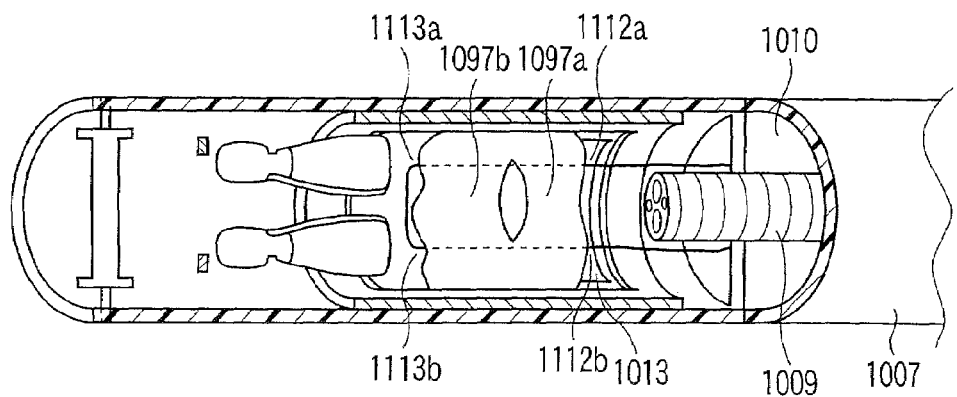
Figure 212:
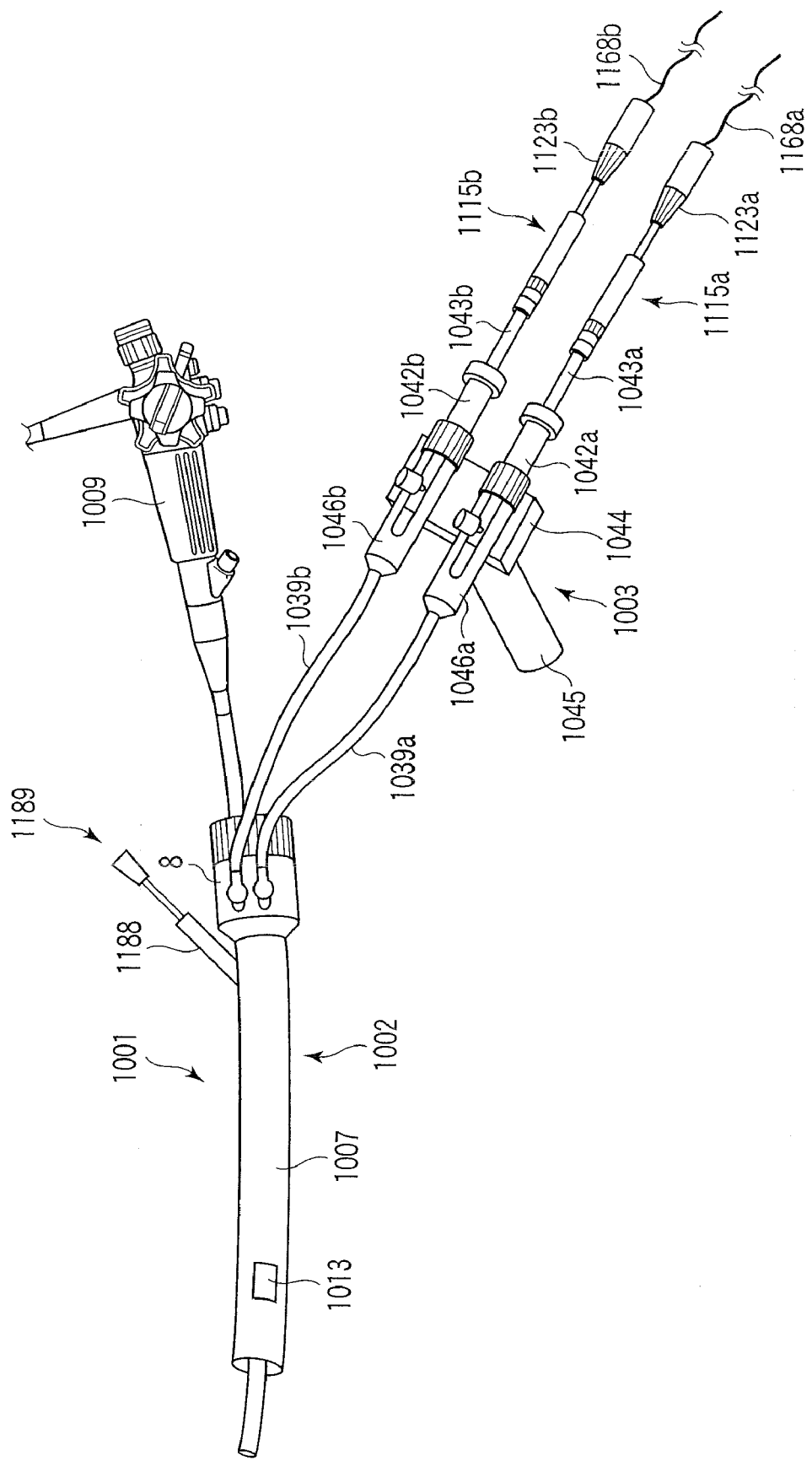
Figure 224:
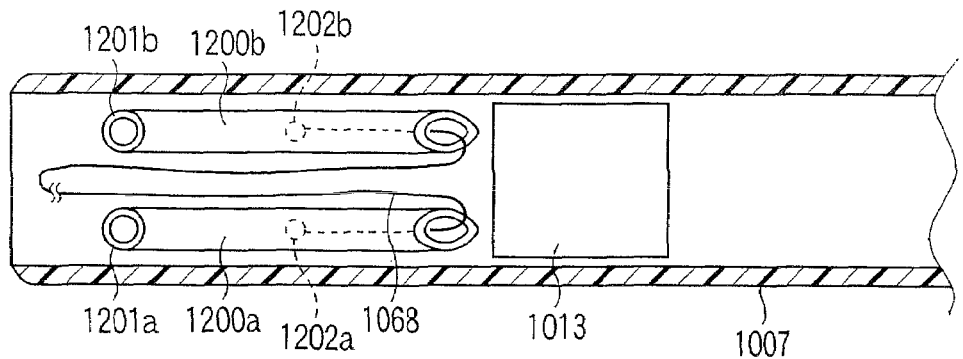
Figure 225:
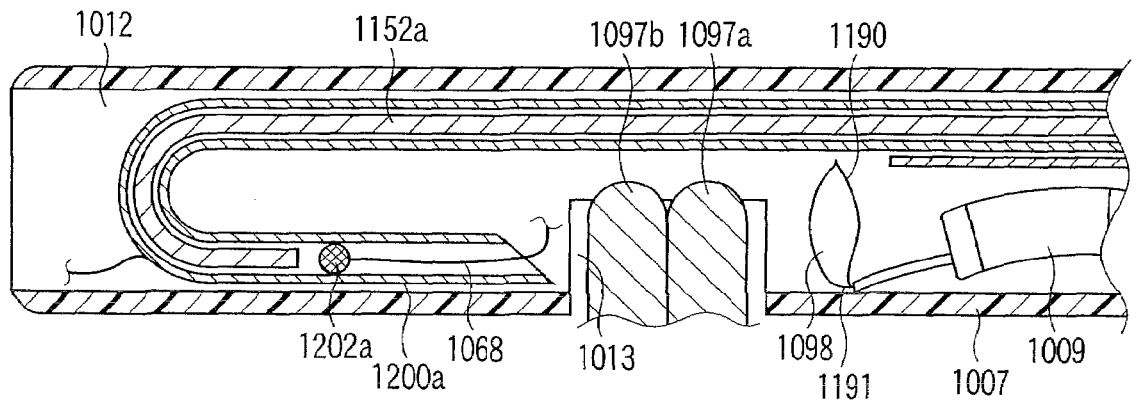
Figure 226:
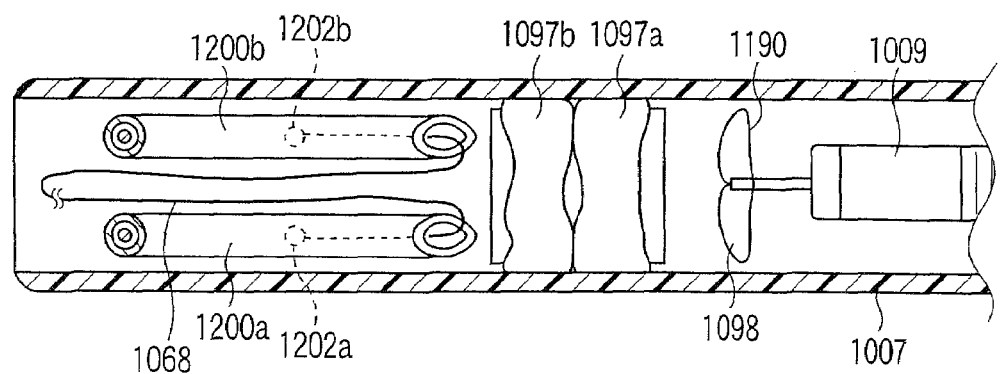
Figure 227:
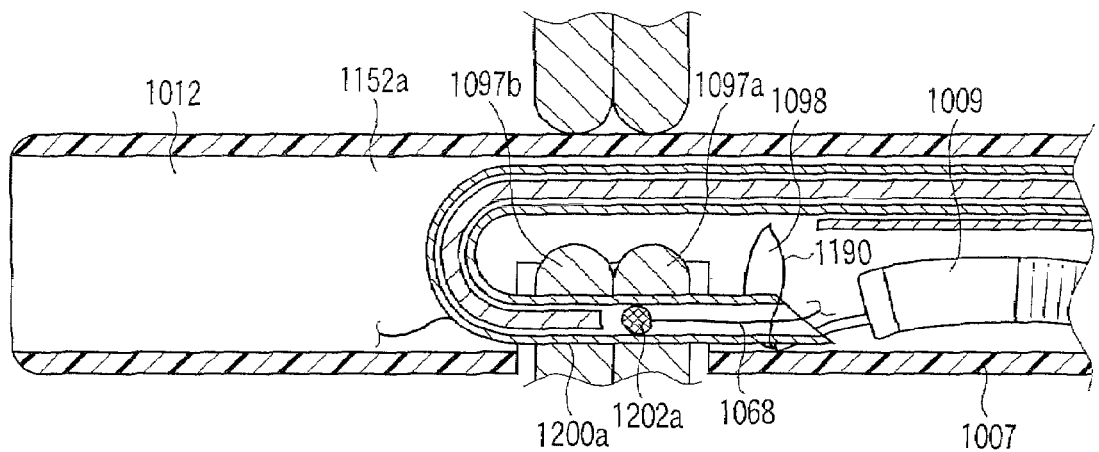
Figure 228:
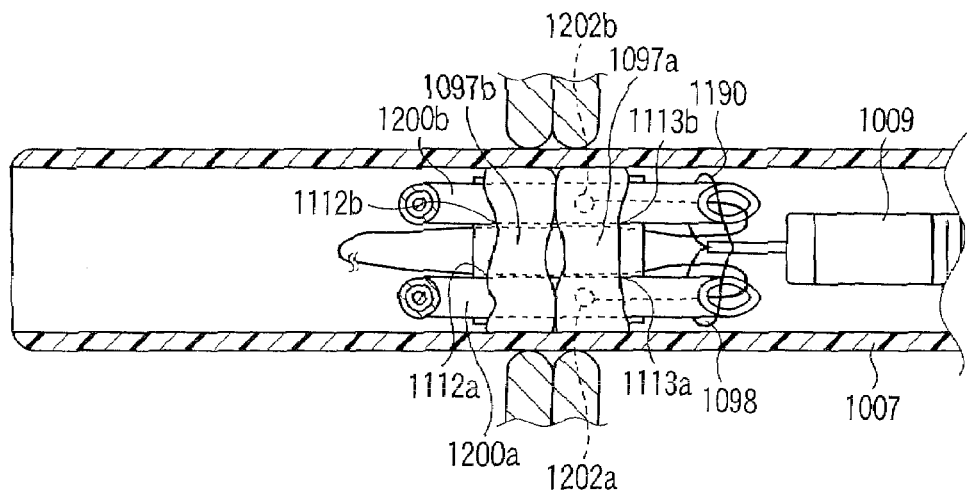
Figure 229:
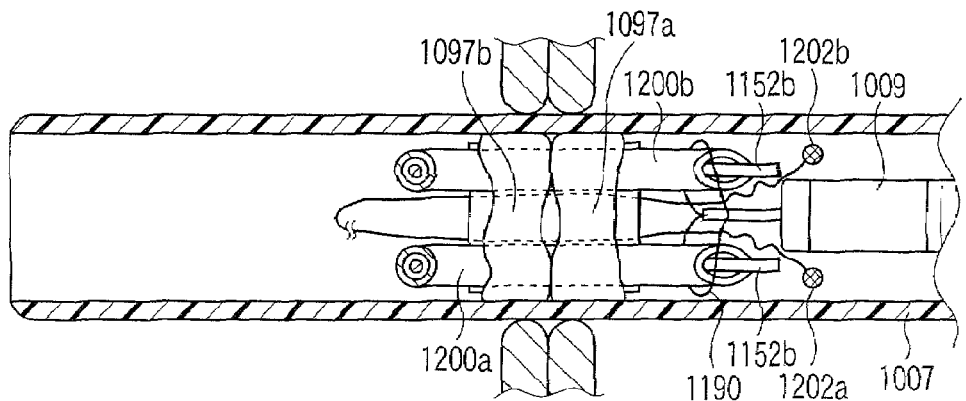
Figure 233:
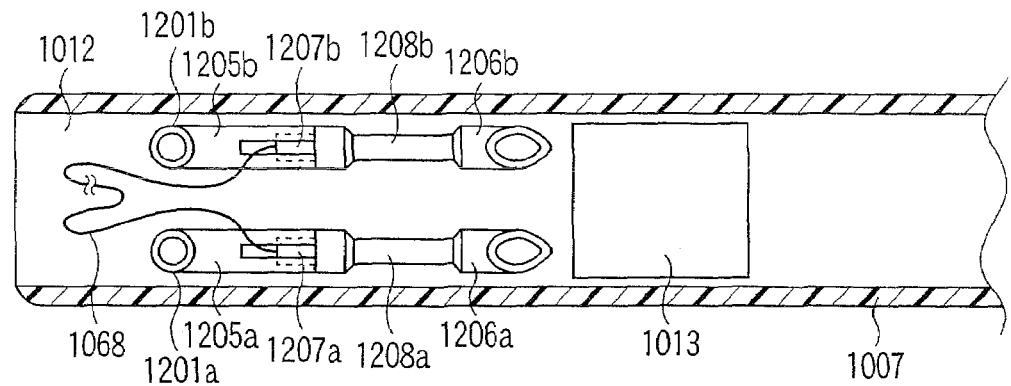
Figure 234:
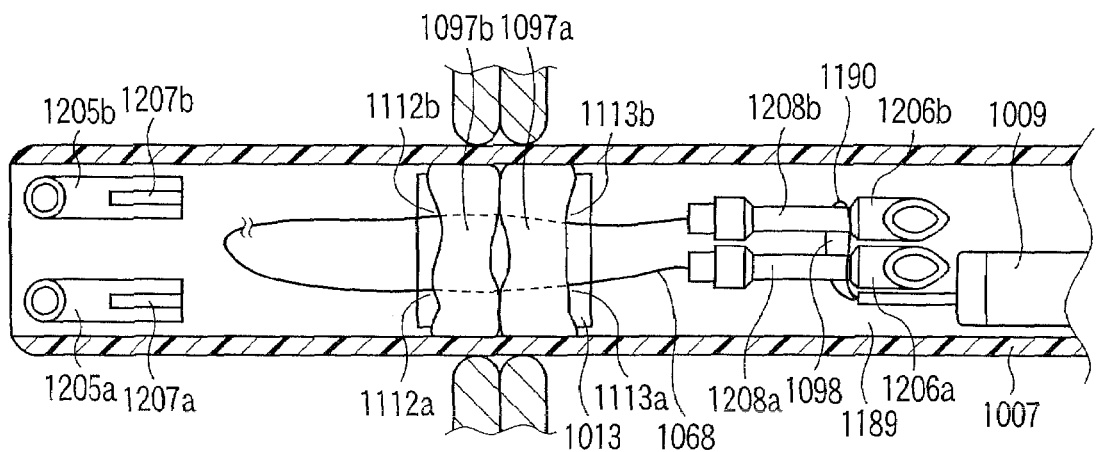
Figure 235:
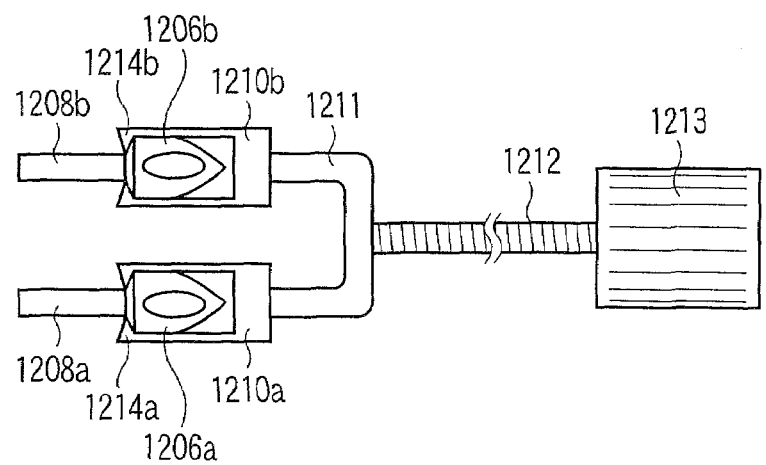
Figure 236:
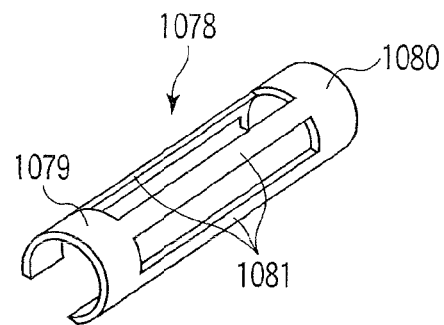
Figure 237:
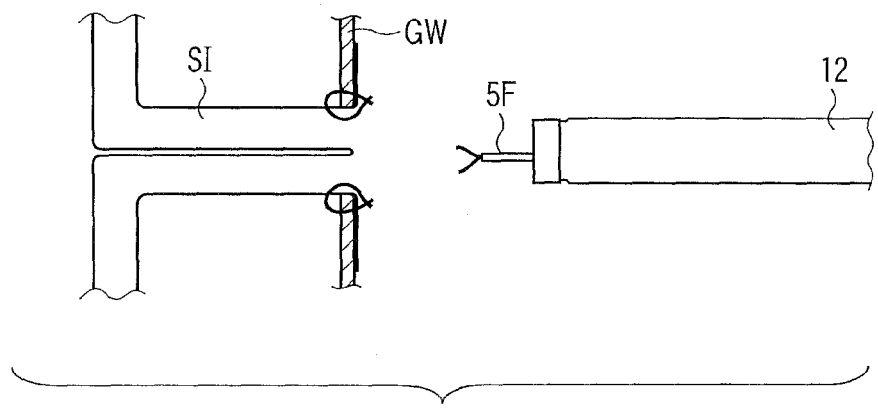
Figure 238:
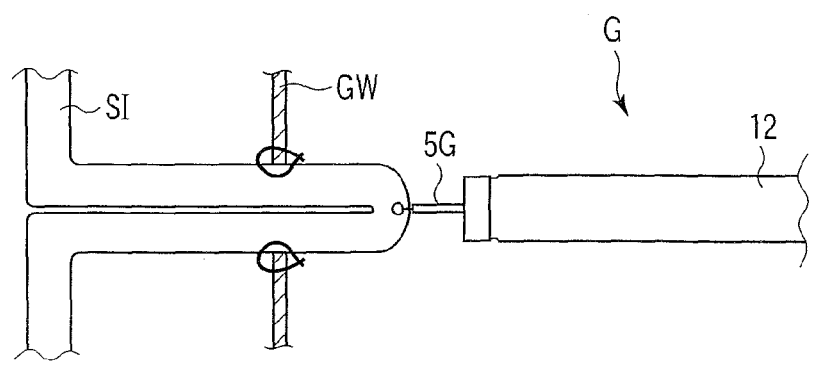

FIG. 152 is a vertical cross-sectional view of a sheath portion in the system of FIG. 141;

FIG. 153 is a vertical cross-sectional view taken along the line D-D in FIG. 152;

FIG. 154 is a view showing a thread grasping function by the thread grasping forceps;

FIGS. 155A to 155D are views showing various kinds of structural examples of the distal end portion of the sheath portion;

FIG. 156 is a view similar to FIG. 154 according to a modification of the needle;

FIGS. 157 and 158 are views showing the structure of the distal end portion of the sheath portion;

FIG. 159 is a vertical cross-sectional view of the proximal side of the over-tube;

FIG. 160 is a view showing the distal end portion of the sheath portion from the oblique direction;

FIG. 161 is a vertical cross-sectional view of a slider of the operation portion;

FIGS. 162 to 164 are views showing the suction/centesis function of the suture portion;

FIGS. 165 to 168 are reviews showing the state that the suture thread is inserted to the tissue;

FIGS. 169 to 170 are views showing the state that the suture thread is fixed;

FIGS. 171 to 177 show the tissue centesis system according to a second example, and FIG. 171 is a view showing a part of the over-tube in the form of a cross-sectional view;

FIGS. 172A and 172B are views showing a side opening of a needle sheath;

FIG. 173 is a view showing the distal end portion of a derivation member;

FIG. 174 is a view showing the distal end side of a side hole from the distal end of the needle end portion;

FIG. 175 is a cross-sectional view showing a needle end portion in the sheath portion;

FIG. 176 is a cross-sectional view of a suture wire;

FIG. 177 is an outside drawing of the entire tissue centesis system;

FIGS. 178 to 183 show the tissue centesis system according to a third example, and FIGS. 178A and 178B are cross-sectional views showing the operation of the operation member in the needle sheath;

FIG. 179 is a view showing a marker of the suture thread;

FIG. 180 is a vertical cross-sectional view of the needle;

FIG. 181 is a vertical cross-sectional view of the distal end of the over-tube;

FIG. 182 is an outside drawing of the operation portion;

FIG. 183 is a vertical cross-sectional view showing the proximal side of the needle;

FIGS. 184 to 187 show the tissue centesis system according to a fourth example, and FIG. 184 is a cross-sectional view of a needle guide using a permanent magnet as thread holding means;

FIG. 185 is a cross-sectional view similar to FIG. 184, in which a U-shaped hook is provided as the thread holding means;

FIG. 186 is a view showing only the distal end of the needle in the form of a section view;

FIGS. 187A and 187B are views of the operation member having a grasping portion as the thread holding means provided at the distal end thereof;

FIG. 188 is an explanatory view of a fifth example in which a T bar is provided at the distal end of the suture thread;

FIGS. 189 to 195 show the tissue centesis system according to sixth example, and FIG. 189 is an outside drawing showing the entire tissue centesis system;

FIG. 190 is a view showing a part of the over-tube in the form of a section view;

FIG. 191 is a vertical cross-sectional view of the distal end of the needle;

FIG. 192 is a vertical cross-sectional view showing the proximal side of the needle;

FIGS. 193 and 194 are cross-sectional views showing the suture function;

FIG. 195 is a view showing a ligature state of a suture tissue;

FIGS. 196 to 202 show the tissue centesis system according to a seventh example, and FIG. 196 is an outside drawing of the entire tissue centesis system;

FIG. 197 is a view showing a part of the over-tube in the form of a section view;

FIG. 198 is a vertical cross-sectional view of FIG. 197;

FIG. 199 is a view showing the distal end portion of the needle piercing a suture tissue;

FIGS. 200 and 201 are views showing the state of removing the needle piercing the suture tissue;

FIG. 202 is a view showing the state of removing the end portion of the suture thread to the outside of a body;

FIGS. 203 to 211 show the tissue centesis system according to an eighth example, and FIG. 203 is a view showing a part of the over-tube in the form of a section view;

FIG. 204 is a vertical cross-sectional view of FIG. 203;

FIGS. 205A and 205B are views showing a notch formed to the needle main body;

FIGS. 206 to 208 are views showing the function of the needle and the needle guide piercing the suture tissue;

FIGS. 209 and 210 are views showing a suture function obtained by the suture thread wound around a drum;

FIG. 211 is a view showing a modification of the needle guide;

FIGS. 212 to 218 show the tissue centesis system according to a ninth example, and FIG. 212 is an outside drawing of the entire tissue centesis system;

FIGS. 213 to 215 are views for illustrating the function of the operation member;

FIGS. 216 and 217 are views showing the relationship between the suture tissue and the knot;

FIG. 218 is a view of a modification;

FIGS. 219 to 220 show a suture operation by the tissue centesis system according to a 10th example;

FIGS. 221 to 231 show the tissue centesis system according to an 11th example, and FIG. 221 is an outside drawing of the entire tissue centesis system;

FIG. 222 is a vertical cross-sectional view of the sheath portion;

FIG. 223 is a transverse cross-sectional view taken along the line E-E in FIG. 222;

FIG. 224 is a cross-sectional view along a plane orthogonal to each of FIGS. 222 and 223;

FIGS. 225 to 230 are explanatory views showing the state of suturing a suture tissue;

FIGS. 231A and 231B are views showing modifications of the needle main body;

FIGS. 232 and 233 are vertical cross-sectional views showing the inner structure of the tissue centesis system according to a 12th example along planes which cross each other;

FIG. 234 is a view showing the needle and the thread piercing the suture tissue;

FIG. 235 is an outside drawing of a thread gripper 209;

FIG. 236 is a view showing the shape of a annular proximal portion according to the first embodiment;

FIG. 237 is a view showing one of the anastomosis procedures by the anastomosis system according to an 11th embodiment; and FIG. 238 is a view showing one of the anastomosis procedures by the anastomosis system according to a 12th embodiment.

DETAILED DESCRIPTION OF THE INVENTION

Embodiments of the present invention will now be described hereinbelow with reference to the accompanying drawings.

First Embodiment

FIGS. 1 to 40 show an anastomosis system according to a first embodiment of the present invention. Incidentally, although the system according to each embodiment described below uses an endoscopic suture machine, any treatment instrument such as a grasping forceps, a thread cutting forceps, a scissor forceps, a hot biopsy forceps or a rotational clip device may be used instead of this machine.

Figure 1:
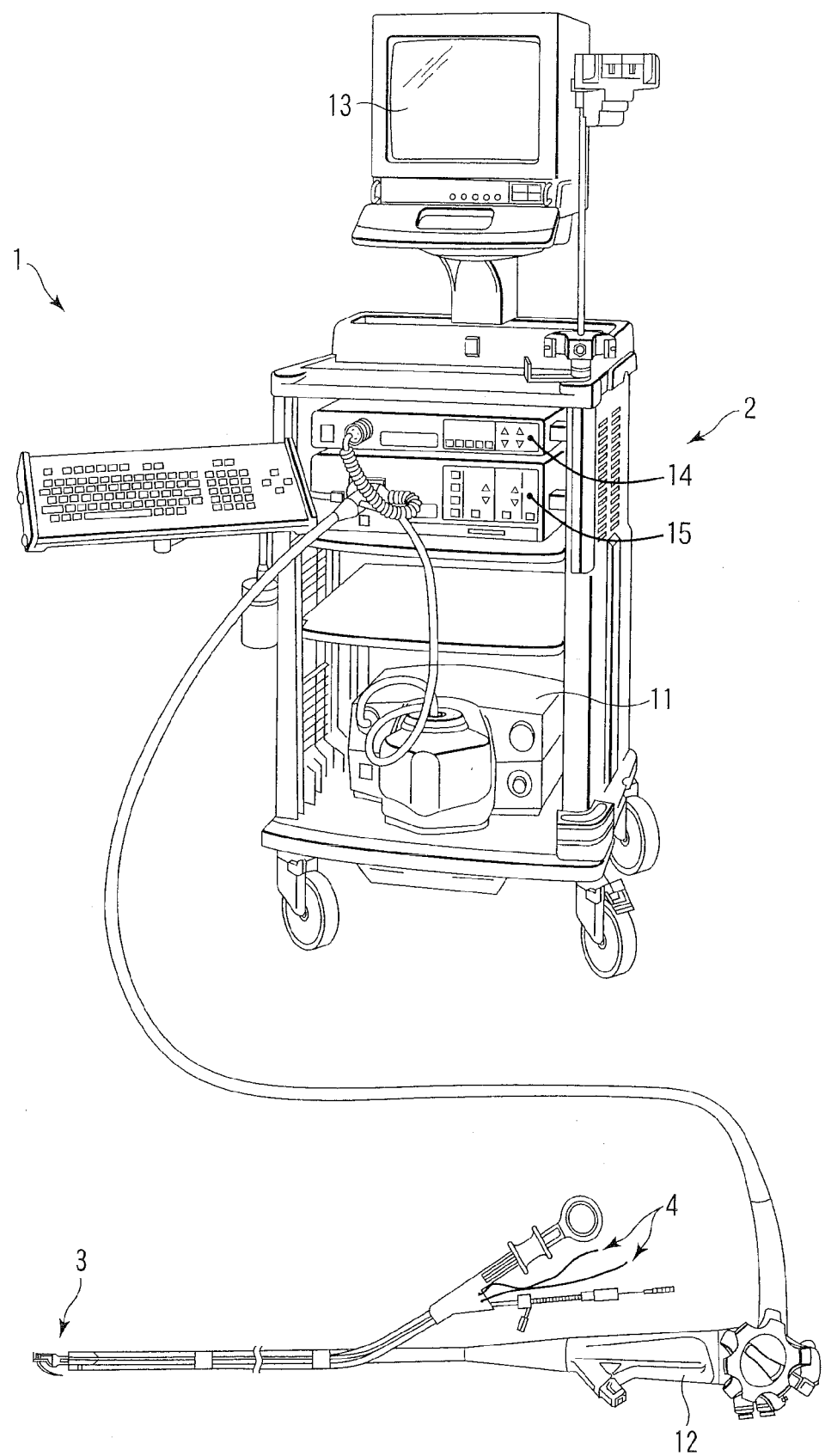
FIG. 1 is an explanatory view showing an entire structure of an endoscopic anastomosis system according to a first embodiment of the present invention.

As shown in FIG. 1, an anastomosis system 1 according to this embodiment includes an endoscopic system 2, a suture machine 3, and a suture thread 4. As similar to a generally used electronic endoscopic system, the endoscopic system 2 is provided with an endoscope 12, an image processing device 14, a light source device 15, an observation monitor 13 and a suction unit 11. The endoscope 12 is connected to the light source device 15 through a universal cord. An image signal supplied from a CCD camera 10 (see FIG. 8) at the distal end portion is processed in the image processing device 14, and it is then displayed in the monitor 13. As is best shown in FIG.

2, an endoscope having one forceps channel 6 is used as the endoscope 12, but an endoscope having two forceps channels may be used instead.

Figure 8:
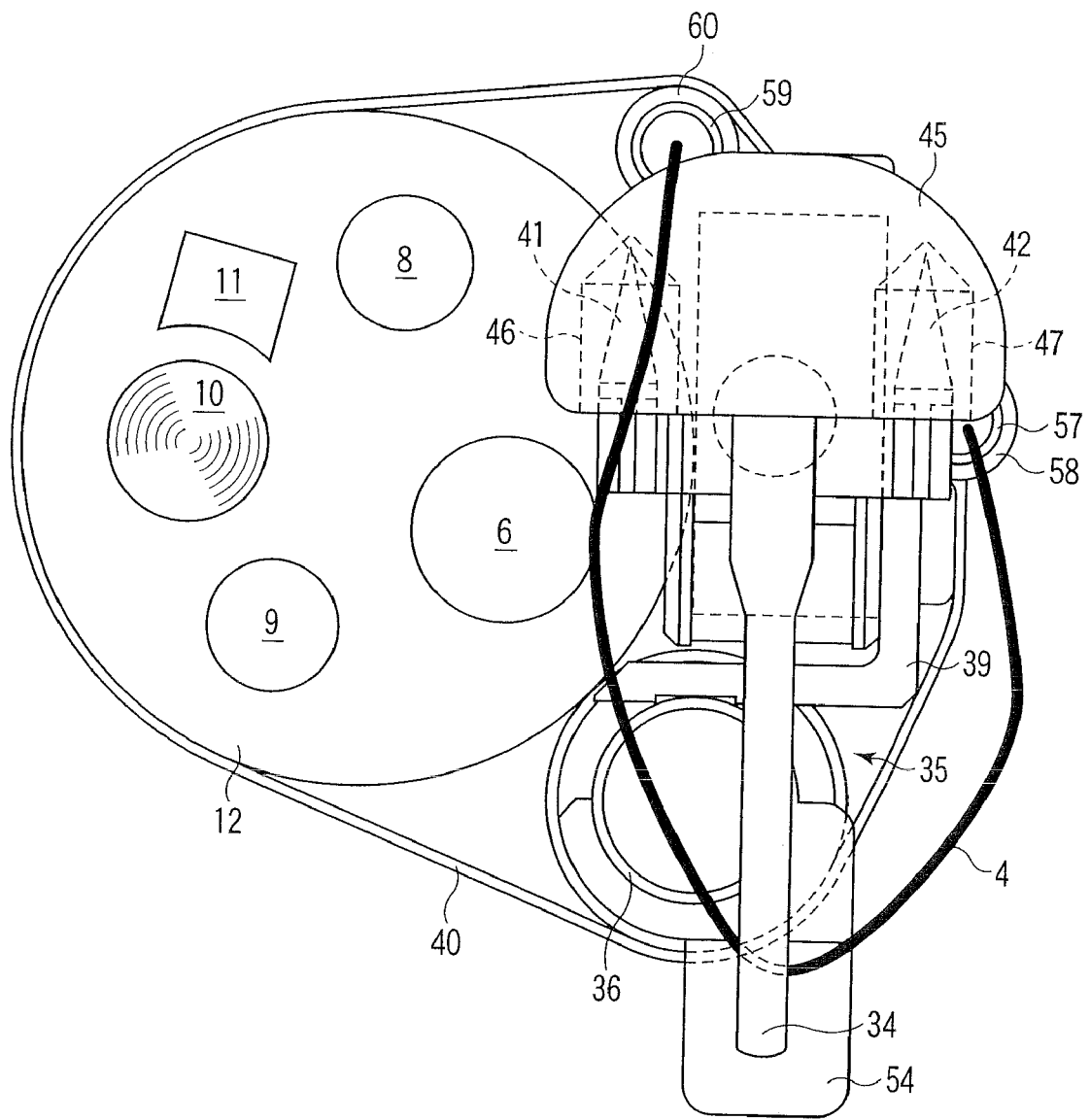
FIG. 8 is a view seen from the direction of an arrow B in FIG. 2.

Further, as shown in FIG. 8, in the endoscope 12 are arranged a CCD camera 10, light guides 8 and 9, a forceps channel 6, and a nozzle 11 for cleansing the lens of the CCD camera at the distal end portion thereof. It is to be noted that a fiber endoscope with an eyepiece may be used in place of the electronic endoscope using the CCD. As shown in FIG. 8, although the suture machine 3 is detachably fixed to the distal end of the endoscope 12 by a fixing member 40, the suture machine 3 and the endoscope 12 may have an integral structure instead.

As shown in FIGS. 3 to 7, the suture machine 3 includes a later-described flexible tube 73 and a holding member 18 which is fixed to the distal end portion of this tube and holds a later-described needle. To this holding member 18 are formed two support plate portions 18a which are opposed with a slit 31 (see FIG. 7) therebetween, and a hole 19 (see FIG. 5) which communicates with the slit 31 between the support plate portions and an inner hole of the flexible tube 73. A push rod 20 is arranged in the hole 19 so as to be capable of moving forward and backward in the axial direction.

One end of each of first and second connection members 22 and 23 is pivoted to the end of the push rod 20 through a pin 21. The other ends of the first and second connection members 22 and 23 are pivoted to proximal end portions of first and second arm members 24 and 25 through pins 26 and 27, respectively. Furthermore, a first operation member 16 integrally formed with the first arm member 24 is rotatably connected to the support plate portion 18a through a pin 28. Similarly, a second operation member 17 integrally formed with the second arm member 25 is rotatably connected to the support plate portion 18a though a pin 29.

Figure 7:
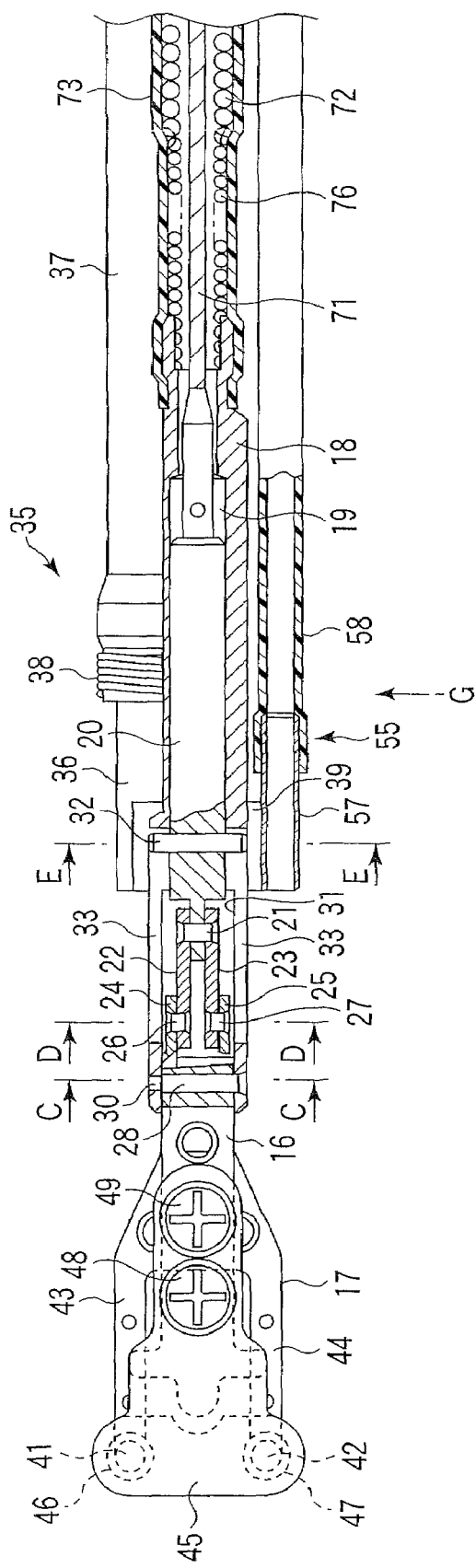
FIG. 7 is a cross-sectional view taken along the line A-A in FIG. 5.

As shown in FIG. 7 by using the example of the pin 28, each of the pins 28 and 29 has an end portion formed of a thin-diameter portion 30. As a result, a size of the slit 31 formed between the support plate portions 18a of the holding member 18 can be maintained to be slightly larger than a sum of thicknesses of the first operation member 16 and the second operation member 17. The first operation member 16 and the second operation member 17 can move in the slit 31 without generating the friction of a large order.

As shown in FIG. 7, the push rod 20 is connected to an elongated flexible member 71. Moreover, the holding member 18 is connected with coils 72 and 76 which form axial holes. Opposed end surfaces of these coils 72 and 76 are connected by preferable means such as laser welding, brazing, soldering or adhesion. The coil 76 is formed of a wire having a thinner diameter than the coil 72, and the distal end side of the suture machine 3 is consequently more flexibly formed. These coils 72 and 76 are covered with the flexible tube 73 along substantially the entire length, and held appressed to the flexible tube 73. The tube 73 restricts expansion and contraction of the coils 72 and 76 in the axial direction, and the force used for opening/closing the first operation member 16 and the second operation member 17 consequently becomes large.

Figure 2:
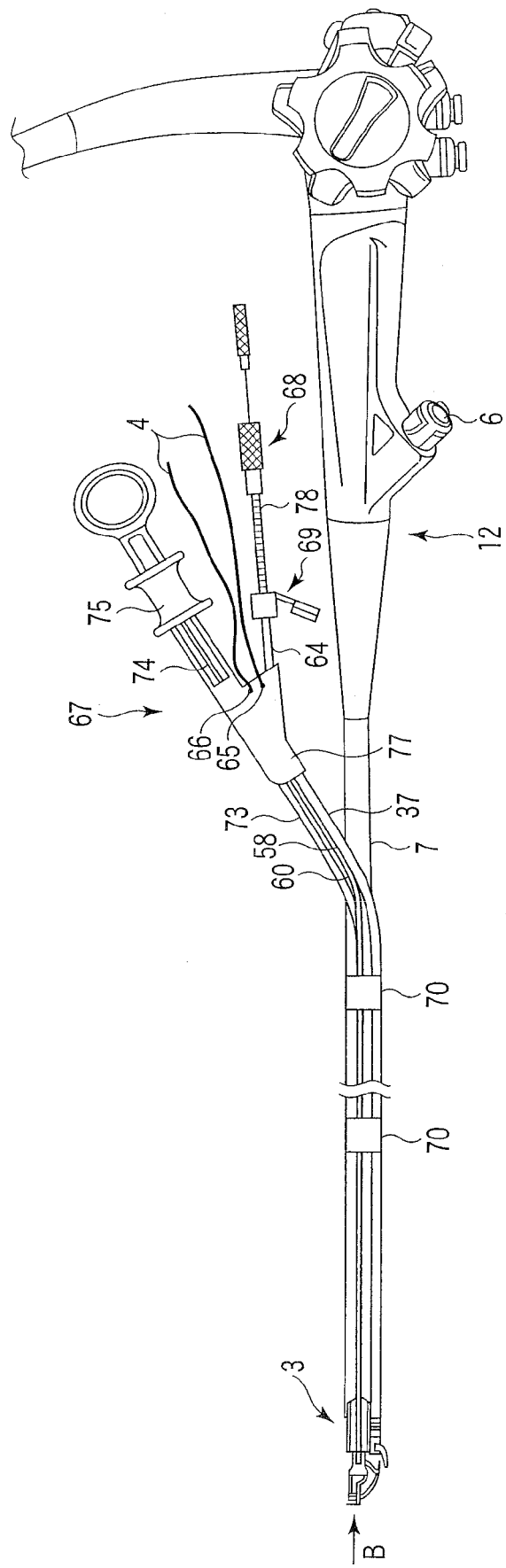
FIG. 2 is an enlarged view of an endoscope and a suture machine illustrated in FIG. 1.

As shown in FIG. 2, the proximal end portions of the tube 73 and the coils 72 are fixed to an operation portion main body 77 of a suture machine operation portion 76. In addition, the proximal end portion of the transmission member 71 is inserted into the operation main body 77, further inserted into a pipe 74 which is capable of sliding with respect to the operation portion main body, and connected to this pipe 74 in this state. This pipe 74 is connected to a movable member 75 through a non-illustrated connection member. Therefore, when the movable member 75 is moved forward/backward with respect to the operation portion main body 77, the first operation member 16 and the second operation member 17 can be opened/closed through the transmission member 71.

Figure 5:
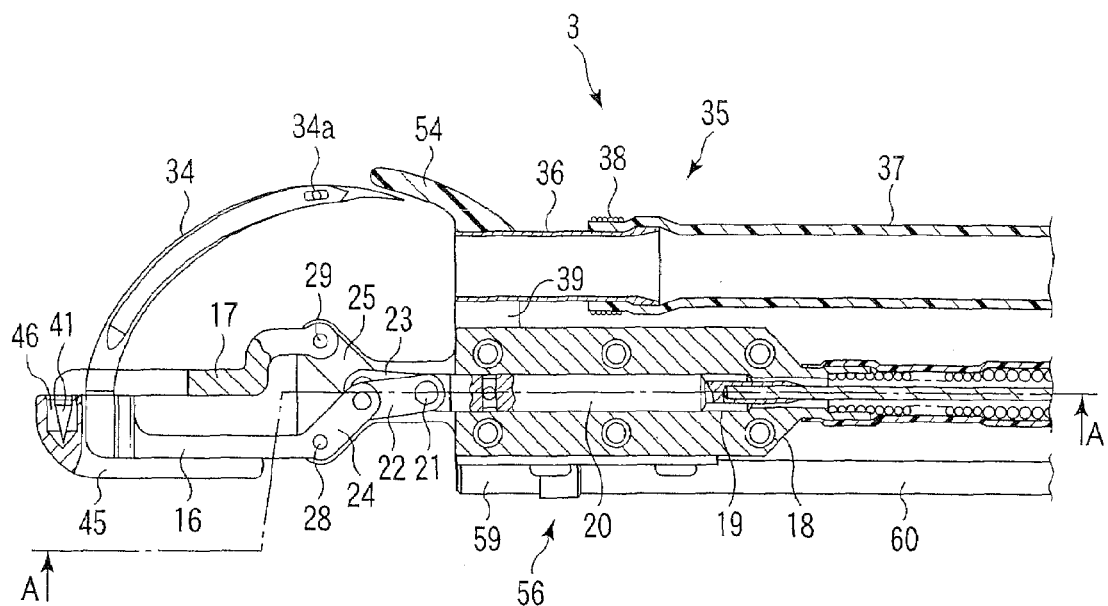
FIG. 5 is a cross-sectional view showing an internal structure of the suture machine illustrated in FIG. 3.
Figure 6:
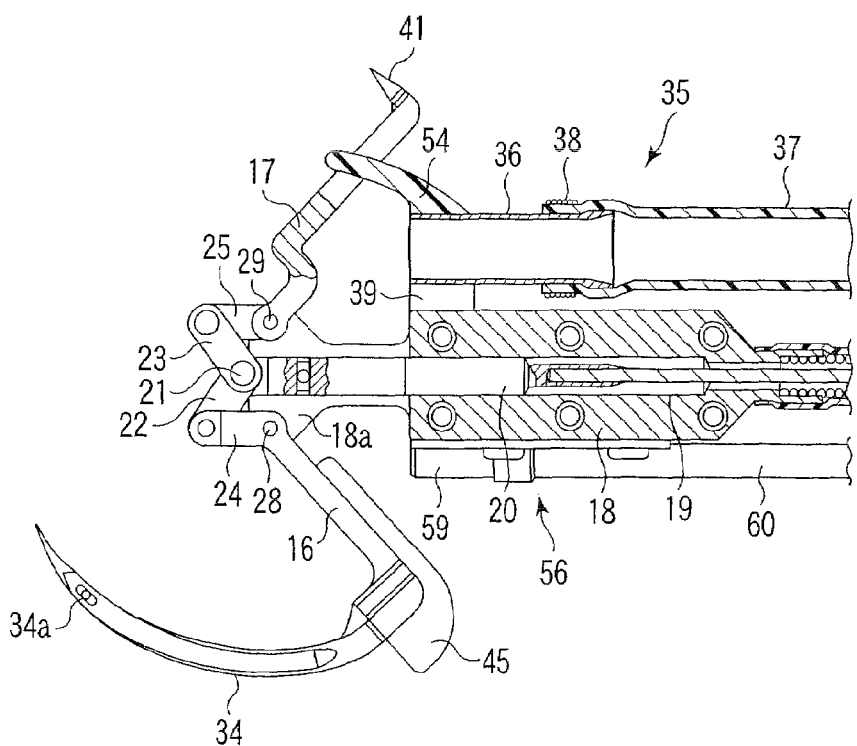
FIG. 6 is a cross-sectional view showing an internal structure of the suture machine illustrated in FIG. 4.

As shown in FIGS. 5 and 6, the first and second arm members 24 and 25 can pass between the pins 28 and 29 and be opened to an angle illustrated in FIG. 6. It is needless to say that an angle between the first and second arm members 24 and 25 can be further enlarged or decreased by appropriately setting the lengths of the first and second arm members 24 and 25 and the lengths of the first and second connection members 22 and 23.

Figure 3:
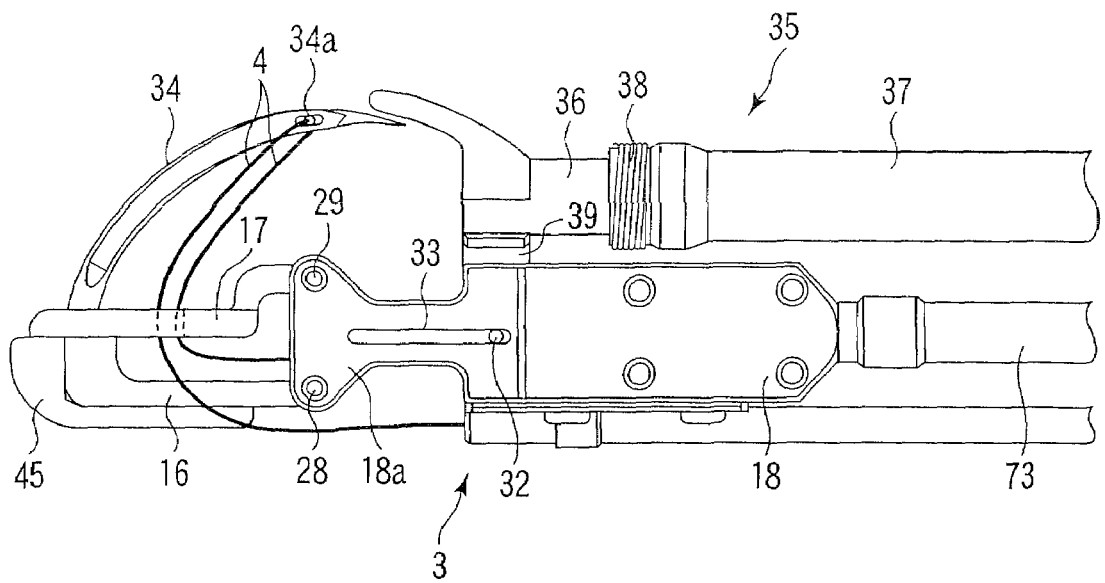
FIG. 3 is an explanatory view showing the state that first and second operation members in the suture machine are closed.
Figure 4:
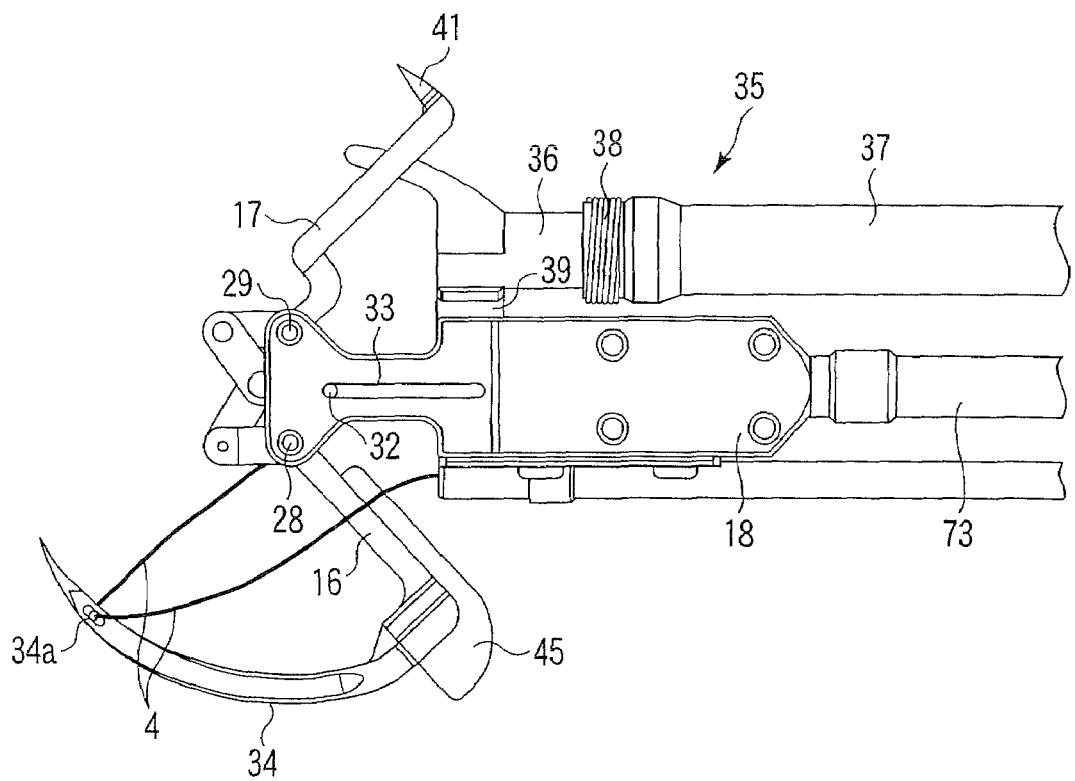
FIG. 4 is an explanatory view showing the state that the first and second operation members in the suture machine are opened.
Figure 11:
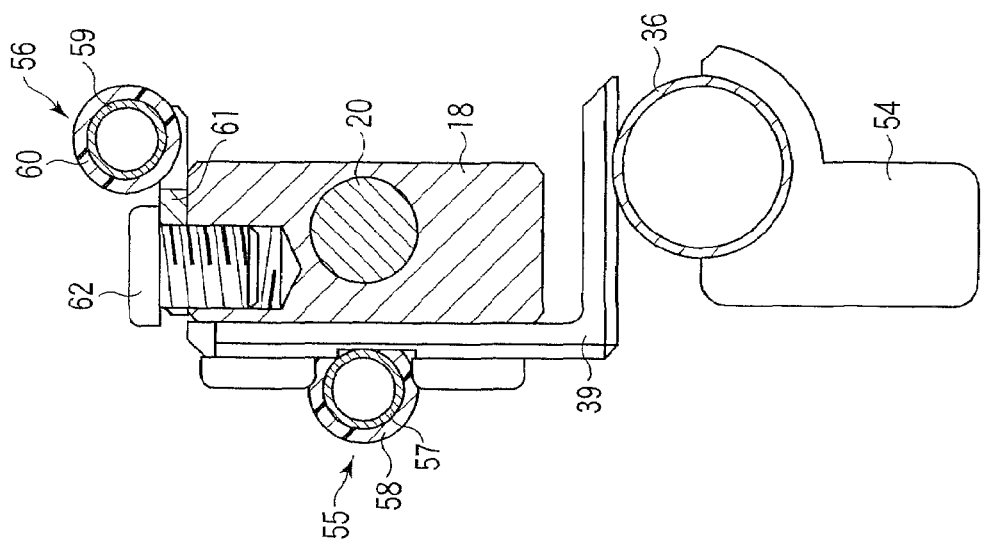
FIG. 11 is a cross-sectional view taken along the line E-E in FIG. 7.

As shown in FIGS. 7 and 11, a stopper pin 32 is fixed to the push rod 20. As shown in FIGS. 3, 4 and 7, the stopper pin 32 is guided in the slit 33 which is formed to the holding member 18 and extends in the longitudinal direction, and can restrict the movement of the first and second operation members 16 and 17 in the opening direction.

A curved needle 34 is fixed to the distal end of the first operation member 16. This curved needle 34 may be detachable with respect to the first operation member 16 instead. A needle hole 34a into which the suture thread 4 can be inserted is formed to the distal end side of the curved needle 34. Additionally, as shown in FIG. 8, a wall thickness of the curved needle 34 is reduced in order to improve penetration into a living tissue.

As shown in FIGS. 5 to 8A, the second operation member 17 has bifurcated fixed arms 43 and 44, and fixed needles 41 and 42 are fixed to the ends of the fixed arms 43 and 44, respectively. In this embodiment, although the fixed needles 41 and 42 are integrally fixed to the fixed arms 43 and 44, they may be detachable to these arms. On the other hand, as shown in FIG. 7, a protection member 45 to which holes 46 and 47 are formed is fixed to the first operation member 16 by screws 48 and 49. As shown in FIGS. 5 and 6, this protection member 45 covers the needle ends of the fixed needles 41 and 42 and prevents the fixed needle 41 and 42 from being caught by, e.g., a living tissue when the first and second operation members 16 and 17 are closed.

Figure 13:
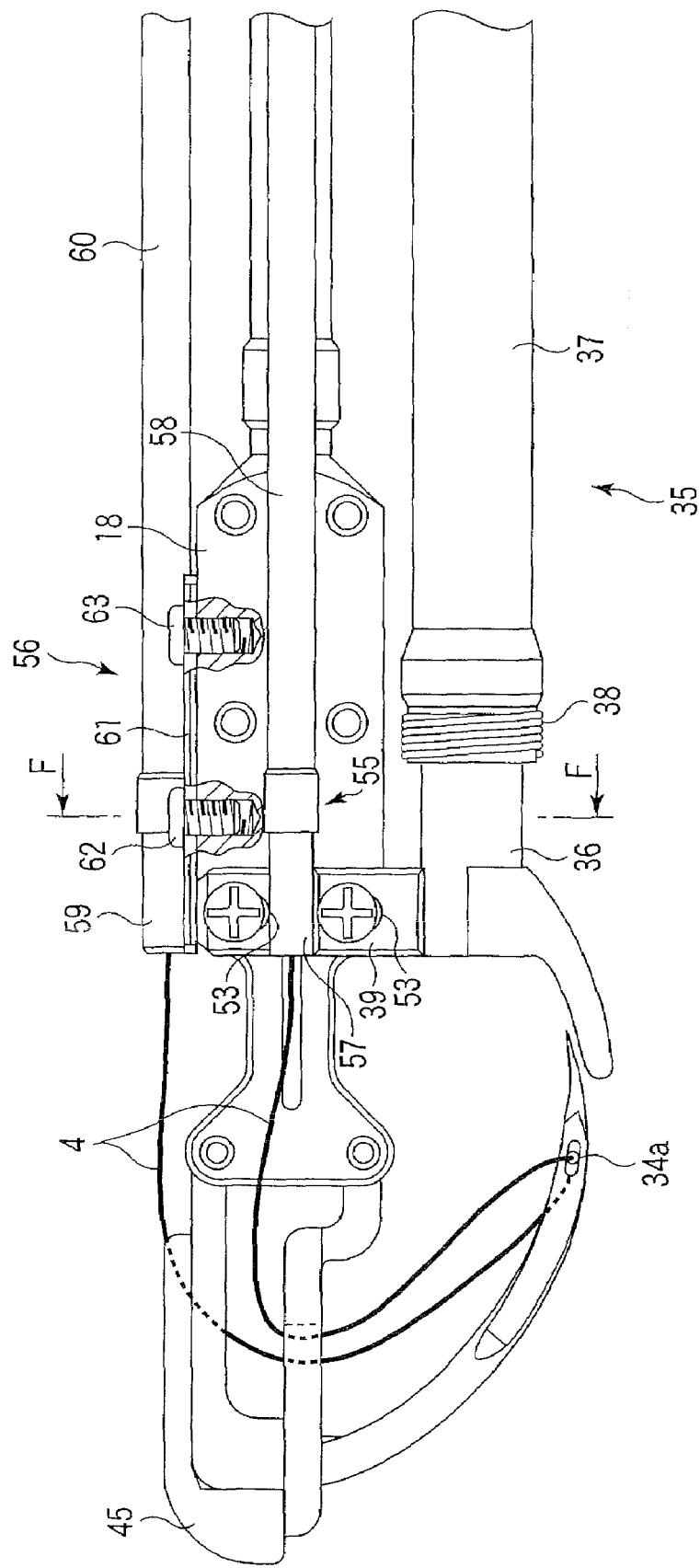
FIG. 13 is a view seen from the direction of an arrow G in FIG. 7.

As shown in FIGS. 5 and 11, a channel member 35 is fixed to the holding member 18 through an L-shaped support member 39. This channel member 35 has a pipe 36 which is formed of a relatively hard material and arranged at the distal end portion thereof and a tube 37 which is formed of a relatively soft material and fastened by a fixed thread 38 after being press-fitted into the pipe 36, and this fixed thread 38 is fixed to the tube 37 by an adhesive agent. The pipe 36 enters a concave portion 52 of a support member 39 (see FIG. 11) and is fixed to the support member 39 by appropriate means such as brazing, soldering or adhesion. As shown in FIGS. 11 and 13, two long holes 53 through which screws 50 and 51 can pass are formed to the support member 39, and the support member 39 can be fixed to the support member 18 by the screws 50 and 51 so as to be capable of adjusting a position relative to the holding member 18.

Further, as shown in FIGS. 10 and 11, a protection member 54 is fixed to the pipe 36 by preferable means such as brazing, soldering or adhesion. This protection member 54 covers the needle end of the curved needle 34 and prevents the curved needle 34 from being caught by a living tissue or the like when the first and second operation members 16 and 17 are closed.

As shown in FIGS. 11 and 13, a thread guide 55 having an axial hole through which the suture thread 4 can pass is attached to the support member 39. This thread guide 55 is constituted by a pipe 57 which is formed of a relatively hard material and a tube 58 which is formed of a relatively soft material, and the pipe 57 is fixed to the tube by appropriate means such as press-fitting or adhesion. Furthermore, the pipe 57 is fixed to the support member 39 by preferable means such as brazing, soldering or adhesion.

Figure 12:
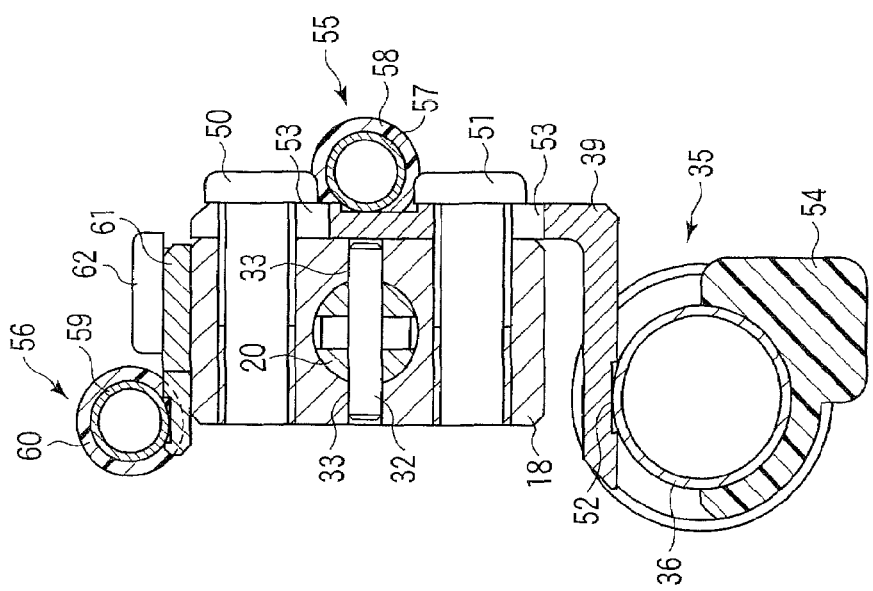
FIG. 12 is a cross-sectional view taken along the like F-F in FIG. 13.

As shown in FIGS. 11 to 13, as similar to the thread guide 55, a thread guide 56 is fixed to the holding member 18 by screws 62 and 63. This thread guide 56 is constituted by a pipe 59 which is formed of a relatively hard material, a tube 60 which is formed of a relatively soft material and a plate-like support member 61, and the support member 61 and the pipe 59 are fixed by preferable means such as brazing, soldering or adhesion.

As shown in FIG. 2, the tube 37 communicates with a mouth ring 64 connected to the operation portion main body 77 on the proximal end thereof. A forceps stopper 69 is provided on the proximal side of the mouth ring 64. Moreover, the tubes 58 and 60 communicate with holes 65 and 66 formed to the operation portion main body 77 on the proximal sides thereof, respectively.

The suture machine 3 according to this embodiment is fixed to an insertion portion 7 of the endoscope 12 at several positions by other fixing members 70 as shown in FIG. 2 as well as the above-described fixing member 40 (see FIG. 8). By detachably forming these fixing members 70, the suture machine 3 can be detachable with respect to the insertion portion 7 of the endoscope 12. Of course, the suture machine 3 and the insertion portion 7 may be integrally formed so as not to be removed.

Figure 14:
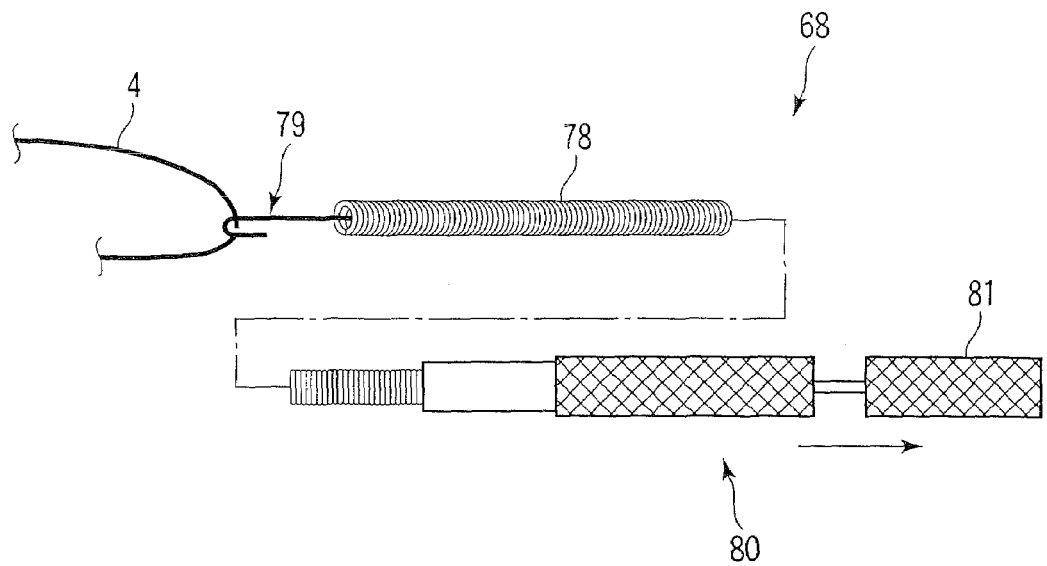
FIG. 14 is a view showing the state that a suture thread is caught by a hook of a thread holder.
Figure 15:
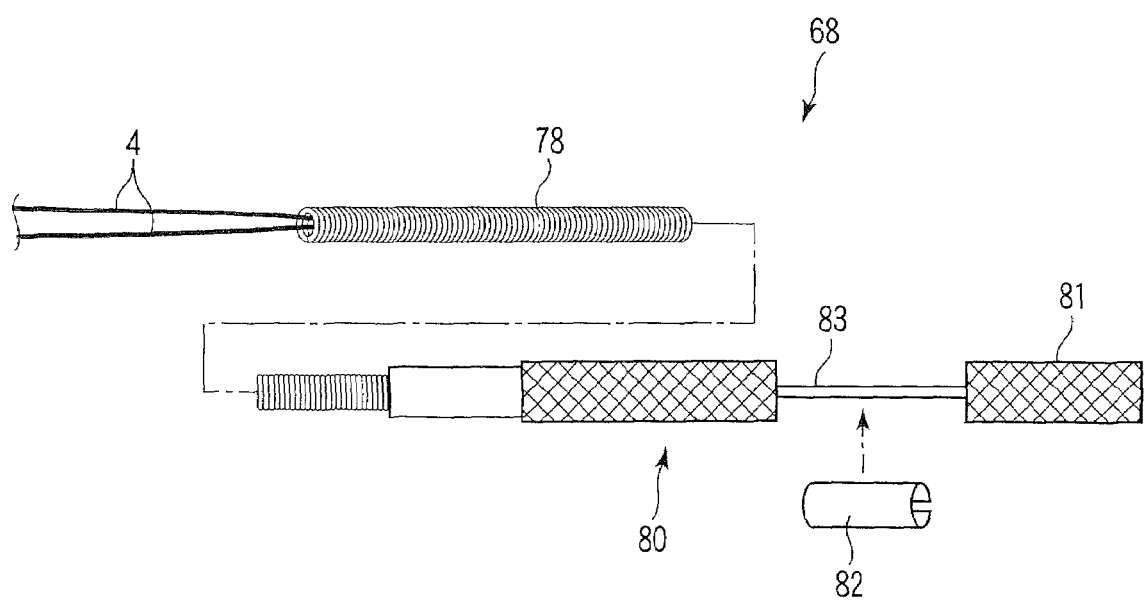
FIG. 15 is a view showing the state that the suture thread is drawn into a sheath by the hook of the thread holder.

As shown in FIGS. 2, 14 and 15, a thread gripper 68 for gripping the suture thread 4 includes a hook 79 which can move forward/backward in a flexible tubular member 78 formed by a coil or the like, and a thread gripper operation portion 80 which is used for operating the hook 79. The hook 79 is accommodated in or caused to protrude from the flexible tubular member 78 by moving forward/backward a grip 81 which is movably arranged to the thread gripper operation portion 80 through, e.g., a pipe 83. The suture thread 4 can slide on the hook 79 when being caught by the hook 79. In addition, the hook 79 can be locked so as not to protrude from the flexible tubular member 78 by fitting a stopper 82 which avoids forward movement of the grip 81 into, e.g., the pipe 83. Such a thread gripper 68 is formed to have an outside diameter with which it can pass through the channel 35.

Figure 16:
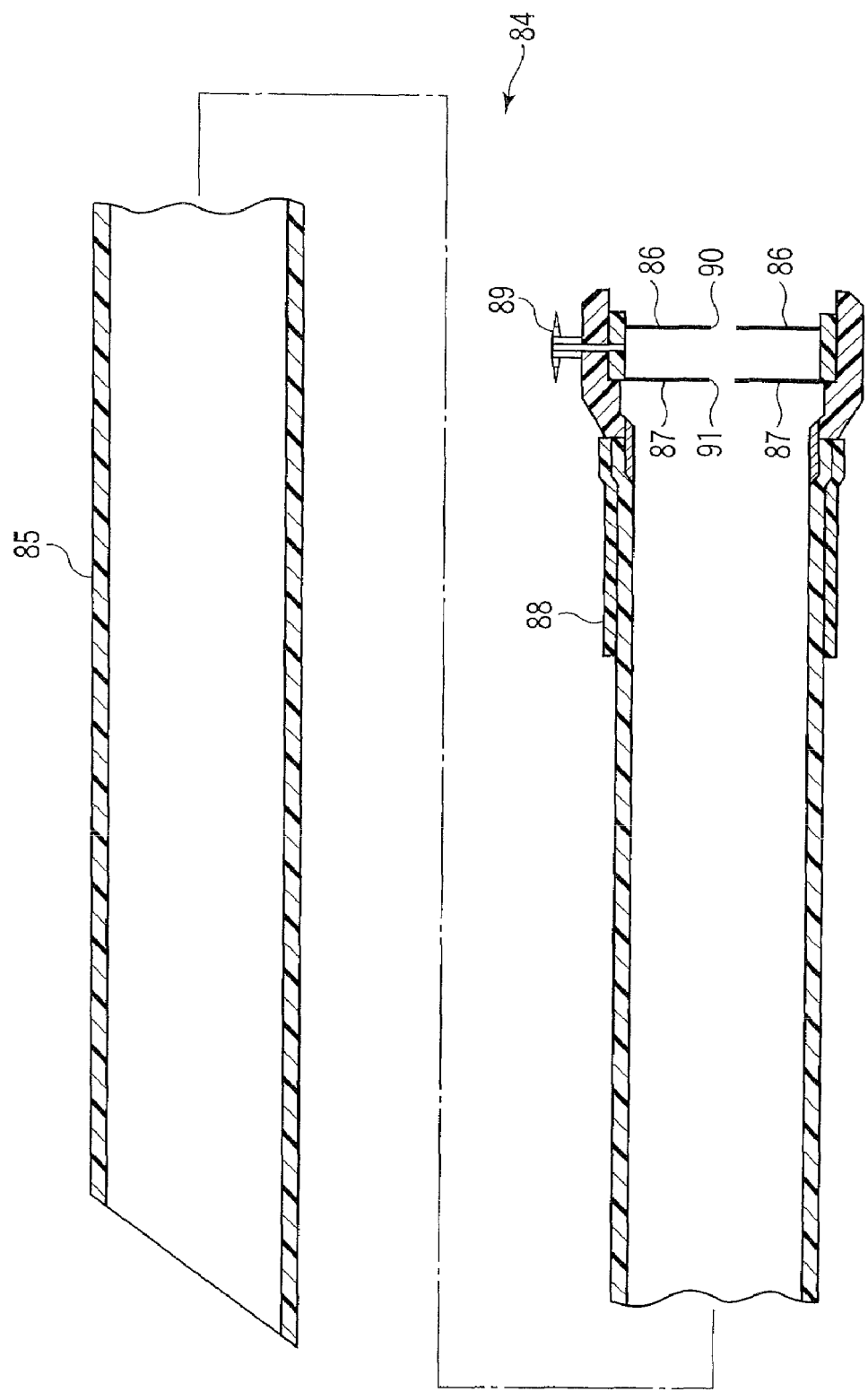
FIG. 16 is a schematic vertical cross-sectional view of an over-tube.

FIG. 16 shows an over-tube 84 which is an insertion auxiliary instrument used for inserting the insertion portion 7 including the suture machine 3 into a body.

The over-tube 84 according to this embodiment includes an over-tube sheath or a flexible tubular member 85 processed into a shape that the end can be readily inserted into a body cavity, e.g., a tapered shape, two valves 86 and 87 respectively having circular holes 90 and 91 arranged on the proximal side of the flexible tubular member 85, and a mouth ring 89 which communicates with an axial hole of the flexible tubular member 85. This mouth ring 89 can be used for connecting a non-illustrated suction unit through, e.g., a tube when a suction function or the like is required. It is desirable to seal this mouth ring 89 with a non-illustrated cover when it is not used.

This flexible tubular member 85 has a hollow structure whose cross section is, e.g., circular, formed of a polymeric resin material such as polytetrafluoro-ethylene (PTFE), ePTFE, polyurethane, styrene-based elastomer, olefin-based elastomer or silicone, and has at least one lumen into which the endoscope 1 is inserted. Its length is 300 to 500 mm which is such an extent that the flexible tubular member can be inserted from a natural opening of a human body and reach a target part in the body, and 1000 to 2000 mm is preferable in particular. Its outside diameter is 3 to 30 mm which is such an extent that the flexible tubular member can be inserted from a natural opening of a human body, and 3 to 25 mm is preferable in particular. Its inside diameter is 3 to 30 mm which is such an extent that the endoscope 1 can be inserted, and 3 to 25 mm is particularly preferable.

A proximal portion of the over-tube 84 is formed of a hard pipe-like member, and fixed to the distal end portion of the flexible tubular member 85 by preferable means such as press-fitting, adhesion, ultrasonic fusion, thermal fusion, a solvent adhesive agent or screw cramp. In order to efficiently carry out the suction operation or air supply operation through the endoscope 12, two valves 86 and 87 arranged at the proximal portion of the over-tube 84 can maintain air-tightness in the body with respect to the outside of the body.

A suction port 89 is a tubular member to which a non-illustrated suction tube connected to, e.g., a non-illustrated suction machine can be connected thereto, or a non-illustrated cap can be attached thereto in order to maintain air-tightness in the body.

Figure 19:
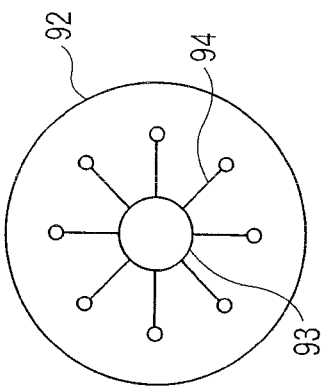
FIG. 19 is a view showing a modification of a valve attached to the over-tube.

As shown in FIG. 19, it is possible to provide a plurality of slits 94 around a hole 93 in place of the above-described valves 86 and 87 and use a valve 92 which allows passage of a member having a larger diameter than the hole 93.

In addition, an over-tube 95 shown in FIGS. 20 and 21 may be used in place of the over-tube 84. This over-tube 95 includes a flexible tubular member 96, a soft hood member 97 arranged on the proximal side of the flexible tubular member 96, and a fixing member 98 which fixes the hood member to the insertion portion 7 including the suture machine 3 in the substantially sealed state. This over-tube 95 is beneficial for maintaining the air-tightness in the body cavity. When the endoscope is pushed out in a direction indicated by an arrow in FIG. 21 after inserting the over-tube 95 into the body cavity, the suture machine 3 fixed to the endoscope can be caused to protrude from the flexible tubular member 96.

Figure 53:
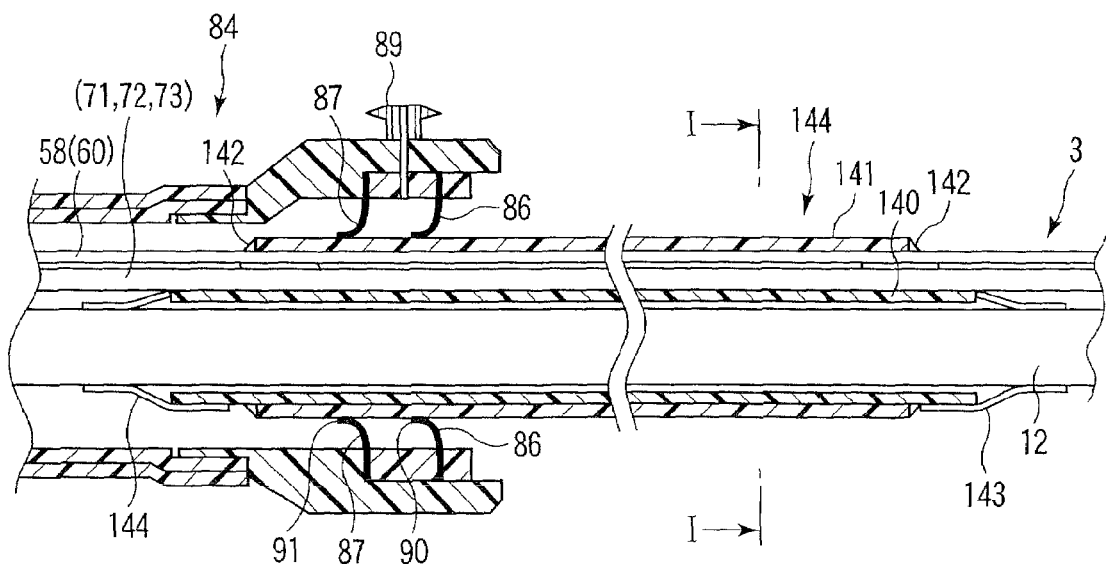
FIG. 53 is a cross-sectional view showing the state that sealing means is incorporated to the proximal side of an auxiliary insertion instrument depicted in FIG. 16.
Figure 54:
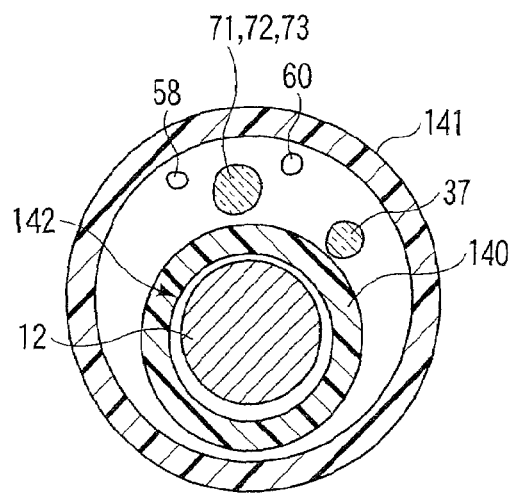
FIG. 54 is a cross-sectional view taken along the line I-I in FIG. 53.

Additionally, as shown in FIGS. 53 and 54, sealing means 144 may be provided on the proximal side of the suture machine 3 and the endoscope 12.

This sealing mean 144 includes an inner tube having an inside diameter which enables passage of the endoscope 12, and an outer tube 141 which has a larger inside diameter than the inner tube 140 and into which the inner tube is inserted. An outside diameter of the outer tube 141 is slightly larger than the inside diameters of the holes 90 and 91 of the valves 86 and 87. Tubes 37, 58, 60, 73 or the like are passed through the space formed between the inner tube 140 and the outer tube 141 A sealing member 142 is filled in the space between these tubes. The space between the both ends of the inner tube 140 and the endoscope 12 are sealed by a tape 143. As a result, the space between the over-tube 84, the suture machine and the endoscope 12 is assuredly sealed and air is prevented from leaking when air is supplied to the body cavity and the body cavity is expanded.

The procedures of gastrojejunostomy by using the above-described anastomosis system will now be described mainly with reference to FIGS. 22 to 40.

Figure 17:
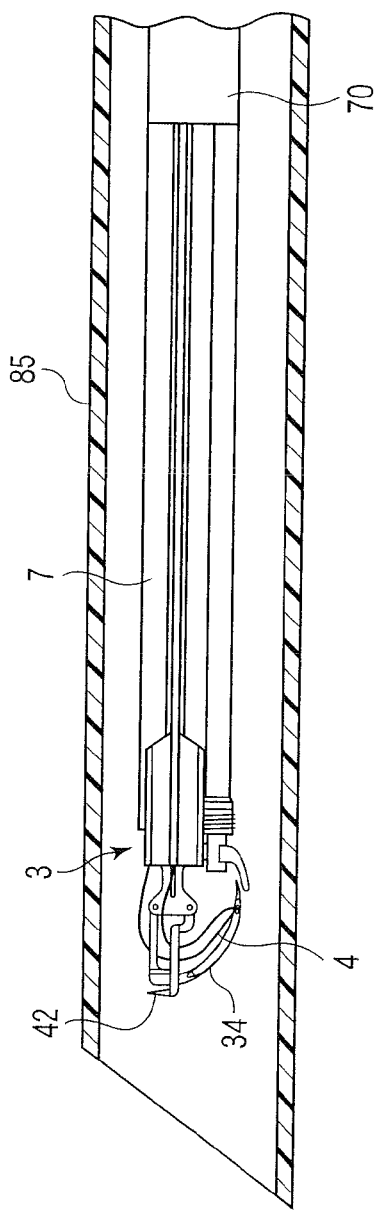
FIG. 17 is an explanatory view showing the state that the endoscope having the suture machine attached thereto is accommodated in the over-tube.

(1) It is preferable to insert the endoscope 12 into the over-tube 84 shown in FIG. 16 together with the suture machine 3 assembled in the state depicted in FIG. 2 and arrange in the state illustrated in FIG. 17. At this moment, the suture thread 4 is inserted into a needle hole 34*a* of the curved needle 34, and the respective end portions are maintained in the state that they are pulled to the outside of the suture machine 3 from the holes 65 and 66 of the operation portion main body 77 through the thread guides 55 and 56. Further, the endoscope 12 is connected to the image processing device 14 and the light source device 15 or the like (FIG. 1) through the universal cord. Thereafter, the inside of the body cavity is observed by the monitor 13, whilst the over-tube 84 having the suture machine 3 and the endoscope 12 accommodated there is inserted into the stomach S through the mouth of the human body.

Figure 22:
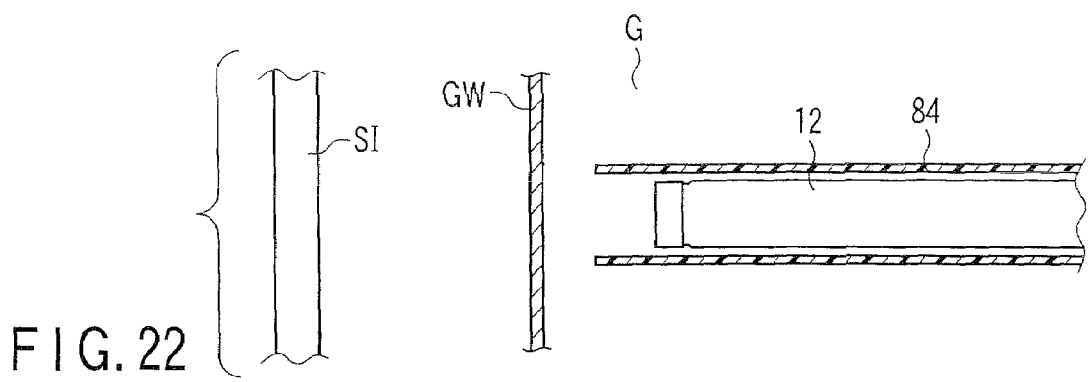

(2) As shown in FIG. 22, the over-tube 84, i.e., the flexible tubular member 85 is moved toward a necessary part in the stomach.

Figure 23:
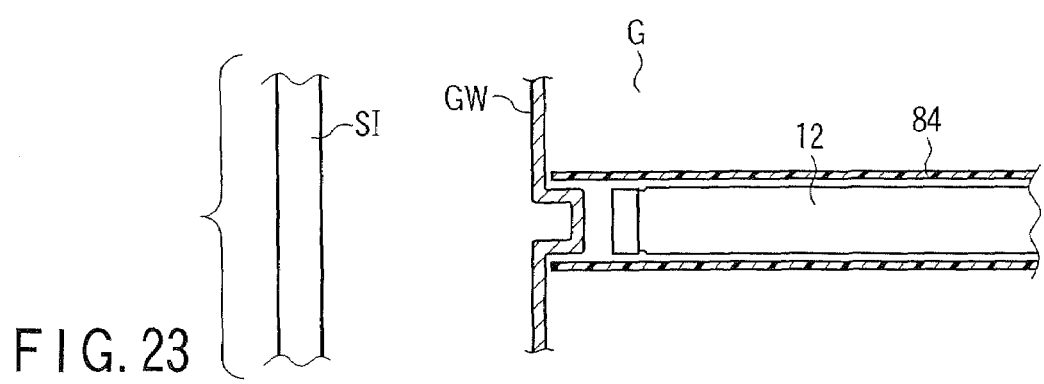

(3) As shown in FIG. 23, after further moving the over-tube 85 forward and bring the distal end portion into contact with the gastric wall GW, the gastric wall GW is sucked by using a non-illustrated suction unit through the mouth ring 89 of the over-tube 84 or the suction function of the endoscope 12. The gastric wall GW is sucked into the flexible tubular member 85 of the over-tube 84 and forms a recession. When sucking the gastric wall, a path having a larger cross-sectional area than that of the channel of the endoscope 12 is formed by connecting a non-illustrated suction tube to the mouth ring 89 even though the endoscope 12 is inserted. Therefore, the suction operation can be carried out through a path or the inner hole in the over-tube 84 having less duct resistance, thereby forming a larger recession in a short time.

Figure 24:
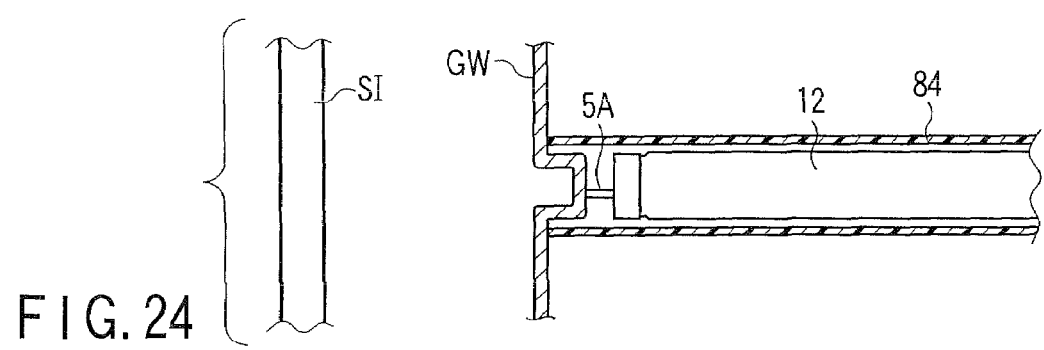

(4) As shown in FIG. 24, a needle-shaped knife 5A is inserted from the forceps opening channel 6 of the endoscope 12 (see FIGS. 2 and 8) and caused to protrude from the distal end portion of the endoscope 12. This needle-shaped knife 5A is brought into contact with the gastric wall GW having the recession formed thereto, and a high-frequency current is supplied from a non-illustrated high-frequency power supply in order to perforate the gastric wall GW. When the recessed portion of the gastric wall GW is held by the over-tube 84, the gastric wall is assuredly fixed by the over-tube 84 and distanced from any other internal organ such as the small intestine SI which is in contiguity with the gaster G. As a result, a necessary part of the gastric wall GW can be perforated without damaging any other internal organ which is in contiguity with the gastric wall GW. The needle-shaped knife 5A which perforates the gastric wall GW may have a regular structure.

Figure 25:
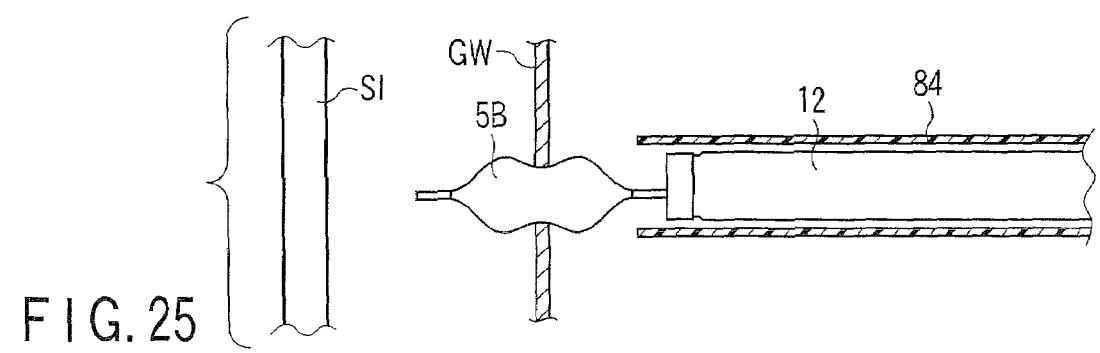

(5) After perforating the gastric wall GW, a balloon dilator 5B is inserted into the gaster G in place of the needle-shaped knife 5A. This balloon dilator 5B is inserted into the perforated portion of the gastric wall GW, and the perforated portion is expanded to the size that the distal end portion of the endoscope 12 can be inserted. FIG. 25 shows this state. The balloon dilator 5B which expands the perforated portion may have a regular structure, and it is preferable that the balloon dilator 5B has a peanut-like shape as shown in the drawing. After such a balloon dilator 5B is inserted until its central part pierces the gastric wall GW, it is expanded into the peanut-like shape shown in FIG. 25 by feeding a fluid from a non-illustrated inflation device. After the balloon dilator 5B is expanded to the size which enables insertion of the endoscope 12 into the perforated portion of the gastric wall GW, supply of the fluid is stopped.

Figure 26:
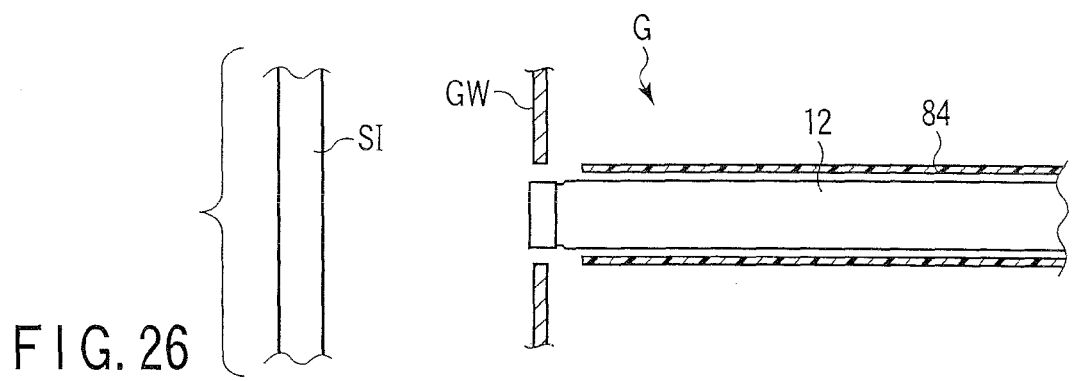

(6) As shown in FIG. 26, the distal end portion of the endoscope 12 is inserted into the expanded perforated portion. Furthermore, the distal end portion of this endoscope 12 is inserted to the outside of the gastric wall GW, i.e., the abdominal cavity, and the distal end portion of the endoscope 12 is caused to be opposed to a part of the small intestine to be anastomosed.

Figure 27:
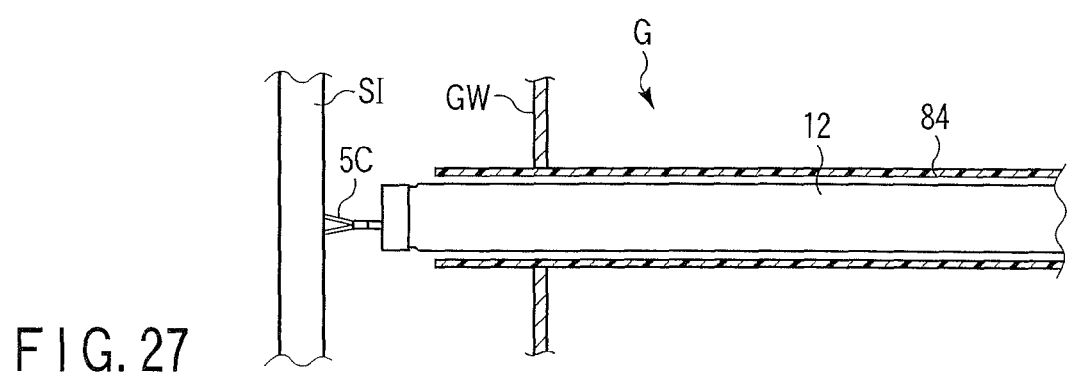

(7) Then, as shown in FIG. 27, a grasping forceps 5C is inserted into the abdominal cavity through the forceps opening channel 6 of the endoscope 12, for example. The small intestine SI is held by the grasping forceps 5C and brought to the gastric wall GW side. At this moment, it is preferable to pull a part of the small intestine SI from the perforated portion of the gastric wall to the inside of the gaster G and enter the state shown in FIG. 28.

Figure 28:
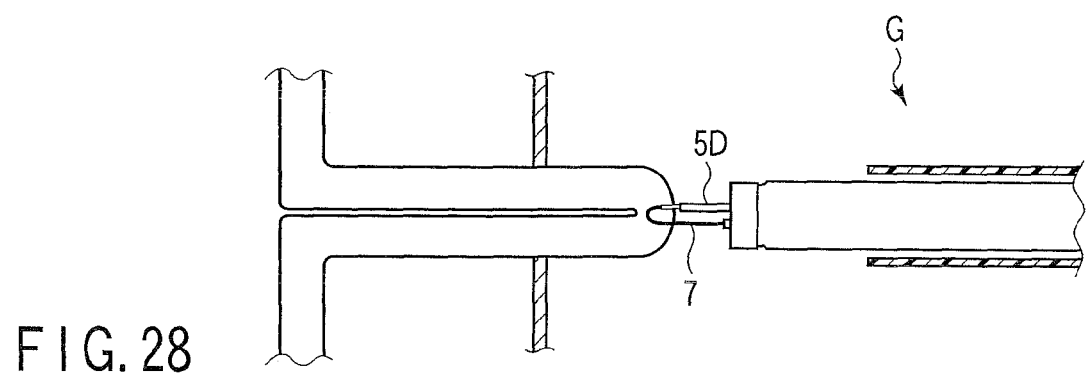

(8) As shown in FIG. 28, a needle 5D is pushed through the small intestine SI pulled to the inside of the gaster G, and the thread 7 is inserted into the small intestine. This thread 7 suspends the small intestine and prevents the small intestine from protruding to the outside from the gastric wall GW. The both end portions of the thread 7 can be extended to the outside of the body and fixed to a part outside the body.

Figure 29:
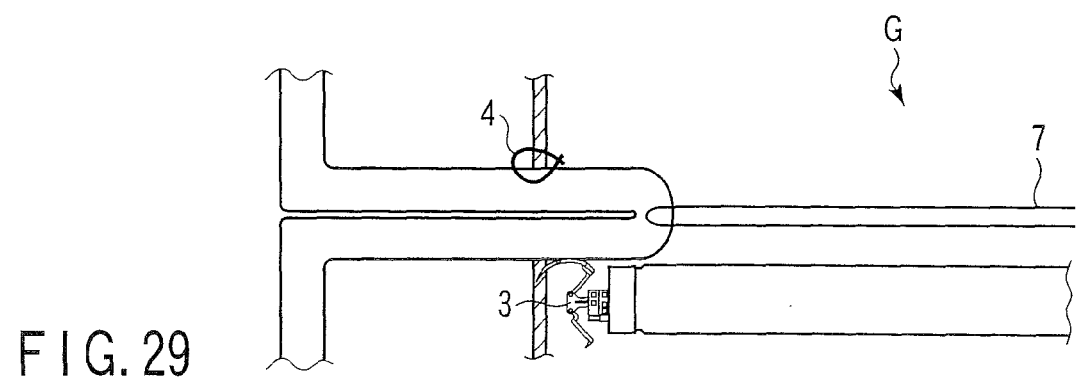

(9) As shown in FIG. 29, the circumferential portion of the small intestine SI suspended by the thread 7 is stitched to the inner peripheral part of the perforated portion of the gastric wall GW. This suture can be carried out by using the above-described curved needle suture machine 3. The suture procedures using the suture machine 3 will be described later. It is to be noted that the above-described procedures (1) to (8) can be carried out by using a regular endoscope to which the suture machine 3 is not fixed without using the endoscope 12 having the suture machine 3 fixed thereto. In this case, the suture can be carried out by inserting the endoscope 12 having the suture machine 3 fixed thereto as shown in FIG. 2 from the mouth only in the procedure which requires the suture machine 3.

(10) Then, as shown in FIG. 30, the needle-shaped knife 5A is inserted into the gaster G, and a necessary part of the small intestine SI pulled to the inside of the gaster G is dissected. Incidentally, although it is preferable to remove the suspension thread 7 after dissecting the small intestine by using the needle-shaped knife 5A, it may be removed before dissecting. That is because the small intestine SI is sutured along the inner circumferential part of the perforated portion of the gastric wall GW.

(11) Subsequently, as shown in FIG. 31, the curved needle suture machine 3 is used to suture the gastric wall GW so as to open the small intestine mucous membrane from the cut part formed by the needle-shaped knife 5A.

(12) By removing the suture machine 3 which has finished suture from the gaster G together with the endoscope 12, the gastrojejunostomy is terminated. FIG. 32 shows this state.

By performing the gastrojejunostomy by using the endoscope 12 which is orally inserted into the gaster G in this manner, the burden on a patient can be greatly reduced without a need to dissect a body surface of a living body.

The suture operation using the curved needle suture machine 3 in the above procedures (9) and (11) will now be described in detail.

Figure 18:
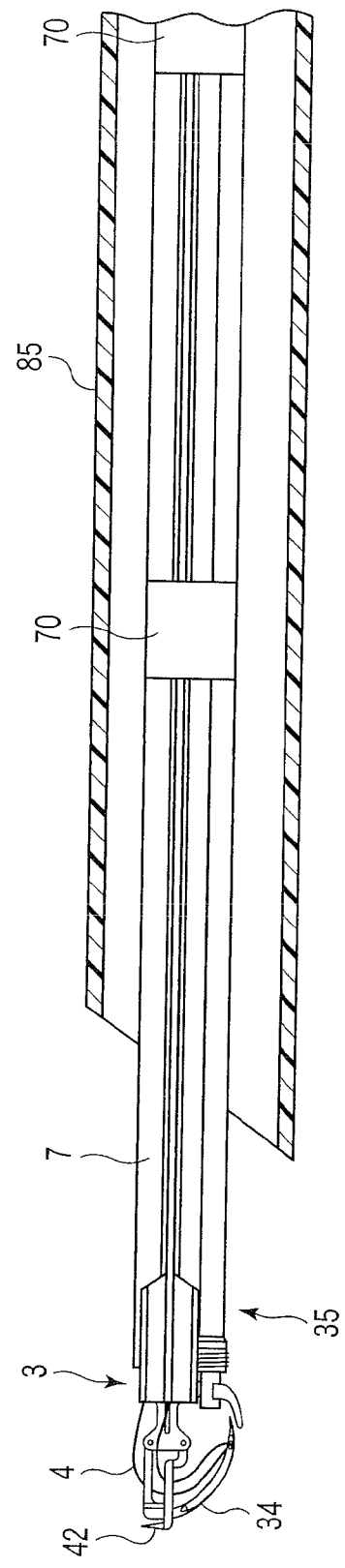
FIG. 18 is an explanatory view showing the state that the endoscope having the suture machine attached thereto is caused to protrude from the over-tube.

(a) Before the suture operation, as shown in FIG. 18, the suture machine 3 is caused to protrude from the flexible tubular member 85 of the over-tube by moving forward the endoscope.

(b) The suture machine 3 is moved close to a suture part, the movable member 75 shown in FIG. 2 is pushed, and the first and second operation members 16 and 17 are opened as illustrated in FIG. 4. The subsequent suture procedures are illustrated in FIGS. 33 to 40.

Figure 33:
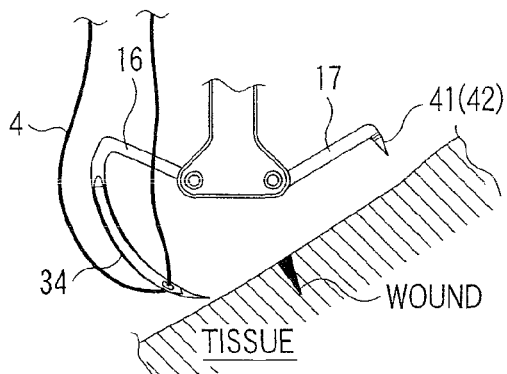
FIGS. 33 to 38 show the suture procedures using the suture machine.
Figure 34:
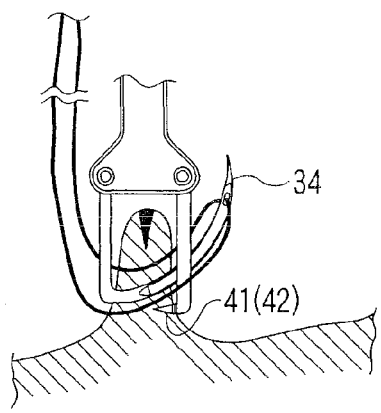

(c) As shown in FIG. 33, the movable member 75 is operated while pressing the curved needle 34 and the fixed needles 41 and 42 against the suture part, and the first and second operation members 16 and 17 are closed as shown in FIG. 34.

Figure 35:
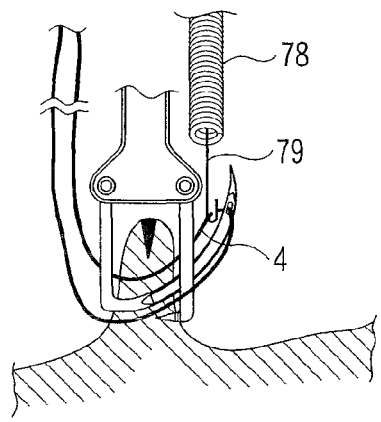
Figure 36:
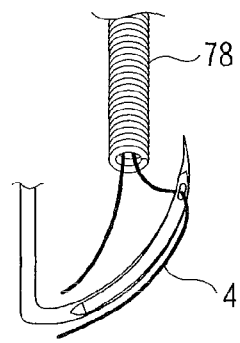

(d) As shown in FIG. 35, the suture thread 4 which has come out of a tissue is caught by the hook 79 of the thread gripper 68 inserted through the forceps stopper 69, and pulled into the flexible tubular member 78 together with the hook 79 as shown in FIG. 36.

Figure 37:
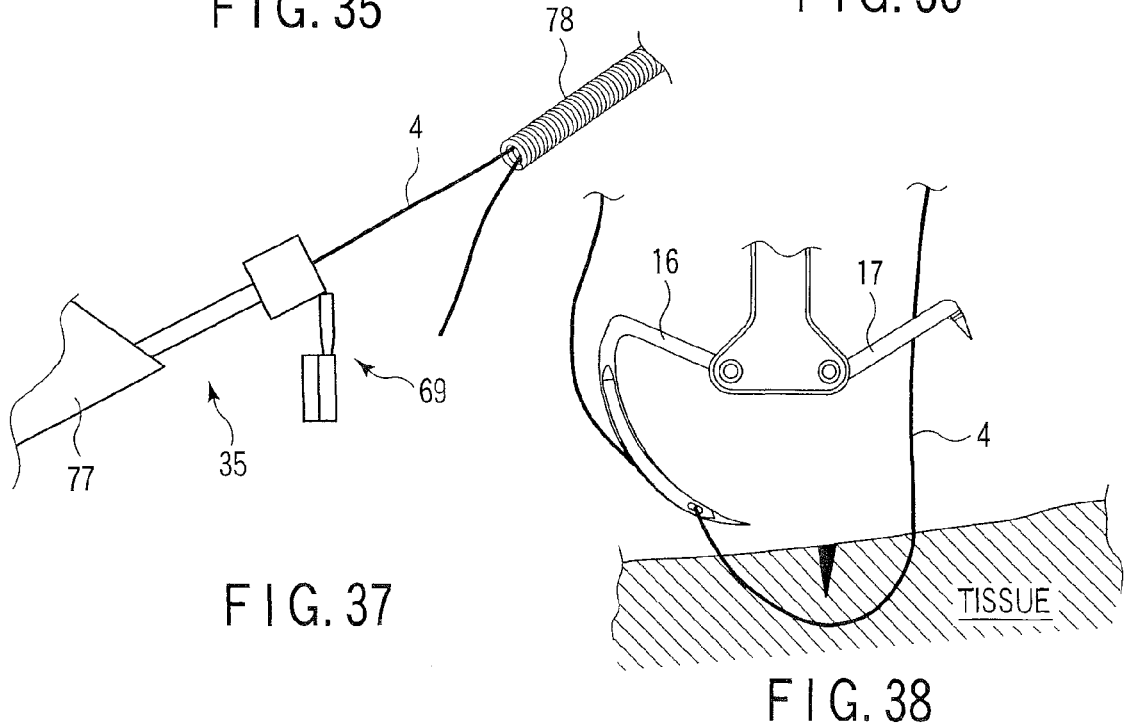

(e) As shown in FIG. 37, the thread gripper 68 is pulled to the outside of the body from the channel 35, and the suture thread 4 is pulled from the forceps stopper 69. At this moment, the suture thread 4 slides on the hook 79, and one end of the suture thread 4 is consequently moved into the channel 35 from one of the thread guides 55 and 56 and pulled to the outside of the body from the channel 35 together with the thread gripper 68. The other end of the suture thread 4 is held being inserted in the other one of the thread guides 55 and 56.

Figure 38:
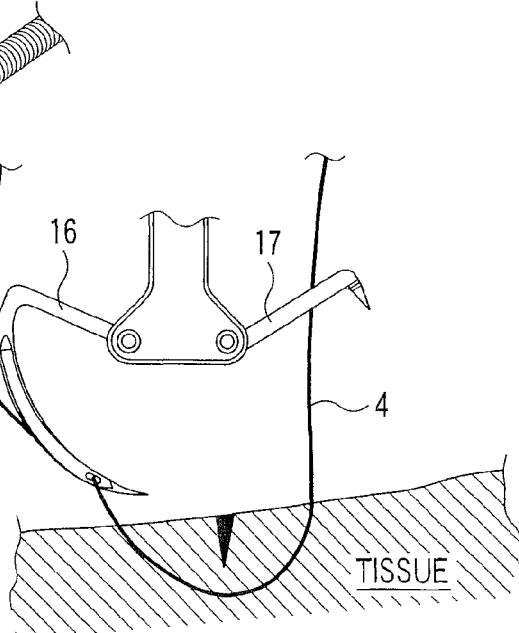

(f) As shown in FIG. 38, the first and second operation members 16 and 17 are opened by operating the movable member 75, and the curved needle 34 and the fixed needles 41 and 42 are removed from the suture part.

Figure 39:
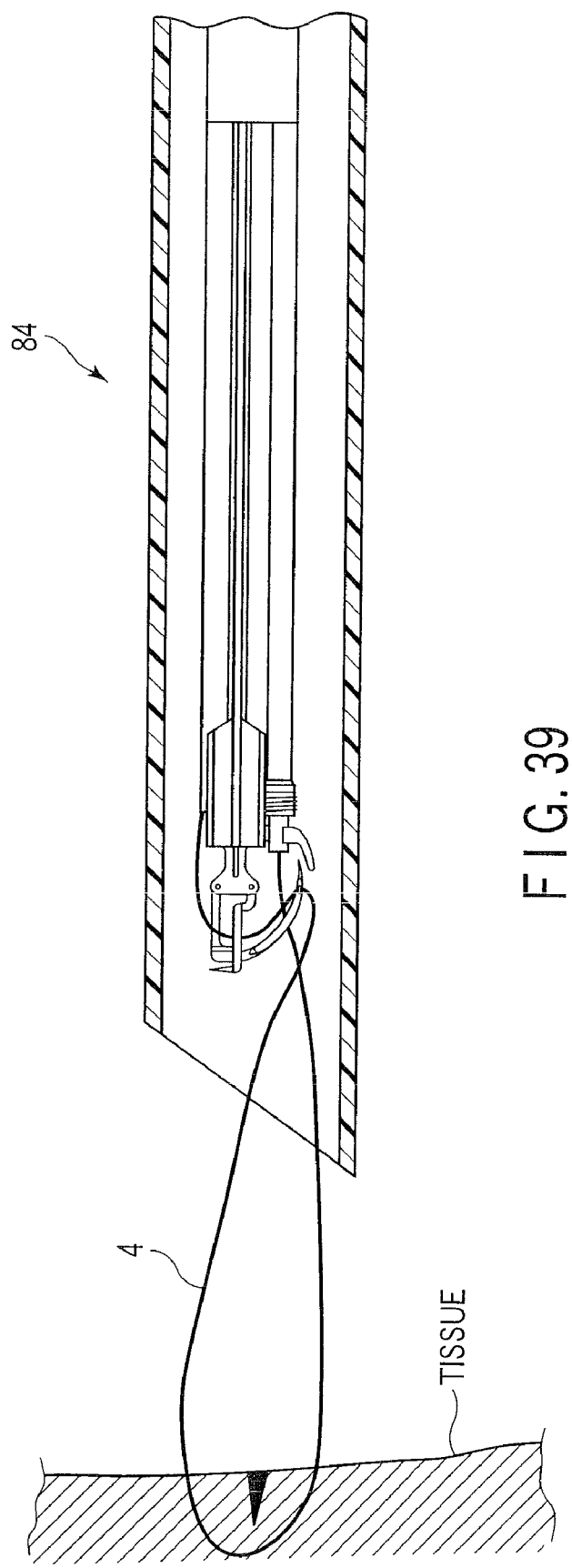
FIG. 39 is a view showing the state that the suture machine is removed to the outside of the body cavity together with the over-tube.

(g) As shown in FIG. 39, the suture machine 3 is again pulled into the flexible tubular member 85, and the suture machine 3 is removed from the body cavity together with the flexible tubular member 85.

Figure 40:
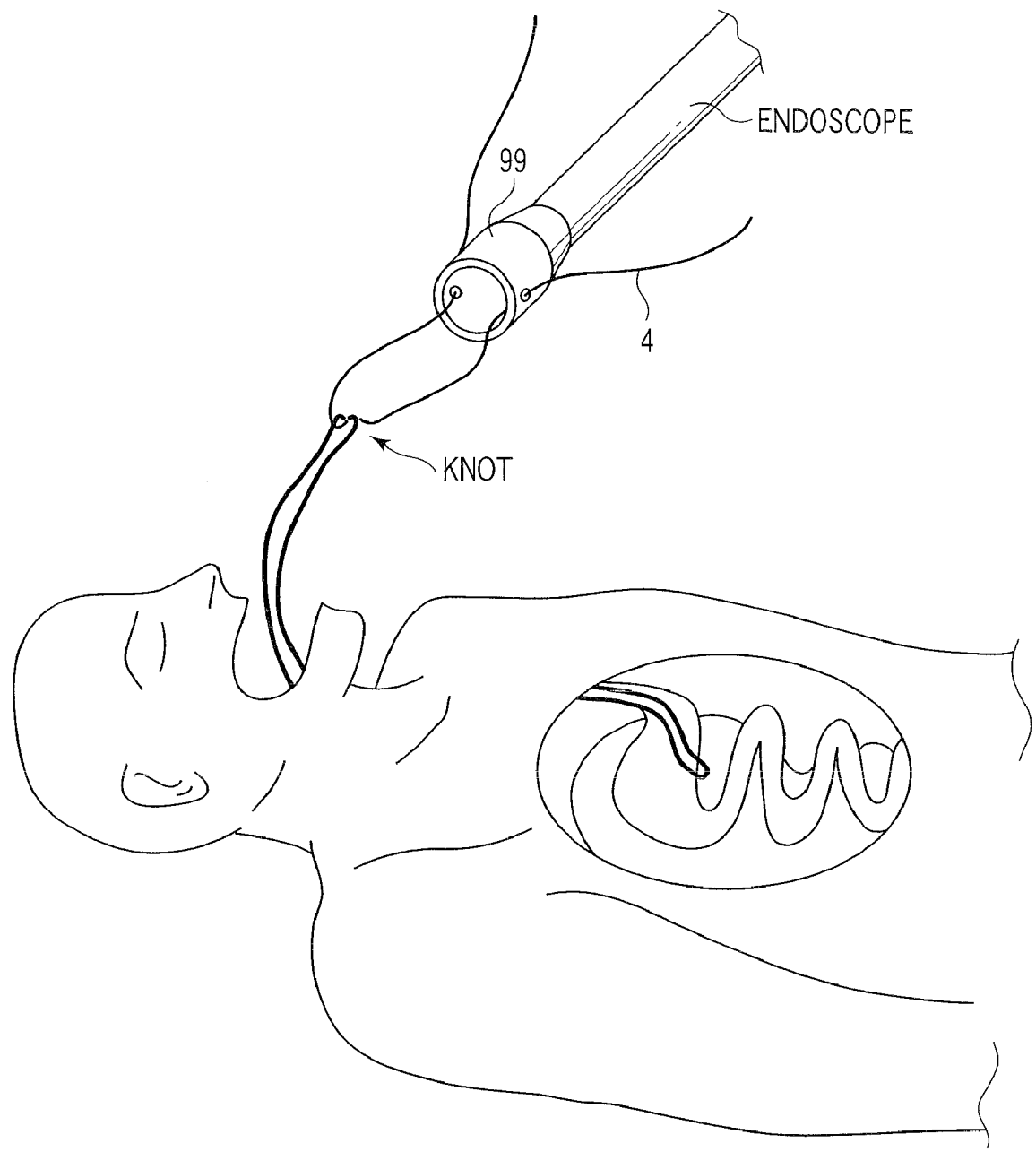
FIG. 40 is a view showing the state that a knot is fed into the body by using a knot pusher.

(h) A knot is formed to the suture thread 4 outside the body, and this knot is fed into the body cavity in several installments by using such a knot pusher 99 as shown in FIG. 40. The knot pusher 99 shown in FIG. 40 has a hood-like cylindrical member attached to the distal end portion of the endoscope, and holes are formed on the side surface of this cylindrical member at two positions. Of course, the knot pusher 99 is not restricted to the illustrated one, and a knot pusher having any structure or shape can be used as long as it can feed the knot into the body. Moreover, the knot itself such as a Grinch knot or Lauders knot may be movably formed. In this case, the knot can be fed into the body by using appropriate means.

(i) At last, the endoscope to which the suture machine 3 is not attached is inserted, and the remaining part of the suture thread 4 is cut by using the scissor forceps or the like.

According to the anastomosis system 1 of this embodiment, since the first and second operation members 16 and 17 which hold the curved needle 34 and the fixed needles 41 and 42 are integrally formed to the first and second arm members 24 and 25 which can pass between the pins 28 and 29, a large opening/closing angle can be formed between the first and second operation members 16 and 17. As a result, even if the size is small for the endoscope, it is possible to form the suture machine having one or more needles which can move over a sufficiently large angle which is required in the suture technique.

In addition, since expansion and contraction of the coils 72 and 76 connected to the holding member 18 which rotatably supports the first and second operation portions 16 and 17 are restricted by the flexible tube 73, large force can be transmitted through the coils 76 and 72. As a result, the large force required in the suture technique can be transmitted to the needles 34, 41 and 42 through the coils 76 and 72 and the first and second operation members 16 and 17.

Additionally, since the suture machine 3 is fixed to the insertion portion of the endoscope 12, it is possible to readily carry out the suture operation using the flexible endoscope which is very difficult in the prior art.

Since there is no need to perform a surgical operation, the very minimally invasive suture treatment can be conducted with respect to a patient. Further, this system can be also used to anastomosis of an intraluminal organ other than gastrojejunostomy.

It is to be noted that the above suture can be carried out by using various kinds of anastomosis systems. Eight preferable modifications of the anastomosis system will now be described hereinafter.

[First Modification]

FIGS. 41 to 46 illustrate the anastomosis system according to a first modification. Incidentally, since various kinds of modifications described below are basically similar to the above-described embodiment, like reference numerals denote like parts, thereby omitting the detailed explanation thereof.

Figure 42:
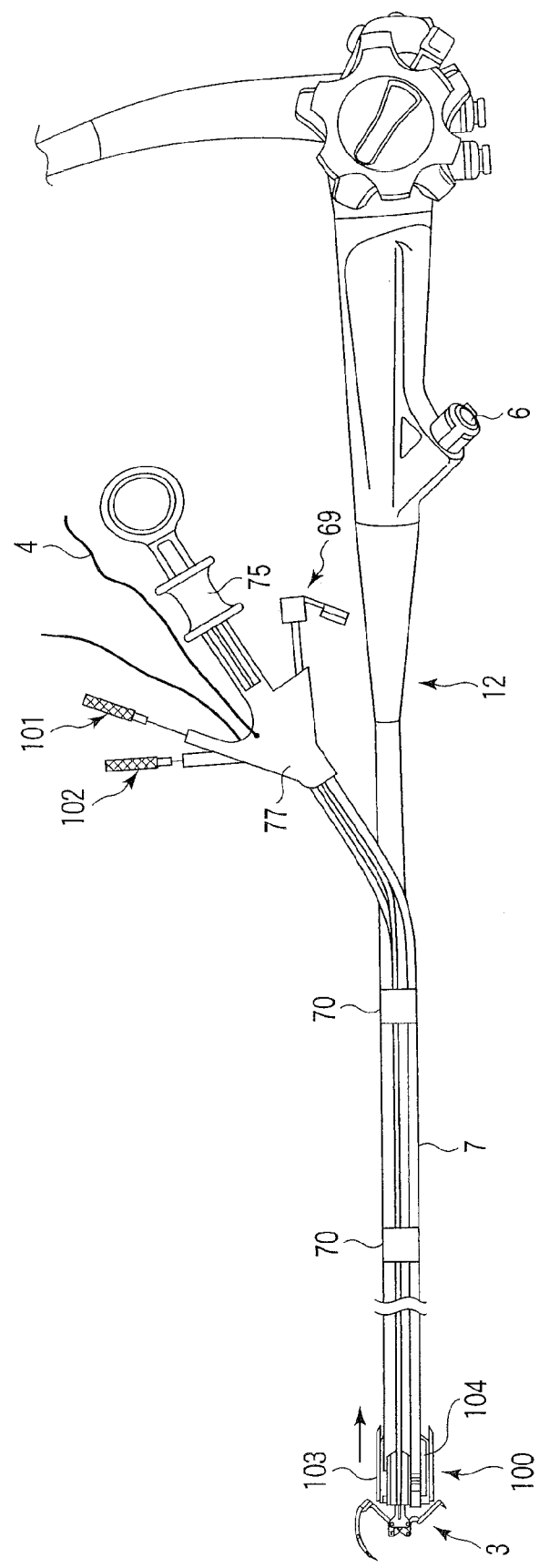
FIG. 42 is an explanatory view showing the state that the suture machine in the endoscopic anastomosis system is caused to protrude.

As shown in FIGS. 41 and 42, the system according to this modification is attached to the distal end portion of the insertion portion 7 of the endoscope 12 and includes a protection member 100 which covers the distal end portion of the suture machine 3. This protection member 100 includes, e.g., a cylindrical fixed portion 104 which can be detachably fixed to the distal end of the insertion portion 7 and a movable portion 103 which is slidably attached on the outer periphery of the fixed portion 104.

Figure 45:
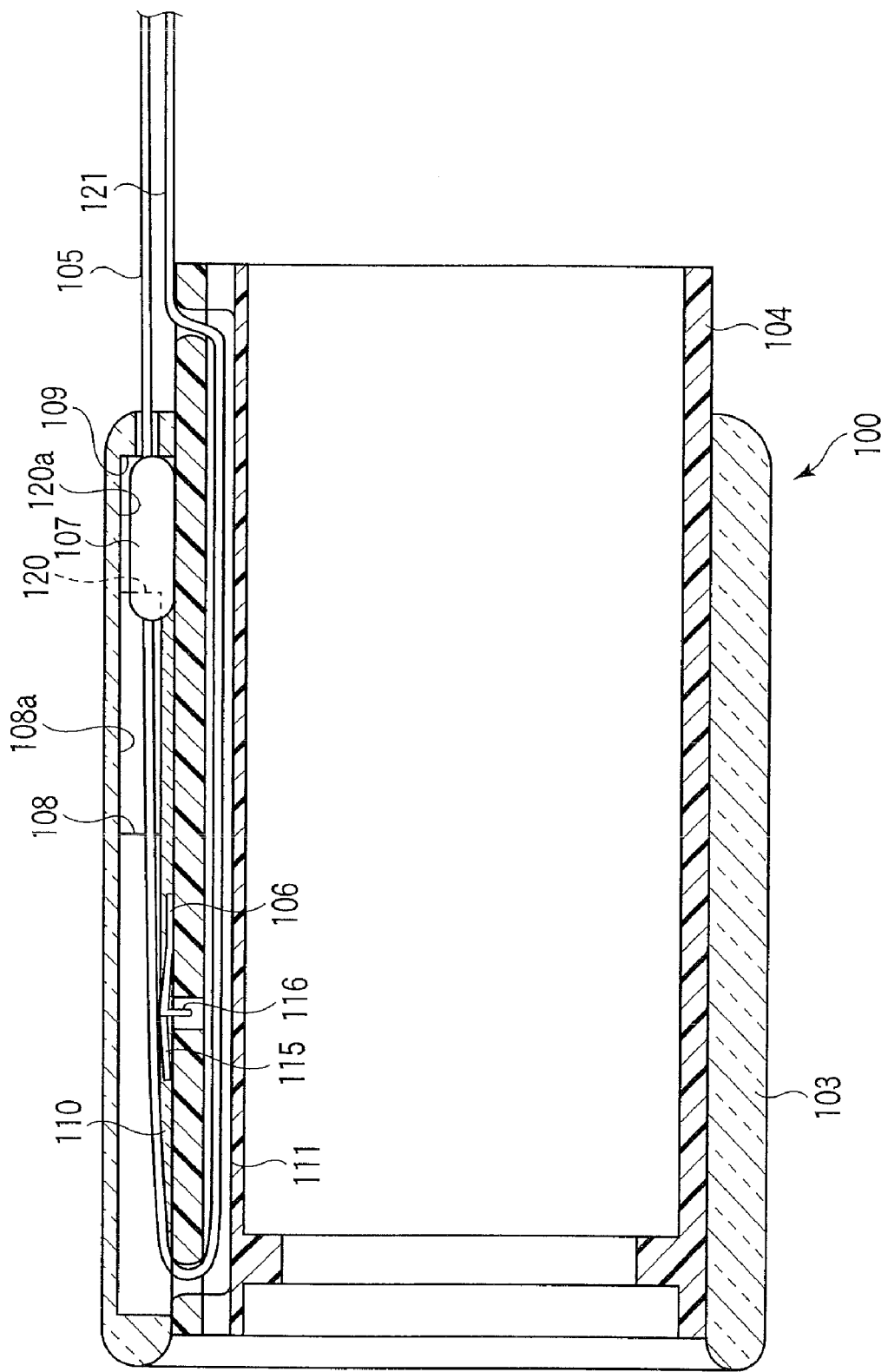

As shown in FIGS. 43 to 45, to the wall part of the fixed portion 104 are formed an axial hole 111 and radial holes 113 and 114 which cause the axial hole to communicate with the outer peripheral surface in the vicinity of each end portion. Furthermore, to the outer peripheral part of the fixed portion 104 is fixed a lock member 106 shown in FIG. 46 through non-illustrated screws or the like which are inserted through, e.g., attachment holes 118 and 119. This lock member 106 includes engagement portions 116 and 117 which are arranged being substantially in an upright stance with respect to the outer peripheral surface of the fixed portion when fixed to the fixed portion 104, and an inclined portion 115 which is gradually declined toward the end from the space between the engagement portions. The entire lock member 106 is formed of an elastic material such as metal. An opening portion 112 is formed on the outer peripheral surface of the fixed portion 104 at a position corresponding to the engagement portions 116 and 117. As a result, when pressed toward the outer peripheral surface of the fixed portion 104, the engagement portions 116 and 117 are accommodated in the opening 112, and the entire lock member 106 becomes flat.

On the other hand, the movable portion 103 has a concave portion 120a whose distal end side is defined by an engagement wall 120 capable of engaging with engagement portions 116 and 117 of the lock member 106, and a concave portion 108a whose distal end side is defined by an engagement wall 108. Rear end sides of these concave portions 108 and 120a are defined by an engagement wall 109. Further, in the concave portion 108a are accommodated an inclination portion 115 of the lock member 106 and a moving member 107 which controls engagement/release between the lock member 106 and the engagement wall 120.

The moving member 107 according to this modification is formed into a substantially cylindrical shape or flat shape by using, e.g., a hard material, and its length is greater than the axial dimension of the concave portion 120a. Also, it is preferable to form a length which enables the moving member 107 to be accommodated in the concave portion 108a without pushing the inclination portion 115 when the engagement portions 116 and 117 and the engagement wall 120 engage with each other. Transmission members 105 and 121 are extended from the end portions of the moving member 107, respectively. The transmission member 105 is extended from the concave portion 120a through a thin hole which pierces the engagement wall 109, and the transmission member 121 is extended to the inner peripheral side of the movement portion 103 from a slit 110 which communicates with the concave portion 108a and further extended to the outer peripheral portion of the fixed portion through a radial hole 113, an axial hole 111 and a radial hole 114 of the fixed portion 104. These transmission members 105 and 121 extend to the operation portion main body 77 shown in FIGS. 41 and 42 through a non-illustrated appropriate flexible tube and coupled with protection member operation portions 101 and 102.

As shown in FIG. 43, this protection member 100 restricts movement of the movable portion 103 in the right-hand direction of the drawing when the engagement wall 120 formed on the movable portion 103 is brought into contact with the engagement portions 116 and 117 of the lock member 106 fixed to the fixed portion 104. As a result, as shown in FIG. 41, the needle fixed at the distal end portion of the suture machine is covered with the movable portion 103 and hence not exposed to the outside.

When the protection member operation portion 101 connected to the transmission member 105 is pulled in this state, the moving member 107 moves in the right-hand direction as shown in FIG. 44. At this moment, since the moving member 107 runs on the inclination portion 115 of the lock member 106, the engagement portions 116 and 117 are accommodated in the opening 112, thereby releasing engagement with the engagement wall 120. The movable portion 103 can move to the read end side, namely, in the right-hand direction of the drawing. Moreover, when the protection member operation portion 101 is pulled, the moving member 107 is brought into contact with the engagement wall 109 as shown in FIG. 45, the movable portion 103 moves in the right direction together with the moving member 107 and enters the state shown in FIG. 42. At this moment, the lock member 106 is in contact with the inner peripheral surface on the both sides of the slit 110 formed to the movable portion 103. On the contrary, when the protection member operation portion 102 connected to the proximal side of the transmission member 121 is pulled, the moving member 107 moves to the left side and engages with the engagement wall 108, and the movable portion 103 moves to the left side together with the moving member 107. When the engagement wall 120 moves beyond the opening 112, the lock member 106 returns to the state shown in FIG. 43 by its elasticity. Again, the engagement portions 116 and 117 protrude from the outer peripheral surface of the fixed portion 104, and movement of the movable portion 103 in the right side direction can be restricted.

The suture procedures by the anastomosis system according to the first modification will now be described.

(a) After attaching the above-described protection member 100 to the suture machine and the endoscope assembled as described above, the protection member operation portion 102 is pulled. As a result, the movement portion 103 is caused to protrude to the distal end side and enters the state shown in FIG. 41. In this state, the system is inserted into the body cavity while observing the inside of the body cavity through the endoscope 12.

(b) After inserting into the body cavity, the protection member operation portion 101 is pulled and movement portion 103 is moved back, thereby entering the state shown in FIG. 42. Consequently, the distal end portion of the suture machine 3 is exposed, and the suture operation can be carried out in accordance with the procedures similar to those according to the first embodiment.

(c) After completion of the suture, the protection member operation portion 102 is pulled, and the movement portion 103 is caused to protrude in the state shown in FIG. 41. In this state, the suture machine and the endoscope are removed from the body cavity.

In this modification, since the movement portion 103 of the protection member 100 moves in the axial direction, the outside diameter of the apparatus can be reduced in addition to the advantage of the first embodiment. In addition, the technique can be further simplified.

[Second Modification]

FIG. 47 shows a protection member 122 for use in the anastomosis system according to a second modification.

The protection member 122 according to this modification includes a fixed portion 124 fixed to the distal end portion of the insertion portion 7 and a movable portion 123 which can slide on the fixed portion 124, and an annular space 128 sealed from the outside is formed between the fixed portion and the movable portion. A mouth ring 125 communicating with the annular space 128 is attached to the outer peripheral portion of the movable portion 123, and a fluid 127 can be injected to or discharged from the annular space 128 through a tube 126 connected to the mouth ring 125. This fluid 127 may be a liquid or a gas.

In this modification, as to the protection member 122, when the preferable fluid 127 such as physiological saline is filled in a non-illustrated fluid injection device such as a syringe and this fluid is injected into the annular space 128, the movable portion 128 slides to the right-hand side of the drawing. On the contrary, when a vacuum is formed in the fluid injection device 129 and the fluid 127 is discharged from the annular space 128, the movable portion 123 can slide to the left side.

By using this protection member 122, the advantages similar to those of the foregoing embodiments can be obtained.

[Third Modification]

FIGS. 48 to 56 show the anastomosis system according to a third modification.

Figure 48:
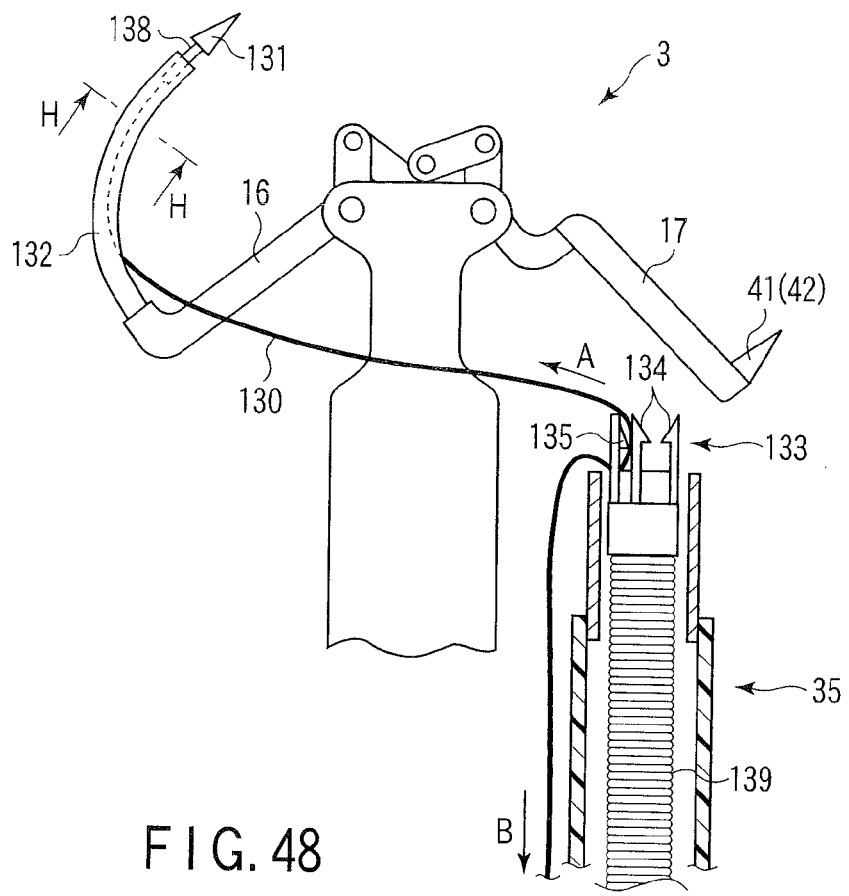
Figure 52:
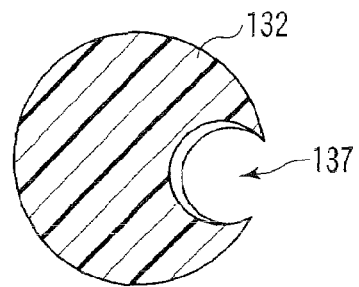

As shown in FIG. 48, in this modification, a needle holder 132 is fixed to the first operation member 16 of the suture machine 3, and a detachable needle 131 is detachably connected to the end of the needle holder 132. This detachable needle 131 has a shaft portion 138, and one end of the suture thread 130 is fixed to the end of the shaft portion 138. As shown in FIG. 52, this suture thread 130 has a groove 137 opened on the inner peripheral side of the needle holder 132 along substantially the entire length, and the suture thread 130 is detachably extended in the groove 137.

On the other hand, the other end of the suture thread 130 is extended to the vicinity of the proximal side of the endoscope through thread locking means 135 formed to a needle/thread fixture 133. This thread locking means 135 is formed so as to be capable of freely moving the suture thread 130 in the direction indicated by an arrow B, i.e., the direction to pull in the suture thread and so as not to move the suture thread in the direction indicated by an arrow A, namely, the direction to feed the suture thread.

Figure 49:
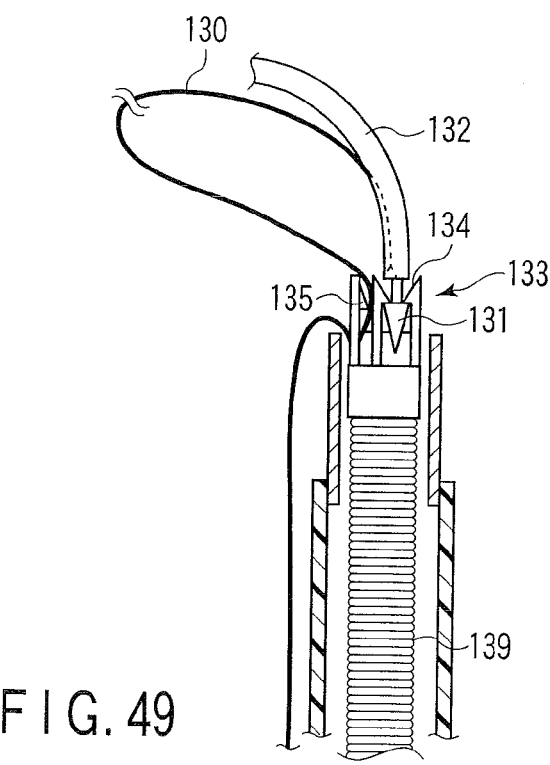

Furthermore, as shown in FIG. 49, needle locking means 134 capable of engaging the detachable needle 131 is also formed to the needle/thread fixture 133. It is preferable to form the needle locking means 134 by an elastic member or the like. In this modification, this needle fixture 133 is detachably attached to the distal end of a needle/thread fixture main body 139. This needle/thread fixture main body 139 can be inserted into the body cavity through a preferable channel 35. Further, although the needle/thread fixture 133 is engaged and fixed by being press-fitted to the needle/thread fixture main body 139, it can be held and fixed by using a preferred treatment instrument such as grasping forceps instead.

This anastomosis system can be used as follows.

(a) The suture machine 3 is inserted into the body cavity with its distal end portion particularly being protected by the over-tubes 84 and 95 according to the first embodiment, the protection member 100 according to the first modification, the protection member 122 according to the second modification or the like. In this case, as similar to the above examples, the inside of the body cavity can be likewise observed through the endoscope 12.

(b) When performing the suture, the first operation member 16 and the second operation member 17 are closed so as to press the detachable needle 131 and the fixed needles 41 and 42 against the suture part, and the detachable needle 131 is pushed through a living tissue.

(c) As shown in FIG. 49, the detachable needle 131 after centesis protrudes from the living tissue. Thereafter, when the needle/thread fixture main body 139 is pushed toward the distal end side, the detachable needle 131 is inserted into the needle locking means 134 of the needle/thread fixture 133 and thereby engaged and fixed.

(d) When the first operation member 16 and the second operation member 17 are opened, since the detachable needle 131 is engaged and fixed to the needle locking means 134, the detachable needle 131 comes off the needle holder 132, and the suture thread 130 departs from the groove 137 of the needle holder 132. As a result, as shown in FIG. 50, a part of the suture thread 130 between the needle/thread fixture 133 and the thread locking means 135 forms a loop and remains in the living tissue.

(e) As shown in FIG. 50, the needle/thread fixture main body 139 is moved toward the living tissue while pulling the end of the suture thread 130 arranged outside the body toward the proximal side. As a result, the loop of the suture thread 130 is narrowed down, and the living tissue is tied to the state shown in FIG. 51.

(f) At last, the remaining suture thread 130 is cut by a thread cutter 136. The needle/thread fixture 133 left in the body cavity can be removed when removing the thread.

According to the system of this modification, in addition to the advantages of the first embodiment and the respective modifications, since it is not necessary to form a knot outside the body and feed it into the body, the time required for the technique can be shortened, thereby further facilitating the treatment. Moreover, the constriction state of the tissue can be easily adjusted.

[Fourth Modification]

Figure 55:
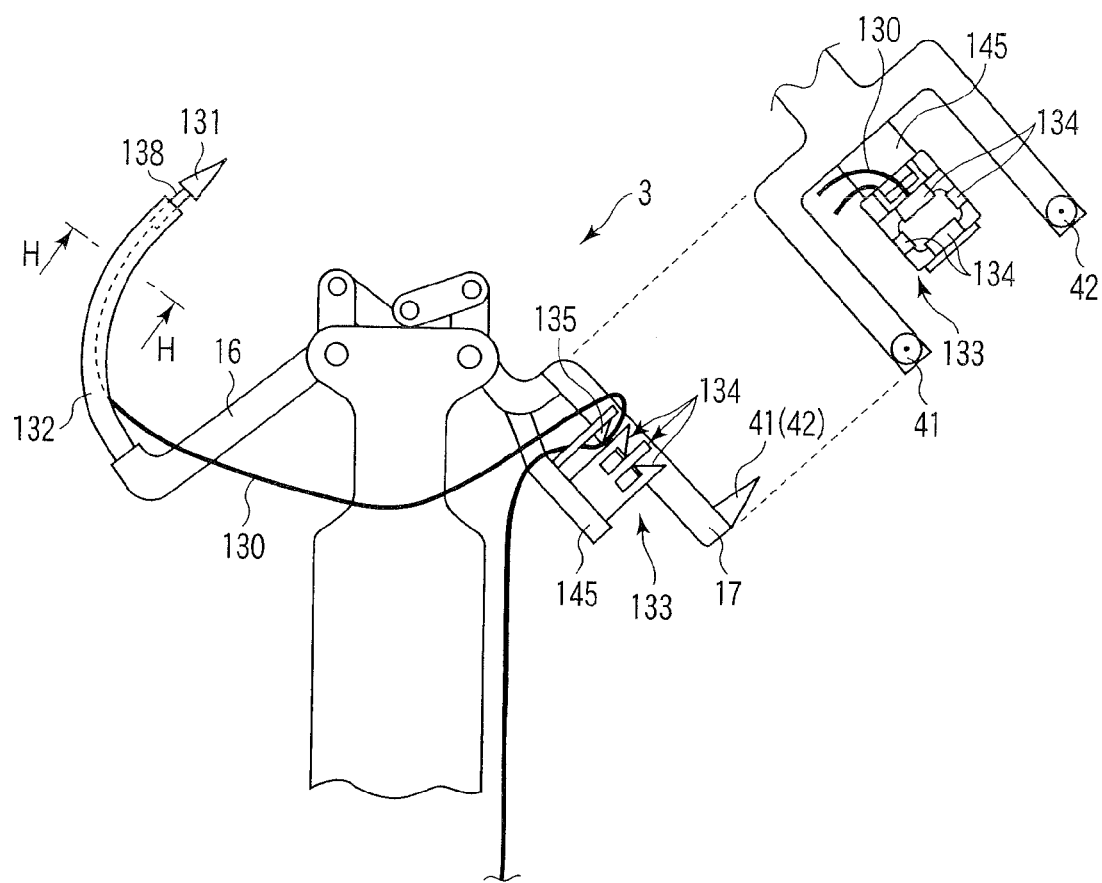
FIG. 55 is a view showing the suture machine for use in an endoscopic anastomosis system according to a fourth modification.
Figure 56:
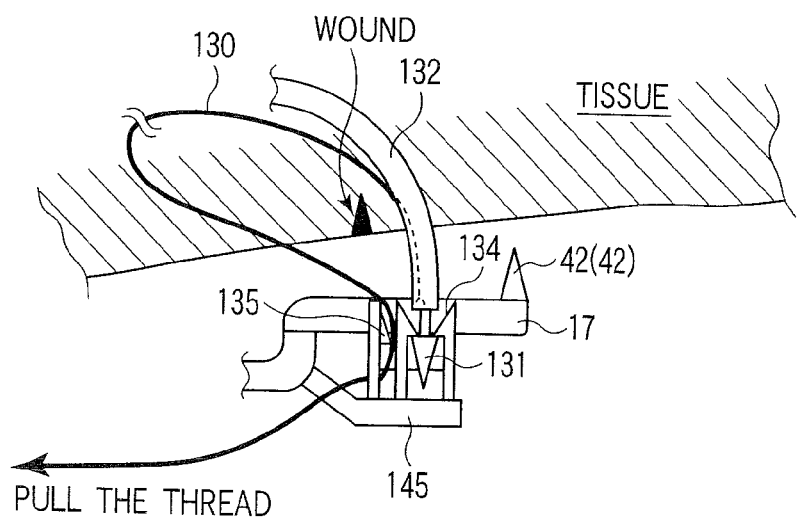
FIG. 56 is a view showing the state that the detachable needle is engaged with the needle/thread fixture after a tissue is stuck.

FIGS. 55 and 56 show a fourth modification. This fourth modification is basically similar to the above-described third modification and different from it in the following points.

As shown in FIG. 55, the needle/thread fixture 133 according to this modification is detachably attached to a holding member 145 formed to the second operation member 17.

This anastomosis system can be used as follows.

(a) When inserting the suture machine 3 into the body cavity, the distal end portion of the suture machine 3 is particularly protected by the above-described over-tubes 84, 95, the protection member 100, the protection member 122 or the like. Since the needle/thread fixture 133 is attached to the second operation member 17, for example, the needle/thread fixture main body 139 or the regular grasping forceps or the like does not have to be used.

(b) When performing the suture, as similar to the third modification, the first operation member 16 and the second operation member 17 are closed so as to press the detachable needle 131 and the fixed arms 41 and 42 against the suture part, and the detachable needle 131 is pushed through the tissue.

(c) As shown in FIG. 56, the detachable needle 131 protruding from the living tissue after centesis is inserted into and engaged with the needle locking means 134 of the needle/thread fixture 133 held in the holding member 145.

(d) When the proximal side of the suture thread 130 is pulled, one end of the suture thread 130 is fixed to the detachable needle 131, and the groove 137 of the needle holder 132 is opened on the inner peripheral side. Therefore, the living tissue is constricted.

(e) When the first operation member 16 and the second operation member 17 are opened, since the detachable needle 131 is engaged with and fixed to the needle locking means 134, the detachable needle 131 and the needle/thread fixture 133 come off the holding member 145 and enter the state shown in FIG. 51.

(f) At last, the remaining suture thread 130 is cut by the thread cutter 136.

In this modification, the advantage similar to that of the third modification can be obtained. Furthermore, in this modification, since the needle/thread fixture 133 does not have to be independently held, the suture technique can be further facilitated.

[Fifth Modification]

FIGS. 57 to 60 show a fifth modification. This fifth modification is basically similar to the third modification but different from it in the following points.

Figure 57:
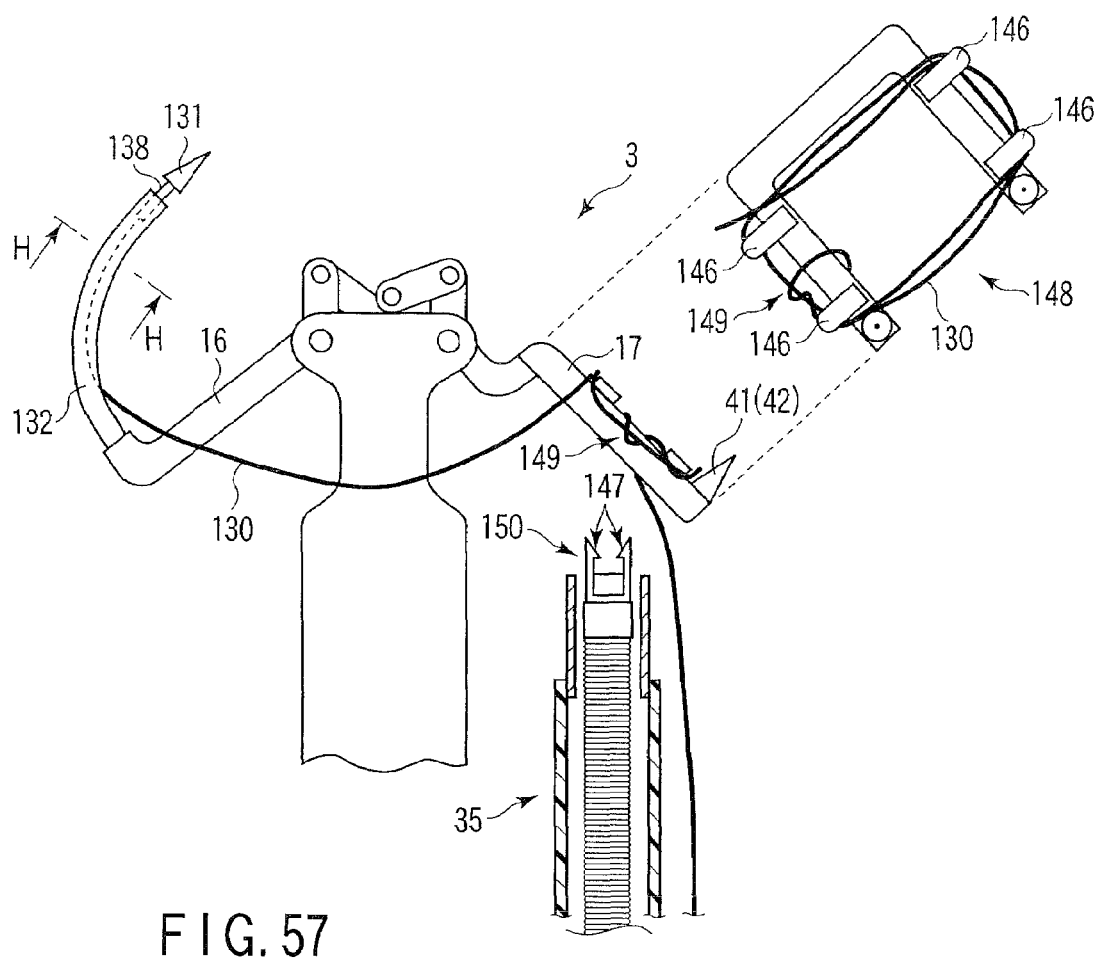
FIG. 57 is a view showing the suture machine for use in an endoscopic anastomosis system according to a fifth modification.
Figure 58:
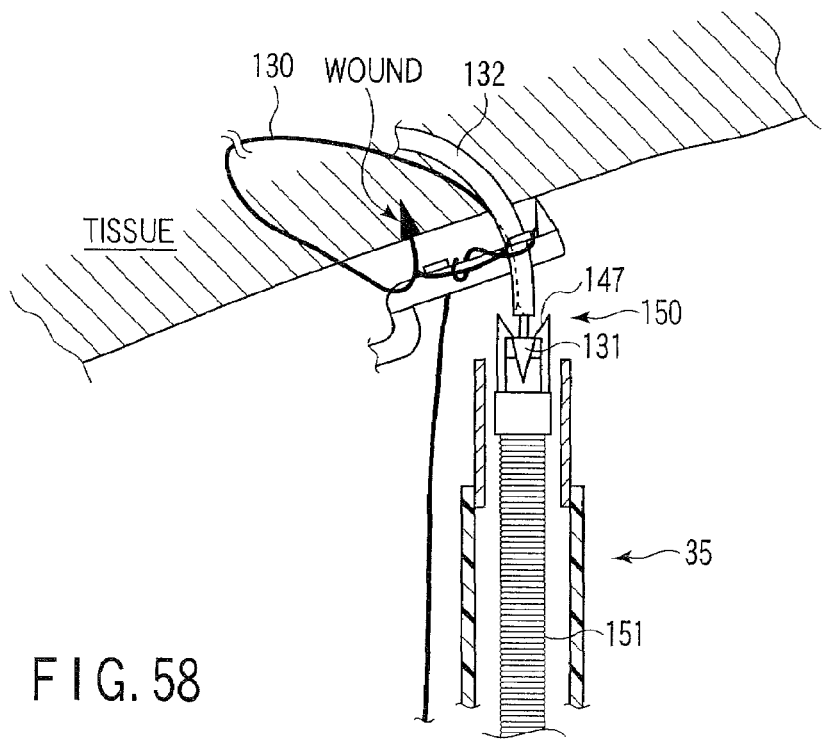
FIG. 58 is a view showing the state that the detachable needle is engaged with the needle fixture after a tissue is stuck.
Figure 61:
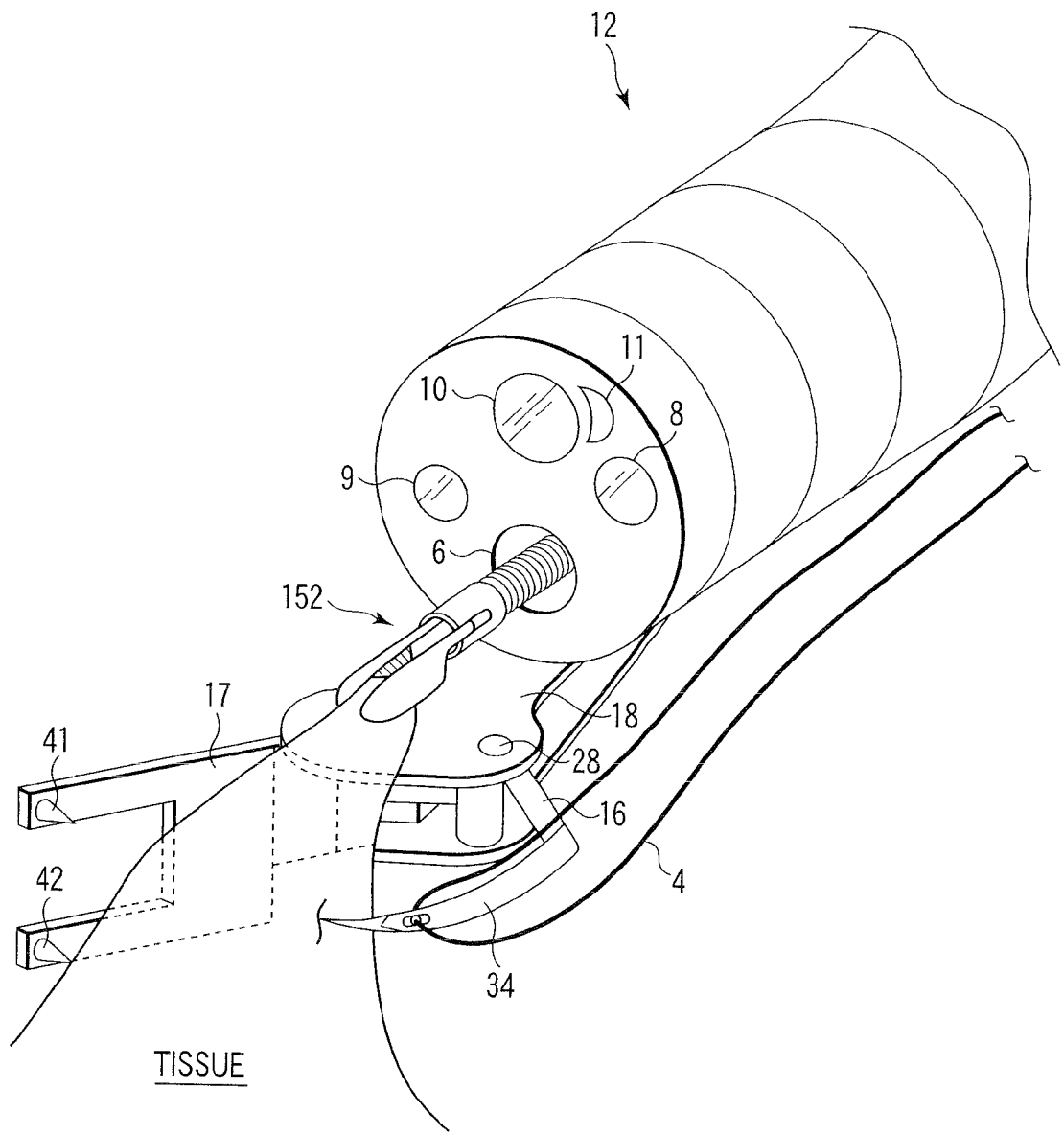
FIG. 61 is a view showing the state that a tissue is pulled by the grasping forceps.

As shown in FIG. 57, in this modification, four engagement members 146 used for holding at least one loop previously formed to the suture thread 130 are provided to the second operation member 17. These engagement members 146 are formed into the claw shape by an elastic material and fixed on the side opposed to the first operation member 16 in such a manner that one pair is opposed to the other pair. A part of the suture thread 130 is caught by the engagement members 146 and, for example, two large loops 148 are formed. The detachable needle 131 can pass through the large loops 148. In addition, at least one small loop 149 used for forming a later-described knot is formed to the circumferential part of the suture thread 130 forming the large loops 148.

A needle fixture 150 includes needle fixing means 147 which can engage with the detachable needle 131 and a tubular member 151 to which this needle fixing means is fixed. This needle fixture 150 is formed so as to be capable of being inserted into a preferred channel 35. Instead of this, the needle fixture 150 may be fixed to the suture machine 3. In this case, the position at which the needle fixture 150 is fixed is a position at which the detachable needle 131 can engage with the needle fixing means 147.

This endoscopic anastomosis system can be used as follows.

(a) When inserting the suture machine 3 into the body cavity, as similar to the above, it is protected by the over-tubes 84 and 95, the protection member 100, the protection member 122 or the like.

(b) When the detachable needle 131 is pushed through the living tissue, the first operation member 16 and the second operation member 17 are closed so as to press the detachable needle 131 and the fixed needles 41 and 42 against the suture part.

(c) As shown in FIG. 56, the detachable needle 131 after centesis protrudes from the living tissue. Thereafter, the tubular member 151 is pushed out toward the distal end side, and the detachable needle 131 is inserted into the needle fixing means 147 of the thread fixture 150 held by the tubular member 151 and then engaged and fixed.

(d) As shown in FIG. 59, when the first operation member 16 and the second operation member 17 are opened, since the detachable needle 131 is engaged with the needle engaging means 147, the detachable needle 131 comes off the needle holder 132, and the large loops 148 come off the engagement member 146. As a result, the small loop 149 forms a knot on the suture thread 130 in cooperation with the large loops 148.

(e) Thereafter, as shown in FIG. 60, the knot 149 is fastened by pulling the proximal side of the suture thread 130 and the needle fixture 150 in order to suture an incision.

(f) At last, as shown in FIG. 60, the remaining suture thread 130 is cut by the thread cutter 136.

This system according to the fifth modification can obtain the advantages similar to those of the third modification. Additionally, members other than the suture thread 130 do not have to be kept in the body.

Incidentally, as described above with respect to each of the foregoing embodiments, when suturing the living tissue, for example, the grasping forceps 152 can be inserted into the body cavity from the forceps channel 6 of the endoscope 12 as shown in FIG. 161, the first and second operation members 16 and 17 can be closed with the living tissue being pulled by the grasping forceps 152, and the detachable needle 131 can be pushed through the living tissue. The subsequent procedures are similar to those described with respect to each modification.

[Sixth Modification]

FIGS. 62 to 67 show a sixth modification, and this system is different from the third modification in the structure of the suture machine 3. Further, a needle/thread fixture 153 is arranged instead of the needle/thread fixture 133.

Figure 62:
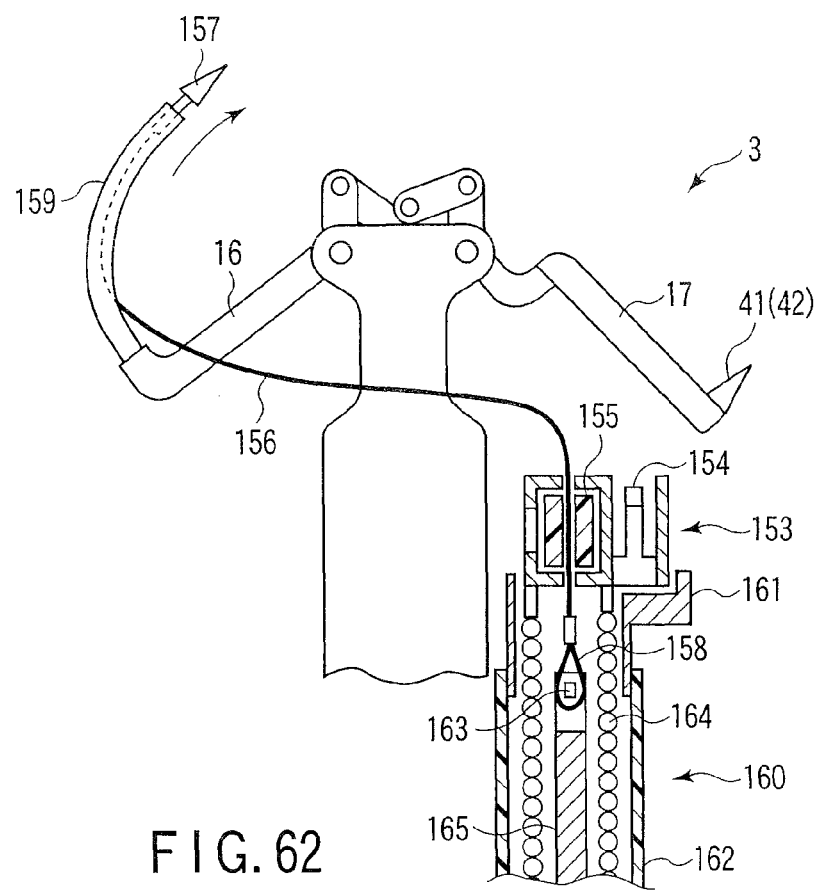
FIG. 62 is a view showing the suture machine for use in an endoscopic anastomosis system according to a sixth embodiment.
Figure 65:
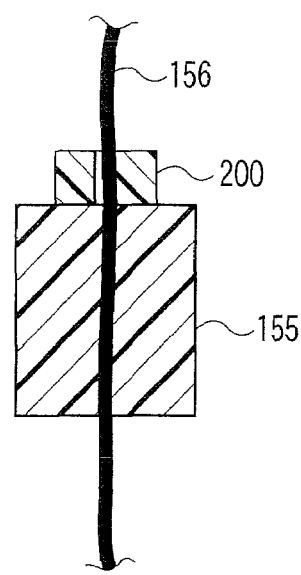
FIG. 65 is a view showing the structure of each thread locking means.

As shown in FIG. 62, the needle/thread fixture 153 includes thread locking means 155 and needle locking means 154. This thread locking means 155 is constituted by an elastic tubular member having a thin axial hole, and the suture thread 156 is inserted into the axial hole in the state that the suture thread is press-fitted. As a result, the thread locking means 155 can engage the suture thread 156 at an arbitrary position. This thread locking means 155 can be formed of, e.g., a silicone tube. On the other hand, when the sufficient strength can not be obtained from only the silicone tube because tube is apt to be cracked after ligation for example, a reinforcing member 200 such as a tube made of PTFE resin may be arranged coaxially with the thread locking means 155 as shown in FIG. 65.

A loop portion 158 is formed to the one end of the suture thread 156 on the proximal side, and the loop portion 158 is detachably engaged with an engagement portion 163. This engagement portion 163 is fixed to a transmission member 165, and arranged in the coil 164 so as to be capable of moving forward/backward. The proximal side of the transmission member 165 is connected to an operation portion (not shown) which can be operated outside the body, and the engagement portion 163 can be moved forward/backward along the coil 164 by moving the operation portion forward/backward. Furthermore, the channel 160 into which the transmission member 165 is inserted has a flexible tubular member 162 and a receiving portion 161 fixed to the distal end of the tubular member 162, and the needle/thread fixture 153 is held through this reception portion 161.

Figure 64:
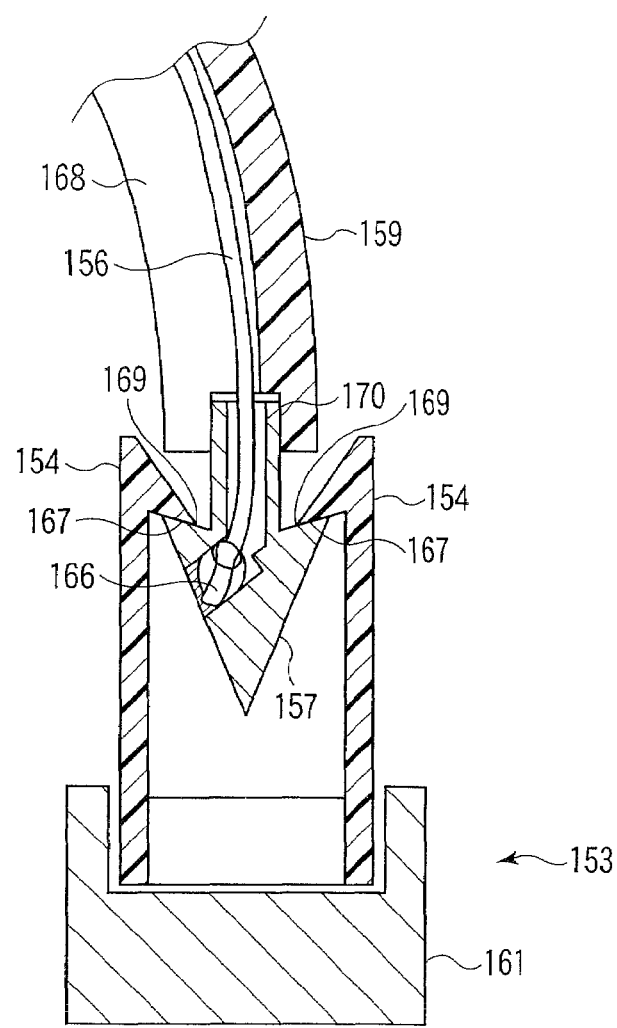
FIG. 64 is a cross-sectional view taken along the line J-J in FIG. 63.

As shown in FIG. 64, an inclination portion 167 is formed to the needle locking means 154. Furthermore, an inclination portion 169 is similarly formed to the detachable needle 157. Therefore, the needle locking means 154 and the detachable needle 157 hardly come off each other when they are engaged with each other through the inclination portions 167 and 169. Moreover, in this modification, there is provided a through hole 170 which pierces the shaft portion of the detachable needle 157 and is opened to a tapered plane of the distal end portion. This through hole 170 is formed to have a structure with a step and, for example, a knot 166 formed to the other end of the suture thread 156 can be accommodated in the through hole 170 as shown in FIG. 64 so as not to move to the other end side and the knot 166 can be engaged with and fixed to the step portion. The knot 166 of this suture thread 156 can be fixed to the detachable needle 157 by a preferable adhesive agent. In addition, a groove 168 similar to that shown in FIG. 41 is formed to the needle holder 159 which holds the detachable needle 157 so that the suture thread 156 can be removed from the needle holder 159.

This endoscopic anastomosis system can be used as follows.

(a) When inserting the suture machine 3 into the body cavity, the suture machine 3 is inserted with its distal end portion being protected in particular.

(b) The first operation member 16 and the second operation member 17 are closed so as to press the detachable needle 157 and the fixed needles 41 and 42 against the suture part, and the detachable needle 157 is pushed through the tissue. Of course, this operation can be observed through the endoscope 12.

Figure 63:
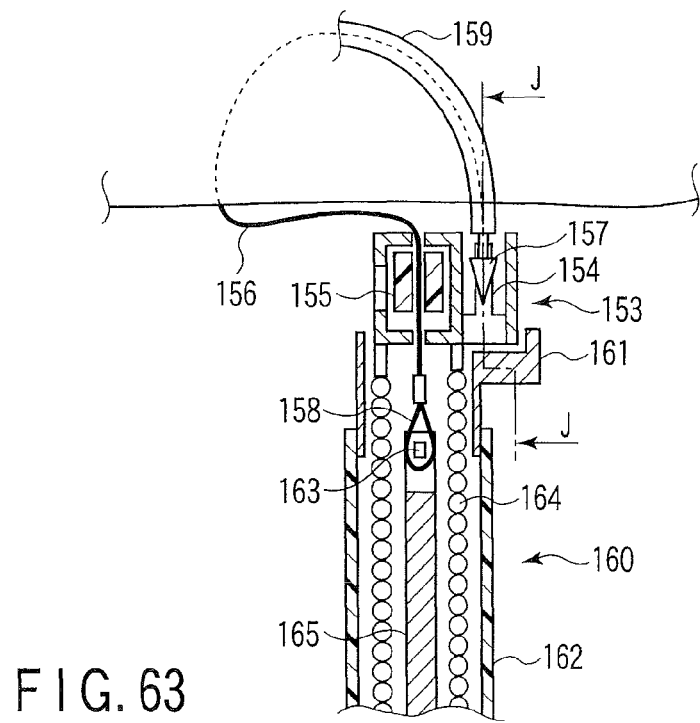
FIG. 63 is a view showing the state that the detachable needle is engaged with the needle/thread fixture after a tissue is stuck.

(c) As shown in FIG. 63, the detachable needle 157 protrudes from the living tissue. Then, the coil 164 is pushed out toward the distal end side, and the detachable needle 157 is inserted into the needle locking means 154 of the needle/thread fixture 153 held at a predetermined position and then engaged and fixed.

Figure 66:
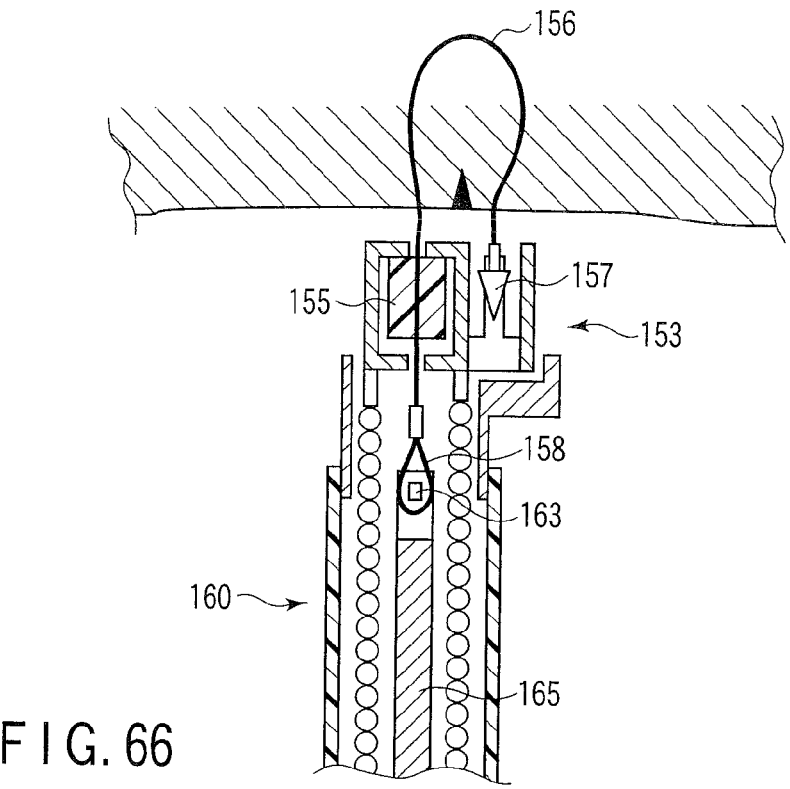
FIG. 66 is a view showing the state that a needle holder is removed from the tissue.

(d) When the first operation member 16 and the second operation member 17 are opened, since the detachable needle 157 is engaged with and fixed to the needle locking means 154, the detachable needle 157 comes off the needle holder 159 and enters the state shown in FIG. 66.

Figure 67:
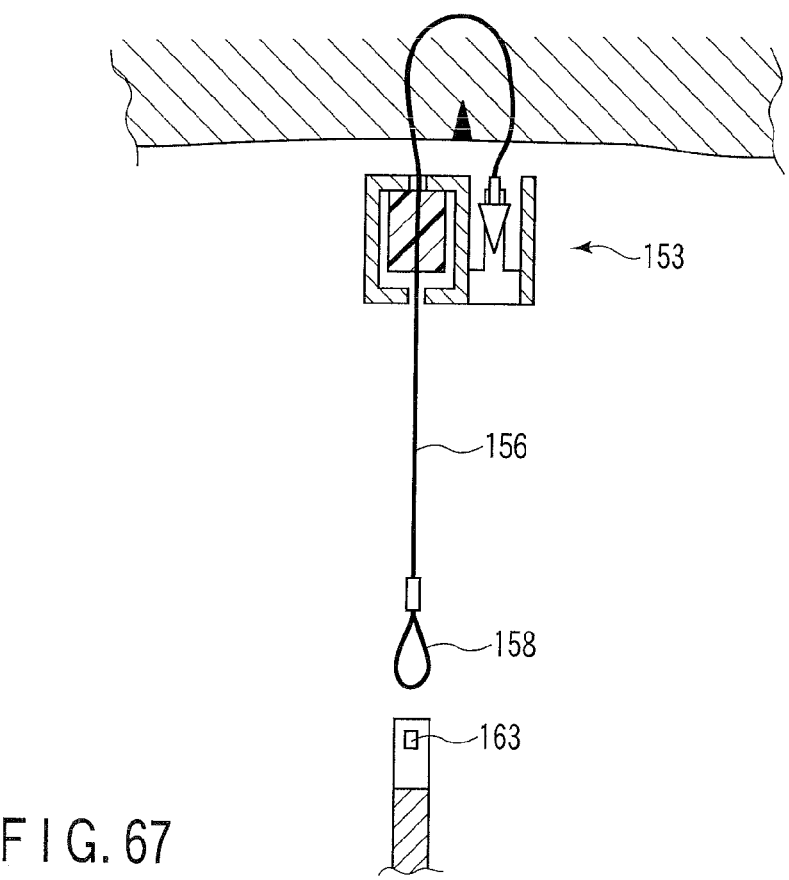
FIG. 67 is a view showing the state the tissue is tied.

(e) The transmission member 165 is pulled toward the proximal side by a non-illustrated operation portion, and the living tissue is constricted until it reaches the state shown in FIG. 67. Then, the distal end portion of the transmission member 165 is caused to protrude from the channel 160, and the loop portion 158 is removed from the engagement portion 163.

(f) At last, the remaining thread 156 is cut by the needle cutter 136.

The system according to this sixth modification can obtain the advantages similar to those of the third modification.

Additionally, in this modification, since the length of the suture thread 156 may be small, the suture operation can be facilitated.

[Seventh Modification]

FIGS. 68 to 74 show the endoscopic anastomosis system according to a seventh modification.

Figure 68:
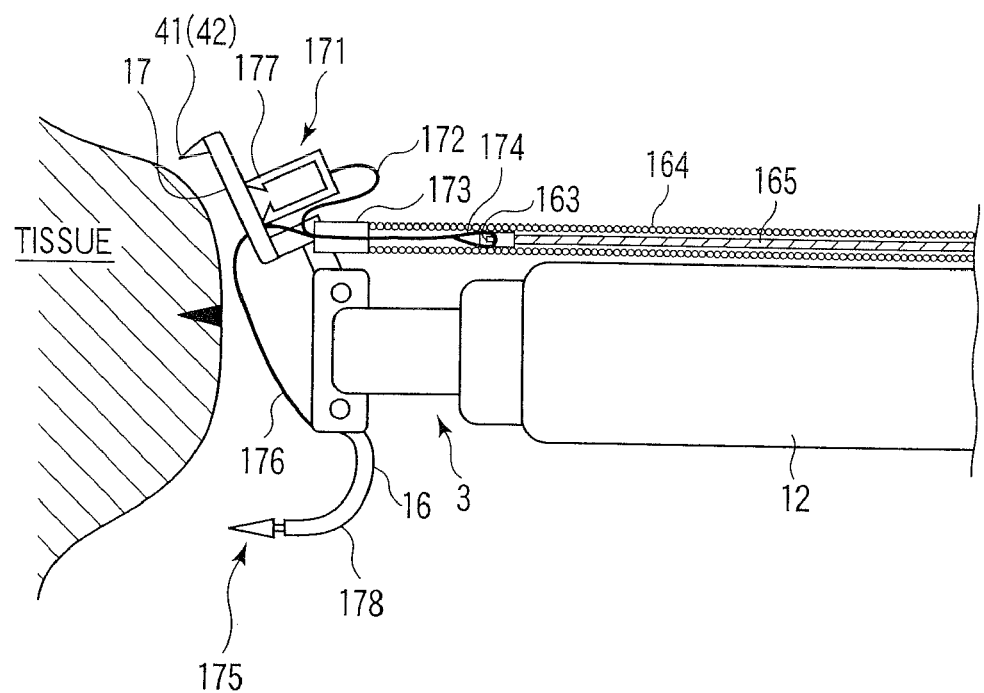

As shown in FIG. 68, a needle/thread fixture 171 is detachably loaded to the second operation member 17 in place of the holding member 145 according to the fourth modification (see FIG. 55). Needle fixing means 177 is formed to the needle/thread fixture 171. One end of the suture needle 172 is fixed to the needle/thread fixture 171. Further, the other end of the suture thread is extended into the coil 164 through thread locking means 173 similar to that in the sixth modification, and a loop portion 174 is formed thereto.

To the first operation member 16 is fixed a needle holder 178 which holds the detachable needle 175 at the end portion thereof. One end of the other suture thread 176 is fixed to the detachable needle 175, and the other end of this suture thread is also extended into the coil 164 through the thread locking means 173, and a loop portion 174 is formed thereto. These loop portions 174 engage with the engagement portion 163 of the transmission member 165 as similar to the sixth modification.

When performing the suture by using this endoscopic system, the following procedures are used.

(a) As similar to the above, the suture machine 3 is inserted into the body cavity with its distal end portion being protected by the over-tubes 84 and 95, the protection member 100, the protection member 122 or the like in particular.

Figure 69:
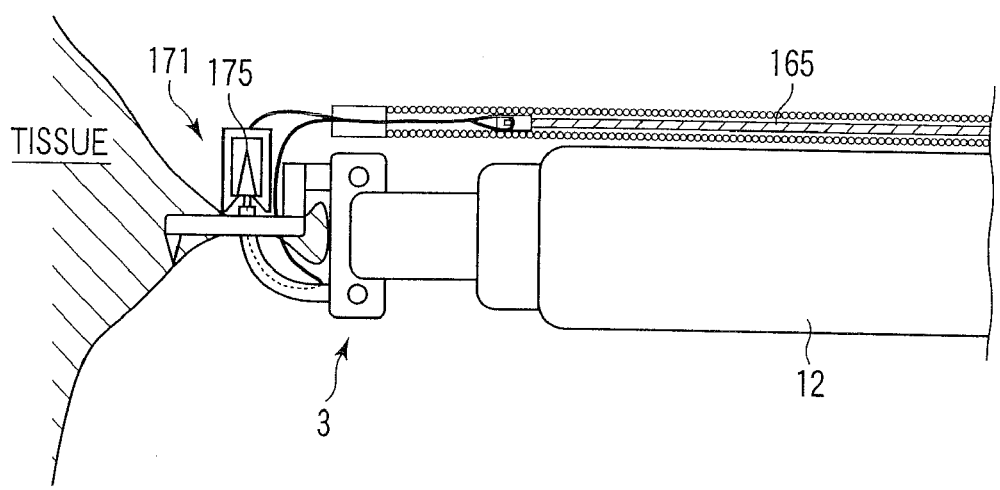

(b) As shown in FIG. 69, the first and second operation members 16 and 17 are closed so as to press the detachable needle 175 and the fixed arms 41 and 42 against the suture part, and the detachable needle 175 is pushed through the living tissue.

(c) As shown in FIG. 69, the detachable needle 175 after centesis is inserted into needle fixing means 177 of the needle/thread fixture 171 held at a predetermined position, and then engaged and fixed.

Figure 70:
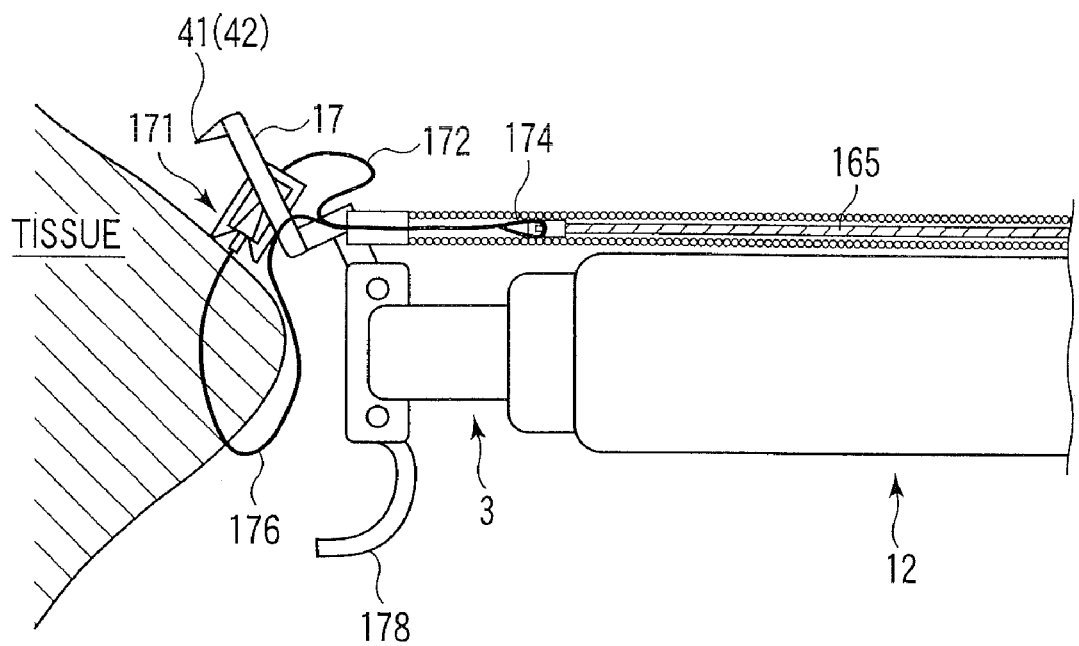

(d) As shown in FIG. 70, when the first and second operation members 16 and 17 are opened, the needle/thread fixture 171 comes off the second operation member 17 with the detachable needle 175 being engaged to the needle/thread fixture 171.

Figure 71:
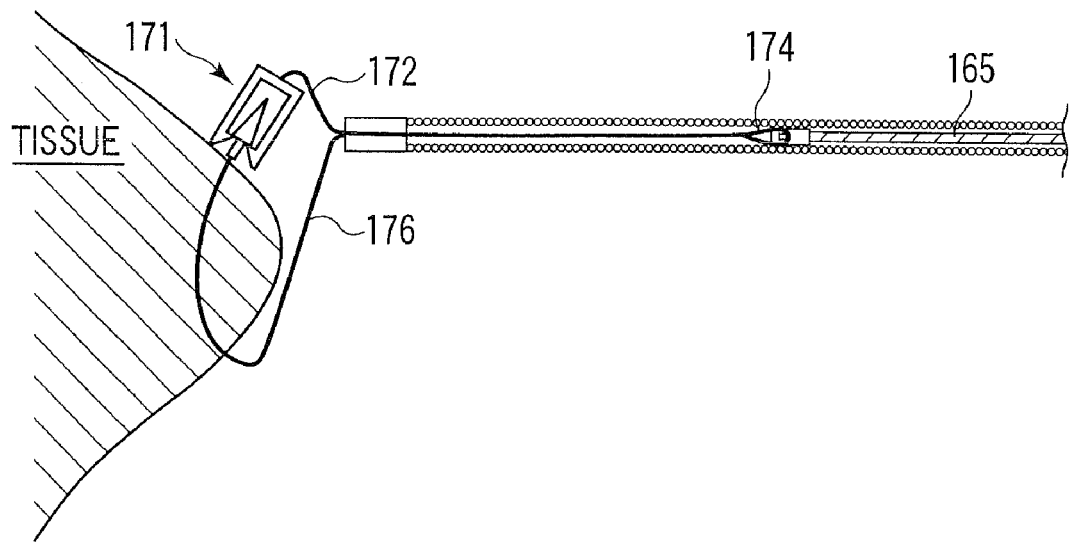

(e) The transmission member 165 is pulled by a non-illustrated operation portion from the state shown in FIG. 71, and the living tissue is constricted by the suture thread 176 until it reaches the state shown in FIG. 72. Subsequently, as shown in FIG. 73, the distal end portion of the transmission member 165 is pushed out from the coil 164. The loop portions 174 are removed from the engagement portion 163 of the transmission member. Only the loop portion 174 of one suture thread can be further pulled if necessary.

(f) At last, as shown in FIG. 74, the remaining suture threads 172 and 176 are cut by the thread cutter 136.

The system according to the seventh modification can likewise obtain the advantages similar to those of the third modification. Furthermore, in this modification, since the lengths of the suture threads 172 and 176 may be small, the suture operation can be further facilitated.

[Eighth Modification]

Figure 75:
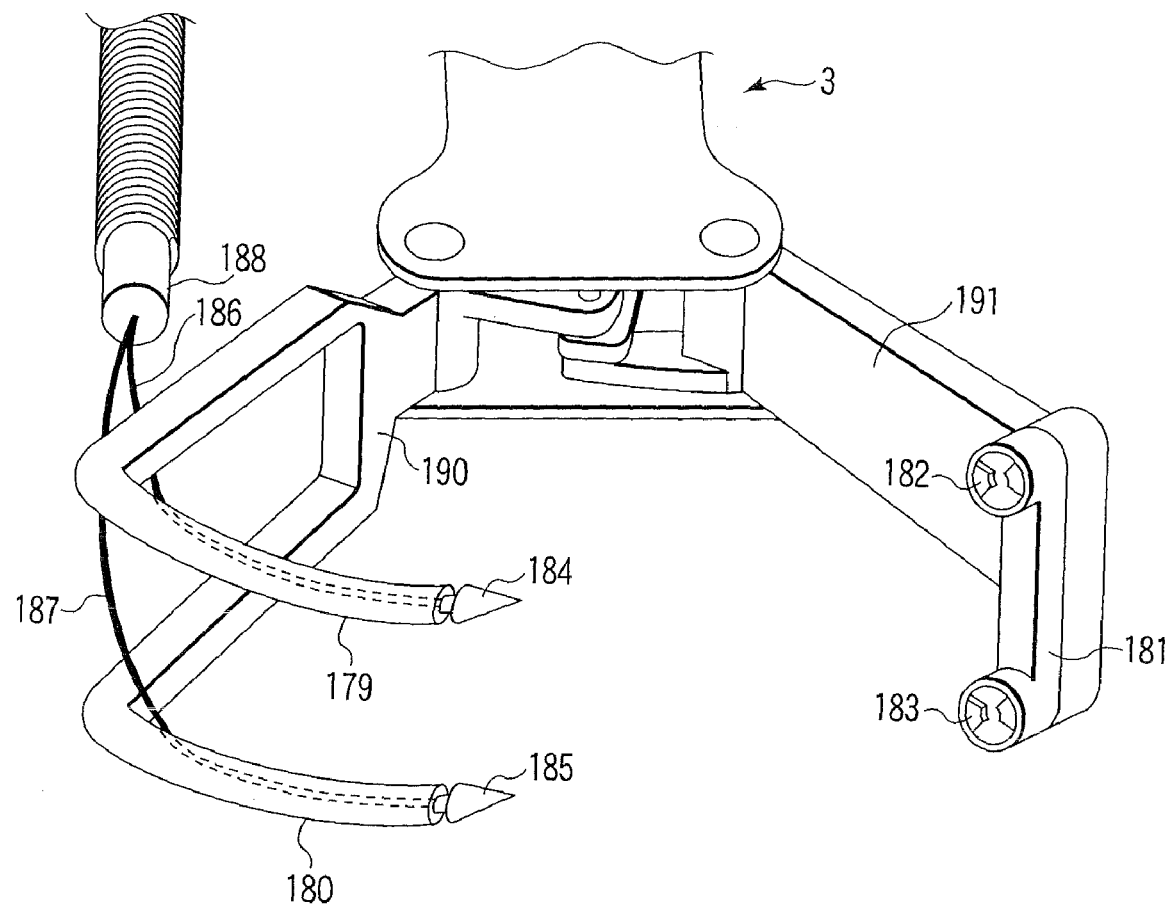
FIG. 75 is a view showing the suture machine for use in an endoscopic anastomosis system according to an eighth modification.
Figure 76:
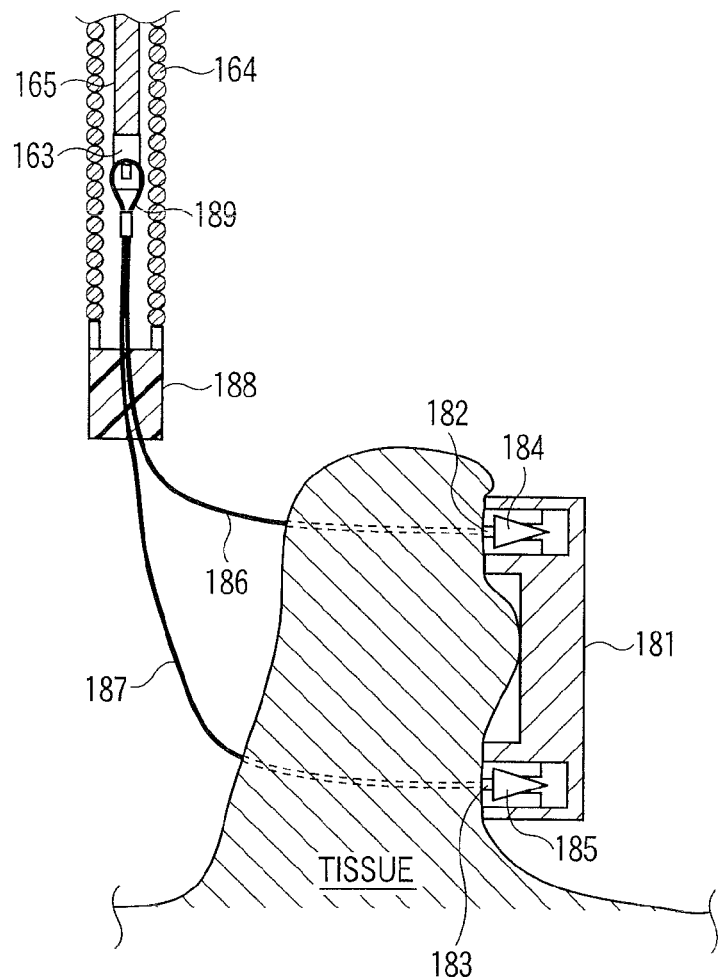
FIG. 76 is a view showing the state that the detachable needle is engaged with the needle fixture after centesis of the tissue.
Figure 77:
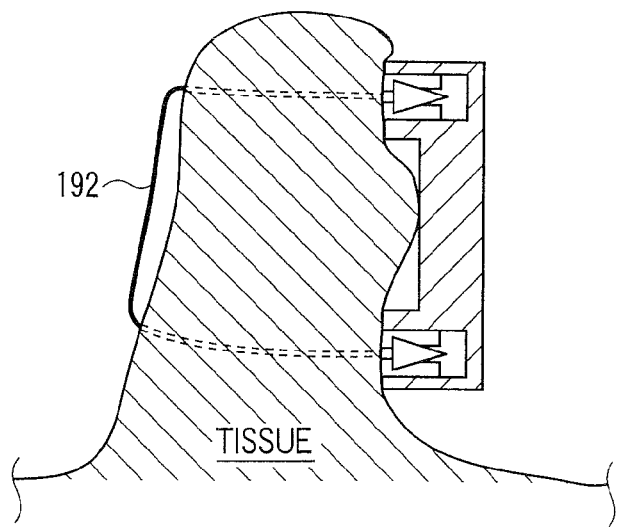
FIG. 77 is a view showing the tissue being sutured.

FIGS. 75 to 77 show the endoscopic anastomosis system according to an eighth modification.

The eighth modification is different from the seventh modification in the following points.

As shown in FIG. 75, in this modification, to the first operation member 190 are arranged needle holders 179 and 180 having detachable needles 184 and 185 attached thereto. As shown in FIG. 52, a groove which is opened to the inner side is provided to each of the needle holders 179 and 180. Furthermore, on end of each of the suture threads 186 and 187 is fixed to each of the two detachable needles 184 and 185 by the method similar to that of the sixth modification.

A needle fixture 181 is detachably attached to the second operation member 191. Needle locking means 182 and 183 for engaging and fixing the detachable needles 184 and 185 are formed to the needle fixture 181.

As shown in FIG. 76, the other end of each of the suture threads 186 and 187 is extended into the coil 164 through thread locking means 188 similar to the thread locking means 155 of the sixth modification, and a loop portion 189 is formed thereto. This loop portion 189 is likewise engaged with the engagement portion 163 of the transmission member 165 as similar to the sixth modification.

When performing the suture by using this endoscopic system, the following procedures are used.

(a) As similar to the above, the suture machine 3 is inserted into the body cavity with its distal end portion particularly protected by the over-tubes 84 and 95, the protection member 100, the protection member 122 or the like.

(b) The first and second operation members 190 and 191 are closed so as to press the needle locking means 182 and 183 and the detachable needles 184 and 185 against the suture part, and the detachable needles 184 and 185 are pushed through the tissue.

(c) As shown in FIG. 76, the detachable needles 184 and 185 after centesis are inserted into and engaged with needle locking means 182 and 183 of the needle fixture 181 held at a predetermined position.

(d) Since the detachable needles 184 and 185 are engaged with and fixed to the needle fixture 181 when the first and second operation members 190 and 191 are opened, the detachable needles 184 and 185 come off the needle holders 179 and 180. Further, the needle fixture 181 also comes off the second operation member 191. As a result, the state shown in FIG. 76 is obtained.

(e) Thereafter, as similar to the sixth modification, the thread locking means 188 is pressed against the living tissue, the engagement portion 163 is pulled through the transmission member 165, and the living tissue is constricted. Thereafter, the engagement portion 163 is pushed out of the coil 164 and the loop portion 189 is caused to come off.

(f) At last, as similar to the third modification, the remaining suture threads 186 and 187 are cut by the thread cutter 136.

On the other hand, as shown in FIG. 77, the constriction force may be adjusted by using the length of one suture thread 192 in place of the two suture threads 186 and 187. In this case, the thread locking means 188 or the engagement portion 163, the coil 164, the transmission member 165, the loop portion 189 and the like are no longer necessary.

The system according to the eighth modification can likewise obtain the advantages similar to those of the third modification. Furthermore, in this modification, the two suture threads 186 and 187 can be simultaneously sutured by the two detachable needles 184 and 185.

Second Embodiment

FIG. 78 shows the anastomosis system according to a second embodiment.

The anastomosis system according to this embodiment is different from the above-described anastomosis system in that a transparent cap 193 is provided at the distal end portion of the endoscope 12. As this transparent cap 193, it is possible to use an appropriate one which can be closely attached to the distal end portion of the endoscope 12.

When performing the gastrojejunostomy by using the anastomosis system according to the second embodiment, it is possible to carry out it in accordance with the procedures similar to those (1) to (12) in the first embodiment. In the procedure illustrated in FIG. 23, however, the gastric wall GW is sucked into the transparent cap 193. In this case, a curvature function of the endoscope 12 can be used. Therefore, the direction of the distal end portion of the endoscope can be freely changed, thereby improving the approach property with respect to the gastric wall GW.

Third Embodiment

FIG. 79 shows the anastomosis system according to the third embodiment.

This anastomosis system according to this embodiment can also perform the gastrojejunostomy in accordance with procedures similar to those (1) to (12) in the first embodiment, but the gastric wall GW is dissected to a necessary length by the needle-shaped knife 5A instead of complying with the procedures (3) to (5) illustrated in FIGS. 23 to 25.

In this case, the gastric wall GW can be cut out in an arbitrary size.

Fourth Embodiment

FIGS. 80 and 81 show the anastomosis system according to the fourth embodiment and the procedures using this system.

Figure 82:
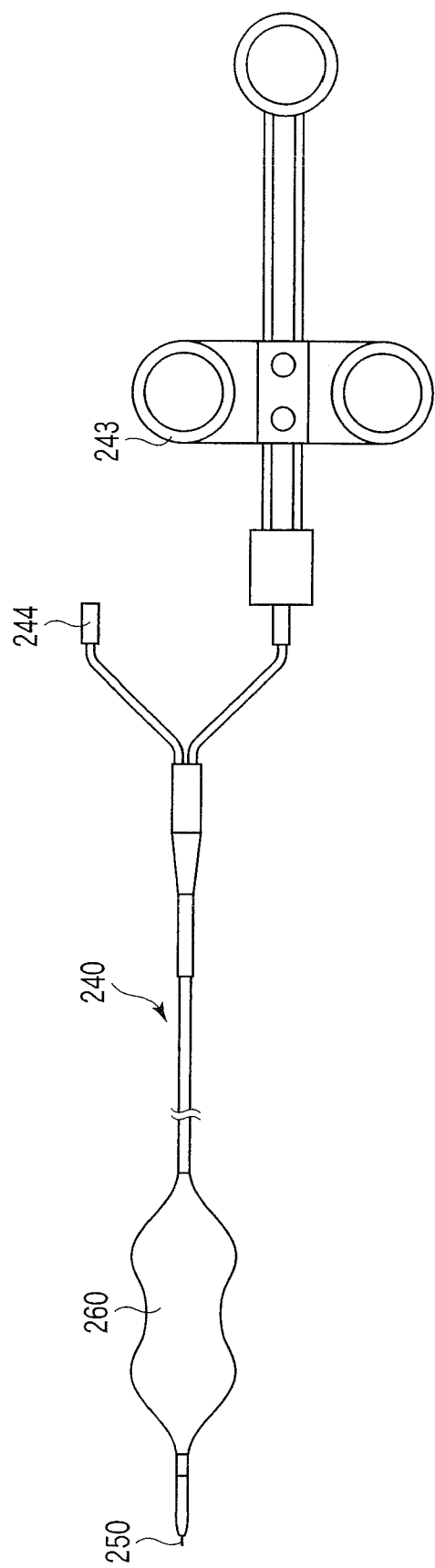
FIG. 82 is a schematic view showing a balloon dilator with a needle-shaped knife for use in the anastomosis system according to the fourth embodiment.
Figure 83:
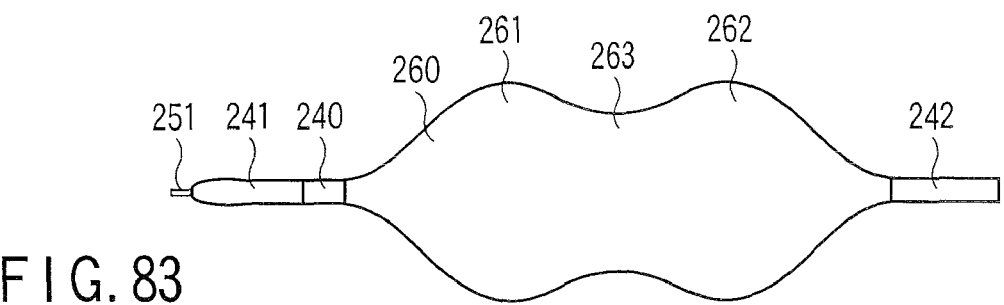
FIG. 83 is an enlarged view showing a distal end portion of the balloon dilator.

This embodiment uses the procedures (4) and (5) in the first embodiment and a balloon dilator with a needle-shaped knife 240 shown in FIGS. 82 and 83.

As shown in FIGS. 82 and 83, the balloon dilator with the needle-shaped knife 240 for use in the anastomosis system according to this embodiment is constituted by a high-frequency knife 250 inserted into a sheath 242, a balloon dilator 260 fixed to the sheath 242, a knife operation portion 243 and a water feed port 244.

The sheath 242 is, for example, a tube sheath having a circular cross section, made of an insulative polymeric resin (high molecular polyamide, high-density/low-density polyethylene, polyester, polytetrafluoro-ethylene, tetrafluoroethylene-perfluoroalkylvinylether copolymer, tetrafluoroethylene-hexafluoropropylene copolymer or the like), and has at least two lumens. Of the lumens, the high-frequency knife 250 can be inserted into one lumen, and a fluid used for expanding the balloon dilator 260 can be passed to the other lumen.

Further, the distal end portion 241 of the balloon dilator with the needle-shaped knife 240 is formed into a tapered shape.

Figure 87:
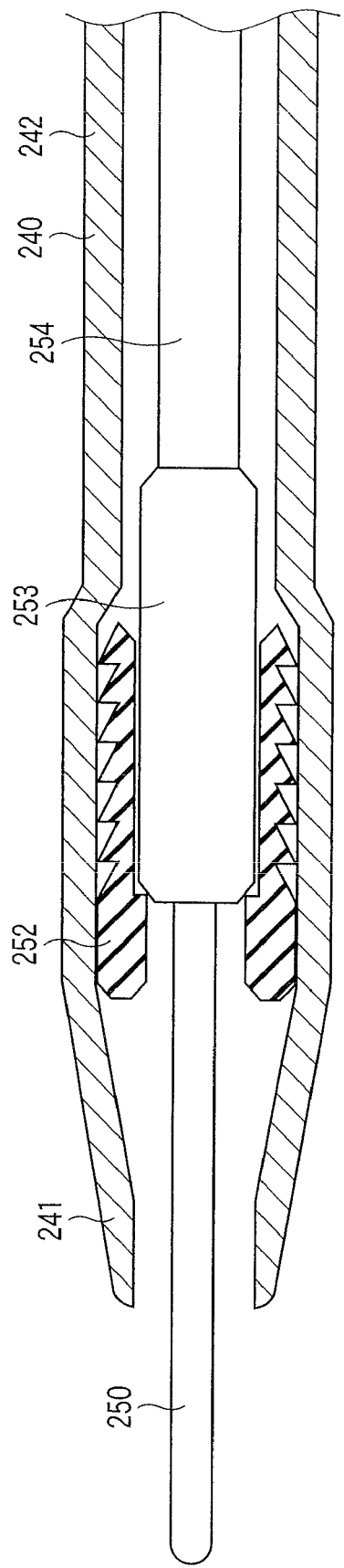
FIG. 87 is an enlarged cross-sectional view of the balloon dilator with the needle-shaped knife of FIG. 82.
Figure 88:
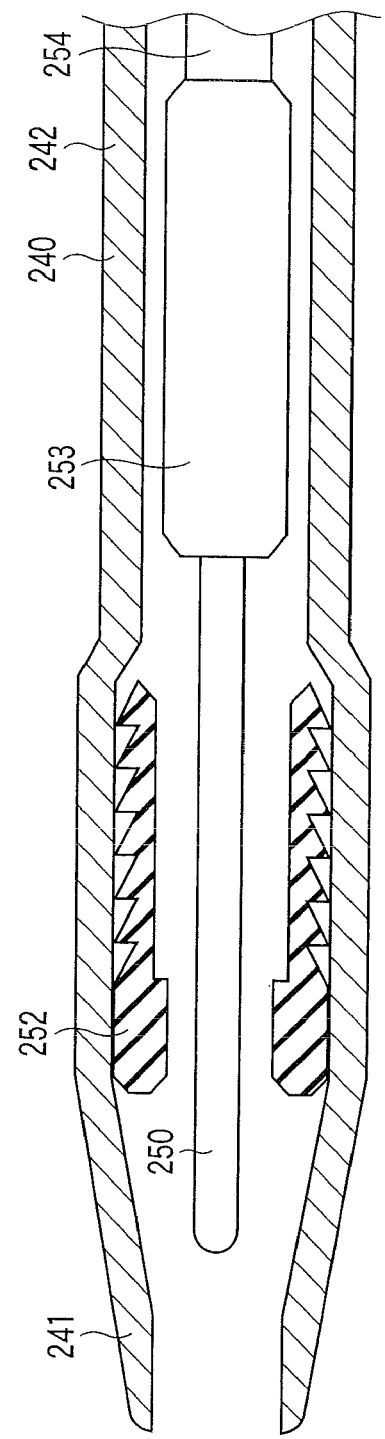

As shown in FIGS. 87 and 88, the high-frequency knife 250 is fixed to the wire 254 through a wire side stopper 253 at the proximal end thereof. The wire 254 is removably attached to the knife operation portion 243. The knife operation portion 243 is connected to a non-illustrated high-frequency power supply through a non-illustrated high-frequency cord.

The high-frequency knife 250 is made of, e.g., conductive metal and may have a circular or paddle-like cross-section. In case of the circular cross section, it is preferable for the outside diameter to have a value of $\phi 0.1$ to 10 mm, and desirably 0.3 mm to 1.0 mm. In case of the paddle-like cross section, it is preferable for the length of one side to have a value of 0.2 to 10 mm, and the side length of 0.2 to 0.5 mm×0.5 to 1.0 mm is particularly desirable.

The wire side stopper 253 is a substantially tubular member made of, e.g., conductive metal, and it is preferable for its length to have a value of 1 to 20 mm and desirably 3 mm to 10 mm in particular.

The wire 254 is, e.g., a conductive metal (stainless or the like) wire and constituted by a single wire or a twisted wire. The circular cross section is preferable. The outside diameter is $\phi 0.1$ to 15 mm which allows the wire to enter the sheath 42, and $\phi 0.3$ mm to $\phi 3$ mm is preferable in particular. The length is 300 mm to 5000 mm, and 1000 mm to 2000 mm is preferable in particular.

The high-frequency knife 250 can be inserted into or removed from the sheath 242. When the high-frequency knife 250 is inserted into the sheath 242, the wire side stopper 253 fixed to the high-frequency knife 250 is brought into contact with a sheath side stopper 252, thereby restricting sliding of the high-frequency knife 250 to the distal end thereof.

The balloon dilator 260 is a balloon made of a polymeric resin, and has distal end side maximum outside diameter portion 261, a central portion 263 and a proximal side maximum outside diameter portion 262. The outside diameters of the distal end side maximum outside diameter portion 261 and the proximal side maximum outside diameter 262 are larger than the outside diameter of the central portion 263 when expanded. As to the outside diameter of the central portion 263, the outside diameter which allows insertion of the over-tube is 3 to 100 mm when the endoscope 12 and the transparent cap 195 or the over-tube are also used, and the outside diameter of 5 to 30 mm is particularly preferable. As to the outside diameter of the distal end side maximum outside diameter portion 261 and the proximal side maximum outside diameter portion 262 when expanded, each outside diameter is 5 to 120 mm which is a size larger than that of the central portion and prevents displacement, and the outside diameter of 7 to 50 mm is particularly preferable. The balloon dilator 260 can be expanded when it receives the pressure due to a fluid from a non-illustrated inflation device removably connected to the water feed port 244 at the proximate end of the sheath 242.

Figure 84:
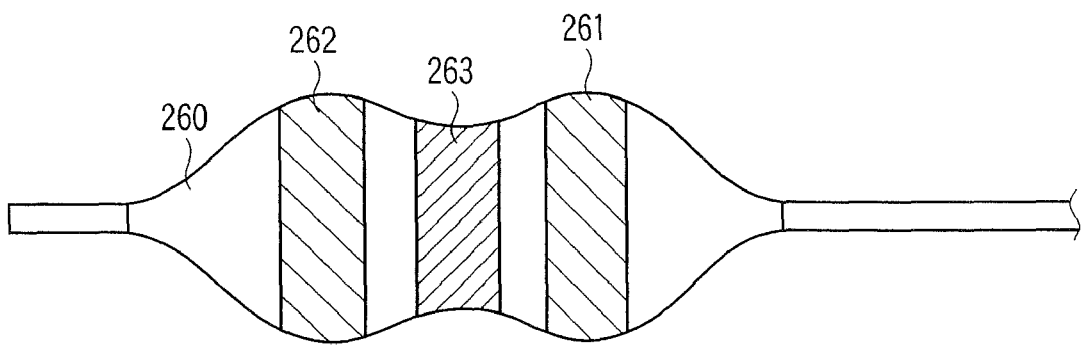
FIGS. 84 to 86 are views showing various kinds of examples of marking applied to the balloon dilator.
Figure 85:
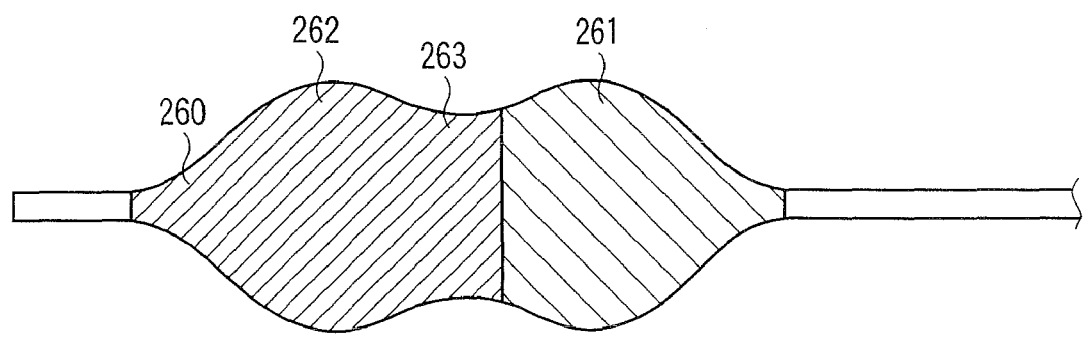
Figure 86:
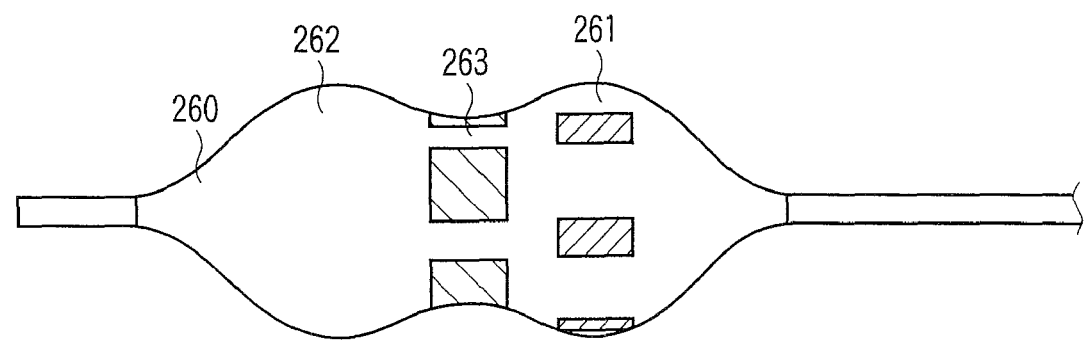

This balloon dilator 260 can be readily positioned by applying marking such as shown in FIGS. 84 to 86. FIG. 84 shows application of the ring-like marking to each of the distal end side maximum outside diameter portion 261, the central portion 263 and the proximal side maximum outside diameter 262 of the balloon dilator 260. FIG. 85 shows the color coding that the position of the central portion 263 of the balloon dilator 260 can be recognized. FIG. 86 shows application of the marking indicative of the central portion 263 and the proximal side maximum outside diameter 262 of the balloon dilator 260. The characteristics of these types of marking can be combined. Application of the marking to the balloon dilator 260 having the distal end side maximum outside diameter portion 261, the central portion 263 and the proximal side maximum outside portion 262 is not restricted to this technique, and it is generally effective. These types of marking can be confirmed in the radioscopy by using or mixing a radiopaque material such as tungsten, platinum, barium sulfate, bismuth oxide or the like.

The gastrojejunostomy using such a balloon dilator with the needle-shaped knife 240 can change the above procedures (4) and (5) as follows.

As shown in FIG. 80, the balloon dilator with the needle-shaped knife 240 is inserted into the forceps channel 6 (see FIGS. 2 and 8) in place of the needle-shaped knife 5A, and caused to protrude from the distal end portion. At this moment, the high-frequency knife 250 is inserted in the state that it is being pulled in from the distal end surface of the balloon dilator with the needle-shaped knife 240 by the operation of the knife operation portion 243 so as not to damage the channel (see FIG. 88), and it protrudes from the distal end surface of the balloon dilator with the needle-shaped knife 240 by the operation of the knife operation portion 243 with the balloon dilator with the needle-shaped knife 243 projecting from the distal end portion of the endoscope 12 (see FIG. 87). Also, with the high-frequency knife 250 being in contact with the gastric wall GW on which the recession is formed, the high-frequency current is caused to flow by a non-illustrated high-frequency power supply in order to perforate the gastric wall GW.

After perforating the gastric wall GW, the balloon dilator with the needle-shaped knife 240 is caused to further protrude, and the sheath 42 is inserted to the outside of the gastric wall, namely, the abdominal cavity. When the central portion 263 of the balloon dilator 260 provided to the sheath 242 is inserted until it reaches the gastric wall GW, the opening portion of the gastric wall GW is extended until it reaches such a sufficient dimension which allows insertion of the endoscope 12 by expanding the balloon dilator 260 by feeding the fluid by a non-illustrated inflation device. FIG. 81 shows this state.

When the sufficient extension is attained, the endoscope 12 is advanced to the procedure (6) shown in FIG. 26 according to the first embodiment. By using the balloon dilator with the needle-shaped knife 240 in this manner, the trouble of exchanging the needle-shaped knife and the balloon dilator can be saved. The displacement of the balloon dilator 260 in the expansion process can be avoided by providing the central portion 263, the distal end side maximum outside diameter portion 261 and the proximal side maximum outside diameter portion 262 which are larger than the outside diameter of the central portion 263. Further, the balloon dilator 260 of the balloon dilator with the needle-shaped knife 240 can be readily positioned on the gastric wall GW by applying marking such as shown in FIGS. 84 to 86 to the balloon dilator 260.

Figure 89:
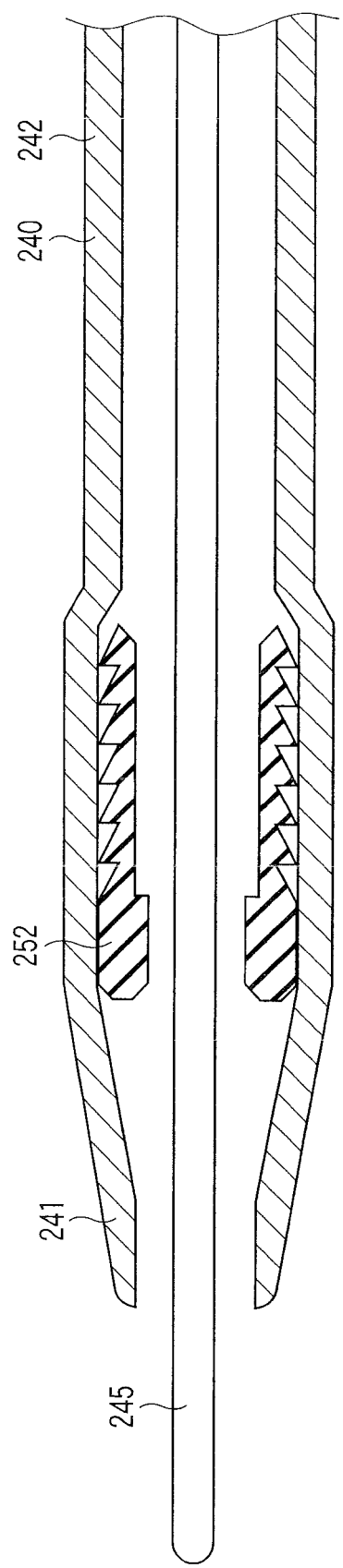
FIG. 89 is an enlarged cross-sectional view showing the state that a guide wire is inserted.
Figure 90:
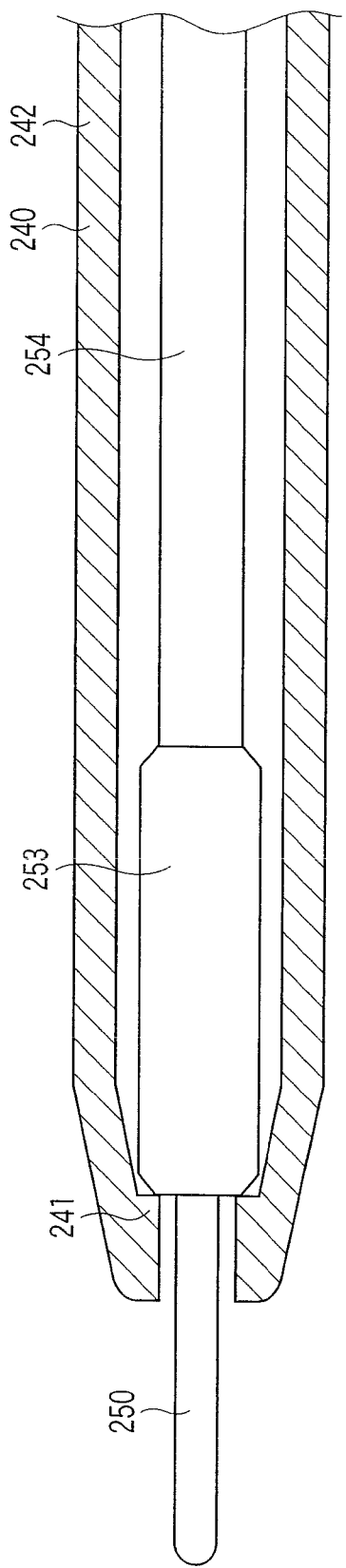
FIG. 90 is an enlarged cross-sectional view showing the state that the balloon dilator with the needle-shaped knife according to a modification.

Incidentally, as shown in FIG. 89, in regard to the sheath side stopper 52, it is preferable to form a member with no stopper such as the guide wire 245 which guides the sheath 242 to a target part so as to be capable of being inserted without restraint. Therefore, it is preferable to form the inside diameter of each of the small-diameter portion of the inner hole of the sheath side stopper 252 and the distal end portion 41 larger than that of the guide wire 45 or the like. Further, as shown in FIG. 90, the sheath side stopper 252 can be omitted by forming a step portion which can engage with the wire side stopper 253 to the distal end portion 241 of the balloon dilator with the needle-shaped knife 240.

Fifth Embodiment

Figure 91:
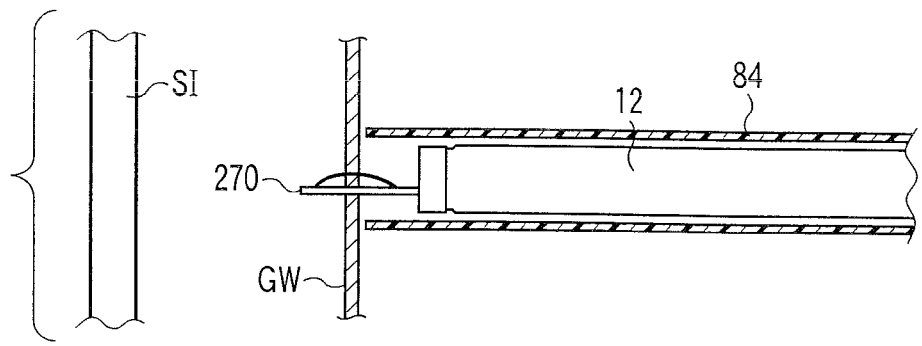
FIG. 91 is a view showing a part of the gastrojejunostomy procedures using the anastomosis system according to a fifth embodiment.

FIG. 91 shows the anastomosis system according to a fifth embodiment.

This anastomosis system according to this embodiment uses an arched knife 5E in the procedure (5) illustrated in FIG. 25 according to the first embodiment. The arched knife 5E is inserted into a bore hole formed in the preceding procedure, and this bore hole is cut open to a necessary dimension. As this arched knife 5E, a regular knife having the same structure as that of a papillotomy knife may be used. Since the bore hole is cut open by using the arched knife 5E in this manner, an opening with an arbitrary dimension can be formed to the gastric wall GW.

Sixth Embodiment

Figure 92:
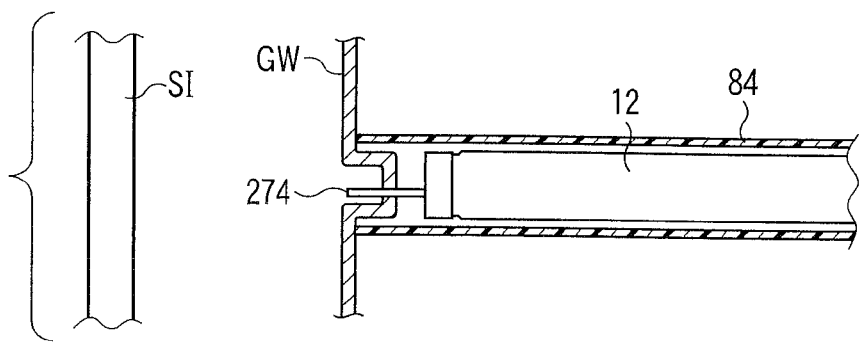
FIG. 92 is a view similar to FIG. 24, using the anastomosis system according to a sixth embodiment.
Figure 93:
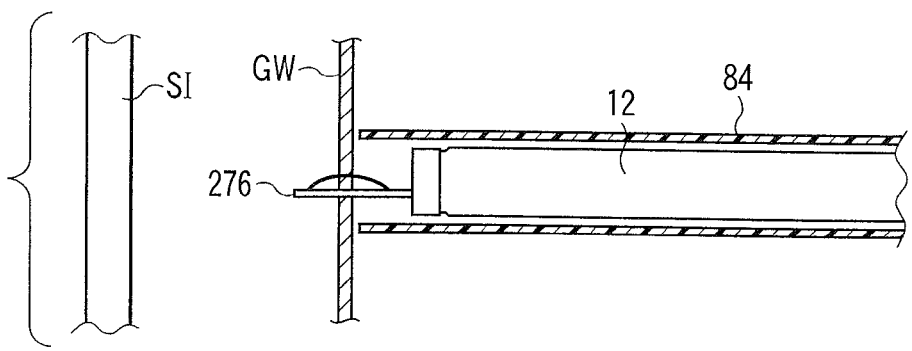
FIG. 93 is a view similar to FIG. 25, using the anastomosis system according to the sixth embodiment.
Figure 97:
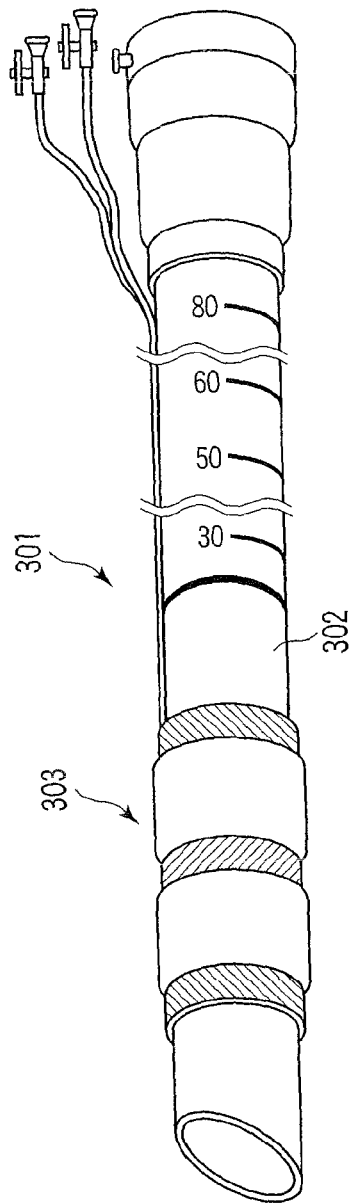
FIG. 97 is a general drawing of the over-tube for use in the anastomosis system according to the eighth embodiment.
Figure 98:
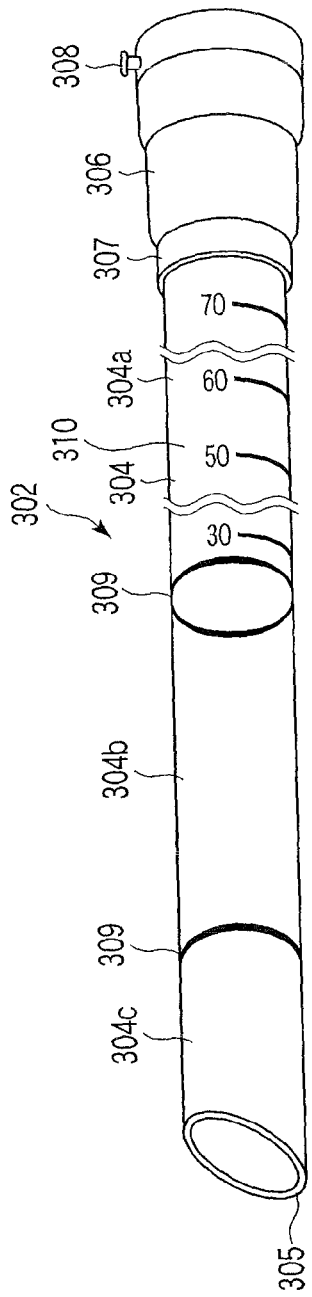
FIGS. 98 and 99 are perspective views of each part forming the over-tube of FIG. 97.
Figure 99:
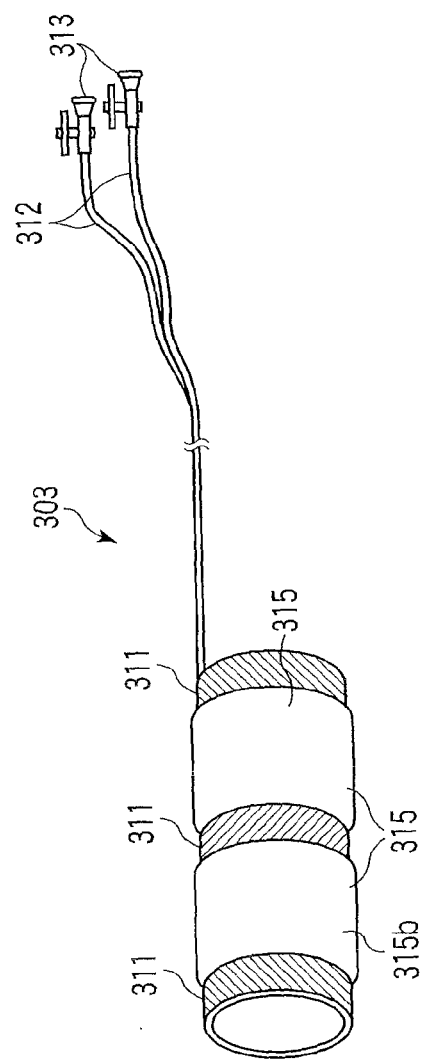

FIGS. 92 to 94 show the anastomosis system according to a sixth embodiment.

This anastomosis system according to this embodiment uses an arched knife with a needle-shaped knife 270 in the procedures (4) and (5) illustrated in FIGS. 24 and 25 according to the first embodiment.

As shown in FIG. 94, the arched knife with the needle-shaped knife 270 used in the anastomosis system according to this embodiment is constituted by a needle-shaped knife 274 inserted into the sheath 272, an arched knife 276 exposed to the side portion of the sheath 272, a needle-shaped knife operation portion 278 and an arched knife operation portion 280.

In this anastomosis system, the needle-shaped knife 274 of the arched knife with the needle-shaped knife 270 is used to perforate the gastric wall GW in the procedure (4) as shown in FIG. 92. Then, in the procedure (5), as shown in FIG. 93, the arched knife with the needle-shaped knife 270 is not removed but further inserted into the gastric wall GW until the arched knife 276 reaches the gastric wall. In this embodiment, the trouble of counterchanging the needle-shaped knife and the arched knife can be saved.

Seventh Embodiment

FIG. 95 shows the anastomosis system according to a seventh embodiment.

The anastomosis system according to this embodiment has the same structure as the anastomosis system according to the first embodiment. The procedures according to the first embodiment include insertion of the over-tube 84 into the abdominal cavity as a procedure (6A) after the procedure (6) illustrated in FIG. 26 and removal of the over-tube 84 from the abdominal cavity as a procedure (8A) after the procedure (8). As a result, insertion and removal of the endoscope 12 and counterchanging can be facilitated.

It is to be noted that the similar advantages can be obtained even if the procedure (6A) is carried out after the procedure (7) according to the first embodiment and the procedure (8A) is performed after the procedure (9).

Eighth Embodiment

FIG. 96 shows the anastomosis system according to an eighth embodiment.

This anastomosis system according to this embodiment uses an over-tube with a double balloon 301 in place of the over-tube 84. By using the over-tube with the double balloon 301, the over-tube 301 can be fixed to the gastric wall GW when performing the procedure (6A). As a result, the over-tube can be prevented from coming off the gastric wall at the time of insertion and removal of the endoscope 12 or counterchanging.

FIGS. 97 to 105 show the embodiment of the over-tube with the double balloon 301.

As shown in FIGS. 97 to 100, the over-tube with the double balloon 301 according to this embodiment is constituted by an elongated shaft portion 302 having the flexibility which can be inserted into the body cavity, and a balloon portion 303 which can be attached to and detached from the outer periphery of the shaft portion 302. The inside diameter of the balloon portion 303 is formed to have a dimension which is slightly smaller than the outside diameter of the shaft portion 302, and the balloon portion 303 can be fixed to the outer peripheral portion of the shaft portion 302 by press-fitting. In this embodiment, the distal end of this balloon portion 302 is arranged at a position distanced from the distal end of the shaft portion 302 by 20 mm.

The shaft portion 302 is constituted by a tubular main body 304 and an operation handle 306. The tubular main body 304 has a proximal side portion 304a which is desirable when it is made of ePTFE, a transparent intermediate portion 304b which is preferable when it is made of polyurethane, and a distal end portion 304c which is preferable when it is made of ePTFE. The proximal side portion 304a and the intermediate portion 304b, and the intermediate portion 304b and the distal end portion 304c are connected by each joint portion denoted by reference numeral 309, and inner holes of the respective portions form one inner hole which coaxially communicate with each other.

An indication 310 indicative of a length from the endmost portion 305 is applied to the outer periphery of the proximal side portion 304a of the tubular main body 304. Furthermore, an operation handle 306 is joined to the proximal side of the proximal side portion 304a, a bend prevention member 307 which can be thermally constricted is caused to cover a part in the vicinity of the outer periphery of the joint portion between the proximal side portion 304a and the operation handle 306. When the bend prevention member 307 is heated being arranged to the outer periphery portion of the proximal side portion 304a, it is constricted and fastens a part in the vicinity of the outer periphery portion of this joint portion. Moreover, a lure-type mouth ring 308 used for feeding the fluid from the outside to the inside of the inner hole is provided to the operation handle 306, and two valves 330 which are preferable when made of fluorine rubber and distanced away from each other in the axial direction are provided so as to sandwich the mouth ring 308 therebetween. In this embodiment, a length from the distal end portion of the bend prevention member 307 to the endmost portion 305 of the tubular main body 304 is set to 650 mm, and an outside diameter of the shaft portion 302 is set to 17 mm. In addition, the shaft portion 302 or the tubular main body 304 has the flexibility which allows the curvature operation of the endoscope inserted inside, and hence the curvature operation can be carried out according to needs even if the endoscope is being inserted in the over-tube 301.

Incidentally, as to a material forming the shaft portion 302, a material such as styrene-based elastomer, olefin-based elastomer or silicone can be used in addition to the above-described material.

Additionally, the balloon portion 303 includes an expandable and constrictable semitransparent balloon 315 which is preferable when made of silicone and has an inner layer and an outer layer. The inner layer and the outer layer of the balloon 315 have the both end portions and the intermediate portion attached to each other by an adhesion portion 311, and form two balloons 315a and 315b distanced from each other along the axial direction of the over-tube 301. Two ducts 312 used for supplying and/or discharging a fluid which is a liquid and/or a gas to the respective balloons 315a and 315b are arranged on the outer peripheral portion of the shaft portion 302 in contiguity with each other so as to extend in the same direction. These ducts 312 may be integrated at the intermediate portion. Further, a mouth ring 313 is connected to the proximal side portion of the ducts 312. In this embodiment, the respective balloons 315a and 315b are formed so as to expand to the outside diameter of approximately 45 mm when a fluid of approximately 40 milliliter is injected into them. Furthermore, an axial length of the adhesion portion 311 at the intermediate portion forming a gap between the two balloons 315a and 315b is set to approximately 5 mm. Moreover, the respective balloons 315a and 315b are formed so as to have the outside diameter of approximately 20 mm when the balloon portion 303 is put onto the outer periphery portion of the shaft portion 302.

Incidentally, as a material of the balloon 315, a material such as styrene-based elastomer or latex can be used in addition to the above-described material.

Then, description will now be given as to the method of fixing the over-tube with the double balloon 301 according to this embodiment on the gastric wall with reference to FIGS. 101 to 105.

The fluid is first discharged from the respective balloons 315a and 315b, and the balloon portion 303 is constricted. In this state, the endoscope 12 is inserted into the inner hole of the over-tube 301. Thereafter, as shown in FIG. 101, the over-tube with the double balloon 301 is inserted into the gaster together with the endoscope 12 from the mouth of a patient to which the mouth piece 390 is put as shown in FIG. 101.

Then, as shown in FIG. 102, the over-tube with the double balloon 301 is curved with the endoscope 12 by operating the curvature mechanism of the endoscope 12, and the distal end surface of the endoscope is caused to be opposed to a necessary part of the gastric wall GW which can be a target. The balloon dilator 5B is inserted into the bore hole formed in the procedure (4) as shown in FIG. 103, and the balloon dilator 5B is expanded, thereby extending this hole (procedure (5)).

Figure 104:
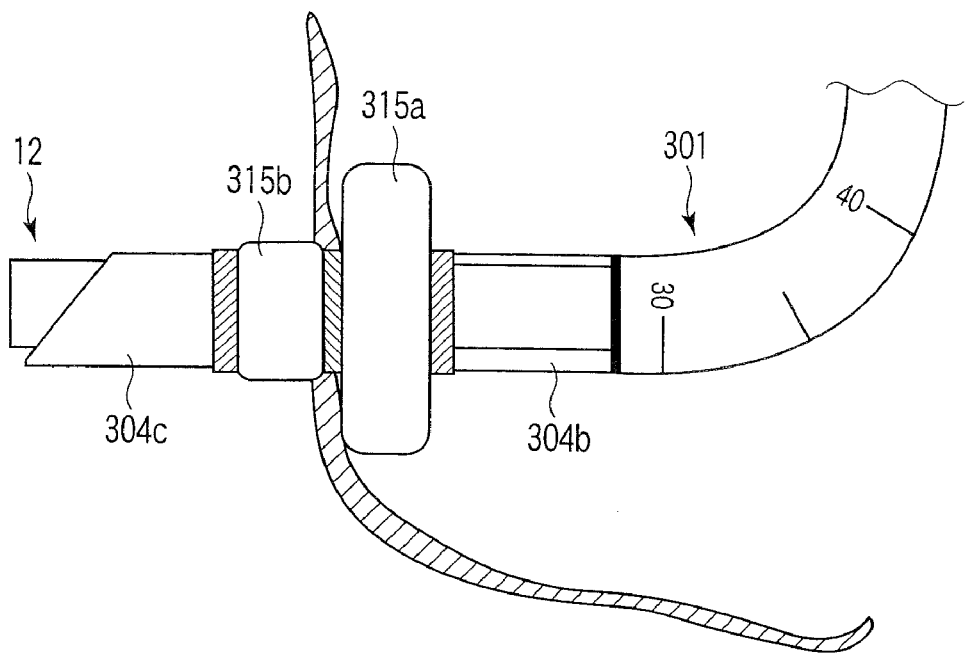

Subsequently, as shown in FIG. 104, the distal end portion of the over-tube 301 is inserted into the extended hole by moving forward the over-tube 301. At this moment, the over-tube 301 is moved forward based on an endoscopic image obtained from the endoscope 12 and information concerning an insertion length measured by the indication 310 provided on the outer surface of the over-tube 301. Then, the fluid is fed to the balloon 315a on the proximal end side from a non-illustrated syringe attached to the mouth ring 313, and the balloon 315a is expanded to, e.g., the outside diameter of 45 mm. At this moment, the distal end portion of the endoscope 12 may be moved back to a position of the transparent intermediate portion 304b, and expansion may be carried out while confirming the state of expansion of the balloon 315a from the inside of the inner hole of the over-tube 301 by using the endoscopic image.

Figure 105:
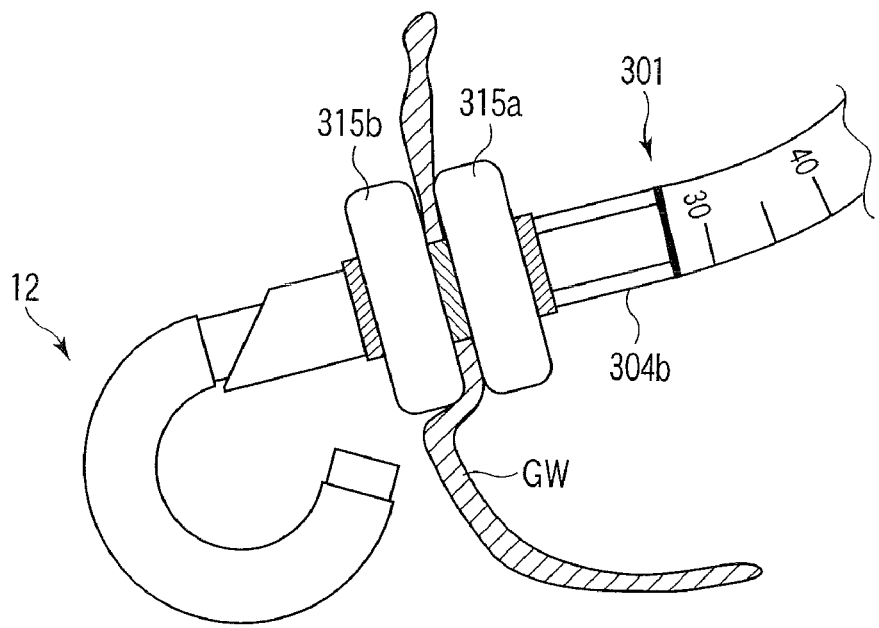

Then, when the over-tube 301 is moved forward with the balloon 315a being expanded, the balloon 315a is brought into contact with the gastric wall GW. The balloon 315b on the distal end side is arranged on the outer side of the stomach. Subsequently, as shown in FIG. 105, the gastric wall GW is sandwiched between the balloons 315a and 315b on the proximal end side and the distal end side by expanding the balloon 315b on the distal end side, and the distal end portion of the over-tube 301 is consequently fixed to the gastric wall GW. Thereafter, the processing can advance to the procedure (7) in the first embodiment.

Incidentally, before proceeding to the procedure (7), the endoscope 12 may be moved forward/backward with respect to the over-tube 301 if necessary, and a predetermined organ in the abdominal cavity can be diagnosed by using the endoscope 12. At this moment, a non-illustrated treatment forceps can be inserted into the forceps channel of the endoscope 12 and caused to protrude from the distal end opening of the endoscope 12 in order to perform treatment. Then, as shown in FIG. 106, a cut tissue t can be held by the grasping forceps 5C and put out of the body cavity together with the endoscope 12.

According to the over-tube 301 according to this embodiment, it has a sufficient length which allows oral extension to the gastric wall, and the over-tube can be smoothly passed through the pharynx portion since it has a small outside diameter. Moreover, the endoscope 12 can be guided to the abdominal cavity by pushing the distal end portion of the over-tube 301 through the gastric wall. In addition, since a gap between the two balloons 315a and 315b arranged at the distal end portion is 5 mm, the over-tube 301 can be fixed with the gastric wall GW being sandwiched in just proportion, and air-tightness between the inside of the stomach and the abdominal cavity can be assured. Additionally, since the over-tube 301 has the high flexibility, it can be bent by the curvature operation of the endoscope 12. Therefore, the over-tube 301 and the endoscope 12 can be guided to a target part. Further, since the shaft portion 302 and the balloon portion 303 can be attached/detached without restraint, the balloon portion 303 can be used again by attaching the new one even if the balloon portion 303 is damaged.

[First Modification of Over-Tube with Double Balloon]

FIGS. 107 to 113 show a first modification of the over-tube with the double balloon 301. Incidentally, since the various modifications described below are basically similar to the over-tube with the double balloon 301 according to the eighth embodiment, description will be mainly given as to different parts. Also, like reference numerals denote like parts, thereby omitting the detailed explanation.

Figure 110:
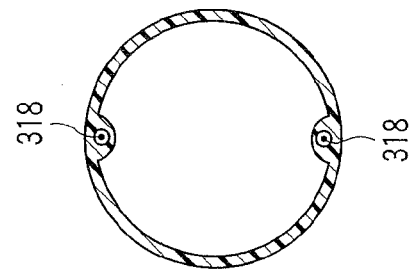
FIG. 110 is a transverse cross-sectional view taken along the line K-K of the shaft portion of FIG. 108.
Figure 108:
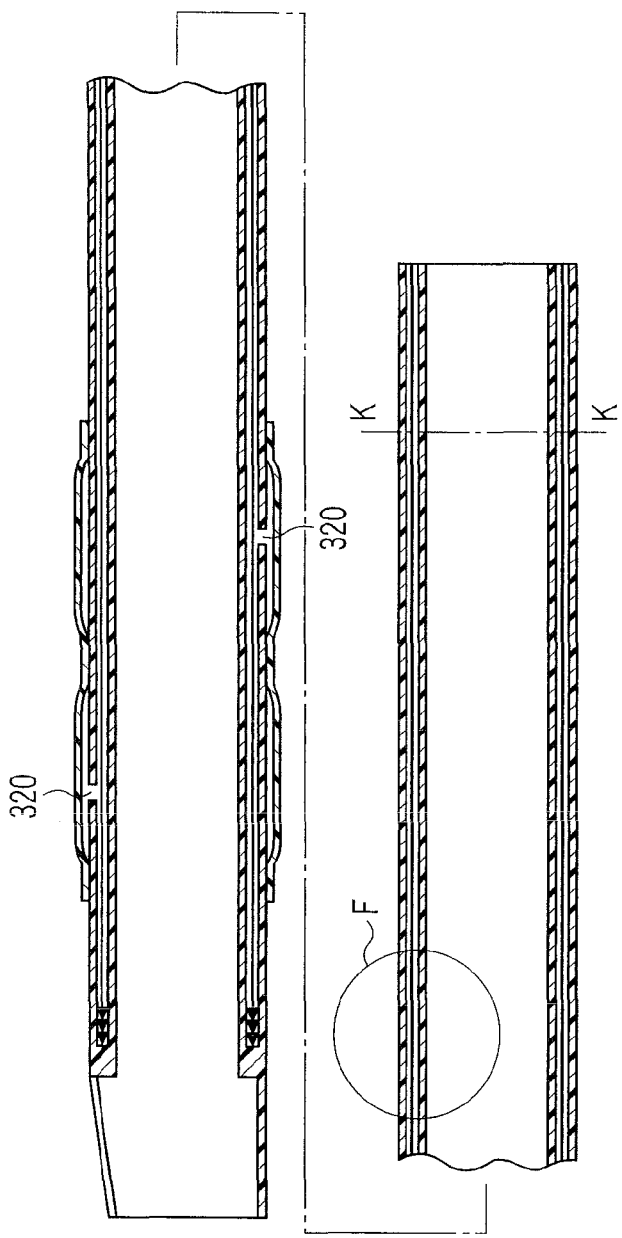
FIG. 108 is an enlarged cross-sectional view of a shaft portion of the over-tube of FIG. 107.

The over-tube 301 according to the first modification, the shaft portion 302 and the balloon portion 303 are integrally formed as shown in FIG. 107. Furthermore, as shown in FIGS. 108 and 110, two small lumens and one large lumen are formed to the shaft portion 302, and the end sides of the two small lumens are closed in the vicinity of the distal end of the over-tube 301, and the proximal end sides of the same communicate with the mouth ring 313. Moreover, the two small lumens communicate with the balloons 315a and 315b through a side hole 320 which is a radial hole formed to the wall portion of the over-tube 301. In addition, the operation wire 318 is inserted into each of the two small lumens, and the distal end portion of the operation wire 318 is fixed to the shaft portion 302 by the closed portion of the small lumens on the distal end side. Additionally, the proximal end side of each operation wire 318 is fixed to an angle operation portion 316 provided on an operation portion operation handle 306.

Figure 109:
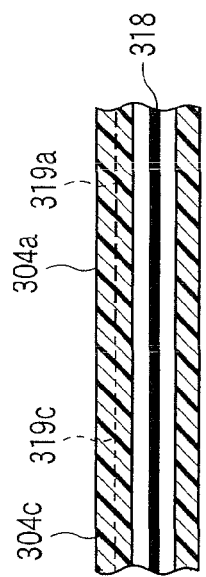
FIG. 109 is an enlarged cross-sectional view of a wall portion of the shaft portion indicated by a circle J in FIG. 108.
Figure 111:
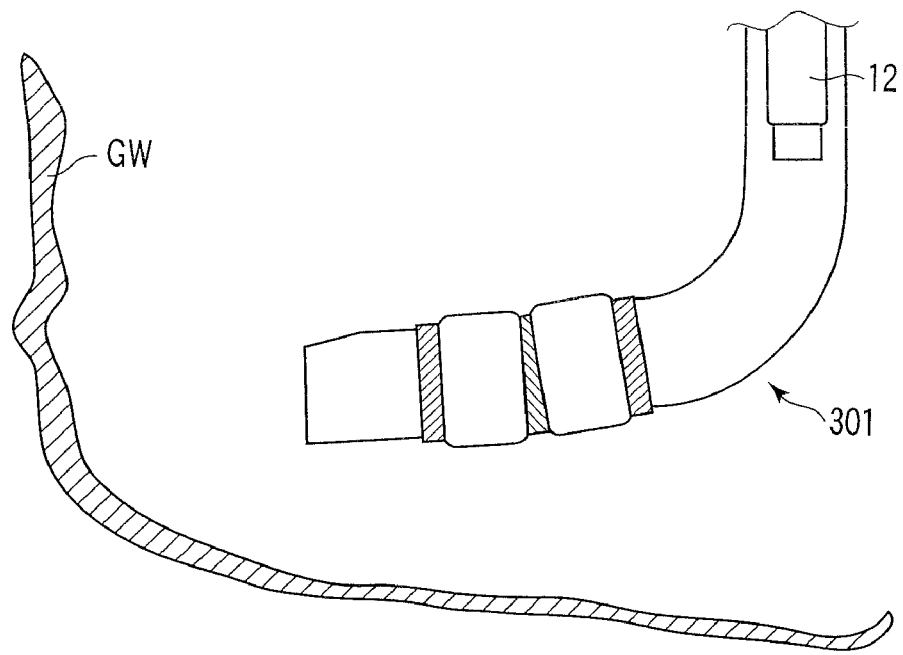
FIGS. 111 and 112 are conceptual views showing the part in the vicinity of the distal end portion, illustrating observation or treatment of the inside of the abdominal cavity by the over-tube of FIG. 107.

Further, as shown in FIG. 109, a reinforcing layer (for example, a coil made of stainless) is embedded in the wall portion of the shaft portion 302. In this modification, this reinforcing layer has reinforcing layers 319a and 319c which are respectively arranged on the proximal side portion 304a side and the distal end portion 304c side of the over-tube 301. The proximal end side reinforcing layer 319a is configured to have a larger wall thickness than the distal end side reinforcing layer 319c, and the distal end portion 304c is constituted to have the higher flexibility than the proximal side portion 304a as a whole. Here, the braided structure may be used for the reinforcing layer, and its material may be a resin or a thread.

Further, the angle operation portion 316 is rotatably provided to the operation portion operation handle 306 on the proximal end side of the shaft portion 302. An angle lock portion 317 which can restrict the rotational operation of the angle operation portion 316 is provided in contiguity with the angle operation portion 316.

Figure 112:
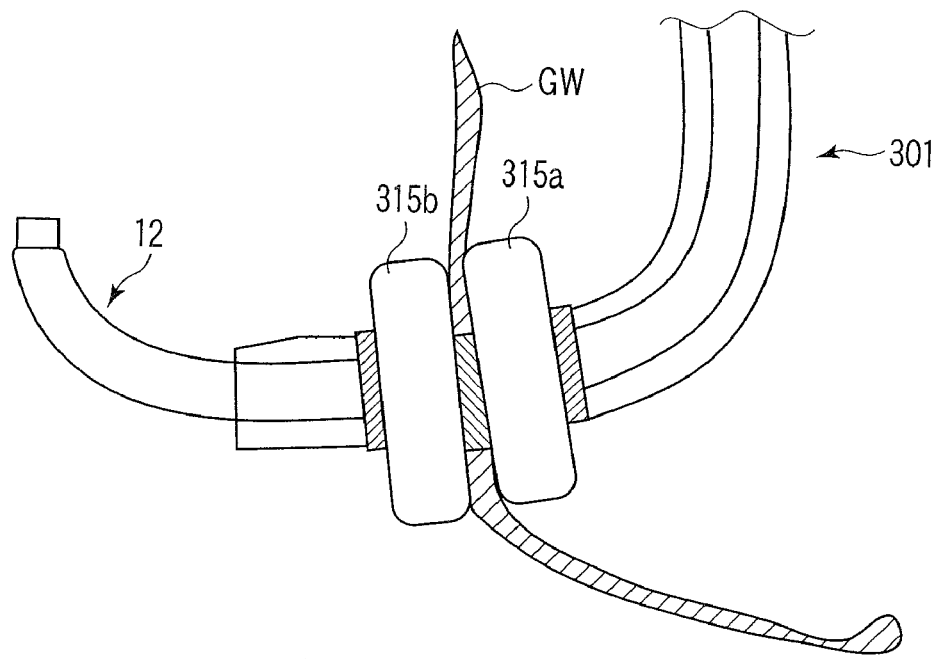
Figure 116:
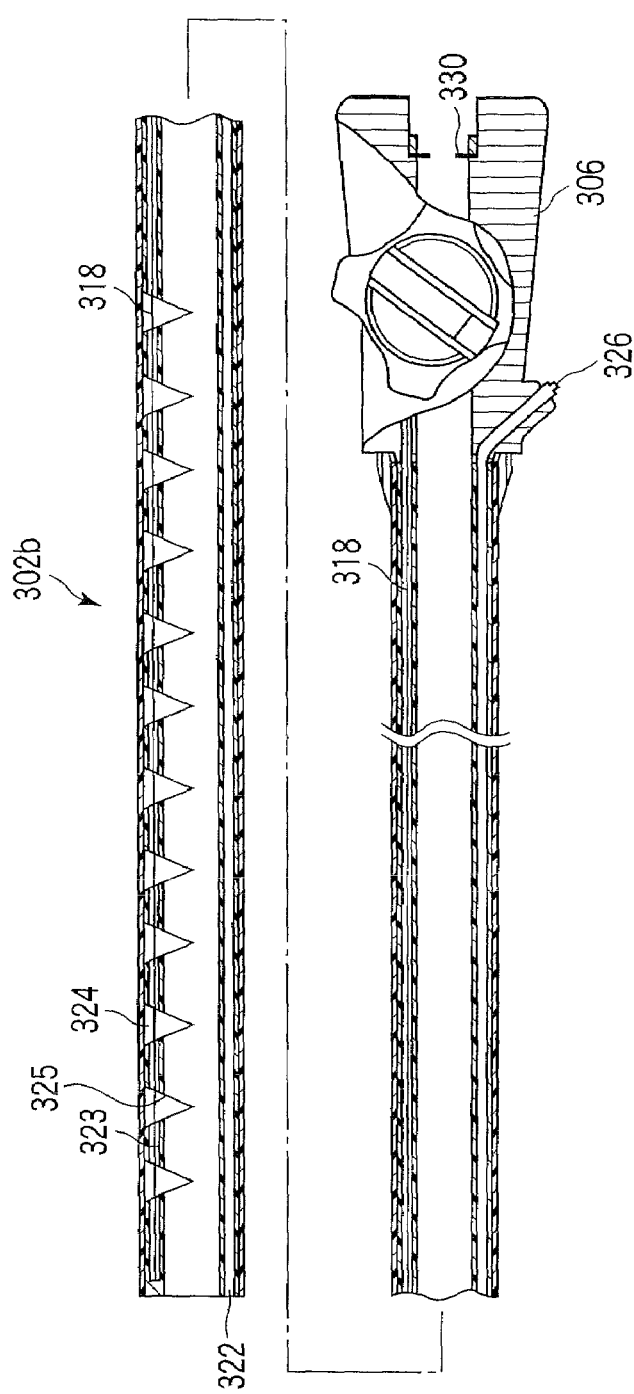
FIG. 116 is a vertical cross-sectional view of an inner tube module illustrated in FIG. 115.
Figure 117:
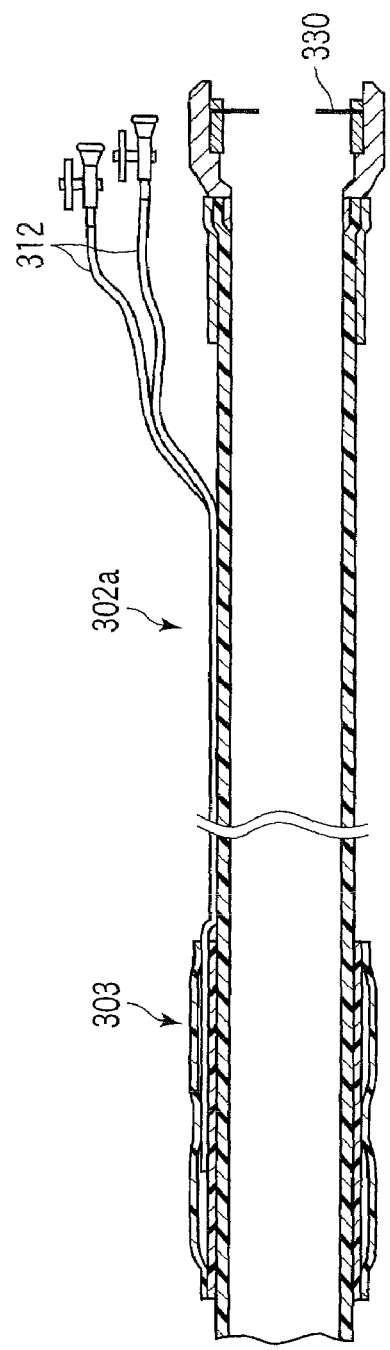
FIG. 117 is a vertical cross-sectional view of an outer tube module illustrated in FIG. 114.

The function different from that of the over-tube 301 according to the eighth embodiment will now be described with reference to FIGS. 112 and 113.

After the over-tube 301 of the endoscope according to this modification is orally inserted into the stomach, one of the two operation wires 318 extended so as to be opposed to the radial direction is pulled to the proximal end side and the other one is pushed to the distal end side by rotating the angle operation portion 316. As a result, as shown in FIG. 112, the shaft portion 302 itself is curved. In this modification, since an area of the shaft portion 302 on the proximal side portion 304a side has less flexibility than an area of the same on the distal end portion 304c side, the area on the proximal side portion 304a side is not curved but the area on the distal end portion 304c side is bent. By operating the angle lock portion 317 in the state that the distal end surface of the over-tube 301 is opposed to a desired gastric wall part, the curved shape of the over-tube 301 can be fixed. Thereafter, the endoscope 112 is advanced to a necessary part of the gastric wall GW by moving forward the endoscope 12 in the over-tube 301. Perforation and expansion of the gastric wall GW and fixation of the over-tube 301 to the gastric wall GW are similar to those in the eighth embodiment. FIG. 113 shows how the distal end portion of the over-tube 301 is fixed to the gastric wall GW and the endoscope 12 is operated in the abdominal cavity on the outer side of the stomach.

According to the over-tube 301 of this modification, in addition to the advantage obtained by the anastomosis system according to the eighth embodiment, the over-tube 301 can be directly curved since the over-tube 301 itself has the curvature operation mechanism. Therefore, there can be obtained the advantage that the over-tube 301 can be directed to a desired part with the higher accuracy than that of the eighth embodiment which indirectly bends the over-tube 301 by using the endoscope 12. Furthermore, since the over-tube 301 can be maintained in a necessary curved shape, the distal end portion of the over-tube 301 maintains the substantially vertical posture relative to the gastric wall GW even if the endoscope 12 is removed from the over-tube 301. Therefore, the burden on the gastric wall GW from the balloon portion 303 is small, and there is the advantage that the over-tube 301 can be further assuredly fixed to the gastric wall GW. Moreover, since the reinforcing member is provided, the follow-up property relative to rotation with the axial line of the over-tube 301 in the longitudinal direction at the center is improved, thereby improving the insertion and positioning property.

In addition, in this modification, since the liquid feed pipe used for expanding the balloons 315a and 315b is embedded in the shaft portion 302, the outside diameter of the part of the over-tube 301 other than the balloon portion 303 can be formed small, thereby obtaining the higher insertion property than that in the eighth embodiment.

[Second Modification of Over-Tube with Double Balloon]

FIGS. 113 to 120 show a second modification of the over-tube with the double balloon according to the present invention.

As shown in FIGS. 113 to 117, the over-tube 301 according to this modification is constituted by an outer tube module 302a, and an inner tube module 302b which can move forward and backward in the inner hole of the outer tube module 302a without restraint and is inserted with the air-tightness maintained.

The balloon portion 303 whose distal end is arranged at a position distanced from the distal end of the outer tube module 302a by approximately 10 mm is integrally jointed to the outer tube module 302a. An operation handle 306a having a valve 330 (see FIG. 117) arranged in the inner hole is provided on the proximal end side of the outer tube module 302a. The outer tube module 302a has the entire length set to approximately 700 mm, the inside diameter set to approximately 18 mm and the outside diameter set to approximately 20 mm.

The inner tube module 302b has a large-diameter inner hole at the center, a forceps channel 322, and a small-diameter inner hole having an operation wire 318 accommodated therein. The inner tube module 302b has at a position away from the distal end by approximately 30 mm to 180 mm an inner layer 323 (see FIG. 117) having a plurality of slits 325 extending in the circumferential direction of the inner tube module 302b formed thereto. The outer side of the inner layer 323 is covered with an outer layer 324 which is soft and capable of expanding and contracting. Each inner hole of the inner tube module 302b is shielded from the outside by the outer layer 324. Additionally, an operation handle 306 is provided on the proximal end side of the inner tube module 302b, and an angle operation portion 316 to which the proximal side portion of the operation wire 318 is connected is provided on the operation handle 306. Further, the proximal side portion of the forceps channel 322 is opened on the operation handle 306 as a forceps opening 326. The inner tube module 302b according to this embodiment has the entire length set to approximately 900 mm and the outside diameter set to approximately 17.5 mm.

Figure 118:
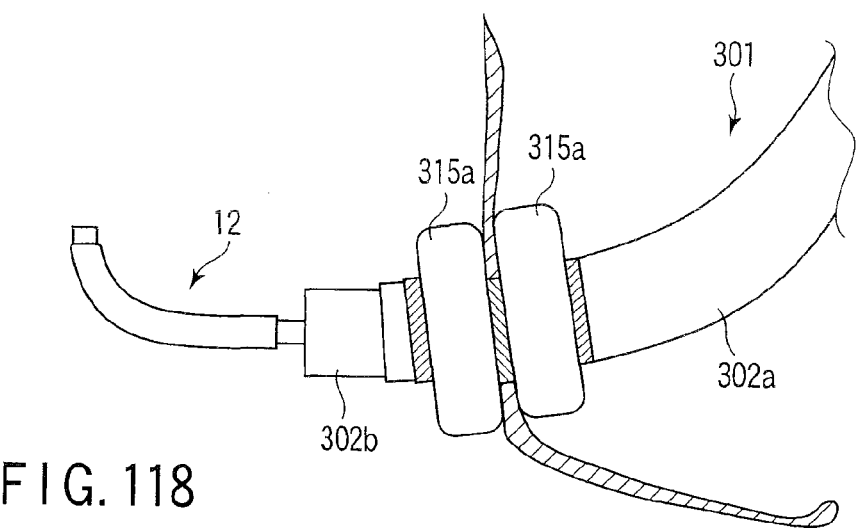
FIGS. 118 to 120 are conceptual views showing the part in the vicinity of the distal end portion, illustrating observation or treatment of the inside of the abdominal cavity by the over-tube depicted in FIG. 113.

Subsequently, the function of the over-tube 301 according to the second modification will now be described with reference to FIGS. 118 to 120.

The over-tube 301 according to this modification is put onto the outer side of the endoscope 12 in advance. Then, after orally inserting the endoscope 12 into the stomach, the over-tube 301 is moved forward along the endoscope 12, and the distal end portion of the over-tube 301 is inserted into the stomach. Subsequently, as similar to the eighth embodiment and the first modification, after providing the bore hole portion to the desired gastric wall GW, the over-tube 301 is fixed to the gastric wall GW by expanding the balloons 315a and 315b (FIG. 118). Here, when the endoscope 12 and the inner tube module 302b are moved forward with respect to the outer tube module 302a, the respective end portions of the endoscope 12 and the inner tube module 302b are caused to protrude to the abdominal cavity from the inside of the stomach.

Figure 119:
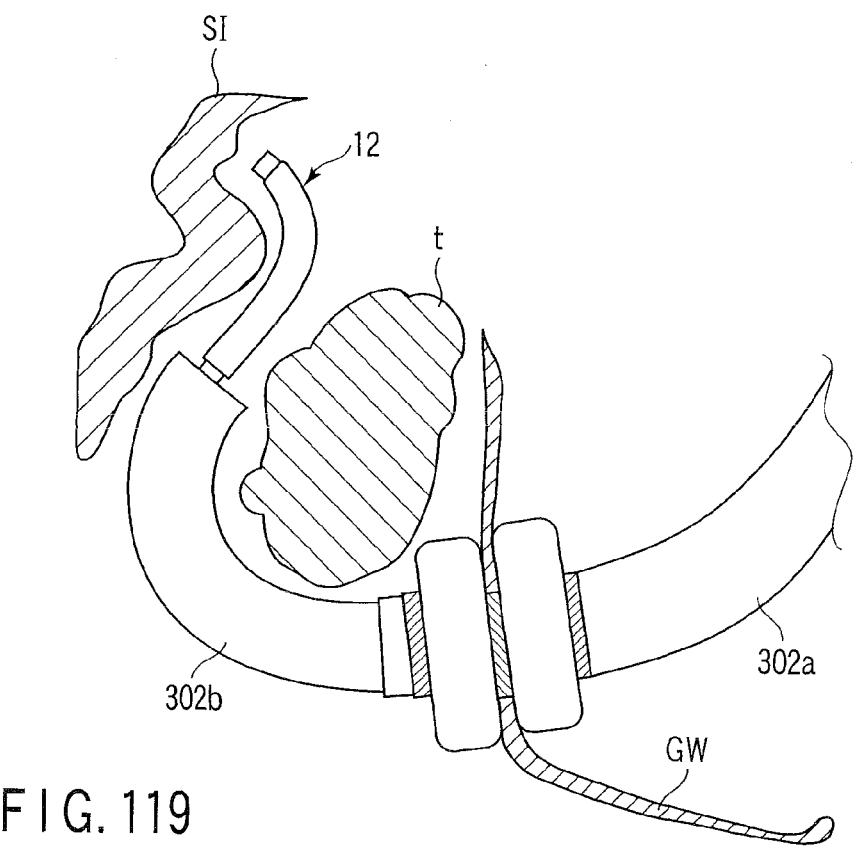
Figure 120:
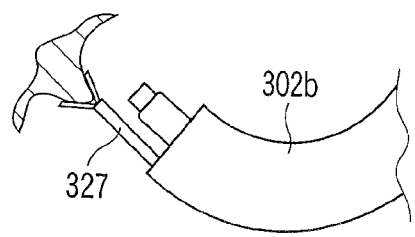

Further, as shown in FIG. 119, when the operation wire 318 is pulled by operating the angle operation portion 316 on the operation handle 306 of the inner tube module 302b, the widths of a plurality of slits 325 of the inner tube module 302b are narrowed. As a result, the inner tube module 302b is curved, and the endoscope 12 is guided to, e.g., a desired part of the intestine SI. Then, as shown in FIG. 120, the forceps 327 is inserted to the forceps channel 322 from the forceps opening 326 to protrude from the distal end of the inner tube module 302b, and the necessary treatment can be hence carried out to the intestine SI. Other functions are similar to those of the eighth embodiment and the first modification.

According to this modification, in addition to the advantages of the eighth embodiment and the first modification, the over-tube 301 can move the outer tube module 302a and the inner tube module 302b relatively in the axial direction, and the inner tube module 302b has the curvature function. Therefore, even if a desired intestine SI exists at a position away from the gastric wall bore hole portion, there can be obtained the advantage that the endoscope 12 can be guided by the over-tube 301. Furthermore, since the over-tube 301 has the forceps channel 322, there can be obtained the advantage that the treatment and the operation can be performed independently from the endoscope 12.

[Third Modification of Over-Tube]

FIGS. 121 to 129 show a third modification of the over-tube.

Figure 121:
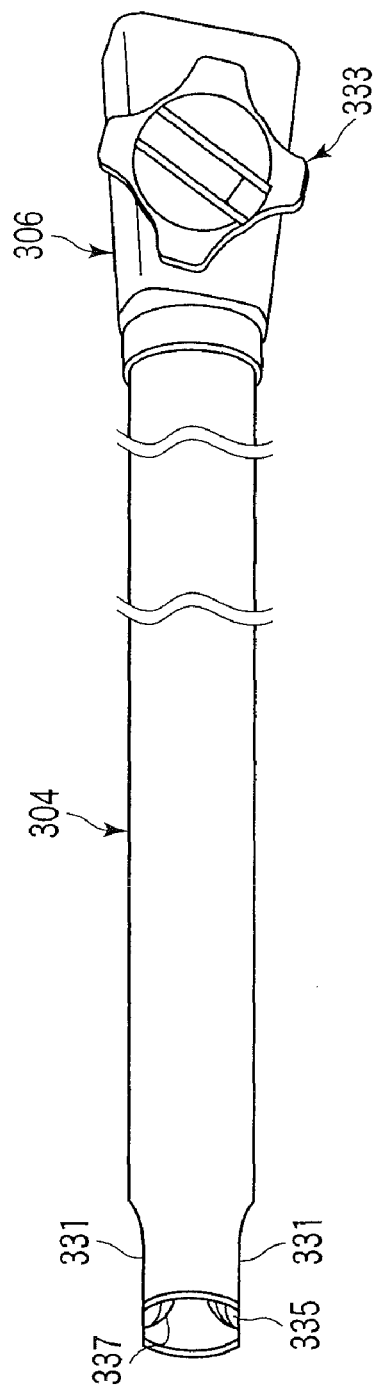
FIG. 121 is a perspective view for illustrating the overall structure of the over-tube according to a third modification.

As shown in FIG. 121, the over-tube 301 for the endoscope according to this modification has a flexible tubular main body 304. At least one slit 331 which is two slits opposed to each other preferably in the radial direction is formed at the distal end portion of the tubular main body 304. Further, in the inner hole at the distal end portion of the over-tube 301, a pair of shafts 336 each facing a horizontal axial direction vertical to the long axial direction of the over-tube 301 have their both ends fixed to the tubular main body 304 and are oppositely arranged in substantially parallel to each other. Furthermore, a pulley 339 is rotatably provided to the outer periphery of each of the shafts 336, and a curved needle 335 having a curved sharp end is attached to the pulley 339. This curved needle 335 has a concave hook 337 in the vicinity of the distal end thereof. The distal end slit 331 is provided at such a position as that it does not interfere with the wall of the tubular main body 304 even if the curved needle 335 rotates around the shafts 336. Moreover, one end of a needle operation wire 338 is connected to and wound around each pulley 339 in order to transmit the drive force from the proximal end side of the over-tube 301 to the curved needle 335, and the other end of each needle operation wire 338 is slidably inserted into a small hole of the tubular main body 304 and connected to the needle operation portion 333 on the operation handle 306 on the proximal end side.

Subsequently, referring to FIGS. 122 to 129, description will be given as to the function of the over-tube 301 for the endoscope according to this modification. The over-tube 301 is also provided with a suture closing function for the bore hole portion in addition to the fixation function relative to the gastric wall.

Figure 122:
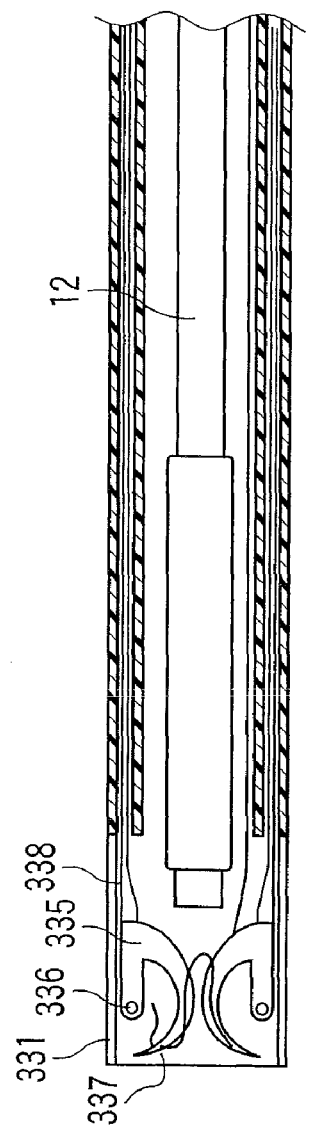
FIG. 122 is a vertical cross-sectional view showing the part in the vicinity of the distal end portion of the over-tube depicted in FIG. 121.

At first, as shown in FIGS. 122 and 123, one end of the suture thread 340 is determined as a free end, the intermediate portion of the same is caught on each hook 337 of the two curved needle 335, and the other end is caused to protrude from a non-illustrated opening portion on the proximal end side to the outside of the body through the inner hole of the tubular main body 304. Thereafter, with the curved needle 335 being retracted in the inner hole of the tubular main body 304, insertion into the stomach is carried out by oral forward movement. Then, perforation of the gastric wall GW and expansion of the bore hole portion can be similarly carried out as in the eighth embodiment.

Subsequently, with the distal end portion of the over-tube 301 being inserted in the bore hole portion, the needle operation portion 333 is rotated, and the two needle operation wires 338 are slid forward and backward. The pulley 339 and the curved needle 335 connected to the needle operation wire 338 are rotated, and the curved needle 335 is caused to protrude to the outer peripheral side as shown in FIG. 126 and pushed through the gastric wall GW. As a result, the distal end portion of the over-tube 301 is fixed to the gastric wall GW. When the curved needle 335 moves to the outer peripheral side, a large gap is formed in the inner hole at the distal end of the tubular main body 304. Then, the endoscope 12 is pushed out from the distal end portion of the tubular main body 304 by moving the endoscope 12 forward as shown in FIG. 125, and the endoscope 12 reaches the abdominal cavity. In this state, the diagnosis in the abdominal cavity is conducted.

Subsequently, as shown in FIG. 126, after moving the endoscope 12 backward to the proximal end side, the pulley 339 is rotated in accordance with the curved needle 335 until the hook 337 is accommodated in the inner hole of the tubular main body 304 by operating the needle operation portion 333. In this state, the grasping forceps 321 inserted into a non-illustrated endoscopic channel of the endoscope 12 is caused to protrude to the inside of the inner hole of the tubular main body 304 and hold the suture thread 340 positioned at the distal end of the curved needle 335. Then, after removing the curved needle 335 from the gastric wall GW by rotating the needle operation portion 333 in the backward direction, the both ends of the suture thread 340 are taken out to the outside of the body cavity from a non-illustrated opening portion of the operation handle by moving backward the grasping forceps 321 holding the suture thread 340 to the proximal end side as shown in FIGS. 127 and 128. Subsequently, after forming a Grinch knot by operating the both ends of the suture thread 340, this knot is fed to the distal end side by pulling one end. As a result, the diameter of the loop of the suture thread 340 piercing the gastric wall GW is reduced, and the gastric wall GW is sutured and closed as shown in FIG. 129.

At last, the suture thread 340 is cut by operating the cutting forceps which is inserted into the non-illustrated endoscopic channel of the endoscope 12 and caused to protrude from the distal end of the endoscope 12 while visually confirming the suture portion by again inserting the endoscope 12 into the over-tube 301. Then, the suture closing is terminated.

According to the over-tube 301 of this modification, not only the over-tube 301 is assuredly fixed to the gastric wall GW, but closing can be also easily performed according to needs.

[Fourth Modification of Over-Tube]

FIGS. 130 to 139 show a fourth modification of the over-tube.

As shown in FIGS. 131 to 134, a pair of snare lumens 345 which are opposed to each other preferably in the radial direction are integrally formed to the tubular main body 304. As shown in FIGS. 130 and 131, the distal end portion of each of the snare lumens 345 is opened on the proximal end side of the distal end slit 331, and the proximal end of the same communicates with the forceps opening 326 on the operation handle 306. A flexible snare tube 342 with a snare wire 343 having the loop shape at its distal end accommodated therein is inserted into each snare lumen 345 so as to be capable of being inserted/removed without restraint. The proximal end side of the snare tube 342 protrudes from the forceps opening 326, and the snare wire 343 protrudes from the proximal end of the snare tube 342. The proximal end portion of the snare wire 343 is jointed to the handle 344 (FIG. 131).

As shown in FIGS. 131 and 132, the central portion of a link 341 is fixed to each pulley 339. The end portion of the needle operation wire 338 is rotatably attached to each of the both end portions of each link 341.

The function of the over-tube 301 according to the fourth modification will now be described with reference to FIGS. 132 and 135 to 139.

The suture thread 340 having an engagement portion 346 (see FIGS. 137 and 138) at one end thereof is first caught on the curved needle 335 as similar to the third modification, and the distal end portion of the over-tube 301 is inserted into the bore hole portion of the gastric wall GW as similar to the third modification. Subsequently, the needle operation wire 338 is slid forward and backward by rotating the needle operation portion 333. The link 341 fixed to the distal end of the needle operation wire 338 rotates around the shaft 336, the curved needle 335 is pushed through the gastric wall GW, and the over-tube 301 is fixed to the gastric wall GW. The subsequent diagnosis and treatment are similar to those in the third modification.

Figure 135:
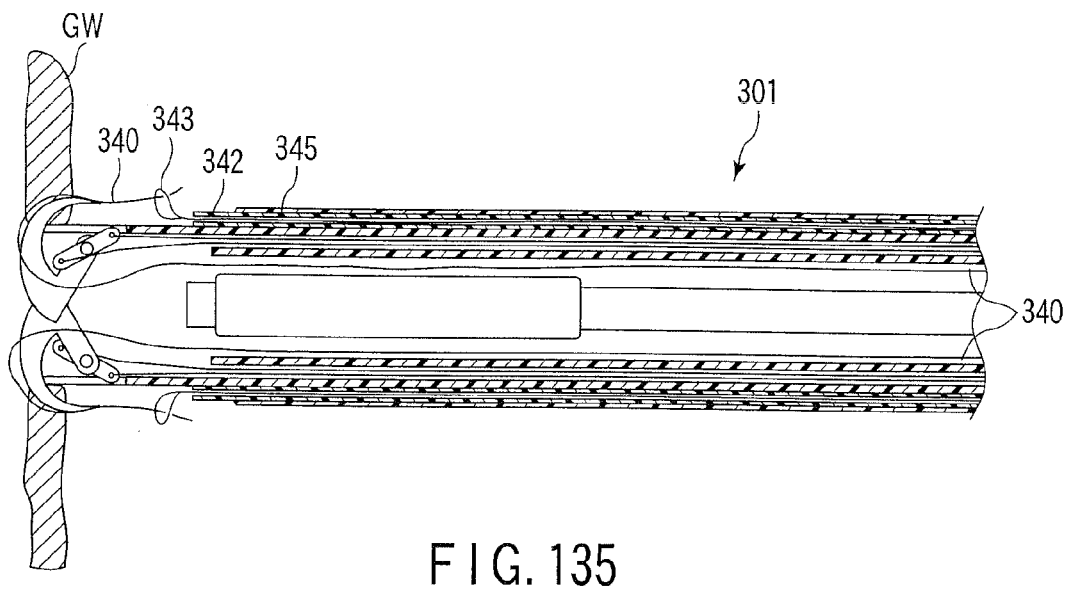
Figure 136:
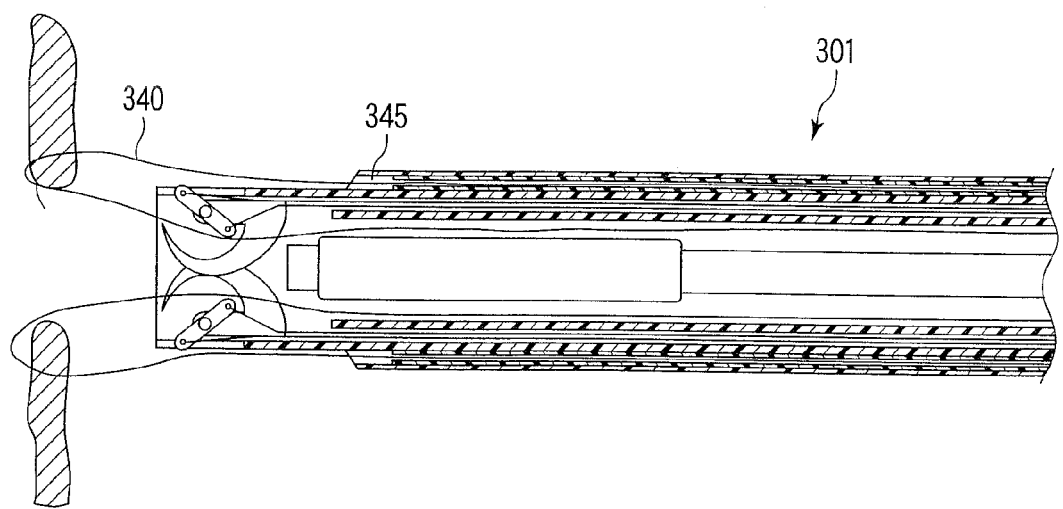

Then, as shown in FIG. 135, the snare tube 342 is caused to protrude from the distal end opening of the snare lumen 345 by moving forward the snare tube 342. Moreover, the distal end portion of the snare wire 343 protruding from the distal end opening of the snare tube 342 is extended and opened in the form of a loop by moving forward the snare wire 343. The suture thread 340 is arranged in the loop of the snare wire 343 by operating the snare tube 342 and the snare wire 343 forward and backward. In this state, when the snare tube 342 is moved forward, the suture thread 340 is fixed being sandwiched between the snare tube 342 and the snare wire 343.

Then, the curved needle 335 is removed from the gastric wall GW by operating the needle operation portion 333 to rotate. In addition, when the snare tube 342 and the snare wire 343 are moved back to the proximal end side and removed from the forceps opening 326, the free end side of the suture thread 340 is removed to the outside of the body cavity. When the suture thread 340 is further pulled to the proximal end side, the engagement portion 346 at the other end of the suture thread 340 is fed to the gastric wall GW (see FIGS. 137 and 138).

Then, the over-tube 301 is removed to the outside of the body wall, and the over-tube 301 and the endoscope 12 are again inserted into the stomach along the suture thread 340. Additionally, the end of the suture thread 440 removed to the outside the body cavity is knotted as similar to the third modification, and the suture and closing of the bore hole portion of the gastric wall GW are completed by feeding the knot (FIG. 139).

According to this modification, in addition to the advantages of the third modification, since the rotation drive portion of the curved needle 335 is constituted by the link 341, the larger running torque can be given to the curved needle 335, thereby facilitating the centesis operation using the curved needle 335. Further, since there are provided the snare tube 342 and the snare wire 343 as means for holding the suture thread 340, there can be obtained the advantage that the suture closing operation is enabled irrespective of presence/absence of the forceps channel of the endoscope 12.

Ninth Embodiment

FIG. 140 shows the anastomosis system according to a ninth embodiment of the present invention.

In the anastomosis system according to this embodiment, the procedures (7) and (8) illustrated in FIGS. 27 and 28 in the first embodiment are substituted by the procedures of stitching the small intestine SI by using the curved needle suture machine 3 and suspending the small intestine. Other procedures remain unchanged.

According to this embodiment, the small intestine suspending thread can be caused to readily penetrate.

10th Embodiment

The anastomosis system according to a 10th embodiment carries out at least one of the procedure (9) and the procedure (12) in the first embodiment by using the straight needle suture machine.

The straight needle suture machine for use in this anastomosis system has been developed in order to achieve the following objects. That is, the first object is to provide a suture machine which can assuredly suture a tissue in a living body. The second object is to provide a suture machine which can facilitate approach and confirmation of the centesis needle to a suture part and perform the subtle control. The third object is to provide a suture machine with the easy treatment operation and the short treatment time. The fourth object is to provide a suture machine with a range of a tissue in a living body being set as large as possible. Further, the fifth object is to provide a suture machine which reduces the pain given to a patient at the time of insertion into the body.

In order to achieve these objects, there is provided a tissue centesis system comprising a distal end portion to which at least one side opening is provided, a flexible sheath having a lumen into which the endoscope can be inserted, two centesis means which are arranged in the flexible sheath and have sharp edges which can move from a first position to the second position, and centesis operating means for moving the centesis means.

[First Example of Straight Needle Suture Machine]
(Structure)

FIGS. 141 to 170, FIG. 223 and FIGS. 236 to 238 show a first example of a suture machine, i.e., a tissue centesis system for use in the anastomosis system according to the 10th embodiment.

The suture machine, namely, the tissue centesis system 1001 according to the first example is constituted by an over-tube 1002, an operation portion 1003, inner sheaths 1004a and 1004b, a needle 1005, a needle 1006 and an endoscope 1009.

The over-tube 1002 is constituted by a sheath portion 1007 and an endoscope insertion portion 1008.

The sheath portion 1007 has an endoscopic lumen 1010 into which the endoscope 1009 can be slidably inserted and two needle lumens 1011a and 1011b into which the inner sheaths 1004a and 1004b can be slidably inserted, and has the flexibility so as to be capable of following up bend of the endoscope 1009.

The endoscopic lumen 1010 and the needle lumens 1011a and 1011b are formed by an outer wall 1015a and a partition 1014.

The endoscopic lumen 1010 and the needle lumens 1011a and 1011b link up at a position away from the distal end of the sheath portion 1007 toward the proximal side by a fixed distance L, and they form one treatment lumen 1012 on the distal end side from that position. It is desirable that the distance L falls within a range of 30 to 100 mm. The treatment lumen 1013 is surrounded by the outer wall 1015b.

The sheath portion 1007 is formed of a plastic material which is relatively soft and superior in the transparency such as polyurethane, polyvinyl chloride, polyurethane-based elastomer, polystyrene-based elastomer or polyolefin-based elastomer, and the outer side of the sheath portion 1007 can be observed by the endoscope 1009 inserted into the endoscopic lumen 1010 through the sheath portion 1007.

Although it is more preferable that the entire sheath portion 1007 is transparent, parts other than a range between the distal end side which is away from the distal end of the later-described side opening 1013 by approximately 5 cm and the proximal side which is away from the proximal end of the side opening 1013 by approximately 5 cm may not be transparent in the worst case.

The sheath portion 1007 has the outside diameter which allows insertion into the body of a patient. This is approximately 10 to 25 mm, and preferably approximately 15 to 18 mm.

Figure 151:
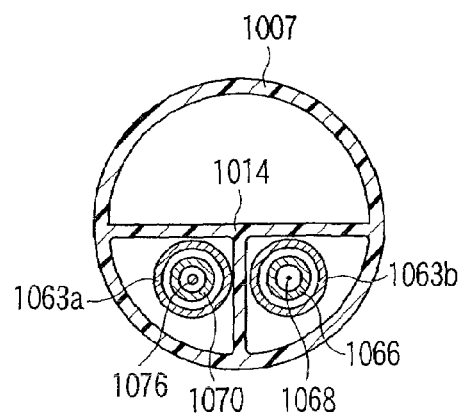

Each of the endoscopic lumen 1010 and the needle lumens 1011a and 1011b may have the inside diameter which allows insertion of the endoscope 1009 and the inner sheaths 1004a and 1004b, and such an inside diameter may have any shape shown in FIGS. 151 and 223.

A wall thickness of each of the partition 1014 and the outer walls 1015a and 1015b is approximately 0.2 to 3 mm, and more preferably 0.5 to 1.5 mm.

It is desirable that the distal end of the sheath portion 1007 is soft in order to facilitate insertion, and the distal end side can be made flexible by making the wall thickness of the outer wall 1015b smaller than that of the outer wall 1015a.

The needle lumens 1011a and 1011b extend substantially in parallel to each other in the sheath portion 1007.

A gap between the centers of the needle lumens 1011a and 1011b is fixed, it is set in such a manner that a gap between ends of the needles 1005 and 1006 inserted into the needle lumens 1011a and 1011b becomes fixed in a range of approximately 5 to 20 mm.

A side opening 1013 is provided on the outer wall 1015b close to the distal end side away from the distal end openings of the endoscopic lumen 1010 and the needle lumens 1011a and 1011b.

A distance from the distal end openings of the endoscopic lumen 1010 and the needle lumens 1011a and 1011b from the proximal side of the side opening 1013 is desirably approximately 5 mm.

The central axis of the side opening 1013 in the longitudinal direction is provided so as to be positioned in the middle of the needle lumen 1011a and the needle lumen 1011b.

Although it is desirable that the shape of the side opening 1013 is a rectangle which extends in the longitudinal direction as shown in FIG. 142, this shape may be an ellipse or a circle. When the side opening 1013 is rectangular, corners of the side opening 1013 may be rounded.

The length of the side opening 1013 in the longitudinal direction is 5 to 30 mm, and approximately 10 to 20 mm is desirable.

The width of the side opening 1013 is 3 to 23 mm, and approximately 13 to 16 mm is desirable.

Furthermore, it is more preferable if marking with a color such as blue or green which can be easily recognized in the body is applied along the outer periphery of the side opening 1013 so that the side opening 1013 can be readily recognized in an endoscopic image.

Moreover, it is desirable that the distal end of the sheath portion 1007 has a shape which can be readily inserted into the body.

This shape may be a tapered shape as shown in FIG. 155A.

In addition, it may be a shape to which a notch is provided to a part of the outer periphery of the distal end as shown in FIG. 155B.

Additionally, as shown in FIG. 155C, strip-like cut portions may be provided to the entire circumference of the distal end.

Further, as shown in FIG. 155D, it may be a shape that the distal end is obliquely cut.

Furthermore, the proximal ends of the endoscopic lumen 1010 and the needle lumens 1011a and 1011b are provided at positions on the distal end side away from the proximal end of the sheath portion 1007 by approximately 5 to 30 mm, and the proximal side forms a sheath connection portion 1017 having a connection lumen 1016.

Moreover, sheath slits 1030a and 1030b which communicate with the needle lumens 1011a and 1011b are provided in the vicinity of the proximal ends of the needle lumens 1011a and 1011b.

The endoscope insertion portion 1008 is connected to the proximal end of the sheath portion 1007.

The endoscope insertion portion 1008 is constituted by a holding member 1018, a sheath fixing member 1019, a valve 1020 and a valve fixing member 1021, and an endoscope insertion opening 1022 is formed at the proximal end.

The holding member 1018 is an annular member having an inner cavity, and an extended-diameter portion 1023, a female screw portion 1024, a tapered portion 1025 and a reduced-diameter portion 1026 are provided on the inner surface of the holding member 1018.

The inside diameter of the reduced-diameter portion 1026 is slightly larger than the outside diameter of the sheath portion 1007, and the sheath portion 1007 can be inserted into the reduced-diameter portion.

Further, slits 1032a and 1032b which extend in the longitudinal direction are provided to the holding member 1018.

The slits 1032a and 1032b are set to such size and positions as that the slits are opened on sheath slits 1030a and 1030b when the holding member 1018 is attached to the sheath portion 1007. It is desirable that the gap and the width of the slits 1032a and 1032b are equal to or above the gap and width of the sheath slits 1030a and 1030b of the sheath portion 1007.

A sheath fixing member 1019 has a cylindrical shape with the inner cavity into which the endoscope 1009 can be inserted. A distal end tapered portion 1027, a straight portion 1028 and a proximal male screw portion 1029 are provided on the outer surface of the sheath fixing member 1019.

A taper angle of the distal end tapered portion 1027 is substantially the same as an angle of the tapered portion 1025.

The distal end tapered portion 1027 and the straight portion 1028 of the holding member 1018 are press-fitted into the connection lumen 1016, and the proximal male screw portion 1029 is screwed into a female screw portion 1024 in this state. When the holding member 1018 is press-fitted into the sheath connection portion 1017, the slits 1032a and 1032b are attached so as to be positioned on sheath slits 1030a and 1030b.

As a result, the sheath connection portion 1017 is held between the tapered portion 1025 and the distal end tapered portion 1027 and fixed to the holding portion 1018.

A valve 1020 is fitted to the inner side of the extended-diameter portion 1023 on the proximal side of the sheath fixing member 1019. Furthermore, a valve fixing member 1021 is screwed in the proximal side of the valve 1020 and fixed to the extended-diameter portion 1023 by using an adhesive agent or the like. The valve 1020 is held between the sheath fixing member 1019 and the valve fixing member 1021 and fixed to the holding portion 1018.

The valve 1020 has a ring-like shape and is formed of various kinds of rubber such as silicone rubber, fluorine rubber or various kinds of thermoplastic elastomer.

The inside diameter of the valve 1020 is smaller than the outside diameter of the endoscope 1009 so that the air-tightness can be maintained between the valve 1020 and the endoscope 1009 when the endoscope 1009 is inserted.

The wall thickness of the valve 1020 is 0.5 to 5 mm, and approximately 1 mm is desirable.

The valve fixing member 1021 has an inner cavity which is larger than the outside diameter of the endoscope 1009, and the outside diameter is slightly smaller than the inside diameter of the extended-diameter portion 1023.

The valve fixing member 1021 and the extended diameter portion 1023 may be fixed by providing a screw portion to each of them and fastening such screws.

Although the holding portion 1018, the sheath fixing member 1019 and the valve fixing member 1021 are formed of various kinds of metal such as stainless or aluminium or various kinds of plastic materials such as polypropylene, ABS, polycarbonate, polyacetal or polysulfone, it is more preferable to form these members by using a plastic material having the light weight and the rigidity.

A protection tube 1031 is fixed to the distal end of the holding portion 1018. The protection tube 1031 extends to the distal end side of the holding portion 1018 and covers the sheath portion 1007, which prevents the sheath portion 1007 from kinking at the distal end of the holding portion.

The protection tube 1031 is formed of various kinds of plastic such as polyurethane, PVC, silicone, fluorocarbon resin, polyolefin-based resin or the like.

The protection tube 1031 may be a heat contraction tube.

The length from the distal end of the sheath portion 1007 to the distal end of the protection tube 1031 is approximately 0.3 to 2 m, and it is preferably approximately 1 m.

Connection pipes 1033a and 1033b are connected to the inside of the respective needle lumens 1011a and 1011b through sheath slits 1030a and 1030b and slits 1032a and 1032b by adhesion or the like.

The connection pipes 1033a and 1033b are bent in the form of S as shown in FIG. 159 or bent in the dogleg form.

The connection pipes 1033a and 1033b are formed of metal such as stainless. Their inside diameters are larger than the outside diameter of each of the later-described inner sheaths 1004a and 1004b so that the inner sheaths 1004a and 1004b can be smoothly inserted into these connection pipes.

Further, a range from the ends of the sheath slits 1030a and 1030b to the proximal ends of the needle lumens 1011a and 1011b is a sealing portion 1034 in which an adhesive agent or filler is filled, and this portion maintains the air-tightness in the sheath portion 1007 at the sheath slits 1030a and 1030b.

At this moment, it is desirable that the proximal end of the sealing portion 1034 is tapered. In this case, when the endoscope 1009 is inserted into the over-tube 1002, it can be smoothly inserted without the distal end of the endoscope 1009 being caught by the sealing portion 1034.

Connection ports 1035a and 1035b are connected to the proximal ends of the connection pipes 1033a and 1033b.

The connection ports 1035a and 1035b have inner cavities 1036a and 1036b so that the inner sheaths 1004a and 1004b can be smoothly inserted into these cavities.

Furthermore, threaded holes 1037a and 1037b are provided on the side walls of the connection ports 1035a and 1035b, and set screws 1038a and 1038b are screwed into these holes. End plugs 1040a and 1040b of connection sheaths 1039a and 1039b of the later-described operation portion 1003 are detachably fixed to the inner cavities 1036a and 1036b by the set screws 1038a and 1038b.

The operation portion 1003 is constituted by the connection sheaths 1039a and 1039b, inner sheath sliders 1042a and 1042b, needle sliders 1043a and 1043b, a base 1044, a grip 1045, and slider receivers 1046a and 1046b.

The grip 1045 is fixed to the lower surface of the base 1044. The grip 1045 is positioned on the central axis (longitudinal direction) of the base 1044. Although the grip 1045 may have any shape as long as an operator can readily get a grip on it, the shape which is gently curved toward the proximal side is preferable.

The two slider receivers 1046a and 1046b are aligned and fixed on the top face of the base 1044 with a gap therebetween. At this moment, the slider receivers 1046a and 1046b are fixed at positions away from the central axis (longitudinal direction) of the base 1044 by the equidistance.

It is desirable that the slider receivers 1046a and 1046b are arranged in parallel to each other or in such a manner that a distance between the proximal ends is larger than a distance between the ends.

The slider receivers 1046a and 1046b have annular housings 1047a and 1047b, and annular rings 1048a and 1048b are connected to the proximal ends of these housings.

Male thread portions and female thread portions are respectively provided on the proximal end outer surfaces of the housings 1047a and 1047b and the distal end inner surfaces of the rings 1048a and 1048b, and these thread portions are screwed to each other.

O-ring receiving planes 1049a and 1049b are provided on the inner surfaces of the rings 1048a and 1048b. Moreover, O-rings 1050a and 1050b are held between the proximal ends of the housings 1047a and 1047b and the O-ring receiving planes 1049a and 1049b.

Connection sheaths 1039a and 1039b are connected to the ends of the housings 1047a and 1047b. Connection between the housings 1047a and 1047b and the connection sheaths 1039a and 1039b may or may not be detachable.

The connection sheaths 1039a and 1039b are hollow and have the flexibility.

The connection sheaths 1039a and 1039b are formed by a tube made of plastic resin such as fluorocarbon, polyethylene, polyamide, polyimide, polyurethane or various kinds of thermoplastic elastomer or a metal coil. A plastic tube may be put on the outer side of the metal coil. A plastic tube with the metal mesh may be used in order to avoid kinking.

It is desirable that each of the connection sheaths 1039a and 1039b has the inside diameter of 1 to 2.5 mm, the outside diameter of approximately 1.5 to 3 mm and the length of approximately 0.3 to 1 m.

End plugs 1040a and 1040b are fixed to the ends of the connection sheaths 1039a and 1039b.

The inside diameter of each of the end plugs 1040a and 1040b is substantially the same as the inside diameter of each of the connection sheaths 1039a and 1039b.

Annular grooves 1051a and 1051b are provided on the outer surfaces of the end plugs 1040a and 1040b. When the end plugs 1040a and 1040b are fitted into the inner cavities 1036a and 1036b of the connection ports 1035a and 1035b and the set screws 1038a and 1038b are fastened, the ends of the set screws 1038a and 1038b are fitted into annular grooves 1051a and 1051b.

Slits 1052a and 1052b which extend in the longitudinal direction from the proximal end to the vicinity of the distal end are provided on the side walls of the housings 1047a and 1047b.

The inner sheath sliders 1042*a* and 1042*b* are slidably and detachably arranged in the inner cavities of the housings 1047*a* and 1047*b*.

The inner sheath sliders 1042*a* and 1042*b* are formed by annular inner sheath housings 1053*a* and 1053*b*, inner sheath rings 1054*a* and 1054*b* connected to the proximal ends of these housings, and O-rings 1055*a* and 1055*b* held between the proximal ends of the inner sheath housings 1053*a* and 1053*b* and the inner sheath rings 1054*a* and 1054*b*.

The method of connecting the inner sheath housings 1053*a* and 1053*b*, the inner sheath rings 1054*a* and 1054*b* and the O-rings 1055*a* and 1055*b* has the structure similar to the slider receivers 1046*a* and 1046*b*.

The outside diameter of each of the inner sheath housings 1053*a* and 1053*b* is slightly larger than the inside diameter of each of the O-rings 1050*a* and 1050*b*. When the inner sheath sliders 1042*a* and 1042*b* are arranged in the housings 1047*a* and 1047*b*, the outer surfaces of the inner sheath housings 1053*a* and 1053*b* are appressed against the O-rings 1050*a* and 1050*b*, thereby maintaining the air-tightness between them.

Threaded holes 1056*a* and 1056*b* are provided on the side surfaces of the inner sheath housings 1053*a* and 1053*b*, and set screws 1057*a* and 1057*b* are provided.

The set screws 1057*a* and 1057*b* have screw portions 1058*a* and 1058*b* and screw knobs 1059*a* and 1059*b*. The screw portions 1058*a* and 1058*b* partially pierce respective slits 1052*a* and 1052*b*.

When the screw knobs 1059*a* and 1059*b* are unfastened, the lower surfaces of the screw knobs 1059*a* and 1059*b* are away from the outer surfaces of the housings 1047*a* and 1047*b*, and the screw portions 1058*a* and 1058*b* can slide in the slits 1052*a* and 1052*b* without restraint. At this moment, the inner sheath housings 1053*a* and 1053*b* can slide in the housings 1047*a* and 1047*b*.

When the screw portions 1058*a* and 1058*b* are fastened, the lower surfaces of the screw knobs 1059*a* and 1059*b* pushes the outer surfaces of the housings 1047*a* and 1047*b*, and the inner sheath housings 1053*a* and 1053*b* are fixed to the housings 1047*a* and 1047*b*.

The rings 1048*a* and 1048*b* and the O-rings 1050*a* and 1050*b* are attached so as to be positioned on the circumference between the set screws 1057*a* and 1057*b* of the inner sheath sliders 1042*a* and 1042*b* and the inner sheath rings 1054*a* and 1054*b* in advance.

When the rings 1048*a* and 1048*b* are removed, the inner sheath sliders 1042*a* and 1042*b* can be removed from the inside of the housings 1047*a* and 1047*b*.

Although a sliding range of the inner sheath sliders 1042*a* and 1042*b* is determined in accordance with the length of the slits 1052*a* and 1052*b*, approximately 10 to 30 mm is desirable.

Connection female screws 1060*a* and 1060*b* are provided on the connection inner surfaces of the inner sheath housings 1053*a* and 1053*b* so that the inner sheaths 1004*a* and 1004*b* can be detachably connected.

Needle sliders 1043*a* and 1043*b* are slidably arranged to the inner cavities of the inner sheath sliders 1042*a* and 1042*b*.

The needle sliders 1043*a* and 1043*b* have the inner cavities, and needle connection ports 1061*a* and 1061*b* having the outside diameter larger than other parts are formed to the proximal ends of these sliders.

The inner surfaces of the needle connection ports 1061*a* and 1061*b* are lure-tapered.

Annular stoppers 1062*a* and 1062*b* are fixed to the distal end circumferences of the needle sliders 1043*a* and 1043*b*.

The outside diameter of each of the stoppers 1062*a* and 1062*b* is larger than the inside diameter of each of the O-rings 1055*a* and 1055*b*. When the needle sliders 1043*a* and 1043*b* are pulled toward the proximal side, the stoppers 1062*a* and 1062*b* come into contact with the O-rings 1055*a* and 1055*b*, thereby preventing the sliders from coming off.

Moreover, when the needle sliders 1043*a* and 1043*b* are moved toward the distal end side, the distal end surfaces of the needle connection ports 1061*a* and 1061*b* come into contact with the proximal surfaces of the sheath rings 1054*a* and 1054*b*, thereby preventing these sliders from further moving.

Approximately 20 to 80 mm is desirable for the sliding range of each of the needle sliders 1043*a* and 1043*b*.

The outside diameter of each of the needle sliders 1043*a* and 1043*b* other than the parts of the needle connection ports 1061*a* and 1061*b* is slightly larger than the inside diameter of each of the O-rings 1055*a* and 1055*b*, thereby maintaining the air-tightness between them.

The O-rings 1050*a* and 1050*b* and the O-rings 1055*a* and 1055*b* are formed of various kinds of rubber such as silicone rubber or fluorine rubber or various kinds of thermoplastic elastomer.

In addition, among the members constituting the operation portion 1003, the members other than the connection sheaths 1039*a* and 1039*b*, the O-rings 1050*a* and 1050*b* and the O-rings 1055*a* and 1055*b* are formed of various kinds of metal materials such as stainless or aluminium or various kinds of plastic materials such as ABS, polycarbonate, polyacetal or polysulfone, but it is more preferable that these member are formed of a plastic material having the light weight and the rigidity.

The inner sheaths 1004*a* and 1004*b* are constituted by tubes 1063*a* and 1063*b*, inner sheath pipes 1064*a* and 1064*b* and connection male screws 1065*a* and 1065*b*.

The tubes 1063*a* and 1063*b* are hollow and have the flexibility. They are formed by, e.g., tubes made of plastic such as fluorocarbon resin, polyethylene, polyamide, polyimide, polyurethane or various kinds of thermoplastic elastomer or a metal coils. Plastic tubes with the metal mesh may be used in order to prevent kinking.

Inner sheath pipes 1064*a* and 1064*b* are connected to the proximal ends of the tubes 1063*a* and 1063*b*.

Connection male screws 1065*a* and 1065*b* are connected to the proximal ends of the inner sheath pipes 1064*a* and 1064*b*.

The connection male screws 1065*a* and 1065*b* can be detachably connected to the connection female screws 1060*a* and 1060*b* of the inner sheath housings 1053*a* and 1053*b*.

The outside diameters of the tubes 1063*a* and 1063*b*, the inner sheath pipes 1064*a* and 1064*b* are smaller than the inner cavities of the needle lumens 1011*a* and 1011*b*, the connection pipes 1033*a* and 1033*b*, the connection ports 1035*a* and 1035*b*, the end plugs 1040*a* and 1040*b*, the connection sheaths 1039*a* and 1039*b* and the slider receivers 1046*a* and 1046*b*.

The outside diameter of each of the connection male screws 1065*a* and 1065*b* is smaller than the inner cavity of each of the slider receivers 1046*a* and 1046*b*.

The inside diameters of the tubes 1063*a* and 1063*b*, the inner sheath pipes 1064*a* and 1064*b* and the connection male screws 1065*a* and 1065*b* allow the needle 1005 and the needle 1006 to be smoothly inserted.

It is desirable that the tubes 1063*a* and 1063*b* are formed to have the inside diameter of 0.5 to 2 mm and the outside diameter of approximately 1 to 2.5 mm.

The length of each of the tubes 1063*a* and 1063*b* is set in such a manner that the distal ends of the tubes 1063*a* and 1063*b* are positioned on the proximal side away from the distal end openings of the needle lumens 1011a and 1011b when the inner sheath sliders 1042a and 1042b are completely pulled out from the slider receivers 1046a and 1046b and that the distal ends of the tubes 1063a and 1063b are positioned on the distal end side away from the proximal end of the side opening 1013 by approximately 3 to 15 mm when the inner sheath sliders 1042a and 1042b are caused to protrude until they completely come into contact with the slider receivers 1046a and 1046b.

Incidentally, the inner sheaths 1004a and 1004b and the inner sheath sliders 1042a and 1042b are not necessarily the required structures, and they may not be provided to the tissue centesis system 1001.

The needle 1005 is constituted by a needle main body 1066 and a needle grip 1067.

The needle 1005 can be inserted into the inner sheath 1004 from the needle connection port 1061 of one of the needle sliders 1043a and 1043b.

The needle grip 1067 is connected to the proximal end of the needle main body 1066, and both the needle main body 1066 and the needle grip 1067 have the inner cavities.

The needle main body 1066 is formed by a metal pipe material such as stainless or nitinol which can resist push from the proximal side at the time of centesis and has the flexibility which can follow up bend of the connection sheath 1039 or the needle lumen 1011.

The needle main body 1066 has a sharp-pointed end so as to be capable of performing centesis to a tissue in the body cavity.

The needle main body 1066 is formed to have the inside diameter of approximately 0.5 to 1.5 mm and the outside diameter of approximately 0.7 to 2 mm.

In order to cause the distal end of the needle main body 1066 to readily protrude from the distal end of the inner sheath 1004, it is desirable that the outside diameter of the needle main body 1066 is close to the inside diameter of the inner sheath 1004 as much as possible in the range allowing sliding with the inner sheath 1004.

A lure taper is provided to the distal end outer periphery of the needle grip 1067 so that it can be detachably fitted/fixed to the lure taper of the inner cavity of the needle connection port 1061.

The needle grip 1067 is formed of various kinds of metal materials such as stainless steel or aluminium or various kinds of plastic materials such as polypropylene, ABS, polycarbonate, polyacetal or polysulfone.

Further, the length of the needle 1005 is set in such a manner that the distal end of the needle main body 1066 is positioned on the proximal side away from the distal end of the tube 1063b when the needle slider 1043b having the needle 1005 attached thereto is completely pulled out from the inner sheath slider 1042b. Additionally, the length of the needle 1005 is set in such a manner that the distal end of the needle main body 1066 is positioned on the distal end side away from the distal end of the side opening 1013 by approximately 5 to 25 mm when the inner sheath slider 1042b is completely pulled out from the slider receiver 1046b and the needle slider 1043b is caused to protrude until it completely comes into contact with the inner sheath slider 1042b.

A suture thread 1068 is loaded in the needle 1005 so as to be capable of moving forward and backward in advance. The distal end of the suture thread 1068 is loaded so as to be positioned on the proximal side away from the distal end of the needle main body 1066.

The proximal end of the suture thread 1068 is exposed from the needle grip 1067 to the proximal side, and the exposed length is set so as to be longer than the entire length of the needle 1005 by approximately 50 cm.

Further, a cap 1155 is provided in the vicinity of the proximal end of the grip 1067.

The cap 1155 can be detachably attached to an opening on the proximal side of the grip 1067, and the opening can be sealed when the cap is attached.

The cap 1155 is formed of various kinds of rubber such as silicone rubber or fluorine rubber or a plastic material such as polypropylene, polyethylene, polystyrene or various kinds of thermoplastic elastomer.

With the suture thread 1068 being loaded to the needle 1005, the cap 1155 is put on the opening on the proximal side of the grip 1067.

As a result, the suture thread 1068 is held between the cap 1155 and the grip 1067 and detachably connected to the needle. At the same time, the air-tightness in the opening on the proximal side of the grip 1067 can be maintained.

Furthermore, a knot 1069 is formed in the vicinity of the distal end of the suture thread 1068.

As the suture thread 1068, one generally used for the surgical operation may be employed, and it is made of, e.g., nylon or silk.

The diameter of the suture thread 1068 is approximately 0.2 to 0.5 mm, and approximately 0.25 to 0.3 mm is particularly preferable.

It is preferable that the outside diameter of the knot 1069 is as large as possible in the range which can allow insertion into the needle 1005.

Moreover, it is preferable that the suture thread 1068 has a color which can be recognized in an endoscopic image in the body cavity, and a color such as blue or green is particularly preferable.

An extended-diameter member 1041 which is made of metal or a plastic material and has a ball-like shape may be fixed to the distal end of the suture thread 1068 in place of providing the knot 1069 in the vicinity of the distal end of the suture thread 1068.

The shape of the extended-diameter member 1041 does not have to be a ball-like shape as long as the extended-diameter member 1041 has the outside diameter which allows insertion into the needle main body 1066.

The needle 1006 is constituted by a needle main body 1070, a needle grip distal portion 1071, a needle grip proximal portion 1072, an O-ring 1073 and thread grasping forceps 1074.

The needle 1006 can be inserted into the inner sheath 1004 from one needle connection port 1061 to which the needle 1005 is not inserted.

The structure of the thread main body 1070 and the needle grip distal portion 1071 is similar to that of the needle main body 1066 and the needle grip 1067 of the needle 1005.

The structure of the needle grip distal portion 1071, the needle grip proximal portion 1072 and the O-ring 1073 is similar to the structure of the housing 1047, the ring 1048 and the O-ring 1050 of the slider receiver 1046, and the O-ring 1073 is held between the needle grip distal portion 1071 and the needle grip proximal portion 1072.

The thread grasping forceps 1074 is slidably inserted into the needle main body 1070, the needle grip distal portion 1071 and the needle grip proximal portion 1072 in advance so as to be capable of sliding.

A loop-shaped grasping portion 1075 which is similar to the snare forceps is formed at the distal end of thread grasping forceps 1074.

The grasping portion 1075 is formed by a wire made of metal such as stainless steel or nitinol or a wire made of various kinds of plastic. The wire may be a twisted wire or a single wire. It is good enough that the wire diameter has the dimension capable of pulling the grasping portion 1075 into the needle main body 1070.

Further, when the grasping portion 1075 is caused to protrude from the needle main body 1070, it opens and forms a loop opening 1098.

As to the dimension of the loop opening 1098, its diameter is approximately φ10 to 20 mm.

An operation member 1076 extends from the proximal side of the grasping portion 1075 to the proximal side of the needle grip proximal portion 1073, and an operation knob 1077 is connected to this proximal portion.

The outside diameter of the operation member 1076 is slightly larger than the inside diameter of the O-ring 1073, thereby maintaining the air-tightness between the O-ring 1073 and the operation member 1076.

The operation member 1076 is formed by a thin pipe material or a wire made of metal such as stainless or nitinol which is superior in the rotation follow-up property and the flexibility. It is preferable that the grasping portion 1075 can also rotate when the operation knob 1077 is rotated.

The needle main bodies 1066 and 1070 of the needles 1005 and 1006 may have the structure that a needle formed of stainless or nitinol is attached at the end of a hollow sheath having the flexibility, e.g., a tube made of plastic such as fluorocarbon resin, polyethylene, polyamide, polyimide, polyurethane or various kinds of thermoplastic elastomer or a metal coil. The hollow sheath may be a plastic tube with the metal mesh in order to prevent kinking.

A reinforcing member 1078 is fixed to the treatment lumen 1012 of the sheath portion 1007 in the vicinity of the side opening 1013.

The reinforcing member 1078 is constituted by a distal annular portion 1079, a proximal annular portion 1080, and three beams 1081a, 1081b and 1081c connecting these annular portions.

The reinforcing member 1078 is formed of metal such as stainless, aluminium or brass, a plastic material such as ABS, polypropylene, polycarbonate, acrylic, polyacetal, polysulfone, polyimide or polyamide-imide, or a material which is relatively superior in the rigidity such as FRP or ceramic. In particular, it is desirable that the reinforcing member 1078 is formed of a transparent material such as polycarbonate, norbornene resin or cycloolefin-based resin. In this case, the visual field of the endoscope 1009 is not cut off, and the outer side of the sheath portion 7 can be hence observed.

The distal annular portion 1079 and the proximal annular portion 1080 are coaxially positioned in front and in the rear, and a gap between them is the same as or slightly longer than the length of the side opening 1013 in the longitudinal direction.

The outside diameter of each of the distal annular portion 1079 and the proximal annular portion 1080 is substantially the same as the inside diameter of the treatment lumen 1012, and these portions are fixed to the treatment lumen 1012 by adhesion or welding.

The beams 1081a, 1081b and 1081c extend from the proximal end of the distal annular portion 1079 to the distal end of the proximal annular portion 80 along the longitudinal direction of the sheath portion 7.

The gap between the beam 1081a and the beam 1081c is larger than the width of the side opening 1013 in order to prevent these beams from being exposed in the side opening 1013.

The wall thickness of each of the distal annular portion 1079, the proximal annular portion 1080 and the beams 1081a, 1081b and 1081c is approximately 0.1 to 1 mm.

The distal annular portion 1079, the proximal annular portion 1080 and the beams 1081a, 1081b and 1081c may be separately formed.

A number of the beams 1081 is not restricted to three and may be at least one as long as the bending strength of the beams 1081 has the degree which prevents the sheath portion 1007 from kinking at the part of the side opening 1013.

Further, in order to prevent the needle points of the needle 1005 and the needle 1006 from being caught on the distal annular portion 1079 and the proximal annular portion 1080 when the needle 1005 and the needle 1006 are caused to protrude from the needle lumens 1011a and 1011b, it is preferable that the distal annular portion 1079 and the proximal annular portion 1080 of the reinforcing member 1078 have the C-ring shape (FIG. 236).

A needle guide 1082 and a needle guide 1083 are fixed to the distal annular portion 1079 of the reinforcing member 1078.

The needle guide 1082 is an annular member having the both ends opened and having a guide inner cavity 1084a, and has a guide proximal portion 1085a on the proximal side thereof.

The needle guide 1083 is also an annular member having the both ends opened and having a guide inner cavity 1084b, has a guide proximal portion 1085b on the proximal side thereof, and a bend portion 1086 on the distal end side thereof.

A bend angle of the bend portion 1086 and the guide proximal portion 1085b is approximately 90 degrees.

The needle guide 1082 is different from the needle guide 1083 and has a bend portion 1086, and its distal opening is opened on the same axis as the guide proximal portion 1085a.

Figure 149:
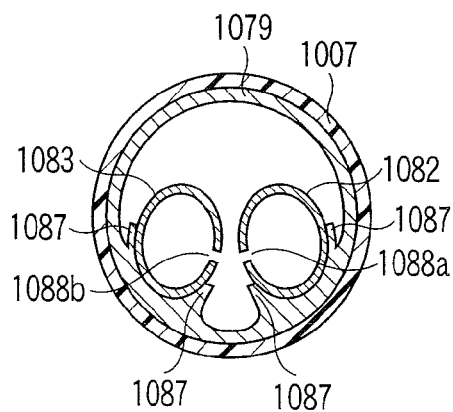
Figure 150:
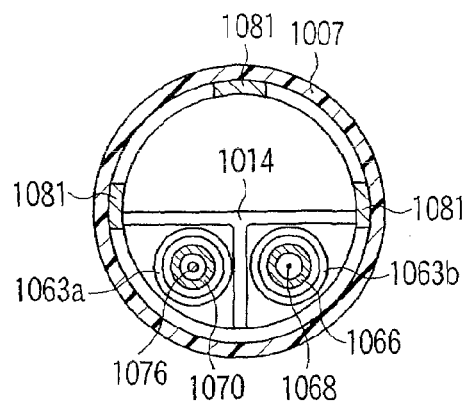

A plurality of support walls 1087 are provided on the inner side of the distal annular portion 1079 as shown in FIG. 149, and guide proximal portions 1085a and 1085b of the needle guide 1082 and 1083 are fixed to the distal annular portion 1079 so as to be sandwiched between the support walls 1087.

At that moment, the needle guide 1083 is fixed to the distal annular portion 1079 in such a manner that the bend portion 1086 faces the central side of the sheath portion 1007 and also faces the other needle guide 1082 side.

Furthermore, the needle guides 1082 and 1083 are fixed to the distal annular portion 1079 in such a manner that the proximal ends of the guide proximal portions 1085a and 1085b are positioned on the distal end side away from the distal end of the side opening 1013. Distances from the distal end of the side opening 1013 to the proximal ends of the guide proximal portions 1085a and 1085b are equal to each other.

Moreover, the needle guides 1082 and 1083 are positioned on substantially the same axis as the central axes of the needles 1005 and 1006 when inserted into the needle lumens 1011a and 1011b.

The needle guides 1082 and 1083 are provided at such position as that the ends of the needle main bodies 1066 and 1070 enter the proximal openings of the guide proximal portions 1085a and 1085b when the needle sliders 1043a and 1043b are caused to completely protrude to the inner sheath sliders 1042a and 1042b.

It is preferable that the cross-sectional shape of each of the guide proximal portions 1085a and 1085b is circular or elliptical as shown in FIG. 149, but it is not restricted to such shapes.

The guide inner cavities 1084a and 1084b are constituted by conical tapered portions 1088a and 1088b, needle inner cavities 1089a and 1089b, needle abutting surfaces 1090a and 1090b and thread inner cavities 1091a and 1091b.

The tapered portions 1088a and 1088b are formed on the proximal side of the guide proximal portions 1085a and 1085b, and their taper angle α is approximately 10 to 90 degrees.

The needle inner cavities 1089a and 1089b are provided on the distal end side of the tapered portions 1088a and 1088b, and their inside diameter is slightly larger than the outside diameter of each of the needle main bodies 1066 and 1070 so that the needle main bodies 1066 and 1070 can fit. The length of each of the needle inner cavities 1089a and 1089b is approximately 5 to 10 mm.

The needle inner cavities 1091a and 1091b are provided on the distal end side of the needle inner cavities 1089a and 1089b and extend to the distal ends of the needle guides 1082 and 1083.

The thread inner cavity 1091a of the needle guide 1082 has the cross-sectional shape obtained by flattening a cylinder as shown in FIG. 154. Both the short diameter and the long diameter of the thread inner cavity 1091a are smaller than the inside diameter of the needle inner cavity 1089a.

Moreover, the needle guide 1082 is fixed to the distal annular portion 1079 in such a manner that the long diameter of the thread inner cavity 1091a extends in a direction vertical to the side opening 1013.

The inside diameter of the thread inner cavity 1091b of the needle guide 1083 is smaller than the inside diameter of the needle inner cavity 1089b and equal to the inside diameter of the needle main body 1066.

The needle abutting surfaces 1090a and 1090b are formed by steps between the needle inner cavities 1089a and 1089b and the thread inner cavities 1091a and 1091b.

Distances from the distal end of the side opening 1013 to the needle abutting surfaces 1090a and 1090b are set smaller than distances from the distal end of the side opening 1013 to the ends of the needle main bodies 1066 and 1070 when the needle main bodies 1066 and 1070 are caused to completely protrude.

The guide slits 1092a and 1092b extend along the entire length of the side surface of each of the needle guides 1082 and 1083.

The guide slits 1092a and 1092b are provided at such positions as that the respective guide slits are opposed to the inner side surfaces (side surfaces on the central axis side of the sheath portion 7) of the needle guides 1082 and 1083 fixed to the end annular portion 1079.

The direction of the guide slit 1092a and the direction of the major axis of the thread inner cavity 1091a are orthogonal to each other.

The widths of the guide slits 1092a and 1092b are smaller than the thickness of the suture thread 1068.

The length of the needle guide 1083 in the longitudinal direction is longer than that of the needle guide 1082, and the distal end opening of the guide inner cavity 1084b is set so as to be positioned on the distal end side away from the distal end opening of the guide inner cavity 1084a by approximately 5 to 10 mm.

The needle guides 1082 and 1083 are formed of a metal material such as stainless, aluminium or brass or a relatively hard plastic material such as polyacetal or polysulfone.

Moreover, the endoscope 1009 inserted into the over-tube 1002 has a suction channel, and its proximal end is connected to a suction source (not shown).

It is preferable if the endoscope 1009 is a flexible endoscope, but it may be a rigid endoscope.

In addition, as the entire tissue centesis system 1001, parts other than the distal end opening of the sheath portion 1007 and the side opening 1013 are configured to be capable of maintaining the air-tightness relative to the outside of the tissue centesis system 1001.

—Modifications—

The grasping portion 1075 of the needle 1006 may be any conformation as long as it has a loop-like shape, and it may has a shape like a basket forceps as shown in FIG. 156.

In this case, the cross-sectional shape of the thread inner cavity 1091a does not have to be one obtained by flattening a cylinder, and it is good enough that the inside diameter of this inner cavity has a circular shape which is smaller than the inside diameter of the needle inner cavity 1089a as similar to the thread inner cavity 1091b as shown in FIG. 156.

Additionally, as shown in FIG. 157, a shell-like end chip 1094 to which a crisscross cut 1093 may be attached to the distal end of the sheath portion 1007.

The end chip 1094 is formed of various kinds of rubber such as silicone rubber or a relatively soft plastic material such as various kinds of thermoplastic elastomer, polyurethane, chloroethene, polyethylene, polyamide or polytetrafluoro-ethylene. Four flaps 1095 are provided to the end chip 1094 by the cut 1093.

When the endoscope 1009 is not inserted into the cut 1093, as shown in FIG. 157, the flaps 1095 are closed so that the end chip 1094 maintains the shell-like shape, and the air-tightness with respect to the outside of the sheath portion 1007 is held.

When the endoscope 1009 is moved forward in the cut 1093, as shown in FIG. 158B, the flaps 1095 are opened so that the endoscope 1009 can be inserted.

Incidentally, the cut 1093 is not restricted to the crisscross shape, and a number of cuts and a number of flaps 1095 are not restricted to four as shown in FIGS. 157 and 158.

Further, as shown in FIG. 160, the sheath distal end portion 1096 including the treatment lumen 1012 of the sheath portion 1007 and the side opening 1013 is formed separately from the sheath portion 1007 and can be detachably connected to the distal end of the sheath portion 1007.

In this case, the endoscopic lumen 1010 and the needle lumens 1011a and 1011b extend to the vicinity of the distal end of the sheath portion 1007.

(Operations)

(a) Assembly of Device (FIGS. 141, 159 and 161)

After putting end plugs 1040a and 1040b of the connection sheaths 1039a and 1039b into the connection ports 1035a and 1035b, the set screws 1038a and 1038b are fastened in order to connect the over-tube 1002 with the operation portion 1003.

Connection male screws 1065a and 1065b of the inner sheaths 1004a and 1004 are screwed into connection female screws 1060a and 1069b of the inner sheath housings 1053a and 1053b, and the inner sheaths 1004a and 1004b are connected to the inner sheath sliders 1042a and 1042b.

Subsequently, with the set screws 1057a and 1057b being loosened, the inner sheath housings 1053a and 1053b are inserted into the housings 1047a and 1047b of the slider receivers 1046a and 1046b, and the rings 1048a and 1048b are screwed into and fixed to the housings 1047a and 1047b.

Then, with the inner sheath sliders 1042a and 1042b being completely pulled out from the slider receivers 1046a and 1046b, the set screws 1057a and 1057b are fastened and fixed.

Thereafter, the needles 1005 and 1006 are inserted from the proximal openings of the needle connection ports 61a and 61b of the needle sliders 43a and 43b.

Then, the needle grip 1067 and the lure taper of the needle grip distal portion 1071a are screwed into the lure tapers on the inner surfaces of the needle connection ports 1061*a* and 1061*b*, and the needle sliders 1043*a* and 1043*b* and the needles 1005 and 1006 are fixed.

Furthermore, the needle sliders 1043*a* and 1043*b* are completely pulled out of the inner sheath sliders 1042*a* and 1042*b*.

An operation knob 1077 of the needle 1006 is completely pulled out of the needle grip proximal portion 1072. At this moment, the grasping portion 1075 is being pulled in the needle main body 1070.

Subsequently, the endoscope 1009 is inserted into the endoscopic lumen 1010 and the treatment lumen 1012 from the endoscope insertion opening 1022 of the over-tube 1002.

The endoscope 1009 is further moved forward, and the distal end of the endoscope 1009 is caused to protrude from the end of the over-tube 1002.

(b) Suction/Centesis of Suture Portion (FIGS. 162 to 164)

The over-tube 1002 having the endoscope 1009 inserted therein is inserted into the body of a patient while observing an endoscopic image, and it is pushed forward to the vicinity of suture tissues 1097*a* and 1097*b*. Incidentally, in the gastrojejunostomy, the suture tissues 1097*a* and 1097*b* are the gastric wall and the jejunum wall. Since the part of the side opening 1013 is reinforced by the reinforcing member 1078, the sheath portion 1007 can be assuredly prevented from kinking at the part of the side opening 1013 when inserting the over-tube 1002.

Then, the distal end of the endoscope 1009 is pulled back to the proximal side of the side opening 1013, and positioning is performed by moving forward/backward or rotating the over-tube 1002 while observing the endoscopic image in such a manner that the side opening 1013 is positioned above the suture tissues 1097*a* and 1097*b*.

In this state, the suture tissues 1097*a* and 1097*b* are pulled into the treatment lumen 1012 from the side opening 1013 by the suction function or the like provided to the endoscope 1009. Since the reinforcing member 1078 is provided, the sheath portion 1007 can be assuredly prevented from being crushed in the vicinity of the side opening 1013 by suction.

Here, confirmation is made upon whether a target centesis part is positioned on the extension line of the needles 1005 and 1006 by observing the suture tissue 1097*a*. If the centesis position deviates, suction is canceled and positioning of the side opening 1013 is again performed. Thereafter, the suture tissues 1097*a* and 1097*b* are again sucked. Before again performing the positioning, the over-tube may be replaced with an over-tube 2 having a different size of the side opening 1013.

In order to facilitate confirmation of which a part of the sucked suture tissue 1097*a* corresponds to a centesis position, this confirmation can be further facilitated by carrying out ink marking or the like by using the endoscope 1009 and a general endoscopic injection needle before inserting the over-tube 1002.

Then, the set screws 1057*a* and 1057*b* of the inner sheath sliders 1042*a* and 1042*b* in the operation portion 1003 are loosened, and the inner sheath sliders 1042*a* and 1042*b* are moved forward toward the distal end side with respect to slider receivers 1046*a* and 1046*b*.

At this moment, since the operation portion 1003 is placed at a position away from the endoscope insertion portion 1008 by the connection sheaths 1039*a* and 1039*b*, an assistant who operates the operation portion 1003 and an operator who operates the endoscope 1009 can perform the operations at distanced positions. As a result, their operations can be prevented from interfering with each other.

When the inner sheath sliders 1042*a* and 1042*b* are pushed forward, the distal ends of the tubes 1063*a* and 1063*b* are pressed against the suture tissue 1097*a*.

Then, the needle sliders 1043*a* and 1043*b* are respectively pushed toward the distal end side with respect to the inner sheath sliders 1042*a* and 1042*b* until the needle connection ports 1061*a* and 1061*b* come into contact with the inner sheath rings 1054*a* and 1054*b*, and the needle main bodies 1066 and 1070 are caused to protrude from the distal ends of the tubes 1063*a* and 1063*b*. At this moment, the needle main bodies 1066 and 1070 protrude substantially in parallel to each other.

The needle sliders 1043*a* and 1043*b* may be simultaneously or separately caused to protrude.

Then, the needle main bodies 1066 and 1070 pierce the suture tissues 1097*a* and 1097*b*.

Furthermore, the needle main bodies 1066 and 1070 are further pushed, and the distal ends of the needle main bodies 1066 and 1070 are inserted into the guide inner cavities 1084*a* and 1084*b* of the needle guides 1082 and 1083 and come into contact with the needle abutting surfaces 1090*a* and 1090*b* of the needle inner cavities 1089*a* and 1089*b*.

Even if the distal end positions of the needle main bodies 1066 and 1070 deviate from the central axes of the guide inner cavities 1084*a* and 1084*b* in consequence of the fact that the needle main bodies 1066 and 1070 pierce the suture tissues 1097*a* and 1097*b*, the distal ends of the needle main bodies 1066 and 1070 are smoothly guided to the inside of the needle inner cavities 1089*a* and 1089*b* by tapered portions 1088*a* and 1088*b*.

Thereafter, suction of the suture tissues 1097*a* and 1097*b* by the suction function of the endoscope 1009 is canceled.

(c) Insertion of Suture Thread into Tissue (FIG. 154 and FIGS. 165 to 168)

The Operation Knob 1077 of the Needle 1006 is pushed toward the distal end side, and the grasping portion 1075 of the thread grasping forceps is caused to protrude from the distal end of the needle main body 1070.

Then, the grasping portion 1075 protrudes from the distal end of the needle guide 1082 through the thread inner cavity 1091*a*. At this moment, since the grasping portion 1075 is opened in the long-diameter direction of the thread inner cavity 1091*a* as shown in FIG. 154, a loop opening 1098 of the grasping portion 1075 is positioned on a flat surface which is substantially vertical to the central axis of the bend portion 1086 of the needle guide 1083.

Then, after removing a cap 1155 from the needle grip 1067 of the needle 1005, the suture thread 1068 exposed from the grip 1067 is pushed toward the distal end side so that distal end of the suture thread 1068 is caused to protrude from the distal end of the bend portion 1083 of the needle guide 1083 through the thread inner cavity 1091*b*.

Moreover, when the suture thread 1068 is pushed forward, the distal end of the suture thread 1068 is inserted into the loop opening 1098.

While conducting observation using the endoscopic image, the suture thread 1068 is pushed forward until the knot 1069 of the suture thread 1068 moves beyond the loop opening 1098 (FIG. 165).

Subsequently, with the suture thread 1068 which extends from the proximal side of the needle grip 1067 being capable of freely moving, the operation knob 1077 is pulled back to the proximal side. The grasping portion 1075 is pulled into the needle main body 1070, and the distal end of the suture thread 1068 is held.

At this moment, the knot 1069 functions as a stopper, thereby preventing the suture thread 1068 from readily coming off the grasping portion 1075.

Then, the needle sliders 1043a and 1043b are pulled back to the proximal side.

The needle sliders 1043a and 1043b may be simultaneously (FIG. 166) or separately (not shown) pulled back.

Then, a part of the suture thread 1068 stretched between the needle main bodies 1066 and 1070 is taken out from the needle guides 1082 and 1083 through guide slits 1092a and 1092b of the needle guides 1082 and 1083.

In addition, that part of the suture thread 1068 extends between centesis out points 1113a and 113b through which the needle main bodies 1066 and 1070 pierce, and is brought into contact with the suture tissue 1097b (FIG. 167).

Then, the needle sliders 1043a and 1043b are completely pulled out from the inner sheath sliders 1042a and 1042b to the proximal side, and the distal ends of the needle main bodies 1066 and 1070 are pulled into the tubes 1063a and 1063b.

Subsequently, the set screws 1057a and 1057b of the inner sheath sliders 1042a and 1042b are unscrewed, and the inner sheath sliders 1042a and 1042b are completely pulled out to the proximal side with respect to the slider receivers 1046a and 1046b.

As a result, the distal ends of the tubes 1063a and 1063b are pulled to the proximal side from the distal end openings of the needle lumens 1011a and 1011b (FIG. 168).

Then, with the suture thread 1068 which extends from the proximal side of the needle grip 1067 being capable of freely moving, the over-tube 1002 and the endoscope 1009 are removed from the body of a patient.

At this moment, the suture thread 1068 moves in the suture tissues 1097a and 1097b from a centesis in point 1112b to a centesis out point 1113b, then from the centesis out point 1113b to a centesis out point 1113a, and from the centesis out point 1113a to the centesis in point 1112a.

Additionally, the operation knob 1077 is again pushed out to the distal end side with respect to the needle grip proximal portion 1072, the grasping portion 1075 is caused to protrude, and the suture thread 1068 is taken out from the grasping portion 1075 (not shown).

(d) Fixation of Suture Thread (FIGS. 169 and 170)

The both ends of the suture thread 1068 exposed to the outside of the body of a patient are tied to form a knot 1099 (not shown).

As the knot 1099, any knot may be used as long as it is generally used in the surgical operation.

The knot 1099 is again pushed into the body of a patient by using a general knot pusher inserted into the forceps channel of the endoscope 1009 while observing this knot by using the endoscope 1009.

When the knot 1099 reaches the vicinity of the suture tissue 1097a, the knot pusher is pressed against the suture tissue 1097a and, at the same time, the both ends of the suture thread 1068 are pulled, thereby fixing the knot 1099.

The above-described operation is performed once or several times, and confirmation is made upon whether the knot 1099 is firmly formed so as not to come loose. Thereafter, the endoscope 1009 and the knot pusher are removed to the outside of the body of a patient.

At last, the suture thread 1068 is cut in the vicinity of the proximal side away from the knot 1099 by using a non-illustrated endoscopic scissor forceps, and the remaining suture thread 1068 is collected to the outside of the body.

By repeating the above-described series of operation in accordance with the length and range requiring the suture in the suture tissues 1097a and 1097b, the suture tissues 1097a and 1097b can be completely sutured.

(Advantages)

The over-tube 1002 has the endoscopic lumen 1010 into which the endoscope 1009 can be inserted, and the endoscope 1009 can be inserted into the treatment lumen 1012 to which the suture tissues 1097a and 1097b are sucked. In this structure, the suture tissues 1097a and 1097b are sucked into the inner cavity of the treatment lumen 1012 positioned on the proximal side on substantially the same axis as the endoscope 1009. Therefore, it is possible to readily and assuredly confirm whether the needles 1005 and 1006 can be pushed through a target centesis part of the suture tissue 1097a before the centesis of the needles 1005 and 1006. Further, it is possible to adjust the suture tissues 1097a and 1097b so as to be readily observed by moving forward or backward or bending the distal end of the endoscope 1009 with respect to the side opening 1013. As a result, subtle control of the centesis position can be effected, thereby performing secure suture. Furthermore, the treatment operation can be simplified, and the treatment time can be also greatly reduced.

Moreover, since the needles 1005 and 1006 are previously arranged in parallel to each other with a fixed gap therebetween by the needle lumens 1011a and 1011b provided in parallel with each other with a fixed gap therebetween, desired fixed gaps can be provided between the centesis in points 1112a and 1112b and the centesis out points 1113a and 1113b. As a result, the secure control is enabled without extremely reducing the stitch interval. Consequently, the treatment operation can be simplified, and the treatment time can be also greatly reduced.

In addition, even if stitching must be carried out for several times, since a distance of stitching for one time can be controlled to be constant, the suture can be assuredly performed with a reduced number of times of stitching.

Additionally, since the endoscope 1009 and the treatment lumen 1012 are substantially coaxially arranged, a larger space into which the suture tissues 1097a and 1097b can be pulled can be obtained without increasing the outside diameter of the over-tube 1002. As a result, the pain given to a patient when inserting the over-tube 1002 can be reduced.

Further, since the over-tube 1002 and the endoscope 1009 are slidably arranged, they can be inserted into the body cavity of a patient with the curved portion of the endoscope 1009 protruding from the distal end opening of the over-tube 1002. As a result, the property of insertion into the body can be improved, and the pain given to a patient at the time of insertion can be reduced.

Furthermore, since the two needles 1005 and 1006 are previously arranged, when the suture tissues 1097a and 1097b are once pulled in from the side opening 1013, the two needles 1005 and 1006 can be immediately pushed through. In this regard, the treatment operation can be simplified, and the treatment time can be greatly reduced.

Moreover, since the needles 1005 and 1006 are pushed through after the inner sheaths 1004a and 1004b are pushed through a target centesis part, confirmation of the target centesis part and positioning on the target centesis part can be facilitated. Therefore, the secure suture can be performed, the treatment operation can be facilitated, and the treatment time can be greatly reduced.

In addition, since at least a part of the sheath portion 1007 in the vicinity of the side opening 1013 is transparent, observation of the outer periphery of the sheath portion 1007 can be performed by using the endoscope 1009, and the positioning of the side opening 1013 can be facilitated, thereby improving the operability and reducing the treatment time.

Additionally, when the distal end portion of the sheath portion 1007 is separately provided as the sheath distal end portion 1096, parts other than the sheath distal end portion 1096 can be commonly manufactured when producing the over-tube 1002 with the side opening 1013 having a different dimension, thereby reducing the manufacturing cost.

Further, since the system is configured to maintain the air-tightness between the distal end opening of the sheath portion 1007, the inside of the tissue centesis system 1001 other than the side opening 1013 and the outside, suction of the suture tissues 1097a and 1097b from the side opening 1013 can be efficiently carried out.

[Second Example of Straight Needle Suture Machine] (FIGS. 171 to 177)

(Structure)

Description will be given as to only parts different from the first example.

Of the two needles, one needle has the same structure as the needle 1005.

A suture wire 1109 is loaded to the needle 1005 in advance.

The suture wire 1109 is constituted by a guide wire 1110, a suture wire 1068, a push wire 1111 and a connection pipe 1112.

The guide wire 1110 is connected to the distal end of the suture thread 1068, and the push wire is connected to the proximal end of the suture thread 1068. These connections are attained by adhesion with the connection pipe 1112 and caulking of the connection pipe 1112.

The suture wire 1109 is loaded in the needle 1005 in such a manner that the distal end of the suture wire 1109 is positioned on the proximal side away from the distal end of the needle main body 1066.

The guide wire 1110 is obtained by coating a plastic resin which is relatively superior in smooth-ness such as fluorocarbon resin or silicone on a core wire made of metal such as stainless whose flexibility is lower than that of the suture thread 1068.

It is preferable that the diameter of the core wire is approximately 0.2 mm and the coating thickness is approximately 0.05 mm.

The length of the guide wire 1110 is approximately 10 cm.

The push wire 1111 is formed of a wire made of metal such as stainless whose flexibility is lower than that of the suture thread 1068, and it is preferable that the outside diameter of the push wire 1111 is as thick as possible in the range allowing insertion into the needle 1005.

Furthermore, the push wire 1111 is set to the length which is longer than the entire length of the needle 1005 by approximately 50 cm, and its end is positioned in a needle grip 1067.

The other needle 1100 is constituted by a needle grip 1067, a needle sheath 1101, a needle end portion 1102 and a guide member 1103.

The needle sheath 1101 is connected to the needle grip 1067, and both the needle sheath 1101 and the needle grip 1067 have the inner cavities.

The guide member 1103 is fixed to the distal end of the needle sheath 1101.

Figure 143:
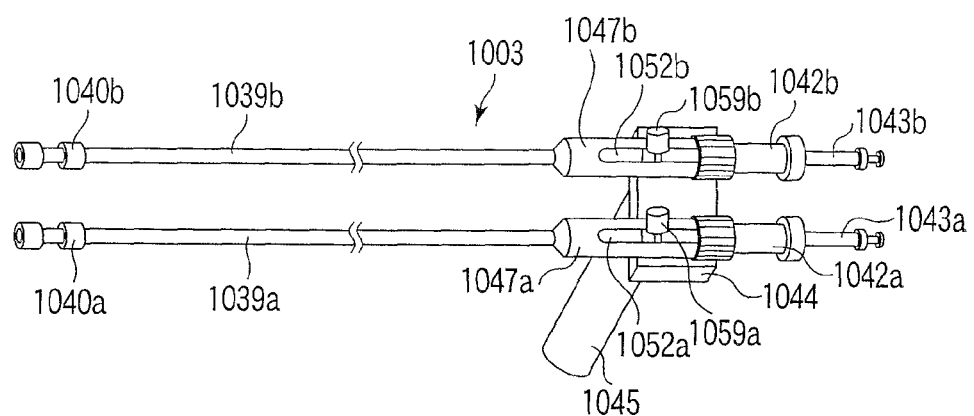
Figure 144:
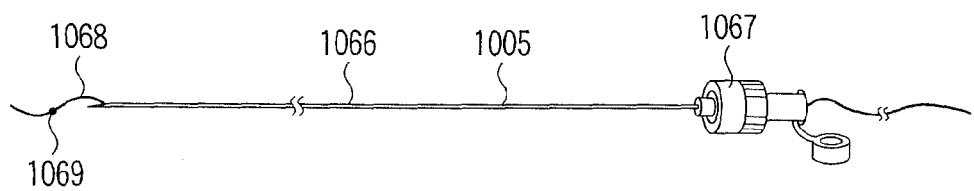
Figure 145:
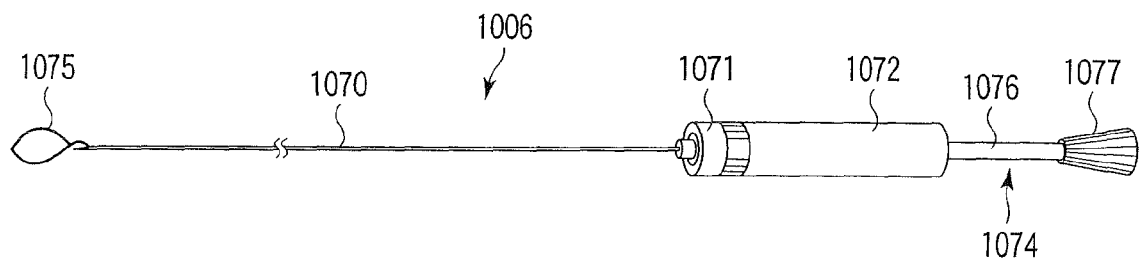
Figure 146:
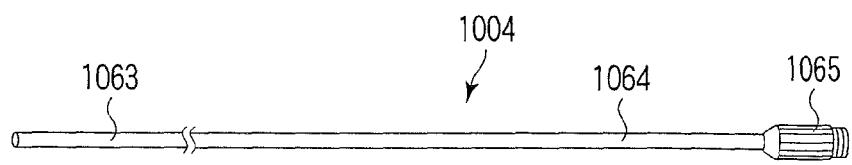
Figure 147:
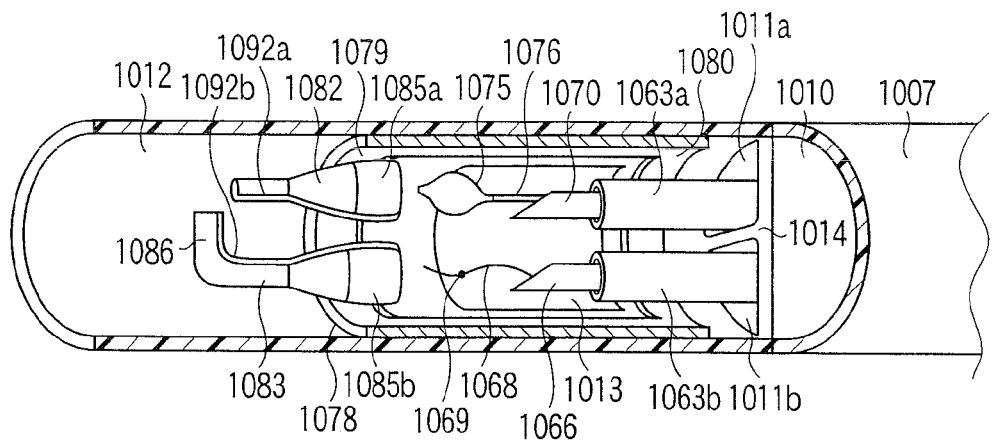
Figure 148:
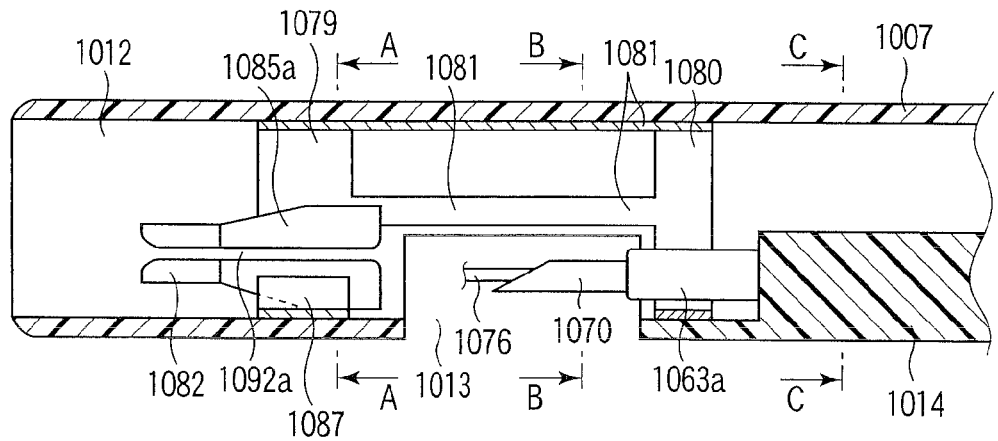

As shown in FIG. 143, the guide member 1103 is a hollow cylindrical member having a tapered plane 1104 at the distal end thereof.

The outside diameter of the guide member 1103 is slightly smaller than the inside diameter of the needle sheath 1101.

The guide member 1103 is attached to the inner cavity of the needle sheath 1101 at such a position as that the tapered plane 1104 of the guide member 1103 is exposed on the distal end side of the needle sheath 1101.

The needle end portion 1102 is fixed to the outer periphery of the guide member 1103 in such a manner that the proximal end of the needle end portion 1102 comes into contact with the distal end of the needle sheath 1101.

The needle end portion 1102 has the inner cavity, and its inside diameter is slightly larger than the outside diameter of the guide member 1103 and it is approximately 0.5 to 1.5 mm.

The outside diameter of the needle sheath 1101 is equal to that of the needle end portion 1102, and this outside diameter is set to such a dimension as that the clearance between itself and the inside diameter of a tube 1063a of the inner sheath 1004 is slightly smaller than the outside diameter of the guide wire 1110.

The needle sheath 1101 and the needle end portion 1102 are formed of pipe members made of metal such as stainless steel or nitinol which can resist pressing from the proximal side at the time of centesis and has the flexibility capable of following up the bend of the connection sheath 1039 or the needle lumen 1011.

The distal end of the needle end portion 1102 has the centesis so as to be capable of puncturing a tissue in the body cavity.

Moreover, a side hole 1105 is provided on the side surface of the needle end portion 1102 positioned above the tapered plane 1104.

The side hole 1105 has, e.g., a rectangular shape shown in FIG. 172, and its dimension allows easy insertion of the guide wire 1110.

The proximal end of the side hole 1105 is tapered, and it is on the same level as the tapered plane 1104.

The length from the distal end of the needle end portion 1102 to the distal end side of the side hole 1105 is set in such a manner that the needle 1100 is positioned on the distal end side away from the proximal side of the side opening 1013 and the distal end opening of the needle lumen 1011a when the needle 1100 comes into contact with a needle abutting surface 1090a as shown in FIG. 174.

In addition, needle guides 1106a and 1106b are provided to a distal end annular portion 1079 of a reinforcing member 1078.

The needle guides 1106a and 1106b have the structure which is substantially similar to that of the needle guide 1083 according to the first embodiment, and an only difference lies in that the bend portion 1086 is not provided.

Additionally, the distal ends of the needle guides 1106a and 1106b are connected by a guide tube 1107 having an inner cavity.

The inside diameter of the guide tube 1107 is substantially the same as that of each of thread inner cavities 1091a and 1091b of the needle guides 1106a and 1106b.

Further, a guide slit 1108 is provided on the side surface on the proximal side of the guide tube 1107, and this slit connects guide slits 1092a and 1092b of the needle guides 1106a and 1106b, thereby forming one slit.

The width of the guide slit 1108 is equal to or smaller than the width of each of the guide slits 1092a and 1092b, and smaller than the outside diameter of the suture wire 1109.

The guide tube 1107 is formed of a plastic material such as fluorocarbon resin, polyethylene, polyamide, polyimide, polyurethane or various kinds of thermoplastic elastomer.

The guide tube 1107 may be one obtained by providing in a post-process a guide slit 1108 to a tube produced by extrusion or one obtained by molding the whole guide slit 1108 by injection molding.

Furthermore, a suction tube 1200 having an inner cavity communicating with the endoscopic lumen 1010 is provided to the endoscope insertion portion 1008 of the over-tube 1002, and the proximal end of the suction tube 1200 can be attached to and detached from a suction source (not shown).

(Operations)

Description will be given as to only parts different from the first example.

In place of using the suction function of the endoscope 1009, the suction tube 1200 is connected to the suction source (not shown) and the suture tissues 1097a and 1097b are sucked from the side opening 1013.

After pushing the needle 1005 and the needle 1100 through the suture tissues 1097a and 1097b, the inner sheath sliders 1042a and 1042b are completely pulled back from the slider receivers 1046a and 1046b, and the distal ends of the inner sheaths 1004a and 1004b are pulled back to the vicinity of the distal end openings of the needle lumens 1011a and 1011b.

Subsequently, the push wire 1111 of the suture wire 1109 exposed from the needle grip 1067 of the needle 1005 is held and pushed forward.

Then, the guide wire 1109 protruding from the distal end of the needle 1005 passes through the thread inner cavity 1091b of the needle guide 1106b, the guide tube 1107 and the thread inner cavity 1091a of the needle guide 1106a, and is moved into the needle end portion 1102 of the needle 1100.

Moreover, the guide wire 1109 moves along the tapered plane 1104 of the guide member 1103 and protrudes from the needle 1100 through the side hole 1105.

Subsequently, after confirming that the distal end of the guide wire 1109 protrudes to the outside of the needle 1100 by using an image of the endoscope 1009, the needle sliders 1043a and 1043b are completely pulled back from the inner sheath sliders 1042a and 1042b.

Then, the needle 1005 and the needle 1100 are removed from the suture tissues 1097a and 1097b, and the needle 1005 and the needle 1100 are pulled into the tubes 1063a and 1063b, respectively.

At this moment, a part of the suture wire 1109 stretched between the needles 1005 and 1100 is taken out from the needle guides 1106a and 1106b through the guide slit 1108 of the guide tube 1107 and the guide slits 1092a and 1092b of the needle guides 1106a and 1106b.

In addition, as similar to FIG. 168 of the first example, that part of the suture wire 1109 extends between the centesis out points 1113a and 1113b through which the needles 1005a and 1100 have passed and comes into contact with the suture tissue 1097b.

Additionally, when the needles 1005 and 1100 are pulled into the tubes 1063a and 1063b, since the clearance between the outer surface of the needle end portion 1102 and the inner surface of the tube 1063a is smaller than the outside diameter of the guide wire 1110, the guide wire 1110 protruding from the needle 1100 is fitted/held in the clearance.

Then, with the suture wire 1109 which extends from the proximal side of the needle grip 1067 being capable of freely moving, the over-tube 1002 and the endoscope 1009 are removed from the body of a patient.

Subsequently, the needle slider 1043a is pushed toward the distal end side, and the needle end portion 1102 is caused to protrude from the distal end of the tube 1063a. Thereafter, the guide wire 1110 is taken out from the needle end portion 1102.

Then, the push wire 1111 extending to the outside of the body of a patient is pulled back in such a manner that the suture thread 1068 pierces the suture tissues 1097a and 1097b.

Further, parts of the suture thread 1068 in the vicinity of the both ends thereof are cut outside the body of a patient, and the guide wire 1110 and the push wire 1111 are cut away.

(Advantages)

In addition to the advantages of the first example, the following advantages can be obtained.

Since the suture wire 1109 is held on the needle 1100 side by the needle 1100 itself and the inner sheath 1004a, the operation of the thread grasping forceps 1074 is no longer necessary as with the first example, thereby improving the operability and reducing the treatment time.

Furthermore, since the resin superior in smoothness is applied and the guide wire 1109 consisting of the metal core wire whose flexibility is lower than that of the suture thread 1068 is provided at the distal end of the suture thread 1068, insertion of the suture wire 1109 into the needle 1005, the needle guide 1106b, the guide tube 1107, the needle guide 1106a and the needle 1100 is facilitated, thereby improving the operability and reducing the treatment time.

Moreover, since the push wire 1111 whose flexibility is lower than that of the suture wire 1068 is connected to the proximal side of the suture thread 1068 and exposed to the proximal end of the needle grip 1067 of the needle 1005, insertion of the suture wire 1109 is facilitated rather than pushing forward the suture thread 1068 as in the first example, thereby achieving improvement in the operability and reduction in the treatment time.

[Third Example of Straight Needle Suture Machine]
(FIGS. 178 to 183)

(Structure)

Description will now be given as to only parts different from the first and second examples.

In this machine, the needles 1005 and 1100 in the second example are changed to needles 1114 and 1115.

The needle 1114 is constituted by a needle end portion 1116, a needle sheath 1101, a needle grip distal portion 1071a, a needle grip proximal portion 1072a, an O-ring 1073a (not shown) and a thread fixture 1117.

The needle sheath 1101 is connected to the distal end of the needle grip distal portion 1071a.

The structure of the needle grip distal portion 1071a, the needle grip proximal portion 1072a and the O-ring 1073a is similar to that of the needle 1006 in the first example.

The outside diameter of the needle distal portion 1116 is slightly smaller than the inside diameter of the needle sheath 1101, and the proximal side of the needle distal portion 1116 is fixed to the inner cavity at the distal end of the needle sheath 1101.

The end surface on the proximal side of the needle end portion 1116 has a conical tapered portion 1118.

In the thread fixture 1117, a thread fixing portion 1119 is provided in place of the grasping portion 1075 of the thread grasping forceps 1074 in the first example.

The thread fixing portion 1119 is connected to the distal end of the operation member 1076.

The outside diameter of the thread fixing portion 1119 is smaller than the outside diameter of the operation member 1076.

The clearance between the outer surface of the thread fixing portion 1119 and the inner surface of the needle sheath 1101 is larger than the later-described outside diameter of the suture thread 1068.

A tapered portion 1121 whose angle is substantially the same as that of the tapered portion 1118 is formed on the distal end surface of the thread fixing portion 1119.

Both the needle end portion 1116 and the thread fixing portion 1119 are formed of a metal material such as stainless steel which rarely transforms or a relatively hard plastic material.

The needle 1115 is constituted by a needle main body 1122, a needle grip distal portion 1071b, a needle grip proximal portion 1072b, an O-ring 1073b, and feeding means 1123.

The needle main body 1122 is connected to the distal end of the needle grip distal portion 1071b.

The structure of the needle grip distal portion 1071b, the needle grip proximal portion 1072b and the O-ring 1073b is similar to that of the needle 1006 in the first example.

The feeding device 1123 is composed of a slider 1124 and an elastic grip 1125.

The slider 1124 has an inner cavity and is formed of a metal material such as stainless steel or a hard plastic material.

The slider 1124 can slide in the inner cavities of the needle main body 1122, the needle grip distal portion 1071b and the needle grip proximal portion 1072b.

In addition, to the distal end of the slider 1124 is provided an enlarged-diameter portion 1126 whose outside diameter is larger than the inside diameter of the O-ring 1073b, and the enlarged-diameter portion 1126 is provided on the distal end side away from the O-ring 1073b.

When the slider 1124 is pulled toward the proximal side from the needle grip proximal portion 1072b, the enlarged-diameter portion 1126 comes into contact with the O-ring 1073b. This prevents the slider 1124 from coming off the needle grip proximal portion 1072b.

To the proximal side of the slider 1124 is connected to the elastic grip 125 formed of various kinds of rubber such as silicone rubber or fluorine rubber or various kinds of thermoplastic elastomer.

Both the slider 1124 and the elastic grip 1125 have the inner cavities.

The suture thread 1068 is previously loaded in the needle 1115 as with the first example.

Each of the slider 1124 and the elastic grip 1125 has the inside diameter which facilitates sliding of the suture thread 1068 therein.

Additionally, as shown in FIG. 181, on the side surface on the proximal side of the guide tube 1127 are provided with a plurality of vertical slits 1128 in addition to the guide slit 1108 similar to that of the guide tube 1107 in the second example.

The vertical slits 1128 extend in a direction which is substantially vertical to the guide slit 1108.

The width of each of the vertical slits 1128 is smaller than the outside diameter of the suture thread 1068 in such a manner that the suture thread 1068 can not pass through the vertical slit.

Further, a mark 1129 is provided to the suture thread 1168 exposed on the proximal side of the elastic grip 1125.

A distance L from the proximal end of the elastic grip 1125 to the mark 1129 is equal to a distance obtained when the distal end of the suture thread 1068 passes through the needle guide 1106a, the guide tube 1127 and the needle guide 1106b and further advances to the proximal side from the distal end surface on the proximal side of the needle end portion 1116 by approximately several mm.

Furthermore, the inner sheath sliders 1042a and 1042b are detachably connected by an inner sheath connection member 1220.

The needle sliders 1043a and 1043b are likewise detachably connected by the needle connection member 1221.

A transparent sheath portion 1130 may be provided to the distal end portion of the needle sheath 1101 of the needle 1114 instead of providing the mark 1130 to the suture thread 1068.

The transparent sheath portion 1130 is formed of a plastic material which is relatively superior in the transparency such as polycarbonate.

In this case, it is more preferable that, for example, a helical mark 1131 is provided to the end of the suture thread 1068.

(Operations)

Description will now be given as to only parts different from the first and second examples.

When the inner sheaths 1004a and 1004b are caused to protrude from the needle lumens 1011a and 1011b, either the inner sheath slider 1042a or 1042b is pushed to the distal end side. Then, the other inner sheath slider connected by the inner sheath connection member 1220 also moves, and the inner sheaths 1004a and 1004b are caused to simultaneously protrude. Simultaneous protrusion of the needles 0114 and 0115 can be likewise performed by operating either the needle slider 1043a or 1043b by using the needle connection member 0221.

After the needle 1114 and the needle 1115 are pushed through the suture tissues 1097a and 1097b, the elastic grip 1125 is squashed and held in such a manner that the elastic grip 1125 grips the suture thread 1068 in the elastic grip 1125. In this state, the slider 1124 is pushed out to the distal end side.

Then, the suture thread 1068 is pushed toward the distal end side in the needle 1114 by the same distance as the moving distance of the slider 1124.

Subsequently, the proximal side of the slider 1124 is held and pulled back to the proximal side. At this moment, the suture thread 1168 does not move.

The same operation is repeated until the mark 1129 of the suture thread 1068 reaches the position of the proximal end of the elastic grip 1125, and the distal end of the suture thread 1068 is advanced in the needle sheath 1101 through the needle guide 1106b, the guide tube 1127, the needle guide 1106a and the needle end portion 1116.

Subsequently, the operation knob 1077 of the thread fixture 1117 is pushed toward the proximal side, and the thread fixing portion 1119 is pushed forward until it comes into contact with the distal end surface on the proximal side of the needle end portion 1116.

Then, as shown in FIG. 178B, the suture thread 1068 is held between the tapered portion 1118 and the tapered portion 1121 and fixed to the needle 1114.

With the suture thread 1068 being fixed to the needle 1114, when the needles 1114 and 1115 are removed from the suture tissues 1097a and 1097b, the part of the suture thread 1068 stretched between the needle 114 and the needle 1115 is taken out from the needle guides 1106a and 1106b through the guide slit 1108 of the guide tube 1127, the vertical slit 1128, and the guide slits 1092a and 1092b of the needle guides 1106a and 1106b.

Further, as similar to FIG. 168 of the first example, that part of the suture thread 1068 extends between the centesis out points 1113a and 1113b through which the needles 1114 and 1115 pierce, and comes into contact with the suture tissue 1097b.

Then, with the suture thread 1068 extending from the proximal side of the elastic grip 1125 being capable of freely moving, the over-tube 1002 and the endoscope 1009 are removed from the body of a patient.

When the transparent sheath portion 1130 is provided to the distal end of the needle sheath 0101, it is confirmed by using an image of the endoscope 1009 that the distal end of the suture thread 1068 has moved to the inside of the transparent sheath portion 1130, and thereafter the operation knob 1077 of the thread fixture 1117 is pushed forward.

In this case, when the mark 1131 is provided at the distal end of the suture thread 1068, the distal end of the suture thread 1068 can be readily confirmed in the endoscopic image.

(Advantages)

In addition to the advantages of the first example, the following advantages can be obtained.

Since the suture thread 1068 is held between the needle end portion 1116 formed of a material which rarely transforms and the thread fixing portion 1119 and fixed to the needle 1114, fixture of the suture thread can be more assuredly attained than the second example.

Furthermore, insertion of the suture thread 1068 into the needle 1115 can be facilitated by using thread feeding means 1123 as compared with inserting the flexible suture thread 1068 into the needle while holding the suture thread 1068 as in the first example, it is possible to achieve improvement in the operability and reduction in the treatment time.

Moreover, at that moment, by providing the mark to the suture thread 1068 or providing the transparent sheath portion 1130 to the needle sheath 1101, it is possible to confirm where the suture thread 1068 should be moved to, thereby achieving improvement in the operability and reduction in the treatment time.

In addition, since the inner sheath sliders 1042a and 1042b and the needle sliders 1043a and 1043b are connected by the inner sheath connection member 1220 and the needle connection member 1221, one operation of the inner sheath slider and the needle slider can suffice, thereby achieving improvement in the operability and reduction in the treatment time.

[Fourth Example of Straight Needle Suture Machine]
(FIGS. 184 to 187)

(Structure)

Description will now be given as to only parts different from the first and second examples.

As similar to the second example, the needle guides 1106a and 1106b are provided to the distal annular portion 1079 of the reinforcing member 1078, and the guide tube 1107 connects these guides to each others.

The two needles are composed of the needle 1132 and the needle 1005 shown in the first example.

The needle 1132 has substantially the same structure as that of the needle 1006 in the first example, and it is different from the needle 1006 in that thread holding means having the different structure is provided in place of the grasping portion 1075 at the distal end of the thread grasping forceps 1074.

In addition, the suture thread 1068 to which engaging means held by the thread holding means is previously loaded at the distal end.

As one thread holding means, there is a structure in which a permanent magnet 1134 formed of, e.g., barium ferrite is provided at the distal end of the operation member 1076 as shown in FIG. 184. Additionally, a permanent magnet 1135 as engaging means is connected to the distal end of the suture thread 1068.

Further, as another thread holding means, a U-shaped hook 1136 is provide at the distal end of the operation member 1076 as shown in FIG. 185. A hook 1137 is likewise connected to the distal end of the suture thread 1068.

The hooks 1136 and 1137 are formed of a metal material such as stainless steel.

Further, as still another thread holding means, there is a structure in which a grasping portion 1138 is provided at the distal end of the operation member 1076 as shown in FIGS. 186 and 187.

The grasping portion 1138 is formed by a tubular member made of a metal material such as stainless steel or nitinol which is relatively superior in the elasticity or a plastic material such as polyethylene, polypropylene, polyamide or fluorocarbon resin.

Furthermore, the grasping portion 1138 has an inner cavity, and the inside diameter on the distal side thereof is smaller than the inside diameter on the proximal side of the same.

Moreover, a cruciform slit 1139 is provided to the grasping portion 1138 and extends in the longitudinal direction to a part of this portion where the inside diameter is large.

In addition, in the non-load state of the grasping portion 1138, the distal end portion of the grasping portion 1138 is formed in the shape which is opened in the circumferential direction with the proximal end of the slit being determined as a starting point, and four claws 1140 are formed.

A convex portion 1141 is formed to the distal end of the claw 1140.

When the needle 1132 is pulled into the grasping portion 1138, the claws 1140 are closed.

An enlarged-diameter member 1142 is connected to the end of the suture thread 1068 as engaging means.

The outside diameter of the enlarged-diameter member 1142 is smaller than the inside diameter on the proximal side of the grasping portion 1138, and larger than the inside diameter on the distal end side.

Additionally, a grip inner cavity 1133 with the inside diameter being enlarged is formed on the proximal side of the thread inner cavity 1091a of the needle guide 1106a.

The inside diameter of the grip inner cavity 1133 is substantially the same as the open width of the claw 1140 in the non-load state.

(Operations)

Description will be given as to only parts different from the first and second examples.

After the needles 1005 and 0132 are pushed through the suture tissues 1097a and 1097b, the suture thread 1068 is caused to protrude from the needle 1005, and pushed toward the needle guide 1106a and the guide tube 1107.

Then, the operation knob 1077 of the needle 1132 is pushed toward the distal end side, and the thread holding means at the distal end of the operation member 1076 is caused to protrude from the needle 1132.

Further, the engagement member at the distal end of the suture thread 1068 and the thread holding means are engaged in the guide tube 1107 or the needle guide 1106a. Subsequently, the operation knob 1077 is pulled back, and the engaging means is pulled into and fixed to the needle 1132.

When the thread holding means and the engagement member are permanent magnets 1134 and 1135, they are engaged by the magnetic force.

When the thread holding means and the engagement member are permanent magnets 1136 and 1137, they are engaged by catching on each other by using their hooks.

When the thread holding means and the engagement member are the grasping portion 1138 and the extended-diameter member 1142, they are engaged in the following manner.

When the operation knob 1077 is pushed forward, the grasping portion 1138 is caused to protrude from the needle 1132, and the claws 1140 are opened in the grip inner cavity 1133.

In this state, the suture thread 1168 is pushed forward so that the extended-diameter member 1142 is positioned on the proximal side away from the convex portion 1141.

Then, when the operation knob 1077 is pulled back, the claws 1140 are pulled into the needle 1132 while being closed. At this moment, the convex portion 1141 is caught on the extended-diameter member 1142, and the extended-diameter member 1142 is also pulled and fixed in the needle 1132.

(Advantages)

The advantages are the same as those of the third example.

[Fifth Example of Straight Needle Suture Machine]

(FIG. 188)

(Structure)

Description will be given as to only parts different from the fourth example.

The two needles are constituted by the needle 1143 and the needle 1005 which is the same as that in the first example.

The suture thread 1068 is loaded in the needle 1005 in advance, and a T bar 1144 is provided at the distal end of the suture thread.

The T bar 1144 is formed of a metal material such as stainless, a bar material, a sheet material or a pipe made of a hard plastic material superior in the smoothness such as polyacetal.

The T bar 1144 has the dimension which allows insertion into the inner cavities of the needle guides 1106a and 1106b and the guide tube 1107.

Furthermore, the distal end of the suture thread 1068 is connected to substantially the center of the T bar 1144.

An engagement member 1146 is provided to the needle 1143 in the vicinity of the distal end of the inner cavity of the needle main body 1145.

Any other structure is similar to the structure of the needle 1005.

The engagement member 1145 has an inner cavity, and a conical tapered surface 1147 is provided on the distal end side of the inner cavity of this member, while an engagement surface 1148 is provided on the proximal side.

The inside diameter of the opening on the proximal side of the engagement member 1145 is slightly larger than the diameter which is a sum of the outside diameter of the T bar 1144 and the outside diameter of the suture thread 1068.

(Operations)

Description will be given as to parts different from the fourth example.

After the needles 1005 and 10143 are pushed through the suture tissues 1097a and 1097b, the suture thread 1068 is caused to protrude from the needle 1005, and moved into the needle guide 1106b, the guide tube 1107, the needle guide 1106a and the needle main body 1145.

Furthermore, when the suture thread 1068 is pushed forward, the T bar 1144 passes through the inner cavity of the engagement member 1146 and moves to the proximal side of the engagement surface 1148.

The tapered surface 1147 facilitates insertion into the opening on the proximal side of the engagement member 1146.

Subsequently, the needles 1005 and 1143 are removed from the suture tissues 1097a and 1097b.

Then, the end portion of the T bar 1144 is caught on the engagement surface 1148 and connected/fixed to the inside of the needle 1143.

(Advantages)

In addition to the advantages of the first example, the following advantages can be obtained.

Since the operation of fixing the suture thread 1068 to the needle 1143 is carried out by only pushing forward the suture thread 1068, improvement in the operability and reduction in the treatment time can be achieved.

[Sixth Example of Straight Needle Suture Machine]

(FIGS. 189 to 195)

(Structure)

Description will be given as to only parts different from the first to fifth examples.

The two needles are constituted by the needle 1149a and 1149b and have the same structure.

The needle 1149 is constituted by the needle main body 1150, the needle grip distal portion 1071, the needle grip proximal portion 1072, the O-ring 1073 and the pusher tube 1151.

The structure of the needle main body 1150, the needle grip distal portion 1071, the needle grip proximal portion 1072 and the O-ring is the same as that of the needle 1006 of the first example.

The pusher tube 1151 is slidably inserted into the needle 1149.

Further, the suture thread 1068 is loaded to the needle 1149 and the pusher tube 1151 in advance.

The pusher tube 1151 is constituted by the sheath 1152, the grip 1153, the stopper 1154 and the cap 1155.

The sheath 1152 is a tubular member having the flexibility which is made of a metal material such as stainless steel or nitinol or a plastic material such as polyethylene, fluorocarbon resin, polyamide or polyimide.

The inside diameter of the sheath 1152 has the dimension which allows the suture thread 1068 to readily slide therein, and it is approximately 0.3 to 1 mm.

Its outside diameter is slightly larger than the inside diameter of the O-ring 1073, the air-tightness can be maintained between the O-ring 1073 and the sheath 1152, and approximately 0.4 to 1.4 mm is preferable.

The grip 1153 is connected to the proximal end of the sheath 1152.

The grip 1153 also has the inner cavity which allows insertion of the suture thread 1068, and this inner cavity communicates with the inner cavity of the sheath 1152.

The grip 1153 is made of various kinds of metal material such as stainless steel or aluminium or various kinds of hard plastic material such as polypropylene, ABS, polycarbonate, polyacetal or polysulfone.

Moreover, a stopper 1154 is provided on the outer periphery of the sheath 1152 on the end side away from the O-ring 1073.

The outside diameter of the stopper 1154 is larger than the inside diameter of the O-ring 1073.

When the pusher tube 1151 is pulled out to the proximal side until the stopper 1154 comes into contact with the O-ring 1073, the distal end of the sheath 1152 is positioned on the proximal side away from the distal end of the needle main body 1150 by approximately 15 to 20 mm.

In addition, when the pusher tube 1151 is pushed out to the distal end side until the grip 1153 comes into contact with the needle grip proximal portion 1072, the distal end of the sheath 1152 protrudes on the distal end side from the distal end of the needle main body 1150 by approximately 5 to 20 mm.

Additionally, a cap 1155 similar to that in the first example is provided in the vicinity of the proximal end of the grip 1153.

The cap 1155 can be detachably put on the suture thread insertion opening 1156, and the suture thread insertion opening 1156 can be sealed when it is put.

A T bar 1157 is connected to the distal end of the suture thread 1068.

The T bar 1157 is formed by a pipe made of metal such as stainless, and its length is larger than a centesis hole produced when the needle main body 1150 pierces the suture tissues 1097a and 1097b. As this length, approximately 5 to 10 mm is preferable.

The inside diameter is approximately 0.3 to 0.5 mm.

The outside diameter of the T bar 1157 is set in such a manner that the dimension obtained by adding this diameter to the outside diameter of the suture thread 1068 is smaller than the inside diameter of the needle main body 1150, and the T bar 1157 can slide in the needle main body 1150.

A side hole 1158 is provided at the central point which is the weight point of the T bar 1157.

The distal end portion of the suture thread 1068 is inserted into the T bar 1157 from the side hole 1158, and exposed from one end portion, thereby forming a knot 1159.

Further, a part of the T bar 1157 in the vicinity of the end into which the suture thread 1068 is inserted is crushed and caulks the suture thread 1068.

In order to firmly fix the T bar 1157 and the suture thread 1068, an adhesive agent is filled into the T bar 1157 from the side hole 1158.

Also, the outer periphery of the knot 1159 is hardened by an adhesive agent.

Furthermore, the both ends of the T bar 1157 are rounded so as not to damage the tissue in the body cavity.

With the pusher tube 1151 being pulled out to the proximal side until the stopper 1154 comes into contact with the O-ring 1073, the T bar 1157 is loaded on the end side away from the sheath 1152 in the inner cavity of the needle main body 1150 in advance.

The suture thread 1068 is inserted into the sheath 1152 from the distal end of the sheath 1152 and extends to the proximal side of the grip 1153.

The length of the suture thread 1068 exposed on the proximal side of the grip 1153 is approximately 10 cm.

Moreover, with the suture thread 1068 being loaded in the needle 1150, the cap 1155 is put on the suture thread insertion opening 1156.

As a result, the suture thread 1068 is held between the cap 1155 and the suture thread insertion opening 1156 and connected to the pusher tube 1151. At the same time, the airtightness of the suture thread insertion opening 1156 is assured.

The needle guide described in the first to fifth examples is not provided to the distal end annular portion 1079 of the reinforcing member 1078 of the over-tube 1002.

(Operations)

Description will be given as to only parts different from the first example.

After the needles 1149a and 1149b are pushed through the suture tissues 1097a and 1097b, the grips 1153a and 1153b are pushed toward the distal end side until the grips 1153a and 1153b come into contact with the needle grip proximal portions 1072a and 1072b.

Then, the sheaths 1152a and 1152b are also pushed toward the distal end side, and the T bars 1157a 1157b are caused to protrude from the distal ends of the needle main bodies 1150a and 1150b and placed in the body cavity on the distal end side of the suture tissue 1097b.

Subsequently, the caps 1155a and 1155b are removed from the suture thread insertion openings 1156a and 1156b, and fixation of the suture thread 1068 and the pusher tube 1151 is released.

As a result, the suture threads 1068a and 1068b can slide on the needles 1149a and 1149b and the pusher tubes 1151a and 1151b.

Then, the needles 1149a and 1149b are removed from the suture tissues 1097a and 1097b and pulled into the needle lumens 1011a and 1011b.

Also, the inner sheaths 1004a and 1004b are pulled into the needle lumens 1011a and 1011b, respectively.

At that moment, the T bars 1157a and 1157b are caught on the suture tissue 1097b, and the suture threads 1068a and 1068b can not come off the suture tissues 1097a and 1097b.

Further, with the suture thread 1068 which extends from the proximal side of the grip 1153 being capable of freely moving, the over-tube 1002 and the endoscope 1009 are removed from the body of a patient.

Thereafter, a knot 1099 is formed to the suture thread 1068 exposed to the outside of the body of a patient as in the first example, and the knot 1099 is pushed into the body by using a general knot pusher, thereby ligating the proximal side of the suture tissue 1097a.

(Advantages)

In addition to the advantages of the first example, the following advantages can be obtained.

Since the suture thread 1068 does not have to be stretched between the two needles, it is possible to achieve improvement in the operability and reduction in the treatment time.

Further, since holding of the suture thread 1068 in the needle which has received the suture thread 1068 is no longer necessary, there is no possibility that the suture thread 1068 comes off when removing the over-tube 1002 from the body of a patient and one end of the suture thread 1068 can not be pulled out of the body of a patient.

Furthermore, since the suture thread 1068 and the T bar 1157 are caused to protrude from the end of the needle 1149 by pushing forward the pusher tube 1151, insertion is facilitated as compared with manually holding and pushing forward the flexible suture thread 1068, thereby achieving improvement in the operability and reduction in the treatment time.

Moreover, since there is no need to provide the needle guide to the over-tube 1002 as in the first to fifth examples, facilitation of manufacture and reduction in the manufacturing cost can be attained.

[Seventh Example of Straight Needle Suture Machine] (FIGS. 196 to 202)

(Structure)

Description will be given as to only parts different from the first and second examples.

The two needles 1160a and 1160b have the same structure.

The needle 1160 is composed of the needle end portion 1102, the needle grip 1067, the guide member 1103 and the pin 1162.

Connection between the needle end portion 1102, the guide member 1103, the needle sheath 1161 and the needle grip 1067 is similar to the structure of the needle 1100 in the second example.

The needle sheath 1161 is obtained by additionally providing a pin hole 1163 to the needle sheath 1100 in the second example.

Furthermore, the two inner sheaths 1164a and 1164b have the same structure.

The inner sheath 1164 has the structure similar to that of the inner sheath 1004 in the first example except that a pin slit 166 which extends in the longitudinal direction is provided on the side surface of the tube 1165.

With the needle 1160 being inserted into the inner sheath 1164 in advance, the pin 1162 is press-fitted/fixed in the pin hole 1163 through the pin slit 1166.

The outside diameter of the pin 1162 is smaller than the width of the pin slit 1166.

A part of the pin 1162 protrudes from the outer surface of the needle sheath 1161, and the protruding portion can slide in the pin slit 1166 in accordance with sliding of the needle 1160 in the inner sheath 1164.

Needle guides 1168a and 1168b are provided to the distal annular portion 1079 of the reinforcing member 1078.

The distal end side of the thread inner cavity 1091 of the needle guide 1168 has a small inside diameter, and a thread fixing surface 1167 is formed by a difference in the inside diameter.

As different from the first example, it is preferable that the width of the guide slit 1092 is larger than the suture thread 1068.

Any other structure is the same as that of the needle guide 1106 of the second example.

It is to be noted that the thread inner cavities 1091*a* and 1091*b* are not communicated with each other through the guide tube 1107 or the like as in the second example.

Hooks 1169*a* and 1169*b* are attached to the both ends of the suture thread 1168 through the connection pipe 1170.

The hook 1169 is formed by a wire made of metal such as stainless steel which, relatively, has the rigidity, and a clinch portion 1171 bent into a V shape is provided at the distal end of the hook 1169.

The hook 1169 and the connection pipe 1170 are loaded in the thread inner cavity 1091 in advance.

The distal end surface of the connection pipe 1170 on the suture thread side is in contact with the thread fixing surface 1167.

The connection pipe 1170 has the outside diameter slightly larger than the inside diameter of the thread inner cavity 1091, and is loaded being lightly fitted on the thread inner cavity. This fitting is set in such a manner that the connection pipe 1170 can be successfully pulled out with the force used when removing the needle 1160 from the suture tissue through which the needle 1160 has been pushed.

At this moment, they are loaded in such a manner that the clinch portion 1171 faces the same direction as the side hole 1105.

The clinch portion 1171 is positioned in the inner cavity of the tapered portion 1088.

The length of the suture thread 1068 is equal to or more than twofold of the length from the side opening 1013 to the proximal end of the slider receiver 1046, and folded and placed in the treatment lumen 1012.

(Operations)

Description will be given as to only parts different from the first example.

The needles 1160*a* and 1160*b* which have been pushed through the suture tissues 1097*a* and 1097*b* move into the needle guides 1168*a* and 1168*b*, and come into contact with and stop at the needle abutting surfaces 1090*a* and 1090*b*.

At that moment, the hooks 1169*a* and 1169*b* are inserted into the inner cavities of the needle end portions 1102*a* and 1102*b*.

The clinch portions 1171*a* and 1171*b* move along the tapered surfaces 1104*a* and 1104*b* of the guide member 1103, and protrude to the outside of the needle end portions 1102*a* and 1102*b* from the side holes 1105*a* and 1105*b*.

Subsequently, the rings 1048*a* and 48*b* of the slider receivers 1046*a* and 1046*b* and the set screws 1057*a* and 1057*b* of the inner sheath sliders 1042*a* and 1042*b* are loosened.

Then, the inner sheath sliders 1042*a* and 1042*b* and the needle sliders 1043*a* and 1043*b* still connected with the needles 1160*a* and 1160*b* are altogether removed from the housings 1047*a* and 1047*b*.

When the needles 1160*a* and 1160*b* are removed from the needle guides 1168*a* and 1168*b*, the clinch portions 1171*a* and 1171*b* are caught on the side holes 1105*a* and 1105*b* and connected to the needles.

With removal of the needles 1160*a* and 1160*b*, the both ends of the suture thread 1068 pierce the suture tissues 1097*a* and 1097*b* and are removed to the outside of the body (FIG. 202).

Then, when the needles are further removed, the suture thread 1068 passes through the guide slits 1092*a* and 1092*b* and comes off the needle guides 1168*a* and 1168*b*. At last, a part of the suture thread 1068 comes into contact with a part between the centesis out points 1113*a* and 1113*b* of the suture tissue 1097*b*.

After the both ends of the suture thread 1068 are removed from the housings 1047*a* and 1047*b*, the hooks 1169*a* and 1169*b* are removed from the needle end portions 1102*a* and 1102*b*, and the suture thread 1068 is cut in order to separate the hooks 1169*a* and 1169*b* from the connection pipe 1170.

With the suture thread 1068 which extends from the proximal side of the housings 1047*a* and 1047*b* being capable of freely moving, the over-tube 1002 and the endoscope 1009 are removed from the body of a patient.

(Advantages)

In addition to the advantages of the first example, the following advantages can be obtained.

Since the suture thread 1068 does not have to be handed over between the two needles, it is possible to achieve improvement in the operability and reduction in the treatment time.

[Eighth Example of Straight Needle Suture Machine]
(FIGS. 203 to 211)

(Structure)

Description will be given as to parts different from the first and seventh examples.

The two needles 1172*a* and 1172*b* have the same structure.

The needle 1172 is constituted by the needle main body 1173, the needle grip 1067 and the pin 1162.

The needle grip 1067 is connected to the proximal end of the needle main body 1173.

A notch 1174 is provided in the vicinity of the distal end of the needle main body 1173.

The notch 1174 has such a shape as shown in FIG. 205 and is constituted by a lead-in opening 1175, a fixing groove 1176 and a hook 1177.

The fixing groove 1176 is formed on the distal end side of the lead-in opening 1175, and its width is slightly smaller than the suture thread 1068.

The hook 1177 is also formed on the distal end side of the lead-in opening 1175, and its distal end portion faces the proximal side of the lead-in opening 1175.

The inner sheath is constituted by the inner sheaths 1164*a* and 1164*b* as similar to the seventh example.

Further, the pin hole 1163 is provided to the needle main body 1173, and the needle main body 1173 is slidably connected to the inner sheath 1164 by the pin 1162 as with the seventh example.

Needle guides 1178*a* and 1178*b* are arranged on the distal annular portion 1079 of the reinforcing member 1078.

The needle guide 1178 has a straight portion 1179 and a curved portion 1180 at the distal end thereof.

The curving direction of the curved portion 1180 corresponds to the direction to which the notch 1174 of the needle 1172 faces.

A guide slit 1181 is provided to the needle guide 1178, and its distal end is placed at a position which is slightly close to the curved portion 1180 side from the border between the straight portion 1179 and the curved portion 1180 and close to the lower side from the central axis of the inner cavity of the curved portion 1180.

The needle guide 1178 is provided with a side hole 1182 on the side surface opposite to the distal end portion of the guide slit 1181 by 180 degrees.

The width of the guide slit 1182 and the size of the side hole 1182 have such dimensions which facilitate insertion of the suture thread 1068.

As different from the seventh example, the needle abutting surface 1090 and the thread inner cavity 1091 are not provided in the inner cavity of the needle guide 1178.

Any other structure is the same as that of the needle guide 1106 according to the second example.

At the distal end of the treatment lumen 1012, a shaft 1183 is attached so as to bridge the two positions on the outer walls 1015.

In this case, the shaft 1183 extends in the direction vertical to the opening direction of the side opening 1013.

A drum 1184 having the flange at the both ends thereof is rotatably attached to the outer periphery of the shaft 1183.

The both ends of the suture thread 1068 pierce the respective guide slits 1181 of the needle guides 1178 and the respective side holes 1182, and are lightly fixed on the inner surface of each outer wall 1015 by temporary fixing member 1185.

Further, a knot 1186 is formed in the vicinity of the distal end portion of the suture thread 1068. The knot 1186 is smaller than the width of the guide slit 1181 and the inside diameter of the side hole 1182, and larger than the width of the fixing groove 1176.

The suture thread 1068 which extends into the treatment lumen 1012 from the guide slit 1181 is wound around the outer periphery of the drum 1184, and lightly fixed by the temporary fixing member 1185.

The length of the suture thread 1068 is similar to that of the seventh example.

—Modification—

The needle guide 1178 may or may not have the curved portion 1180 as shown in FIG. 211. In this case, a notch 1174 and a fixing grove 1176 must be formed at the distal end of the needle main body 1073.

(Operations)

Description will be given as to only parts different from the seventh example.

The needles 1172a and 1172b piercing the suture tissues 1097a and 1097b can move into the needle guides 1178a and 1178b.

As shown in FIG. 206, after the needle distal end comes into contact with the inner surface of the curved portion 1180, the needle 1172 bends, moves in the inner cavity of the curved portion 1180 and stops as shown in FIG. 207.

Then, the rings 1048a and 1048b of the slider receivers 1046a and 1046b and the set screws 1057a and 1057b of the inner sheath sliders 1042a and 1042b are loosened.

Further, the inner sheath sliders 1042a and 1042b and the needle sliders 1043a and 1043b having the needles 1160a and 1160b connected thereto are altogether removed from the housings 1047a and 1047b.

When the needle 1172 consequently starts to be removed from the needle guide 1178, the hook 1177 is caught on the suture thread 1068 stretched between the guide slit 1181 and the side hole 1182.

When the needle 1172 is further moved toward the outside, the suture thread 1068 is fitted to the fixing groove 1176 and fixed to the needle 1172.

Further, the knot 1186 functions as a stopper and strongly prevents the suture thread 1068 from coming off the fixing groove 1172.

At the same time, fixation of the both ends of the suture thread 1068 by the temporary fixing member 1185 is released.

When the needle 1172 is moved toward the outside, the suture thread 1068 is removed from the needle guide 1178 through the guide slit 1181 and the side hole 1182. With the same timing that the both ends of the suture thread 1068 are pulled back to the proximal side, the drum 1184 rotates to feed the suture thread 1068 wound therearound. The both ends of the suture thread 1068 are removed to the outside of the body through the suture tissues 1097a and 1097b.

Then, at last, fixation of the suture thread 1068 to the drum 1184 by the temporary fixing member 1185 is released, and a part of the suture thread 1068 comes into contact with the portion between the centesis out points 1113a and 1113b of the suture tissue 1097b.

(Advantages)

In addition to the advantages of the seventh example, the following advantages can be obtained.

Since the hook 1169 or the like is not provided to the both ends of the suture thread 1068 as in the seventh example, the both ends of the suture thread 1068 do not have to be cut before removing the over-tube 1002 from the body of a patient.

As a result, it is possible to achieve improvement in the operability and reduction in the treatment time.

Further, since the suture thread 1068 is wound around the drum 1184, there is no possibility that the suture thread intertwists and can not be removed when pulling out the suture thread 1068.

[Ninth Example of Straight Needle Suture Machine]
(FIGS. 212 to 218)

(Structure)

Description will be given as to only parts different from the first example.

A convex portion 1193 which protrudes toward the inner side over the circumference is provided in the inner cavity at the distal end of the treatment lumen 1012 of the over-tube 1002.

The convex portion 1193 may be formed integrally with or separately from the sheath portion 1007.

Furthermore, a lumen 1187 is provided in the inner cavity of the sheath portion 1007.

The distal end of the lumen 1187 is positioned on the distal end side away from the side opening 1013. Also, the proximal side is opened on the outer wall 1015 in the vicinity of the endoscope insertion portion 1008. A guide 1188 having the inner cavity is connected to the opening portion. The lumen 1187 communicates with the inner cavity of the guide 1188.

The thread grasping forceps 1189 is slidably inserted into the lumen 1187 and the guide 1188 in advance.

The thread grasping forceps 1189 has a structure that the grasping portion 1190 is connected to the distal end of the operation member 1191 and the operation knob 1192 is connected to the proximal side of the same.

The grasping portion 1190 protrudes and opens from the distal end opening of the lumen 1187 when the operation knob 1192 is pushed out, and it is pulled into the lumen 1187 when the operation knob 1192 is pulled toward the proximal side.

Although the grasping portion 1190 forms a loop opening 1098 when opened, the diameter of this opening is substantially the same as the inner diameter of the treatment lumen 1012.

The grasping portion 1190 is bent in a direction substantially vertical to the longitudinal direction of the operation member 1191, and can be opened along the distal end surface of a convex portion 1193 on the proximal side.

Any other structure concerning the grasping portion 1190 and the operation member 1191 is similar to that of the thread grasping forceps 1074 according to the first example.

Furthermore, although the needle guide is not provided to the distal annular portion 1079 of the reinforcing member 1078 in the drawing, the needle guide may be provided.

In case of providing the needle guide, a needle guide 1082 according to the first example is attached.

The two needles are constituted by the needles 1115a and 1115b according to the third example.

—Modification—

As shown in FIG. 218, in place of inserting the thread grasping forceps 1189 by providing the lumen 1187 to the sheath portion 1007, the thread grasping forceps 0189 may be inserted into the forceps channel (not shown) of the endoscope 1009.

(Operations)

Description will be given as to only parts different from the first example.

After the needles 1115a and 1115b are pushed through/caused to pierce the suture tissues 1097a and 1097b, the operation knob 1192 is pushed toward the distal end side, and the grasping portion 1190 is caused to protrude from the lumen 1187.

As shown in FIG. 213, the grasping portion 1190 is opened along the distal end surface of the convex portion 1193 on the proximal side and the inner surface of the treatment lumen 1012.

Moreover, the suture threads 1068a and 1068b are pushed toward the distal end side and caused to protrude from the needle end by feeding means 1123a and 1123b of the needles 1115a and 1115b.

In addition, when the suture threads 1068a and 1068b are pushed forward, they are inserted into the loop opening 1098 formed by the grasping portion 1190.

Subsequently, the operation knob 1192 is pulled toward the proximal side, and the suture threads 1068a and 1068b are held in the lumen 1187.

In this state, the needles 1115a and 1115b and the inner sheaths 1004a and 1004b are pulled into the needle lumens 1011a and 1011b.

Then, with the suture thread 1068 which extends from the proximal side of the elastic grip 1125 being capable of freely moving, the over-tube 1002 and the endoscope 1009 are removed from the body of a patient. As a result, both the distal ends and the proximal ends of the suture threads 1068a and 1068b are exposed to the outside of the body of a patient.

After the grasping portion 1190 is again opened and the ends of the suture threads 1068a and 1068b are taken out, the ends are tied to form a knot 1194.

Then, the proximal sides of the suture threads 1068a and 1068b taken out from the tissue centesis system 1001 are pulled, and the suture threads in the vicinity of the knot 1194 are brought into contact with the suture tissue 1097b between the centesis out points 1113a and 1113b.

At last, the suture thread 1068 exposed to the outside of the body of a patient is tied to form a knot 1099 as similar to the first example, the knot 1099 is pushed into the body by using a general knot pusher, and the proximal side of the suture tissue 1097a is ligated.

(Advantages)

In addition to the advantages of the first example, the following advantages can be obtained.

Since there is no need to provide the needle guide to the over-tube 1002, facilitation of manufacture and reduction in the manufacturing cost can be achieved.

[10th Example of Straight Needle Suture Machine]
(FIGS. 219 to 220)

(Structure)

Description will be given as to only parts different from the first and ninth examples.

The two needles 1198a and 1198b have the same structure.

The needle 1198 is composed of the needle distal portion 1195, the needle sheath 1101 and the needle grip 1067.

The needle grip 1067 is connected to the proximal end of the needle sheath 1101.

A reduced-diameter portion 1196 having a reduced outside diameter is formed at the proximal end of the needle distal portion 1195.

The outside diameter of the reduced-diameter portion 1196 is slightly larger than the inside diameter of the needle sheath 1101, and the reduced-diameter portion 1196 is connected to the inner cavity at the distal end of the needle sheath 1101 in the state that the reduced-diameter portion 1196 is lightly fitted to this inner cavity.

The length of the needle distal portion 1195 is set shorter than the length of the needle 1198 protruding from the distal end of the side opening 1013 to the distal end side when it is caused to completely protrude.

Additionally, the distal end of the suture thread 1068 is fixed to the proximal end of the needle distal portion 1195 by adhesion or the like.

The suture thread 1068 extends to the proximal side of the needle grip 1067.

A cap 1155 such as described in connection with the sixth example is attached to the proximal end of the needle grip 1067, and it is further preferable if the suture thread 1068 can be fixed to the needle grip 1067 by putting the cap 1155 on the proximal opening of the needle grip 1067.

A needle receiver 1197 is fixed to the distal end side of the side opening 1013 of the treatment lumen 1012.

The needle receiver 1197 is formed of a material with the hardness which facilitates centesis of the needle distal portion 1195, e.g., various kinds of rubber such as silicone rubber or fluorine rubber or various kinds of thermoelastic elastomer.

The distal end surface of the needle receiver 1197 on the proximal side is placed at a position which allows centesis of the needle distal portion 1195 by the depth of approximately 10 mm when the needle 1198 is caused to completely protrude.

Additionally, a quantity of power required for pulling out the needle distal portion 1195 when it is pushed through the needle receiver 1197 is set in such a manner that a quantity of power required for pulling out the needle distal portion 1195 from the needle sheath 1101 becomes also large.

It is more preferable if a small barb (not shown) facing the proximal side is provided on the outer surface of the needle distal portion 1195.

Further, although the reinforcing member 1078 and the needle guide are not provided in the treatment lumen 1012 in the drawing, they may be provided. In this case, it is good enough that the distal end of the needle guide is positioned on the proximal side away from the proximal end of the needle distal portion 1195 which has been pushed through the needle receiver 1197. Furthermore, the needle guide inner cavity must have the inside diameter which allows insertion of the needle distal portion 195.

It is to be noted that the convex portion 1193 is not provided to the sheath portion 7.

(Operations)

Description will be given as to only parts different from the first and ninth examples.

The needles 1198a and 1198b piercing the suture tissues 1097a and 1097b are pushed through the needle receiver 1197.

Then, the needle sliders 1043a and 1043b are pulled back to the proximal side, and the needles 1198a and 1198b are removed.

When the suture thread 1068 is fixed to the needle grip 1067 by using the cap 1155, the cap 1155 is removed from the needle grip 67 before removing the needle.

Then, fitting of the needle distal portion 1195 and the needle sheath 1101 is released, and only the needle distal portion 1195 remains being connected with the needle receiver 1197. If a barb is provided on the outer periphery of the needle distal portion 1195, the needle distal portion 1195 can be prevented from coming off the needle receiver 1197.

Further, with the suture thread 1068 which extends from the proximal side of the needle grip 1097 being capable of freely moving, the over-tube 1002 and the endoscope 1009 are removed from the body of a patient. As a result, both the distal ends and the proximal ends of the suture threads 1068a and 1068b are exposed to the outside of the body of a patient.

(Advantages)

In addition to the advantages according to the first example, the following advantages can be obtained.

Since the operation for stretching the suture thread 1068 between the two needles or the operation for feeding the suture thread 1068 is no longer necessary, it is possible to achieve improvement in the operability and reduction in the treatment time.

Moreover, the needle guide does not have to be provided to the over-tube 1002, thereby facilitating manufacture and reducing the manufacture cost.

[11th Example of Straight Needle Suture Machine]
(FIGS. 221 to 231)

Description Will be Given as to Only Parts different from the first example.

The position of the side opening 1013 is provided on the outer wall 1015 on the opposite side to the needle lumens 1011a and 1011b as different from the first example.

The two needles 1199a and 1199b have the same structure.

The needle 1199 is composed of the needle main body 1200, the needle grip distal portion 71, the needle grip proximal portion 1072, the O-ring 1073 and the pusher tube 1151.

Although the structure of the needle grip distal portion 1071, the needle grip proximal portion 1072, the O-ring 1073 and the pusher tube 1151 is similar to that of the needle 1006 according to the first example, a cap 1155 may not be provided to the pusher tube 1151.

A bent portion 1201 is provided to the distal end portion of the needle main body 1200, and it is bent at 180 degrees so that the needle distal end faces the proximal side.

The bent portion 1201 is gently curved in such a manner that the sheath 1152 of the pusher tube 1151 can slide.

The curvature diameter of the bent portion 1201 is slightly smaller than the inside diameter of the treatment lumen 1012 and formed in such a manner that the distal end of the needle main body 1200 moves directly above the side opening 1013.

With the inner sheath sliders 1042a and 1042b and the needle sliders 1043a and 1043b being assembled in the slider receivers 1046a and 1046b in advance, the needle main body 1200 is slidably inserted into the needle lumens 1011a and 1011b, and the proximal end of the needle main body 1200 is connected to the needle grip distal portions 1071a and 1071b.

The distal end of the needle main body 1200 is set to have such a length as that it is positioned on the distal end side away from the side opening 1013 when the needle slider 1043 is completely pushed out and positioned on the proximal side away from the side opening 1013 when the needle slider 1043 is completely pulled back.

Moreover, the both ends of the suture thread 1068, each of which has a length of approximately 15 mm, are loaded to the distal ends of the needle main bodies 1200a and 1200b.

An extended-diameter member 1202 is attached to the both ends of the suture thread 1068, and it can protrude from the distal end of the needle main body 1200 by pushing forward the pusher tube 1151.

The part exposed from the needle main body 1068 is placed in the treatment lumen 1012.

Incidentally, the inner sheath is not provided in the drawing, but the inner sheath may be provided. In this case, the inner sheath must have the clinch portion as similar to the needle 1199.

Further, although the reinforcing member 1078 or the needle guide is not provided in the treatment lumen 1012 in the drawing, they may be provided. In this case, the needle guide 1082 must be attached to the proximal side of the side opening 1013 in such a manner that the tapered portion 1088 faces the distal end side.

The thread grasping forceps 1189 having the loop-shaped grasping portion 1190, e.g., a general snare forceps is inserted into the forceps channel (not shown) of the endoscope 1009. The structure of the thread grasping forceps 1189 is similar to that of the ninth example.

—Modification—

In place of loading the both ends of the suture thread 1068 in the inner cavity at the distal end of the needle main body 1200, a hook 1203 may be provided on the outer surface at the needle end and the both ends of the suture thread 1068 may be caught thereon, as shown in FIG. 231.

In this case, the pusher tube 1151 is no longer necessary.

(Operations)

With the needle sliders 1043a and 1043b being completely pushed to the end side, the side opening 1013 is positioned above the suture tissues 1097a and 1097b, and thereafter suction is carried out by the endoscope 1009.

Subsequently, after causing the thread grasping forceps 1189 from the forceps channel of the endoscope 1009, the operation knob 1192 is pushed forward to open the grasping portion 1190, and a loop opening 1098 is formed in the vicinity of the sucked suture tissue 1097a.

Then, the needle sliders 1043a and 1043b are pulled back toward the proximal side, and the needle main body 1200 is pushed through the suture tissues 1097a and 1097b.

The suture thread 1068 being parallel with the needle main body 1200 is inserted from the insertion point 1112 of the suture tissue 1097b, and protrudes from the protruding point 1113 of the suture tissue 1097a.

The needle end protruding from the suture tissue 1097a is inserted into the loop opening 1098.

Then, the grip 1153 of the pusher tube 1151 is pushed, the enlarged-diameter member 1202 and the both ends of the suture tissue 1068 are caused to protrude from the needle end.

Subsequently, the operation knob 1192 is pulled back to the proximal side, the grasping portion 1190 is closed, and the both ends of suture threads 1068 are held.

At this moment, the enlarged-diameter member 1202 functions as a stopper and prevents the suture tissue 1068 from coming off the grasping portion 1190.

Furthermore, the needle sliders 1043a and 1043b are again completely pushed toward the distal end side, and the suture tissues 1097a and 1097b are removed from the needle main body 1200.

When the both ends of the suture thread 1068 are engaged with the hook 1203, the both ends of the suture thread 1068 are withdrawn from the needle main body 1200 by removal of the needle main body 1200.

Then, only the endoscope 1009 is removed from the body of a patient. Then, the both ends of the suture thread 1068 are pulled to the outside of the body of a patient, and a part of the suture thread 1068 is brought into contact with the suture tissue 1097*b* between the centesis in points 1112*a* and 1112*b*.

Then, the over-tube 1002 is removed from the body of a patient.

(Advantages)

In addition to the advantages of the first example, the following advantages can be obtained.

In the first example, since the needle is pushed forward at the time of centesis by the needle, the needle bends in the inner sheath, and a quantity of the pushing power on the proximal side may not be possibly sufficiently transmitted to the distal end. On the contrary, since centesis can be carried out by pulling the needle in this example, the needle does not bend, and a quantity of tensile power on the proximal side is directly transmitted to the needle distal end. As a result, the centesis property of the needle with respect to the suture tissue is further improved.

Additionally, since the needle guide does not have to be provided to the over-tube 1002, it is possible to attain facilitation of manufacture and reduction in the manufacturing cost.

[12th Example of Straight Needle Suture Machine]
(FIGS. 232 to 235)

(Structure)

Description will be given as to only parts different from the 11th example.

The two needles 1204*a* and 1204*b* have the same structure.

The needle 1204 is composed of the needle sheath 2105, the needle end portion 1206 and the needle grip 1067.

The needle sheath 1205 has a bent portion 1201 at the distal end thereof as similar to the needle main body 1200 according to the 11th example.

The needle grip 1067 is connected to the proximal side of the needle sheath 1205.

A slit 1207 having the width which allows insertion of the suture thread 1068 is provided at the distal end of the needle sheath 1205.

An annular groove 1208 is provided along the circumference in the vicinity of the center of the needle distal portion 1206.

Further, a reduced-diameter portion 1196 is provided at the distal end side of the needle distal portion 1206 (distal end side of the sheath portion 1007) as similar to the 10th example, and it is lightly fitted and fixed to the inner cavity at the distal end of the needle sheath 1205.

The proximal side of the needle distal portion 1206 is set so as to be positioned on the distal end side of the side opening 1013 when the slider 1043 is completely pushed out.

Furthermore, as similar to the 10th example, one end of the suture thread 1068 is fixed to the proximal end of the needle distal portion 1206, and the suture thread 1068 extends to the outside of the needle through the slit 1207.

In place of the thread grasping forceps 1189 of the 11th example, a thread gripper 1209 may be inserted into the forceps channel of the endoscope 1009.

The thread gripper 1209 is composed of the two grasping portions 1210, the connection portion 1211, the operation member 1212 and the operation knob 1213.

The operation knob 1213 is detachably disposed to the proximal side of the operation member 1212.

The connection portion 1211 is fixed to the distal end side of the operation member 1212.

The operation member 1212 is formed by a metal coil or the like having the flexibility, and it is formed so as to be capable of sliding in the forceps channel of the endoscope 9.

The two grasping portions 1210*a* and 1210*b* are attached to the both ends of the connection portion 2111 substantially in parallel to each other with a fixed gap therebetween.

This gap has substantially the same dimension as the gap between the needles 1204*a* and 1204*b*.

The grasping portion 210 is a tubular member formed of a plastic material such as polypropylene or ABS.

A convex portion 1214 is provided on the entire circumference of the inner surface at the distal end of the grasping portion 1210.

The height of the convex portion is substantially the same as the depth of the annular groove 1208 of the needle distal portion 1206.

(Operations)

Description will be given as to only parts different from the 11th example.

The annular groove portions 1208*a* and 1208*b* of the needle distal portions 1206*a* and 1206*b* protruding the suture tissues 1097*a* and 1097*b* are held by the grasping portion 1190 of the thread grasping forceps 1189, and the endoscope 1009 is removed.

Then, the needle distal portion 1206 is withdrawn from the distal end of the needle sheath 1205. When the endoscope 1009 is further removed, the needle distal portion 1206 and the suture thread 1068 pierce the tissue from the point 1112 to the point 1113.

At last, the both ends of the suture thread 1068 are pulled out to the outside of the body of a patient, and a part of the suture thread 1068 is brought into contact with the suture thread 1097*b* between the centesis points 1112*a* and 1112*b*.

When the thread gripper 1209 is used, the operation knob 1213 is pushed to the distal end side so that the needle distal portion 1206 can be inserted into the inner cavity of the grasping portion 1210.

As a result, the convex portion 1214 of the grasping portion 1210 and the annular groove 1208 of the needle distal portion 1206 are engaged with each other, and the needle distal portion 1206 is held.

(Advantages)

In addition to the advantages of the 11th example, the following advantages can be obtained.

By removing the endoscope 1009, the needle distal portion 1206 is removed from the suture tissues 1097*a* and 1097*b*, and hence the operation for removing the needle by using the needle slider is no longer necessary, thereby achieving improvement in the operability and reduction in the treatment time.

Moreover, when the thread gripper 1209 is used, the thread gripper 1209 can be held by only pushing the thread gripper 1209 into the needle distal portion 1206, and the operation for opening/closing the loop-shaped grasping portion is thereby no longer necessary. As a result, it is possible to achieve improvement in the operability and reduction in the treatment time.

According to the above-described tissue centesis system, the flexible sheath has the lumen which allows insertion of the endoscope, and the endoscope can be inserted into a space into which the suture tissue is sucked. In this structure, the suture tissue is sucked into the lumen inner cavity positioned on the distal side on substantially the same axis with the endoscope. Therefore, it is possible to easily and assuredly confirm whether the centesis means can be successfully pushed through a target part of the suture tissue before centesis by the centesis means. In addition, the suture tissue can be adjusted into a shape which facilitates observation by moving forward/backward or bending the distal end of the endoscope with respect to the side opening. As a result, the subtle control over the centesis position is enabled, thereby performing secure suture. Additionally, the treatment operation is facilitated, and the treatment time can be also greatly reduced.

Further, since the centesis means are arranged in parallel with a fixed gap, the centesis in point and the centesis out point of the centesis means on the suture tissue also have a fixed gap. Consequently, the secure control is enabled without extremely reducing the stitching gap. As a result, the treatment operation is simplified, and the treatment time is also greatly reduced.

Furthermore, even if stitching must be carried out for several times, a distance of one stitch can be controlled to be fixed, thereby assuredly performing the suture with a reduced number of times of stitching.

Moreover, since the endoscope and the space into which the suture tissue is sucked are arranged on substantially the same axis, a larger space capable of sucking the suture tissue can be obtained without increasing the outside diameter of the flexible sheath. As a result, the pain given to a patient at the time of insertion of the flexible sheath can be reduced.

In addition, since the flexible sheath and the endoscope are slidably arranged, they can be inserted into the body cavity of a patient with the curved portion of the endoscope protruding from the opening at the distal end of the flexible sheath. As a result, the insertion property into the body can be improved, and the pain given to a patient at the time of insertion can be reduced.

Additionally, since the two centesis means are arranged in advance, the two centesis means can be immediately pushed through the tissue when the suture tissue is once sucked from the side opening. In this regard, the treatment operation is simplified, and the treatment time is also greatly reduced.

Further, since the inner sheath is brought into contact with a target centesis part and then the centesis means are pushed through the part, confirmation of the target centesis part and positioning on the target centesis part can be facilitated. Thus, the secure suture can be effected and the treatment operation can be simplified. Also, the treatment time can be greatly reduced.

Furthermore, since at least a part of the flexible sheath in the vicinity of the side opening is transparent, the outer periphery of the flexible sheath can be observed by the endoscope, and positioning of the side opening can be facilitated, thereby achieving improvement in the operability and reduction in the treatment time.

Moreover, if the distal end portion of the flexible sheath is a detachable separate body, parts other than the distal end portion can be produced without making any change when manufacturing the tissue centesis systems with the side opening of a different size, thereby reducing the manufacturing cost.

In addition, since parts other than the distal end opening of the flexible sheath and the side opening are configured to maintain the air-tightness relative to the outside, suction of the suture tissue from the side opening can be efficiently performed.

11th Embodiment

FIG. 237 shows one of the procedures according to the anastomosis system according to the 11th embodiment.

The anastomosis system according to the 11th embodiment uses a clip device 5F in both or one of the procedure (9) and the procedure (12) in the first embodiment. A regular endoscopic clip device can be used as long as the clip device 5F can be used in the endoscope 12. Any other points remain unchanged.

According to this anastomosis system of this embodiment, the suture can be readily preformed.

12th Embodiment

FIG. 238 shows one of the procedures according to the anastomosis system of the 12th embodiment.

The anastomosis system according to the 11th embodiment replaces the above-described procedure (10) in the first embodiment as follows.

That is, there is included an additional procedure (10A) by which dissection is carried out by using a needle-shaped knife with a distal end insulation portion 5G after a necessary part of the small intestine SI pulled in the gaster G is pre-cut by a needle-shaped knife 5A in the procedure (10) as described above. The needle-shaped knife with the insulated distal portion 5G is obtained by providing to the distal end of an electrode protruding from the main body member having the electrical insulating property an electrical insulator having a diameter larger than this electrode. According to the needle-shaped knife with the insulated distal portion 5G, the insulating member at the distal end portion prevents puncture to the lower layer which should not be dissected or unnecessary cautery when performing high-frequency incision of a living tissue by using the electrode.

As a result, the suture can be readily carried out.

The present invention has been described in connection with the preferred embodiments illustrated in the various drawings, but any similar embodiments can be also used without departing from the present invention, and the foregoing embodiments can be modified in order to realize the same function as that of the present invention. Therefore, the present invention is not restricted to any single embodiment, and various combinations of the embodiments are possible within the scope intended by the present invention.

What is claimed is:

1. An apparatus for positioning an endoscope relative to a body surface, the apparatus comprising:
    a first tube body;
    a first operation wire arranged to the first tube body and configured to be controlled to bend the first tube body;
    a second operation wire arranged to the first tube body and configured to be controlled to bend the first tube body; and
    a balloon portion comprising:
        a first expandable balloon arranged to an external surface of the first tube body, the first expandable balloon having an expanded configuration; and
        a second expandable balloon arranged to the external surface of the first tube body and separated from the first balloon by a space, the second expandable balloon having an expanded configuration;
        wherein the first expandable balloon and the second expandable balloon are further configured to receive the body surface in the space separating the first expandable balloon and the second expandable balloon and to fix the body surface between the first expandable balloon in the expanded configuration and the second expandable balloon in the expanded configuration, wherein the first tube body defines at least:
- an endoscope receiving lumen configured to receive the endoscope,
- a first operation wire receiving lumen configured to receive the first operation wire and a first fluid,
- a first fluid communication lumen configured to connect the first operation wire receiving lumen with an interior of the first expandable balloon to feed the first fluid into the interior of the first expandable balloon to expand the first expandable balloon into its expanded configuration,
- a second operation wire receiving lumen configured to receive the second operation wire and a second fluid, and
- a second fluid communication lumen configured to connect the second operation wire receiving lumen with an interior of the second expandable balloon to feed the second fluid into an interior of the second expandable balloon to expand the second expandable balloon into its expanded configuration.

2. The apparatus according to claim 1, wherein:
the first fluid is a gas or a liquid, and
the second fluid is a gas or a liquid.

3. The apparatus according to claim 1, further comprising an operation member configured to control the first operation wire and the second operation wire to bend the first tube body, wherein:
- a distal end of the first operation wire is fixed to the first tube body,
- a distal end of the second operation wire is fixed to the first tube body,
- a proximal end of the first operation wire and a proximal end of the second operation wire are fixed to the operation member, and
- the operation member is configured to pull one of the first operation wire and the second operation wire, and push the other of the first operation wire and the second operation wire to bend the first tube body.

4. The apparatus according to claim 1, wherein the first operation wire receiving lumen and the second operation wire receiving lumen are arranged in an axial direction of the first tube body.

5. The apparatus according to claim 1, wherein the first operation wire receiving lumen and the second operation wire receiving lumen are opposed to each other in a radial direction of the first tube body.

6. The apparatus according to claim 1, wherein the first tube body includes a first tube body flexibility varying portion configured to provide a first area of the first tube body closer to a distal end of the first tube body with greater bending flexibility than a second area of the first tube body further from the distal end of the first tube body than the first area, where the first tube body bending flexibility varying portion includes a reinforcing layer arranged to the second area of the first tube body to increase a thickness of the second area of the first tube body in a radial direction of the first tube body relative to a thickness of the first area of the first tube body in the radial direction of the first tube body such that the first area of the first tube body has a greater bending flexibility than the second area of the first tube body.

* * * * *